US008088621B2

(12) United States Patent
Rodriguez et al.

(10) Patent No.: US 8,088,621 B2
(45) Date of Patent: Jan. 3, 2012

(54) ADENOVIRAL FIBER EXCHANGE SHUTTLE SYSTEM

(75) Inventors: Ronald Rodriguez, Glenwood, MD (US); Shawn Edward Lupold, Ellicott City, MD (US); Wasim Haider Chowdhury, Laurel, MD (US); Tarana A. Kudrolli, Frederick, MD (US)

(73) Assignee: The Johns Hopkins University, Baltimore, MD (US)

( * ) Notice: Subject to any disclaimer, the term of this patent is extended or adjusted under 35 U.S.C. 154(b) by 927 days.

(21) Appl. No.: 11/901,275

(22) Filed: Sep. 14, 2007

(65) Prior Publication Data

US 2009/0042257 A1    Feb. 12, 2009

Related U.S. Application Data

(63) Continuation of application No. PCT/US2006/010025, filed on Mar. 16, 2006.

(60) Provisional application No. 60/662,168, filed on Mar. 16, 2005.

(51) Int. Cl.
*C12N 15/87* (2006.01)

(52) U.S. Cl. ........ 435/462; 435/465; 435/466; 435/475; 435/477; 435/488

(58) Field of Classification Search .................. None
See application file for complete search history.

(56) References Cited

U.S. PATENT DOCUMENTS

2003/0166586 A1   9/2003  Sealy
2004/0005591 A1   1/2004  Clark

OTHER PUBLICATIONS

NG, P., et al., "A High-Efficiency Cre/loxP-Based System for Construction of Adenoviral Vectors," Human Gene Therapy, 1999, 10: pp. 2667-2672.
NG, P., et al., "An Enhanced System for Construction of Adenoviral Vectors by the Two-Plasmid Rescue Method," Human Gene Therapy, 2000, 11: pp. 693-699.
Tashiro, F., et al., "Constructing Adenoviral Vectors by Using the circular Form of the Adenoviral genome cloned in a Cosmid and teh Cre-loxP Recombination System," Human Gene Therapy, 1999, 10: pp. 1845-1852.
International Search Report, PCT/US06/10025, Issued Dec. 6, 2006.
Nakano et al., "Production of viral vectors using recombinase-mediated cassette exchange", Nucleic Acids Reserach, vol. 33, e76, pp. 1-8 (2005).
Danthinne et al., "Production of first generation adenovirus vectors: A review", Gene Therapy, vol. 7, pp. 1707-1714 (2000).
Dmitriev et al., "An adenovirus vector with genetically modified fibers demonstrates expanded tropism via utilization of a coxsackievirus and adenovirus receptor-independent cell entry mechanism", Journal of Virology, vol. 72, pp. 9706-9713 (1998).
Langer et al., "A genetic screen identifies novel non-compatible loxP sites", Nucleic Acids Research, vol. 30, pp. 3067-3077 (2002).
Pierce et al. "A positive selection vector for cloning high molecular weight DNA by the bacteriophage P1 system: Improved cloning efficacy", Proc. Nat'l. Acad. Sci. USA, vol. 89, pp. 2056-2060 (1992).
Roelvink et al., "Identification for a Conserved Receptor-Binding Site on the Fiber Proteins of CAR-Recognizing Adenovirdae", Science, vol. 286, p. 1568 (1999).
Tomko et al., "HCAR and MCAR: The human and mouse cellular receptors for subgroup C adenoviruses and group B coxsackieviruses", Proc. Natl. Acad. Sci. USA, vol. 94, pp. 3352-3356 (1997).
van Beusechem et al., "Efficient and Selective Gene Transfer into Primary Human Brain Tumors by Using Single-Chain Antibody-Targeted Adenoviral Vectors with Native Tropism Abolished", Journal of Virology, vol. 76, pp. 2753-2762 (2002).
Wickham et al., "Increased In Vitro and In Vivo Gene Transfer by Adenovirus Vectors Containing Chimeric Fiber Protein", Journal of Virology, vol. 71, pp. 8221-8229 (1997).
Wickham et al., "Integrins avb3 and avb5 Promote Adenovirus Internalization but not Virus Attachment", Cell, vol. 73, pp. 309-319 (1993).
Zeng et al., "AdEasy System Made Easier by Selecting the Viral Backbone Plasmid Preceding Homologous Recombination" Bio Techniques, vol. 31, pp. 260-262 (2001).
Ziff et al., "Coincidence of the Promoter and Capped 5' Terminus of RNA from the Adenovirus 2 Major Late Transcription Unit", Cell, vol. 15, pp. 1463-1475 (1978).
Belousova et al., "Modulation of Adenovirus Vector Tropism via Incorporation of Polypeptide Ligands into the Fiber Protein," Journal of Virology, vol. 76, pp. 8621-8631 (Sep. 2002).
Bergelson et al., "Isolation of a Common Receptor for Coxsackie B Viruses and Adenoviruses 2 and 5," Science, 275, 1320 (1997).
Berget et al., "Spliced segments at the 5' terminus of adenovirus 2 late mRNA," Proc. Natl. Acad. Sci. USA, vol. 74, No. 8, pp. 3171-3175 (Aug. 1977).
Buchholz et al., "A simple assay to determine the functionality of Cre or FLP recombination targets in genomic manipulation constructs," Nucleic Acids Research, vol. 24(15), pp. 3118-3119 (1996).
Chow et al., "An Amazing Sequence Arrangement at the 5' Ends of Adenovirus 2 Messenger RNA," Cell, vol. 12, pp. 1-8 (Sep. 1977).
He et al., "A simplified system for generating recombinant adenoviruses," Proc. Natl. Acad. Sci. USA, vol. 95, pp. 2509-2514 (Mar. 1998).
Krasnykh et al., "Characterization of an Adenovirus Vector Containing a Heterologous Peptide Epitope in the HI Loop of the Fiber Knob," Journal of Virology, vol. 72, pp. 1844-1852 (Mar. 1998).
Mizuguchi et al., "CAR- or av integrin-binding ablated adenovirus vectors, but not fiber-modified vectors containing RGD peptide, do not change the systemic gene transfer properties in mice," Gene Therapy, 9, pp. 769-776 (2002).
Nevins et al., "Groups of Adenovirus Type 2 mRNA's Derived from a Large Primary Transcript: Probable Nuclear Origin and Possible Common 3' Ends," Journal of Virology, vol. 25, pp. 811-823 (Mar. 1978).
Okegawa et al., "The Dual Impact of Coxsackie and Adenovirus Receptor Expression on Human Prostate Cancer Gene Therapy," Cancer Research, 60, pp. 5031-5036 (Sep. 15, 2000).
Lupold et al., "pFEX: A novel fiber exchange system for the creation of modified-fiber gene therapy vectors", Molecular Therapy, vol. 9, Supp. 1, p. S53, Abstract 137 (2004).

*Primary Examiner* — Jim Ketter
(74) *Attorney, Agent, or Firm* — Edwards Wildman Palmer LLP; Peter F. Corless

(57) ABSTRACT

The instant invention provides methods and compositions for generating recombinant adenoviral vectors. The invention also provides kits comprising for the generation of recombinant adenoviral vectors.

61 Claims, 71 Drawing Sheets

Various spacer sequences produce non-compatible *lox* sites to prevent excision. Changes are in *italics*.

Spacer Sequences:

| | |
|---|---|
| P | GCATACAT |
| 511 | G*T*ATACAT |
| m2 | *TGGT*TTCT |
| m3 | *TGGTA*TT*A* |
| M7 | *TT*CTATCT |
| M11 | *TGGTA*TC*G* |

FIG. 2B

Nde I Digestion Demonstrates ColE1/Ad Right Hand Recombination

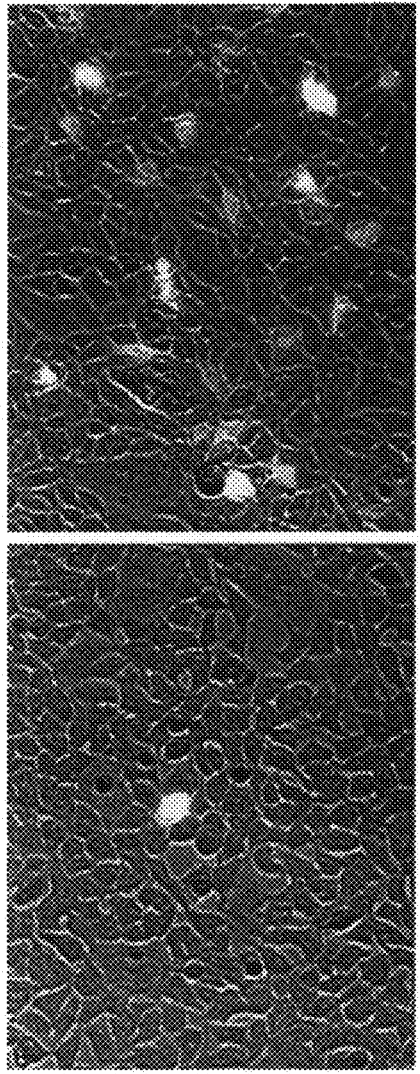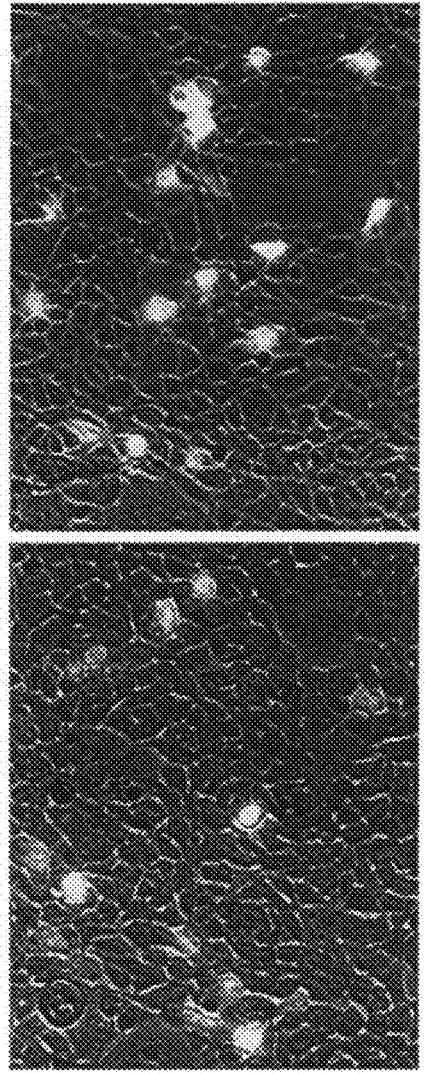
FIG. 23

Table 1: Primers for constructing and sequencing pFex.

| Primer | Sequence | Primer | Sequence |
|---|---|---|---|
| 5' Lox71 | [Phosp]CGTACCGTTCGTATAGCATACAT TATACGAAGTTATA | pFEXfor08 | CCGCAGAATAAGCCACACCC |
| 3' Lox71 | [Phosp]CCGGTATAACTTCGTATAATGTA TGCTATACGAACGGTACGAT | pFEXfor09 | TAACAAAAATACCGCGATCC |
| 5' Lox m2/66 | [Phosp]CCGGTATAACTTCGTATATGGTT TCTTATACGAACGGTA | pFEXfor10 | ACAGCTCCTCGGTCATGTCC |
| 3' Lox m2/66 | [Phosp]GATCTACCGTTCGTATAAGAAAC CATATACGAAGTTATA | pFEXfor11 | CGTTTTCCCAGTTACGTAA |
| AdE-Dist 5' | AACCGGTATACATTGCCCAAGAATAAAG | pFEXrev01 | CACTATAGGGCGAATTGGGC |
| AdE-Dist 3' | TCATAAGTGCGGCGACGATA | pFEXrev02 | GCCCTTTTTACACTGTGAC |
| loxmve1 | GTTGTGTGGAATTGTGAGCGG | pFEXrev03 | TTTATGCAGAAACCCGAGA |
| loxmve2 | CATGTACCGGTGGGGTGCGGATGGACA GGAAC | pFEXrev04 | ATATTGAGAAGGTGGCGAGA |
| pFEXfor01 | CTAACAATTCGTTCAAGCCG | pFEXrev05 | TGTTTGTCACGCCCGCACCT |
| pFEXfor02 | TCAGCGGTTTCATCACTTT | pFEXrev06 | AGAGGTTTATATGGTACCGG |
| pFEXfor03 | CTGACCATTCTTGTGTTGG | pFEXrev07 | ACTTAAGTGAGCTGCCCGGG |
| pFEXfor04 | GTCTCCTTTTTATGTACTGTG | pFEXrev08 | TTATGCCCATGCAACAGAAA |
| pFEXfor05 | TTATACGAAGTTATACCGGT | pFEXrev09 | TATTACACGCCATGATATGC |
| pFEXfor06 | AATAAACTGCTGCCGCCGCC | pFEXrev10 | CGGTGTAGAGGATTATAAATCAATC |
| pFEXfor07 | ATCAATGTTGGCACAACACA | pFEXrev11 | CATGCTTGGTTATGTTTCTA |

FIG. 24

Table 2: Primers for constructing and sequencing Fiber Shuttles

| Primer | Sequence |
|---|---|
| S-lox m2/71-X5 | [Phos]CTAGTACCGTTCGTATATGGTTT CTTATACGAAGTTATC |
| S-lox m2/71-X3 | [Phos]TCGAGATAACTTCGTATAAGAAA CCATATACGAACGGTA |
| N-Lox 66-A-5 | [Phos]GGCCGCATAACTTCGTATAGCAT ACATTATACGAACGGGTAG |
| N-Lox 66-A-3 | [Phos]GTACCTACCGTTCGTATAATGTA TGCTATACGAAGTTATGC |

FIG. 25

Table 3: Current Fiber Shuttle Vectors

| Vector | Antibiotic Resistance | HI Loop Peptide | CAR Binding |
|---|---|---|---|
| RP-Fib-1 | Kanamycin | None | Wild Type |
| RP-Fib-2 | Kanamycin | None | $dT_{489}AYT_{492}$ |
| RP-Fib-3 | Kanamycin | RGD4C | Wild Type |
| RP-Fib-4 | Kanamycin | RGD4C | $dT_{489}AYT_{492}$ |
| RPuc-Fib-1 | Ampicillin | None | Wild Type |
| RPuc-Fib-2 | Ampicillin | None | $dT_{489}AYT_{492}$ |
| RPuc-Fib-3 | Ampicillin | RGD4C | Wild Type |
| RPuc-Fib-4 | Ampicillin | RGD4C | $dT_{489}AYT_{492}$ |

FIG. 26

Table 4: Total transformants from 294 co-transfections. Kan/suc colonies represent desired recombinants, Kan the total pAdTrack-Fex transformants, and Amp the total RPuc-Fib shuttle transformants.

| Sample | Kan/Suc | Kan | Amp |
|---|---|---|---|
| pAdTrack - | 40 | 142000 | 0 |
| pAdTrack + Rpuc-Fib-1 | 2720 | 300000 | 3000000 |
| pAdTrack + Rpuc-Fib-2 | 1820 | 321000 | 3000000 |
| pAdTrack + Rpuc-Fib-3 | 1250 | 183000 | 3000000 |
| pAdTrack + Rpuc-Fib-4 | 2180 | 250000 | 3000000 |
| pAdTrack-Luc - | 0 | 29000 | 0 |
| pAdTrack-Luc + Rpuc-Fib-1 | 1170 | 17000 | 3000000 |
| pAdTrack-Luc + Rpuc-Fib-2 | 780 | 17100 | 3000000 |
| pAdTrack-Luc + Rpuc-Fib-3 | 2620 | 40200 | 3000000 |
| pAdTrack-Luc + Rpuc-Fib-4 | 2690 | 40000 | 3300000 |

FIG. 27

Table 5: Percent recombinants of large pAdTrack-Fex vector.

| Sample | Average | Stdev |
|---|---|---|
| pAdTrack - | 0.03% | |
| pAdTrack + Rpuc-Fib-1 | 0.91% | |
| pAdTrack + Rpuc-Fib-2 | 0.57% | 0.76% | 0.001604 |
| pAdTrack + Rpuc-Fib-3 | 0.68% | |
| pAdTrack + Rpuc-Fib-4 | 0.87% | |
| | | |
| pAdTrack-Luc - | 0.00% | |
| pAdTrack-Luc + Rpuc-Fib-1 | 6.88% | |
| pAdTrack-Luc + Rpuc-Fib-2 | 4.56% | 6.17% | 0.010838 |
| pAdTrack-Luc + Rpuc-Fib-3 | 6.52% | |
| pAdTrack-Luc + Rpuc-Fib-4 | 6.73% | |

FIG. 28

Table 6: Titer of pFex and AdEasy based virus

| Name | Purification Date | Cell Line for Amplification | Purification Method | Titer Date | PFU/ml |
|---|---|---|---|---|---|
| AdTrack-AdEasy | 8/22/2005 | 293 cells | AdenoPure Kit | 9/22/2005 | 2.15E+09 |
| AdTrack-WTFib | 8/22/2005 | 293 cells | AdenoPure Kit | 9/22/2005 | 1.72E+09 |

FIG. 29 pShuttle-Fib (SEQ ID NO:1)

```
GCGCTCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTA
CCATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTG
CGCAACGTTGTTGNNNNNNAAAAAGGATCTTCACCTAGATCCTTTTCACGTAGAAAGCCAGT
CCGCAGAAACGGTGCTGACCCCGGATGAATGTCAGCTACTGGGCTATCTGGACAAGGGAAAA
CGCAAGCGCAAAGAGAAAGCAGGTAGCTTGCAGTGGGCTTACATGGCGATAGCTAGACTGGG
CGGTTTTATGGACAGCAAGCGAACCGGAATTGCCAGCTGGGGCGCCCTCTGGTAAGGTTGGG
AAGCCCTGCAAAGTAAACTGGATGGCTTTCTCGCCGCCAAGGATCTGATGGCGCAGGGGATC
AAGCTCTGATCAAGAGACAGGATGAGGATCGTTTCGCATGATTGAACAAGATGGATTGCACG
CAGGTTCTCCGGCCGCTTGGGTGGAGAGGCTATTCGGCTATGACTGGGCACAACAGACAATC
GGCTGCTCTGATGCCGCCGTGTTCCGGCTGTCAGCGCAGGGGCGCCCGGTTCTTTTTGTCAA
GACCGACCTGTCCGGTGCCCTGAATGAACTGCAAGACGAGGCAGCGCGGCTATCGTGGCTGG
CCACGACGGGCGTTCCTTGCGCAGCTGTGCTCGACGTTGTCACTGAAGCGGGAAGGGACTGG
CTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCAT
TCGACCACCAAGCGAAACATCGCATCGAGCGAGCACGTACTCGGATGGAAGCCGGTCTTGTC
GATCAGGATGATCTGGACGAAGAGCATCAGGGGCTCGCGCCAGCCGAACTGTTCGCCAGGCT
CAAGGCGAGCATGCCCGACGGCGAGGATCTCGTCGTGACCCATGGCGATGCCTGCTTGCCGA
ATATCATGGTGGAAAATGGCCGCTTTTCTGGATTCATCGACTGTGGCCGGCTGGGTGTGGCG
GACCGCTATCAGGACATAGCGTTGGCTACCCGTG
```

```
ATATTGCTGAAGAGCTTGGCGGCGAATGGGCTGACCGCTTCCTCGTGCTTTACGGTATCGCC
GCTCCCGATTCGCAGCGCATCGCCTTCTATCGCCTTCTTGACGAGTTCTTCTGAATTTTGTT
AAAATTTTTGTTAAATCAGCTCATTTTTTAACCAATAGGCCGAAATCGGCAACATCCCTTAT
AAATCAAAAGAATAGACCGCGATAGGGTTGAGTGTTGTTCCAGTTTGGAACAAGAGTCCACT
ATTAAAGAACGTGGACTCCAACGTCAAAGGGCGAAAAACCGTCTATCAGGGCGATGGCCCAC
TACGTGAACCATCACCCAAATCAAGTTTTTTGCGGTCGAGGTGCCGTAAAGCTCTAAATCGG
AACCCTAAAGGGAGCCCCCGATTTAGAGCTTGACGGGGAAAGCCGGCGAACGTGGCGAGAAA
GGAAGGGAAGAAAGCGAAAGGAGCGGGCGCTAGGGCGCTGGCAAGTGTAGCGGTCACGCTGC
GCGTAACCACCACACCCGCGCGCTTAATGCGCCGNNNNNNNNNNNNNNNNNNNNNNNNNNNN
NNNNNNNNNNNNNNNNNNNNNNNNNNNNNNNNNNNNNNNNTTAATTAANNNTCCCTTCCAGCT
CTCTGCCCCTTTTGGATTGAAGCCAATATGATAATGAGGGGGTGGAGTTTGTGACGTGGCGC
GGGGCGTGGGAACGGGGCGGGTGACGTAGTAGTGTGGCGGAAGTGTGATGTTGCAAGTGTGG
CGGAACACATGTAAGCGACGGATGTGGCAAAAGTGACGTTTTTGGTGTGCGCCGGTGTACAC
AGGAAGTGACAATTTTCGCGCGGTTTTAGGCGGATGTTGTAGTAAATTTGGGCGTAACCGAG
TAAGATTTGGCCATTTTCGCGGGAAAACTGAATAAGAGGAAGTGAAATCTGAATAATTTTGT
GTTACTCATAGCGCGTAANNCGCGTTAAGATACATTGATGAGTTTGGACAAACCACAACTA
GAATGCAGTGAAAAAAATGCTTTATTTGTGAAATTTGTGATGCTATTGCTTTATTTGTAACC
ATTATAAGCTGCAATAAACAAGTTAACAACAACAATTGCATTCATTTTATGTTTCAGGTTCA
GGGGGAGGTGTGGGAGGTTTTTTAAAGCAAGTAAAACCTCTACAAATGTGGTATGGCTGATT
ATGATCAGTTATCTAGATCCGGTGGATCTGAGTCCGGACTTGTACAGCTCGTCCATGCCGAG
AGTGATCCCGGCGGCGGTCACGAACTCCAGCAGGACCATGTGATCGCGCTTCTCGTTGGGGT
CTTTGCTCAGGGCGGACTGGGTGCTCAGGTAGTGGTTGTCGGGCAGCAGCACGGGGCCGTCG
CCGATGGGGGTGTTCTGCTGGTAGTGGTCGGCGAGCTGCACGCTGCCGTCCTCGATGTTGTG
GCGGATCTTGAAGTTCACCTTGATGCCGTTCTTCTGCTTGTCGGCCATGATATAGACGTTGT
GGCTGTTGTAGTTGTACTCCAGCTTGTGCCCCAGGATGTTGCCGTCCTCCTTGAAGTCGATG
CCCTTCAGCTCGATGCGGTTCACCAGGGTGTCGCCCTCGAACTTCACCTCGGCGCGGGTCTT
GTAGTTGCCGTCGTCCTTGAAGAAGATGGTGCGCTCCTGGACGTAGCCTTCGGGCATGGCGG
ACTTGAAGAAGTCGTGCTGCTTCATGTGGTCGGGGTAGCGGCTGAAGCACTGCACGCCGTAG
GTCAGGGTGGTCACGAGGGTGGGCCAGGGCACGGGCAGCTTGCCGGTGGTGCAGATGAACTT
CAGGGTCAGCTTGCCGTAGGTGGCATCGCCCTCGCCCTCGCCGGACACGCTGAACTTGTGGC
CGTTTACGTCGCCGTCCAGCTCGACCAGGATGGGCACCACCCCGGTGAACAGCTCCTCGCCC
TTGCTCACCATGGTGGCGACCGGTAGCGCTAGCGGATCTGACGGTTCACTAAACCAGCTCTG
CTTATATAGACCTCCCACCGTACACGCCTACCGCCCATTTGCGTCAATGGGCGGAGTTGTT
ACGACATTTTGGAAAGTCCCGTTGATTTGGTGCCAAAACAAACTCCCATTGACGTCAATGG
GGTGGAGACTTGGAAATCCCCGTGAGTCAAACCGCTATCCACGCCCATTGATGTACTGCCAA
AACCGCATCACCATGGTAATAGCGATGACTAATACGTAGATGTACTGCCAAGTAGGAAAGTC
CCATAAGGTCATGTACTGGGCATAATGCCAGGCGGGCCATTTACCGTCATTGACGTCAATAG
GGGGCGTACTTGGCATATGATACACTTGATGTACTGCCAAGTGGGCAGTTTACCGTAAATAC
TCCACCCATTGACGTCAATGGAAAGTCCCTATTGGCGTTACTATGGGAACATACGTCATTAT
TGACGTCAATGGGCGGGGG
```

```
TCGTTGGGCGGTCAGCCAGGCGGGCCATTTACCGTAAGTTATGTAACGCGGAACTCCATATA
TGGGCTATGAACTAATGACCCCGTAATTGATTACTATTANNNCTAGCAGATCTGGTACCGTC
GACGCGGCCGCGATATCCTCGAGAAGCTTTCTAGAGNNNTAAGGGTGGGAAAGAATATATAA
GGTGGGGGTCTTATGTAGTTTTGTATCTGTTTTGCAGCAGCCGCCGCCGCCATGAGCACCAA
CTCGTTTGATGGAAGCATTGTGAGCTCATATTTGACAACGCGCATGCCCCCATGGGCCGGGG
TGCGTCAGAATGTGATGGGCTCCAGCATTGATGGTCGCCCCGTCCTGCCCGCAAACTCTACT
ACCTTGACCTACGAGACCGTGTCTGGAACGCCGTTGGAGACTGCAGCCTCCGCCGCCGCTTC
AGCCGCTGCAGCCACCGCCCGCGGGATTGTGACTGACTTTGCTTTCCTGAGCCCGCTTGCAA
GCAGTGCAGCTTCCCGTTCATCCGCCCGCGATGACAAGTTGACGGCTCTTTTGGCACAATTG
GATTCTTTGACCCGGGAACTTAATGTCGTTTCTCAGCAGCTGTTGGATCTGCGCCAGCAGGT
TTCTGCCCTGAAGGCTTCCTCCCCTCCCAATGCGGTTTAAAACATAAATAAAAAACCAGACT
CTGTTTGGATTTGGATCAAGCAAGTGTCTTGCTGTCTTTATTTAGGGGTTTTGCGCGCGCGG
TAGGCCCGGGACCAGCGGTCTCGGTCGTTGAGGGTCCTGTGTATTTTTTCCAGGACGTGGTA
AAGGTGACTCTGGATGTTCAGATACATGGGCATAAGCCCGTCTCTGGGGTGGAGGTAGCACC
ACTGCAGAGCTTCATGCTGCGGGGTGGTGTTGTAGATGATCCAGTCGTAGCAGGAGCGCTGG
GCGTGGTGCCTAAAAATGTCTTTCAGTAGCAAGCTGATTGCCAGGGGCAGGCCCTTGGTGTA
AGTGTTTACAAAGCGGTTAAGCTGGGATGGGTGCATACGTGGGGATATGAGATGCATCTTGG
ACTGTATTTTTAGGTTGGCTATGTTCCCAGCCATATCCCTCCGGGGATTCATGTTGTGCAGA
ACCACCAGCACAGTGTATCCGGTGCACTTGGGAAATTTGTCATGTAGCTTAGAAGGAAATGC
GTGGAAGAACTTGGAGACGCCCTTGTGACCTCCAAGATTTTCCATGCATTCGTCCATAATGA
TGGCAATGGGCCCACGGGCGGCGGCCTGGGCGAAGATATTTCTGGGATCACTAACGTCATAG
TTGTGTTCCAGGATGAGATCGTCATAGGCCATTTTTACAAAGCGCGGGCGGAGGGTGCCAGA
CTGCGGTATAATGGTTCCATCCGGCCCAGGGGCGTAGTTACCCTCACAGATTTGCATTTCCC
ACGCTTTGAGTTCAGATGGGGGATCATGTCTACCTGCGGGGCGATGAAGAAAACGGTTTCC
GGGGTAGGGGAGATCAGCTGGGAAGAAAGCAGGTTCCTGAGCAGCTGCGACTTACCGCAGCC
GGTGGGCCCGTAAATCACACCTATTACCGGGTGCAACTGGTAGTTAAGAGAGCTGCAGCTGC
CGTCATCCCTGAGCAGGGGGGCCACTTCGTTAAGCATGTCCCTGACTCGCATGTTTTCCCTG
ACCAAATCCGCCAGAAGGCGCTCGCCGCCCAGCGATAGCAGTTCTTGCAAGGAAGCAAAGTT
TTTCAACGGTTTGAGACCGTCCGCCGTAGGCATGCTTTTGAGCGTTTGACCAAGCAGTTCCA
GGCGGTCCCACAGCTCGGTCACCTGCTCTACGGCATCTCGATCCAGCATATCTCCTCGTTTC
GCGGGTTGGGCGGCTTTCGCTGTACGGCAGTAGTCGGTGCTCGTCCAGACGGGCCAGGGTC
ATGTCTTTCCACGGGCGCAGGGTCCTCGTCAGCGTAGTCTGGGTCACGGTGAAGGGGTGCGC
TCCGGGCTGCGCGCTGGCCAGGGTGCGCTTGAGGCTGGTCCTGCTGGTGCTGAAGCGCTGCC
GGTCTTCGCCCTGCGCGTCGGCCAGGTAGCATTTGACCATGGTGTCATAGTCCAGCCCCTCC
GCGGCGTGGCCCTTGGCGCGCAGCTTGCCCTTGGAGGAGGCGCCGCACGAGGGGCAGTGCAG
ACTTTTGAGGGCGTAGAGCTTGGGCGCGAGAAATACCGATTCCGGGGAGTAGGCATCCGCGC
CGCAGGCCCCGCAGACGGTCTCGCATTCCACGAGCCAGGTGAGCTCTGGCCGTTCGGGGTCA
AAAACCAGGTTTCCCCCATGCTTTTTGATGCGTTTCTTACCTCTGGTTTCCATGAGCCGGTG
TCCACGCTCGGTGACGAAAAGGCTGTCCGTGTCCCCGTATACAGACTACTTGAGAGGCCTGT
CCTCGAGCGGTGTTCCGCGGTCC
```

```
TCCTCGTATAGAAACTCGGACCACTCTGAGACAAAGGCTCGCGTCCAGGCCAGCACGAAGGA
GGCTAAGTGGGAGGGGTAGCGGTCGTTGTCCACTAGGGGGTCCACTCGCTCCAGGGTGTGAA
GACACATGTCGCCCTCTTCGGCATCAAGGAAGGTGATTGGTTTGTAGGTGTAGGCCACGTGA
CCGGGTGTTCCTGAAGGGGGGCTATAAAAGGGGGTGGGGGCGCGTTCGTCCTCACTCTCTTC
CGCATCGCTGTCTGCGAGGGCCAGCTGTTGGGGTGAGTACTCCCTCTGAAAAGCGGGCATGA
CTTCTGCGCTAAGATTGTCAGTTTCCAAAAACGAGGAGGATTTGATATTCACCTGGCCCGCG
GTGATGCCTTTGAGGGTGGCCGCATCCATCTGGTCAGAAAAGACAATCTTTTTGTTGTCAAG
CTTGGTGGCAAACGACCCGTAGAGGGCGTTGGACAGCAACTTGGCGATGGAGCGCAGGGTTT
GGTTTTTGTCGCGATCGGCGCGCTCCTTGGCCGCGATGTTTAGCTGCACGTATTCGCGCGCA
ACGCACCGCCATTCGGGAAAGACGGTGGTGCGCTCGTCGGGCACCAGGTGCACGCGCCAACC
GCGGTTGTGCAGGGTGACAAGGTCAACGCTGGTGGCTACCTCTCCGCGTAGGCGCTCGTTGG
TCCAGCAGAGGCGGCCGCCCTTGCGCGAGCAGAATGGCGGTAGGGGGTCTAGCTGCGTCTCG
TCCGGGGGGTCTGCGTCCACGGTAAAGACCCCGGGCAGCAGGCGCGCGTCGAAGTAGTCTAT
CTTGCATCCTTGCAAGTCTAGCGCCTGCTGCCATGCGCGGGCGGCAAGCGCGCGCTCGTATG
GGTTGAGTGGGGGACCCCATGGCATGGGGTGGGTGAGCGCGGAGGCGTACATGCCGCAAATG
TCGTAAACGTAGAGGGGCTCTCTGAGTATTCCAAGATATGTAGGGTAGCATCTTCCACCGCG
GATGCTGGCGCGCACGTAATCGTATAGTTCGTGCGAGGGAGCGAGGAGGTCGGGACCGAGGT
TGCTACGGGCGGGCTGCTCTGCTCGGAAGACTATCTGCCTGAAGATGGCATGTGAGTTGGAT
GATATGGTTGGACGCTGGAAGACGTTGAAGCTGGCGTCTGTGAGACCTACCGCGTCACGCAC
GAAGGAGGCGTAGGAGTCGCGCAGCTTGTTGACCAGCTCGGCGGTGACCTGCACGTCTAGGG
CGCAGTAGTCCAGGGTTTCCTTGATGATGTCATACTTATCCTGTCCCTTTTTTTCCACAGC
TCGCGGTTGAGGACAAACTCTTCGCGGTCTTTCCAGTACTCTTGGATCGGAAACCCGTCGGC
CTCCGAACGGTAAGAGCCTAGCATGTAGAACTGGTTGACGGCCTGGTAGGCGCAGCATCCCT
TTTCTACGGGTAGCGCGTATGCCTGCGCGGCCTTCCGGAGCGAGGTGTGGGTGAGCGCAAAG
GTGTCCCTGACCATGACTTTGAGGTACTGGTATTTGAAGTCAGTGTCGTCGCATCCGCCCTG
CTCCCAGAGCAAAAAGTCCGTGCGCTTTTTGGAACGCGGATTTGGCAGGGCGAAGGTGACAT
CGTTGAAGAGTATCTTTCCCGCGCGAGGCATAAAGTTGCGTGTGATGCGGAAGGGTCCCGGC
ACCTCGGAACGGTTGTTAATTACCTGGGCGGCGAGCACGATCTCGTCAAAGCCGTTGATGTT
GTGGCCCACAATGTAAAGTTCCAAGAAGCGCGGGATGCCCTTGATGGAAGGCAATTTTTTAA
GTTCCTCGTAGGTGAGCTCTTCAGGGGAGCTGAGCCCGTGCTCTGAAAGGGCCCAGTCTGCA
AGATGAGGGTTGGAAGCGACGAATGAGCTCCACAGGTCACGGGCCATTAGCATTTGCAGGTG
GTCGCGAAAGGTCCTAAACTGGCGACCTATGGCCATTTTTCTGGGGTGATGCAGTAGAAGG
TAAGCGGGTCTTGTTCCCAGCGGTCCCATCCAAGGTTCGCGGCTAGGTCTCGCGCGGCAGTC
ACTAGAGGCTCATCTCCGCCGAACTTCATGACCAGCATGAAGGGCACGAGCTGCTTCCCAAA
GGCCCCCATCCAAGTATAGGTCTCTACATCGTAGGTGACAAAGAGACGCTCGGTGCGAGGAT
GCGAGCCGATCGGGAAGAACTGGATCTCCCGCCACCAATTGGAGGAGTGGCTATTGATGTGG
TGAAAGTAGAAGTCCCTGCGACGGGCCGAACACTCGTGCTGGCTTTTGTAAAAACGTGCGCA
GTACTGGCAGCGGTGCACGGGCTGTACATCCTGCACGAGGTTGACCTGACGACCGCGCACAA
GGAAGCAGAGTGGGAATTTGAGCCCCTCGCCTGGCGGGTTTGGCTGGTGGTCTTCTACTTCG
GCTGCTTGTCCTTGAC
```

FIG. 30 (4 of 16)

```
CGTCTGGCTGCTCGAGGGGAGTTACGGTGGATCGGACCACCACGCCGCGCGAGCCCAAAGTC
CAGATGTCCGCGCGCGGCGGTCGGAGCTTGATGACAACATCGCGCAGATGGGAGCTGTCCAT
GGTCTGGAGCTCCCGCGGCGTCAGGTCAGGCGGGAGCTCCTGCAGGTTTACCTCGCATAGAC
GGGTCAGGGCGCGGGCTAGATCCAGGTGATACCTAATTTCCAGGGGCTGGTTGGTGGCGGCG
TCGATGGCTTGCAAGAGGCCGCATCCCCGCGGCGCGACTACGGTACCGCGCGGCGGGCGGTG
GGCCGCGGGGGTGTCCTTGGATGATGCATCTAAAAGCGGTGACGCGGGCGAGCCCCCGGAGG
TAGGGGGGGCTCCGGACCCGCCGGGAGAGGGGGCAGGGGCACGTCGGCGCCGCGCGCGGGCA
GGAGCTGGTGCTGCGCGCGTAGGTTGCTGGCGAACGCGACGACGCGGCGGTTGATCTCCTGA
ATCTGGCGCCTCTGCGTGAAGACGACGGGCCCGGTGAGCTTGAGCCTGAAAGAGAGTTCGAC
AGAATCAATTTCGGTGTCGTTGACGGCGGCCTGGCGCAAAATCTCCTGCACGTCTCCTGAGT
TGTCTTGATAGGCGATCTCGGCCATGAACTGCTCGATCTCTTCCTCCTGGAGATCTCCGCGT
CCGGCTCGCTCCACGGTGGCGGCGAGGTCGTTGGAAATGCGGGCCATGAGCTGCGAGAAGGC
GTTGAGGCCTCCCTCGTTCCAGACGCGGCTGTAGACCACGCCCCCTTCGGCATCGCGGGCGC
GCATGACCACCTGCGCGAGATTGAGCTCCACGTGCCGGGCGAAGACGGCGTAGTTTCGCAGG
CGCTGAAAGAGGTAGTTGAGGGTGGTGGCGGTGTGTTCTGCCACGAAGAAGTACATAACCCA
GCGTCGCAACGTGGATTCGTTGATATCCCCAAGGCCTCAAGGCGCTCCATGGCCTCGTAGA
AGTCCACGGCGAAGTTGAAAAACTGGGAGTTGCGCGCCGACACGGTTAACTCCTCCTCCAGA
AGACGGATGAGCTCGGCGACAGTGTCGCGCACCTCGCGCTCAAAGGCTACAGGGGCCTCTTC
TTCTTCTTCAATCTCCTCTTCCATAAGGGCCTCCCCTTCTTCTTCTTCTGGCGGCGGTGGGG
GAGGGGGGACACGGCGGCGACGACGGCGCACCGGGAGGCGGTCGACAAAGCGCTCGATCATC
TCCCCGCGGCGACGGCGCATGGTCTCGGTGACGGCGCGGCCGTTCTCGCGGGGCGCAGTTG
GAAGACGCCGCCCGTCATGTCCCGGTTATGGGTTGGCGGGGGGCTGCCATGCGGCAGGGATA
CGGCGCTAACGATGCATCTCAACAATTGTTGTGTAGGTACTCCGCCGCCGAGGGACCTGAGC
GAGTCCGCATCGACCGGATCGGAAAACCTCTCGAGAAAGGCGTCTAACCAGTCACAGTCGCA
AGGTAGGCTGAGCACCGTGGCGGGCGGCAGCGGGCGGCGGTCGGGGTTGTTTCTGGCGGAGG
TGCTGCTGATGATGTAATTAAAGTAGGCGGTCTTGAGACGGCGGATGGTCGACAGAAGCACC
ATGTCCTTGGGTCCGGCCTGCTGAATGCGCAGGCGGTCGGCCATGCCCCAGGCTTCGTTTTG
ACATCGGCGCAGGTCTTTGTAGTAGTCTTGCATGAGCCTTTCTACCGGCACTTCTTCTTCTC
CTTCCTCTTGTCCTGCATCTCTTGCATCTATCGCTGCGGCGGCGGCGGAGTTTGGCCGTAGG
TGGCGCCCTCTTCCTCCCATGCGTGTGACCCCGAAGCCCCTCATCGGCTGAAGCAGGGCTAG
GTCGGCGACAACGCGCTCGGCTAATATGGCCTGCTGCACCTGCGTGAGGGTAGACTGGAAGT
CATCCATGTCCACAAAGCGGTGGTATGCGCCCGTGTTGATGGTGTAAGTGCAGTTGGCCATA
ACGGACCAGTTAACGGTCTGGTGACCCGGCTGCGAGAGCTCGGTGTACCTGAGACGCGAGTA
AGCCCTCGAGTCAAATACGTAGTCGTTGCAAGTCCGCACCAGGTACTGGTATCCCACCAAAA
AGTGCGGCGGCGGCTGGCGGTAGAGGGGCCAGCGTAGGGTGGCCGGGGCTCCGGGGCGAGA
TCTTCCAACATAAGGCGATGATATCCGTAGATGTACCTGGACATCCAGGTGATGCCGGCGGC
GGTGGTGGAGGCGCGCGGAAAGTCGCGGACGCGGTTCCAGATGTTGCGCAGCGGCAAAAAGT
GCTCCATGGTCGGGACGCTCTGGCCGGTCAGGCGCGCGAATCGTTGACGCTCTACCGTGCA
AAAGGAGAGCCTGTAAGCGGGCACTCTTCCGTGGTCTGGTGGATAAATTCGCAAGGGTATCA
TGGCGGA
```

FIG. 30

```
CGACCGGGGTTCGAGCCCCGTATCCGGCCGTCCGCCGTGATCCATGCGGTTACCGCCCGCGT
GTCGAACCCAGGTGTGCGACGTCAGACAACGGGGGAGTGCTCCTTTTGGCTTCCTTCCAGGC
GCGGCGGCTGCTGCGCTAGCTTTTTTGGCCACTGGCCGCGCGCAGCGTAAGCGGTTAGGCTG
GAAAGCGAAAGCATTAAGTGGCTCGCTCCCTGTAGCCGGAGGGTTATTTTCCAAGGGTTGAG
TCGCGGGACCCCGGTTCGAGTCTCGGACCGGCCGGACTGCGGCGAACGGGGGTTTGCCTCC
CCGTCATGCAAGACCCCGCTTGCAAATTCCTCCGGAAACAGGGACGAGCCCCTTTTTTGCTT
TTCCCAGATGCATCCGGTGCTGCGGCAGATGCGCCCCCTCCTCAGCAGCGGCAAGAGCAAG
AGCAGCGGCAGACATGCAGGGCACCCTCCCCTCCTCCTACCGCGTCAGGAGGGGCGACATCC
GCGGTTGACGCGGCAGCAGATGGTGATTACGAACCCCGCGGCGCCGGGCCCGGCACTACCT
GGACTTGGAGGAGGGCGAGGGCCTGGCGCGGCTAGGAGCGCCCTCTCCTGAGCGGTACCCAA
GGGTGCAGCTGAAGCGTGATACGCGTGAGGCGTACGTGCCGCGGCAGAACCTGTTTCGCGAC
CGCGAGGGAGAGGAGCCCGAGGAGATGCGGGATCGAAAGTTCCACGCAGGGCGCGAGCTGCG
GCATGGCCTGAATCGCGAGCGGTTGCTGCGCGAGGAGGACTTTGAGCCCGACGCGCGAACCG
GGATTAGTCCCGCGCGCGCACACGTGGCGGCCGCCGACCTGGTAACCGCATACGAGCAGACG
GTGAACCAGGAGATTAACTTTCAAAAAAGCTTTAACAACCACGTGCGTACGCTTGTGGCGCG
CGAGGAGGTGGCTATAGGACTGATGCATCTGTGGGACTTTGTAAGCGCGCTGGAGCAAAACC
CAAATAGCAAGCCGCTCATGGCGCAGCTGTTCCTTATAGTGCAGCACAGCAGGGACAACGAG
GCATTCAGGGATGCGCTGCTAAACATAGTAGAGCCCGAGGGCCGCTGGCTGCTCGATTTGAT
AAACATCCTGCAGAGCATAGTGGTGCAGGAGCGCAGCTTGAGCCTGGCTGACAAGGTGGCCG
CCATCAACTATTCCATGCTTAGCCTGGGCAAGTTTTACGCCCGCAAGATATACCATACCCCT
TACGTTCCCATAGACAAGGAGGTAAAGATCGAGGGGTTCTACATGCGCATGGCGCTGAAGGT
GCTTACCTTGAGCGACGACCTGGGCGTTTATCGCAACGAGCGCATCCACAAGGCCGTGAGCG
TGAGCCGGCGGCGCGAGCTCAGCGACCGCGAGCTGATGCACAGCCTGCAAAGGGCCCTGGCT
GGCACGGGCAGCGGCGATAGAGAGGCCGAGTCCTACTTTGACGCGGGCGCTGACCTGCGCTG
GGCCCCAAGCCGACGCGCCCTGGAGGCAGCTGGGGCCGGACCTGGGCTGGCGGTGGCACCCG
CGCGCGCTGGCAACGTCGGCGGCGTGGAGGAATATGACGAGGACGATGAGTACGAGCCAGAG
GACGGCGAGTACTAAGCGGTGATGTTTCTGATCAGATGATGCAAGACGCAACGGACCCGGCG
GTGCGGGCGGCGCTGCAGAGCCAGCCGTCCGGCCTTAACTCCACGGACGACTGGCGCCAGGT
CATGGACCGCATCATGTCGCTGACTGCGCGCAATCCTGACGCGTTCCGGCAGCAGCCGCAGG
CCAACCGGCTCTCCGCAATTCTGGAAGCGGTGGTCCCGGCGCGCGCAAACCCCACGCACGAG
AAGGTGCTGGCGATCGTAAACGCGCTGGCCGAAAACAGGGCCATCCGGCCCGACGAGGCCGG
CCTGGTCTACGACGCGCTGCTTCAGCGCGTGGCTCGTTACAACAGCGGCAACGTGCAGACCA
ACCTGGACCGGCTGGTGGGGGATGTGCGCGAGGCCGTGGCGCAGCGTGAGCGCGCGCAGCAG
CAGGGCAACCTGGGCTCCATGGTTGCACTAAACGCCTTCCTGAGTACACAGCCCGCCAACGT
GCCGCGGGGACAGGAGGACTACACCAACTTTGTGAGCGCACTGCGGCTAATGGTGACTGAGA
CACCGCAAAGTGAGGTGTACCAGTCTGGGCCAGACTATTTTTTCCAGACCAGTAGACAAGGC
CTGCAGACCGTAAACCTGAGCCAGGCTTTCAAAAACTTGCAGGGGCTGTGGGGGGTGCGGGC
TCCCACAGGCGACCGCGCGACCGTGTCTAGCTTGCTGACGCCCAACTCGCGCCTGTTGCTGC
TGCTAATAGCGCCCTTCACGGACAGTGGCAGCGTGTCCCGGGACACATACCTAGGTCACTTG
C
```

```
TGACACTGTACCGCGAGGCCATAGGTCAGGCGCATGTGGACGAGCATACTTTCCAGGAGATT
ACAAGTGTCAGCCGCGCGCTGGGGCAGGAGGACACGGGCAGCCTGGAGGCAACCCTAAACTA
CCTGCTGACCAACCGGCGGCAGAAGATCCCCTCGTTGCACAGTTTAAACAGCGAGGAGGAGC
GCATTTTGCGCTACGTGCAGCAGAGCGTGAGCCTTAACCTGATGCGCGACGGGGTAACGCCC
AGCGTGGCGCTGGACATGACCGCGCGCAACATGGAACCGGGCATGTATGCCTCAAACCGGCC
GTTTATCAACCGCCTAATGGACTACTTGCATCGCGCGGCCGCCGTGAACCCCGAGTATTTCA
CCAATGCCATCTTGAACCCGCACTGGCTACCGCCCCTGGTTTCTACACCGGGGATTCGAG
GTGCCCGAGGGTAACGATGGATTCCTCTGGGACGACATAGACGACAGCGTGTTTTCCCCGCA
ACCGCAGACCCTGCTAGAGTTGCAACAGCGCGAGCAGGCAGAGGCGGCGCTGCGAAAGGAAA
GCTTCCGCAGGCCAAGCAGCTTGTCCGATCTAGGCGCTGCGGCCCCGCGGTCAGATGCTAGT
AGCCCATTTCCAAGCTTGATAGGGTCTCTTACCAGCACTCGCACCACCCGCCCGCGCCTGCT
GGGCGAGGAGGAGTACCTAAACAACTCGCTGCTGCAGCCGCAGCGCGAAAAAAACCTGCCTC
CGGCATTTCCCAACAACGGGATAGAGAGCCTAGTGGACAAGATGAGTAGATGGAAGACGTAC
GCGCAGGAGCACAGGGACGTGCCAGGCCCGCGCCCGCCCACCCGTCGTCAAAGGCACGACCG
TCAGCGGGGTCTGGTGTGGGAGGACGATGACTCGGCAGACGACAGCAGCGTCCTGGATTTGG
GAGGGAGTGGCAACCCGTTTGCGCACCTTCGCCCCAGGCTGGGGAGAATGTTTTAAAAAAAA
AAAGCATGATGCAAAATAAAAAACTCACCAAGGCCATGGCACCGAGCGTTGGTTTTCTTGT
ATTCCCCTTAGTATGCGGCGCGCGGCGATGTATGAGGAAGGTCCTCCTCCCTCCTACGAGAG
TGTGGTGAGCGCGGCGCCAGTGGCGGCGGCGCTGGGTTCTCCCTTCGATGCTCCCCTGGACC
CGCCGTTTGTGCCTCCGCGGTACCTGCGGCCTACCGGGGGAGAAACAGCATCCGTTACTCT
GAGTTGGCACCCCTATTCGACACCACCCGTGTGTACCTGGTGGACAACAAGTCAACGGATGT
GGCATCCCTGAACTACCAGAACGACCACAGCAACTTTCTGACCACGGTCATTCAAAACAATG
ACTACAGCCCGGGGGAGGCAAGCACACAGACCATCAATCTTGACGACCGGTCGCACTGGGGC
GGCGACCTGAAAACCATCCTGCATACCAACATGCCAAATGTGAACGAGTTCATGTTTACCAA
TAAGTTTAAGGCGCGGGTGATGGTGTCGCGCTTGCCTACTAAGGACAATCAGGTGGAGCTGA
AATACGAGTGGGTGGAGTTCACGCTGCCCGAGGGCAACTACTCCGAGACCATGACCATAGAC
CTTATGAACAACGCGATCGTGGAGCACTACTTGAAAGTGGGCAGACAGAACGGGGTTCTGGA
AAGCGACATCGGGGTAAAGTTTGACACCCGCAACTTCAGACTGGGGTTTGACCCCGTCACTG
GTCTTGTCATGCCTGGGGTATATACAAACGAAGCCTTCCATCCAGACATCATTTTGCTGCCA
GGATGCGGGGTGGACTTCACCCACAGCCGCCTGAGCAACTTGTTGGGCATCCGCAAGCGGCA
ACCCTTCCAGGAGGGCTTTAGGATCACCTACGATGATCTGGAGGGTGGTAACATTCCCGCAC
TGTTGGATGTGGACGCCTACCAGGCGAGCTTGAAAGATGACACCGAACAGGGCGGGGGTGGC
GCAGGCGGCAGCAACAGCAGTGGCAGCGGCGCGGAAGAGAACTCCAACGCGGCAGCCGCGGC
AATGCAGCCGGTGGAGGACATGAACGATCATGCCATTCGCGGCGACACCTTTGCCACACGGG
CTGAGGAGAAGCGCGCTGAGGCCGAAGCAGCGGCCGAAGCTGCCGCCCCGCTGCGCAACCC
GAGGTCGAGAAGCCTCAGAAGAAACCGGTGATCAAACCCCTGACAGAGGACAGCAAGAAACG
CAGTTACAACCTAATAAGCAATGACAGCACCTTCACCCAGTACCGCAGCTGGTACCTTGCAT
ACAACTACGGCGACCCTCAGACCGGAATCCGCTCATGGACCCTGCTTTGCACTCCTGACGTA
ACCTGCGGCTCGGAGCAGGTCTACTGGTCGTTGCCAGACATGATGCAAGACCCCGTGACCTT
CCGCTCCACGCGCCAGATCAGCAACTTTCCGGTGGTGGGCGCCGAGCTGTTGCCCGTGCA
```

FIG. 30

```
CTCCAAGAGCTTCTACAACGACCAGGCCGTCTACTCCCAACTCATCCGCCAGTTTACCTCTC
TGACCCACGTGTTCAATCGCTTTCCCGAGAACCAGATTTTGGCGCGCCCGCCAGCCCCCACC
ATCACCACCGTCAGTGAAAACGTTCCTGCTCTCACAGATCACGGGACGCTACCGCTGCGCAA
CAGCATCGGAGGAGTCCAGCGAGTGACCATTACTGACGCCAGACGCCGCACCTGCCCCTACG
TTTACAAGGCCCTGGGCATAGTCTCGCCGCGCGTCCTATCGAGCCGCACTTTTTGAGCAAGC
ATGTCCATCCTTATATCGCCCAGCAATAACACAGGCTGGGGCCTGCGCTTCCCAAGCAAGAT
GTTTGGCGGGGCCAAGAAGCGCTCCGACCAACACCCAGTGCGCGTGCGCGGGCACTACCGCG
CGCCCTGGGGCGCGCACAAACGCGGCCGCACTGGGCGCACCACCGTCGATGACGCCATCGAC
GCGGTGGTGGAGGAGGCGCGCAACTACACGCCCACGCCGCCACCAGTGTCCACAGTGGACGC
GGCCATTCAGACCGTGGTGCGCGGAGCCCGGCGCTATGCTAAAATGAAGAGACGGCGGAGGC
GCGTAGCACGTCGCCACCGCCGCCGACCCGGCACTGCCGCCCAACGCGCGGCGGCGGCCCTG
CTTAACCGCGCACGTCGCACCGGCCGACGGGCGGCCATGCGGGCCGCTCGAAGGCTGGCCGC
GGGTATTGTCACTGTGCCCCCCAGGTCCAGGCGACGAGCGGCCGCCGCAGCAGCCGCGGCCA
TTAGTGCTATGACTCAGGGTCGCAGGGGCAACGTGTATTGGGTGCGCGACTCGGTTAGCGGC
CTGCGCGTGCCCGTGCGCACCCGCCCCCGCGCAACTAGATTGCAAGAAAAAACTACTTAGA
CTCGTACTGTTGTATGTATCCAGCGGCGGCGGCGCGCAACGAAGCTATGTCCAAGCGCAAAA
TCAAAGAAGAGATGCTCCAGGTCATCGCGCCGGAGATCTATGGCCCCCCGAAGAAGGAAGAG
CAGGATTACAAGCCCCGAAAGCTAAAGCGGGTCAAAAAGAAAAAGAAAGATGATGATGATGA
ACTTGACGACGAGGTGGAACTGCTGCACGCTACCGCGCCCAGGCGACGGGTACAGTGGAAAG
GTCGACGCGTAAAACGTGTTTTGCGACCCGGCACCACCGTAGTCTTTACGCCCGGTGAGCGC
TCCACCCGCACCTACAAGCGCGTGTATGATGAGGTGTACGGCGACGAGGACCTGCTTGAGCA
GGCCAACGAGCGCCTCGGGGAGTTTGCCTACGGAAAGCGGCATAAGGACATGCTGGCGTTGC
CGCTGGACGAGGGCAACCCAACACCTAGCCTAAAGCCCGTAACACTGCAGCAGGTGCTGCCC
GCGCTTGCACCGTCCGAAGAAAAGCGCGGCCTAAAGCGCGAGTCTGGTGACTTGGCACCCAC
CGTGCAGCTGATGGTACCCAAGCGCCAGCGACTGGAAGATGTCTTGGAAAAAATGACCGTGG
AACCTGGGCTGGAGCCCGAGGTCCGCGTGCGGCCAATCAAGCAGGTGGCGCCGGGACTGGGC
GTGCAGACCGTGGACGTTCAGATACCCACTACCAGTAGCACCAGTATTGCCACCGCCACAGA
GGGCATGGAGACACAAACGTCCCCGGTTGCCTCAGCGGTGGCGGATGCCGCGGTGCAGGCGG
TCGCTGCGGCCGCGTCCAAGACCTCTACGGAGGTGCAAACGGACCCGTGGATGTTTCGCGTT
TCAGCCCCCGGCGCCCGCGCGGTTCGAGGAAGTACGGCGCCGCCAGCGCGCTACTGCCCGA
ATATGCCCTACATCCTTCCATTGCGCCTACCCCGGCTATCGTGGCTACACCTACCGCCCCA
GAAGACGAGCAACTACCCGACGCCGAACCACCACTGGAACCCGCCGCCGCCGTCGCCGTCGC
CAGCCCGTGCTGGCCCCGATTTCCGTGCGCAGGGTGGCTCGCGAAGGAGGCAGGACCCTGGT
GCTGCCAACAGCGCGCTACCACCCCAGCATCGTTTAAAAGCCGGTCTTTGTGGTTCTTGCAG
ATATGGCCCTCACCTGCCGCCTCCGTTTCCCGGTGCCGGGATTCCGAGGAAGAATGCACCGT
AGGAGGGGCATGGCCGGCCACGGCCTGACGGGCGGCATGCGTCGTGCGCACCACCGGCGGCG
GCGCGCGTCGCACCGTCGCATGCGCGGCGGTATCCTGCCCCTCCTTATTCCACTGATCGCCG
CGGCGATTGGCGCCGTGCCCGGAATTGCATCCGTGGCCTTGCAGGCGCAGAGACACTGATTA
AAAACAAGTTGCATGTGGAAAAATCAAAATAAAAGTCTGGACTCTCACGCTCGCTTGGTCC
TGTA
```

FIG. 30 (8 of 16)

```
ACTATTTTGTAGAATGGAAGACATCAACTTTGCGTCTCTGGCCCCGCGACACGGCTCGCGCC
CGTTCATGGGAAACTGGCAAGATATCGGCACCAGCAATATGAGCGGTGGCGCCTTCAGCTGG
GGCTCGCTGTGGAGCGGCATTAAAAATTTCGGTTCCACCGTTAAGAACTATGGCAGCAAGGC
CTGGAACAGCAGCACAGGCCAGATGCTGAGGGATAAGTTGAAAGAGCAAAATTTCCAACAAA
AGGTGGTAGATGGCCTGGCCTCTGGCATTAGCGGGGTGGTGGACCTGGCCAACCAGGCAGTG
CAAAATAAGATTAACAGTAAGCTTGATCCCCGCCCTCCCGTAGAGGAGCCTCCACCGGCCGT
GGAGACAGTGTCTCCAGAGGGGCGTGGCGAAAAGCGTCCGCGCCCCGACAGGGAAGAAACTC
TGGTGACGCAAATAGACGAGCCTCCCTCGTACGAGGAGGCACTAAAGCAAGGCCTGCCCACC
ACCCGTCCCATCGCGCCCATGGCTACCGGAGTGCTGGGCCAGCACACACCCGTAACGCTGGA
CCTGCCTCCCCCGCCGACACCCAGCAGAAACCTGTGCTGCCAGGCCCGACCGCCGTTGTTG
TAACCCGTCCTAGCCGCGCGTCCCTGCGCCGCGCCGCCAGCGGTCCGCGATCGTTGCGGCCC
GTAGCCAGTGGCAACTGGCAAAGCACACTGAACAGCATCGTGGGTCTGGGGGTGCAATCCCT
GAAGCGCCGACGATGCTTCTGAATAGCTAACGTGTCGTATGTGTGTCATGTATGCGTCCATG
TCGCCGCCAGAGGAGCTGCTGAGCCGCCGCGCGCCCGCTTTCCAAGATGGCTACCCCTTCGA
TGATGCCGCAGTGGTCTTACATGCACATCTCGGGCCAGGACGCCTCGGAGTACCTGAGCCCC
GGGCTGGTGCAGTTTGCCCGCGCCACCGAGACGTACTTCAGCCTGAATAACAAGTTTAGAAA
CCCCACGGTGGCGCCTACGCACGACGTGACCACAGACCGGTCCCAGCGTTTGACGCTGCGGT
TCATCCCTGTGGACCGTGAGGATACTGCGTACTCGTACAAGGCGCGGTTCACCCTAGCTGTG
GGTGATAACCGTGTGCTGGACATGGCTTCCACGTACTTTGACATCCGCGGCGTGCTGGACAG
GGGCCCTACTTTTAAGCCCTACTCTGGCACTGCCTACAACGCCCTGGCTCCCAAGGGTGCCC
CAAATCCTTGCGAATGGGATGAAGCTGCTACTGCTCTTGAAATAAACCTAGAAGAAGAGGAC
GATGACAACGAAGACGAAGTAGACGAGCAAGCTGAGCAGCAAAAAACTCACGTATTTGGGCA
GGCGCCTTATTCTGGTATAAATATTACAAAGGAGGGTATTCAAATAGGTGTCGAAGGTCAAA
CACCTAAATATGCCGATAAAACATTTCAACCTGAACCTCAAATAGGAGAATCTCAGTGGTAC
GAAACTGAAATTAATCATGCAGCTGGGAGAGTCCTTAAAAAGACTACCCCAATGAAACCATG
TTACGGTTCATATGCAAAACCCACAAATGAAAATGGAGGGCAAGGCATTCTTGTAAAGCAAC
AAAATGGAAAGCTAGAAAGTCAAGTGGAAATGCAATTTTTCTCAACTACTGAGGCGACCGCA
GGCAATGGTGATAACTTGACTCCTAAAGTGGTATTGTACAGTGAAGATGTAGATATAGAAAC
CCCAGACACTCATATTTCTTACATGCCCACTATTAAGGAAGGTAACTCACGAGAACTAATGG
GCCAACAATCTATGCCCAACAGGCCTAATTACATTGCTTTTAGGGACAATTTTATTGGTCTA
ATGTATTACAACAGCACGGGTAATATGGGTGTTCTGGCGGGCCAAGCATCGCAGTTGAATGC
TGTTGTAGATTTGCAAGACAGAAACACAGAGCTTTCATACCAGCTTTTGCTTGATTCCATTG
GTGATAGAACCAGGTACTTTTCTATGTGGAATCAGGCTGTTGACAGCTATGATCCAGATGTT
AGAATTATTGAAAATCATGGAACTGAAGATGAACTTCCAAATTACTGCTTTCCACTGGGAGG
TGTGATTAATACAGAGACTCTTACCAAGGTAAAACCTAAAACAGGTCAGGAAAATGGATGGG
AAAAAGATGCTACAGAATTTTCAGATAAAAATGAAATAAGAGTTGGAAATAATTTTGCCATG
GAAATCAATCTAAATGCCAACCTGTGGAGAAATTTCCTGTACTCCAACATAGCGCTGTATTT
GCCCGACAAGCTAAAGTACAGTCCTTCAACGTAAAAATTTCTGATAACCCAAACACCTACG
ACTACATGAACAAGCGAGTGGTGGCTCCCGGGTTAGTGGACTGCTACATTAACCTTGGAGCA
CGCTGGTCCCTTGACTATATGGACAACGTCAACCCATTTAACCACCACCGCAATGCTGGCCT
GCGCTA
```

FIG. 30 (9 of 16)

```
CCGCTCAATGTTGCTGGGCAATGGTCGCTATGTGCCCTTCCACATCCAGGTGCCTCAGAAGT
TCTTTGCCATTAAAAACCTCCTTCTCCTGCCGGGCTCATACACCTACGAGTGGAACTTCAGG
AAGGATGTTAACATGGTTCTGCAGAGCTCCCTAGGAAATGACCTAAGGGTTGACGGAGCCAG
CATTAAGTTTGATAGCATTTGCCTTTACGCCACCTTCTTCCCCATGGCCCACAACACCGCCT
CCACGCTTGAGGCCATGCTTAGAAACGACACCAACGACCAGTCCTTTAACGACTATCTCTCC
GCCGCCAACATGCTCTACCCTATACCCGCCAACGCTACCAACGTGCCCATATCCATCCCCTC
CCGCAACTGGGCGGCTTTCCGCGGCTGGGCCTTCACGCGCCTTAAGACTAAGGAAACCCCAT
CACTGGGCTCGGGCTACGACCCTTATTACACCTACTCTGGCTCTATACCCTACCTAGATGGA
ACCTTTTACCTCAACCACACCTTTAAGAAGGTGGCCATTACCTTTGACTCTTCTGTCAGCTG
GCCTGGCAATGACCGCCTGCTTACCCCCAACGAGTTTGAAATTAAGCGCTCAGTTGACGGGG
AGGGTTACAACGTTGCCCAGTGTAACATGACCAAAGACTGGTTCCTGGTACAAATGCTAGCT
AACTACAACATTGGCTACCAGGGCTTCTATATCCCAGAGAGCTACAAGGACCGCATGTACTC
CTTCTTTAGAAACTTCCAGCCCATGAGCCGTCAGGTGGTGGATGATACTAAATACAAGGACT
ACCAACAGGTGGGCATCCTACACCAACACAACAACTCTGGATTTGTTGGCTACCTTGCCCCC
ACCATGCGCGAAGGACAGGCCTACCCTGCTAACTTCCCCTATCCGCTTATAGGCAAGACCGC
AGTTGACAGCATTACCCAGAAAAAGTTTCTTTGCGATCGCACCCTTTGGCGCATCCCATTCT
CCAGTAACTTTATGTCCATGGGCGCACTCACAGACCTGGGCCAAAACCTTCTCTACGCCAAC
TCCGCCCACGCGCTAGACATGACTTTTGAGGTGGATCCCATGGACGAGCCCACCCTTCTTTA
TGTTTTGTTTGAAGTCTTTGACGTGGTCCGTGTGCACCGGCCGCACCGCGGCGTCATCGAAA
CCGTGTACCTGCGCACGCCCTTCTCGGCCGGCAACGCCACAACATAAAGAAGCAAGCAACAT
CAACAACAGCTGCCGCCATGGGCTCCAGTGAGCAGGAACTGAAAGCCATTGTCAAAGATCTT
GGTTGTGGGCCATATTTTTGGGCACCTATGACAAGCGCTTTCCAGGCTTTGTTTCTCCACA
CAAGCTCGCCTGCGCCATAGTCAATACGGCCGGTCGCGAGACTGGGGGCGTACACTGGATGG
CCTTTGCCTGGAACCCGCACTCAAAAACATGCTACCTCTTTGAGCCCTTTGGCTTTTCTGAC
CAGCGACTCAAGCAGGTTTACCAGTTTGAGTACGAGTCACTCCTGCGCCGTAGCGCCATTGC
TTCTTCCCCCGACCGCTGTATAACGCTGGAAAAGTCCACCCAAAGCGTACAGGGGCCCAACT
CGGCCGCCTGTGGACTATTCTGCTGCATGTTTCTCCACGCCTTTGCCAACTGGCCCCAAACT
CCCATGGATCACAACCCCACCATGAACCTTATTACCGGGGTACCCAACTCCATGCTCAACAG
TCCCCAGGTACAGCCCACCCTGCGTCGCAACCAGGAACAGCTCTACAGCTTCCTGGAGCGCC
ACTCGCCCTACTTCCGCAGCCACAGTGCGCAGATTAGGAGCGCCACTTCTTTTTGTCACTTG
AAAAACATGTAAAAATAATGTACTAGAGACACTTTCAATAAAGGCAAATGCTTTTATTTGTA
CACTCTCGGGTGATTATTTACCCCCACCCTTGCCGTCTGCGCCGTTTAAAAATCAAAGGGGT
TCTGCCGCGCATCGCTATGCGCCACTGGCAGGGACACGTTGCGATACTGGTGTTTAGTGCTC
CACTTAAACTCAGGCACAACCATCCGCGGCAGCTCGGTGAAGTTTTCACTCCACAGGCTGCG
CACCATCACCAACGCGTTTAGCAGGTCGGGCGCCGATATCTTGAAGTCGCAGTTGGGGCCTC
CGCCCTGCGCGCGCGAGTTGCGATACACAGGGTTGCAGCACTGGAACACTATCAGCGCCGGG
TGGTGCACGCTGGCCAGCACGCTCTTGTCGGAGATCAGATCCGCGTCCAGGTCCTCCGCGTT
GCTCAGGGCGAACGGAGTCAACTTTGGTAGCTGCCTTCCCAAAAAGGGCGCGTGCCCAGGCT
TTGAGTTGCACTCGCACCGTAGTGGCATCAAAAGGTGACCGTGCCCGGTCTGGGCGTTAGGA
TACAGCGCCTGCATAAAAGCCTTGATCTGCTTAAAAGCCACCTGAGCCTTTGCGCCTTCAGA
GAAGAACATGCCGCAAGACTTG
```

FIG. 30 (10 of 16)

```
CCGGAAAACTGATTGGCCGGACAGGCCGCGTCGTGCACGCAGCACCTTGCGTCGGTGTTGGA
GATCTGCACCACATTTCGGCCCCACCGGTTCTTCACGATCTTGGCCTTGCTAGACTGCTCCT
TCAGCGCGCGCTGCCCGTTTTCGCTCGTCACATCCATTTCAATCACGTGCTCCTTATTTATC
ATAATGCTTCCGTGTAGACACTTAAGCTCGCCTTCGATCTCAGCGCAGCGGTGCAGCCACAA
CGCGCAGCCCGTGGGCTCGTGATGCTTGTAGGTCACCTCTGCAAACGACTGCAGGTACGCCT
GCAGGAATCGCCCCATCATCGTCACAAAGGTCTTGTTGCTGGTGAAGGTCAGCTGCAACCCG
CGGTGCTCCTCGTTCAGCCAGGTCTTGCATACGGCCGCCAGAGCTTCCACTTGGTCAGGCAG
TAGTTTGAAGTTCGCCTTTAGATCGTTATCCACGTGGTACTTGTCCATCAGCGCGCGCGCAG
CCTCCATGCCCTTCTCCCACGCAGACACGATCGGCACACTCAGCGGGTTCATCACCGTAATT
TCACTTTCCGCTTCGCTGGGCTCTTCCTCTTCCTCTTGCGTCCGCATACCACGCGCCACTGG
GTCGTCTTCATTCAGCCGCCGCACTGTGCGCTTACCTCCTTTGCCATGCTTGATTAGCACCG
GTGGGTTGCTGAAACCCACCATTTGTAGCGCCACATCTTCTCTTTCTTCCTCGCTGTCCACG
ATTACCTCTGGTGATGGCGGGCGCTCGGGCTTGGGAGAAGGGCGCTTCTTTTTCTTCTTGGG
CGCAATGGCCAAATCCGCCGCCGAGGTCGATGGCCGCGGGCTGGGTGTGCGCGGCACCAGCG
CGTCTTGTGATGAGTCTTCCTCGTCCTCGGACTCGATACGCCGCCTCATCCGCTTTTTTGGG
GGCGCCCGGGGAGGCGGCGGCGACGGGGACGGGGACGACACGTCCTCCATGGTTGGGGACG
TCGCGCCGCACCGCGTCCGCGCTCGGGGGTGGTTTCGCGCTGCTCCTCTTCCCGACTGGCCA
TTTCCTTCTCCTATAGGCAGAAAAAGATCATGGAGTCAGTCGAGAAGAAGGACAGCCTAACC
GCCCCCTCTGAGTTCGCCACCACCGCCTCCACCGATGCCGCCAACGCGCCTACCACCTTCCC
CGTCGAGGCACCCCCGCTTGAGGAGGAGGAAGTGATTATCGAGCAGGACCCAGGTTTTGTAA
GCGAAGACGACGAGGACCGCTCAGTACCAACAGAGGATAAAAAGCAAGACCAGGACAACGCA
GAGGCAAACGAGGAACAAGTCGGGCGGGGGGACGAAAGGCATGGCGACTACCTAGATGTGGG
AGACGACGTGCTGTTGAAGCATCTGCAGCGCCAGTGCGCCATTATCTGCGACGCGTTGCAAG
AGCGCAGCGATGTGCCCCTCGCCATAGCGGATGTCAGCCTTGCCTACGAACGCCACCTATTC
TCACCGCGCGTACCCCCCAAACGCCAAGAAAACGGCACATGCGAGCCCAACCCGCGCCTCAA
CTTCTACCCCGTATTTGCCGTGCCAGAGGTGCTTGCCACCTATCACATCTTTTTCCAAAACT
GCAAGATACCCCTATCCTGCCGTGCCAACCGCAGCCGAGCGGACAAGCAGCTGGCCTTGCGG
CAGGGCGCTGTCATACCTGATATCGCCTCGCTCAACGAAGTGCCAAAAATCTTTGAGGGTCT
TGGACGCGACGAGAAGCGCGCGGCAAACGCTCTGCAACAGGAAAACAGCGAAAATGAAAGTC
ACTCTGGAGTGTTGGTGGAACTCGAGGGTGACAACGCGCGCCTAGCCGTACTAAAACGCAGC
ATCGAGGTCACCCACTTTGCCTACCCGGCACTTAACCTACCCCCCAAGGTCATGAGCACAGT
CATGAGTGAGCTGATCGTGCGCCGTGCGCAGCCCCTGGAGAGGGATGCAAATTTGCAAGAAC
AAACAGAGGAGGGCCTACCCGCAGTTGGCGACGAGCAGCTAGCGCGCTGGCTTCAAACGCGC
GAGCCTGCCGACTTGGAGGAGCGACGCAAACTAATGATGGCCGCAGTGCTCGTTACCGTGGA
GCTTGAGTGCATGCAGCGGTTCTTTGCTGACCCGGAGATGCAGCGCAAGCTAGAGGAAACAT
TGCACTACACCTTTCGACAGGGCTACGTACGCCAGGCCTGCAAGATCTCCAACGTGGAGCTC
TGCAACCTGGTCTCCTACCTTGGAATTTTGCACGAAAACCGCCTTGGGCAAAACGTGCTTCA
TTCCACGCTCAAGGGCGAGGCGCGCCGCGACTACGTCCGCGACTGCGTTTACTTATTTCTAT
GCTACACCTGGCAGACGGCCATGGGCGTTTGGCAGCAGTGCTTGGAGGAGTGCAACCTCAAG
GAGCTGCAGAAACTGCTAAAGCAAAACTTGAAGGACCTATGGACGGCCTTCAACGAGCGCTC
CGTGGCCGCG
```

FIG. 30

```
CACCTGGCGGACATCATTTTCCCCGAACGCCTGCTTAAAACCCTGCAACAGGGTCTGCCAGA
CTTCACCAGTCAAAGCATGTTGCAGAACTTTAGGAACTTTATCCTAGAGCGCTCAGGAATCT
TGCCCGCCACCTGCTGTGCACTTCCTAGCGACTTTGTGCCCATTAAGTACCGCGAATGCCCT
CCGCCGCTTTGGGGCCACTGCTACCTTCTGCAGCTAGCCAACTACCTTGCCTACCACTCTGA
CATAATGGAAGACGTGAGCGGTGACGGTCTACTGGAGTGTCACTGTCGCTGCAACCTATGCA
CCCCGCACCGCTCCCTGGTTTGCAATTCGCAGCTGCTTAACGAAAGTCAAATTATCGGTACC
TTTGAGCTGCAGGGTCCCTCGCCTGACGAAAAGTCCGCGGCTCCGGGGTTGAAACTCACTCC
GGGGCTGTGGACGTCGGCTTACCTTCGCAAATTTGTACCTGAGGACTACCACGCCCACGAGA
TTAGGTTCTACGAAGACCAATCCCGCCCGCCAAATGCGGAGCTTACCGCCTGCGTCATTACC
CAGGGCCACATTCTTGGCCAATTGCAAGCCATCAACAAAGCCCGCCAAGAGTTTCTGCTACG
AAAGGGACGGGGGGTTTACTTGGACCCCCAGTCCGGCGAGGAGCTCAACCCAATCCCCCCGC
CGCCGCAGCCCTATCAGCAGCAGCCGCGGGCCCTTGCTTCCCAGGATGGCACCCAAAAAGAA
GCTGCAGCTGCCGCCGCCACCCACGGACGAGGAGGAATACTGGGACAGTCAGGCAGAGGAGG
TTTTGGACGAGGAGGAGGAGGACATGATGGAAGACTGGGAGAGCCTAGACGAGGAAGCTTCC
GAGGTCGAAGAGGTGTCAGACGAAACACCGTCACCCTCGGTCGCATTCCCCTCGCCGGCGCC
CCAGAAATCGGCAACCGGTTCCAGCATGGCTACAACCTCCGCTCCTCAGGCGCCGCCGGCAC
TGCCCGTTCGCCGACCCAACCGTAGATGGGACACCACTGGAACCAGGGCCGGTAAGTCCAAG
CAGCCGCCGCCGTTAGCCCAAGAGCAACAACAGCGCCAAGGCTACCGCTCATGGCGCGGGCA
CAAGAACGCCATAGTTGCTTGCTTGCAAGACTGTGGGGGCAACATCTCCTTCGCCCGCCGCT
TTCTTCTCTACCATCACGGCGTGGCCTTCCCCCGTAACATCCTGCATTACTACCGTCATCTC
TACAGCCCATACTGCACCGGCGGCAGCGGCAGCGGCAGCAACAGCAGCGGCCACACAGAAGC
AAAGGCGACCGGATAGCAAGACTCTGACAAAGCCCAAGAAATCCACAGCGGCGGCAGCAGCA
GGAGGAGGAGCGCTGCGTCTGGCGCCCAACGAACCCGTATCGACCCGCGAGCTTAGAAACAG
GATTTTTCCCACTCTGTATGCTATATTTCAACAGAGCAGGGGCCAAGAACAAGAGCTGAAAA
TAAAAAACAGGTCTCTGCGATCCCTCACCCGCAGCTGCCTGTATCACAAAAGCGAAGATCAG
CTTCGGCGCACGCTGGAAGACGCGGAGGCTCTCTTCAGTAAATACTGCGCGCTGACTCTTAA
GGACTAGTTTCGCGCCCTTTCTCAAATTTAAGCGCGAAAACTACGTCATCTCCAGCGGCCAC
ACCCGGCGCCAGCACCTGTCGTCAGCGCCATTATGAGCAAGGAAATTCCCACGCCCTACATG
TGGAGTTACCAGCCACAAATGGGACTTGCGGCTGGAGCTGCCCAAGACTACTCAACCCGAAT
AAACTACATGAGCGCGGGACCCCACATGATATCCCGGGTCAACGGAATCCGCGCCCACCGAA
ACCGAATTCTCTTGGAACAGGCGGCTATTACCACCACACCTCGTAATAACCTTAATCCCCGT
AGTTGGCCCGCTGCCCTGGTGTACCAGGAAAGTCCCGCTCCCACCACTGTGGTACTTCCCAG
AGACGCCCAGGCCGAAGTTCAGATGACTAACTCAGGGGCGCAGCTTGCGGGCGGCTTTCGTC
ACAGGGTGCGGTCGCCCGGGCAGGGTATAACTCACCTGACAATCAGAGGGCGAGGTATTCAG
CTCAACGACGAGTCGGTGAGCTCCTCGCTTGGTCTCCGTCCGGACGGGACATTTCAGATCGG
CGGCGCCGGCCGTCCTTCATTCACGCCTCGTCAGGCAATCCTAACTCTGCAGACCTCGTCCT
CTGAGCCGCGCTCTGGAGGCATTGGAACTCTGCAATTTATTGAGGAGTTTGTGCCATCGGTC
TACTTTAACCCCTTCTCGGGACCTCCCGGCCACTATCCGGATCAATTTATTCCTAACTTTGA
CGCGGTAAAGGACTCGGCGGACGGCTACGACTGAATGTTAAGTGGAGAGGCAGAGCAACTGC
GCCTGAAACACCTGGTCCACTGTCGCCGCCACAAGTGCTTTGCCCGCGACTCCGGTGAGTTT
TGCTACTTTG
```

```
AATTGCCCGAGGATCATATCGAGGGCCCGGCGCACGGCGTCCGGCTTACCGCCCAGGGAGAG
CTTGCCCGTAGCCTGATTCGGGAGTTTACCCAGCGCCCCCTGCTAGTTGAGCGGGACAGGGG
ACCCTGTGTTCTCACTGTGATTTGCAACTGTCCTAACCTTGGATTACATCAAGATCCTCTAG
TTATAACTAGAGTACCCGGGGATCTTATTCCCTTTAACTAATAAAAAAAAATAATAAAGCAT
CACTTACTTAAAATCAGTTAGCAAATTTCTGTCCAGTTTATTCAGCAGCACCTCCTTGCCCT
CCTCCCAGCTCTGGTATTGCAGCTTCCTCCTGGCTGCAAACTTTCTCCACAATCTAAATGGA
ATGTCAGTTTCCTCCTGTTCCTGTCCATCCGCACCCACCGGTATAACTTCGTATATGGTTTC
TTATACGAACGGTACAAGAACAAGAGCTGAAAATAAAAAACAGGTCTCTGCGATCCCTCACC
CGCAGCTGCCTGTATCACAAAAGCGAAGATCAGCTTCGGCGCACGCTGGAAGACGCGGAGGC
TCTCTTCAGTAAATACTGCGCGCTGACTCTTAAGGACTAGTTTCGCGCCCTTTCTCAAATTT
AAGCGCGAAAACTACGTCATCTCCAGCGGCCACACCCGGCGCCAGCACCTGTCGTCAGCGCC
ATTATGAGCAAGGAAATTCCCACGCCCTACATGTGGAGTTACCAGCCACAAATGGGACTTGC
GGCTGGAGCTGCCCAAGACTACTCAACCCGAATAAACTACATGAGCGCGGGACCCCACATGA
TATCCCGGGTCAACGGAATCCGCGCCCACCGAAACCGAATTCTCTTGGAACAGGCGGCTATT
ACCACCACACCTCGTAATAACCTTAATCCCCGTAGTTGGCCCGCTGCCCTGGTGTACCAGGA
AAGTCCCGCTCCCACCACTGTGGTACTTCCCAGAGACGCCCAGGCCGAAGTTCAGATGACTA
ACTCAGGGGCGCAGCTTGCGGGCGGCTTTCGTCACAGGGTGCGGTCGCCCGGGCAGGGTATA
ACTCACCTGACAATCAGAGGGCGAGGTATTCAGCTCAACGACGAGTCGGTGAGCTCCTCGCT
TGGTCTCCGTCCGGACGGGACATTTCAGATCGGCGGCGCCGGCCGTCCTTCATTCACGCCTC
GTCAGGCAATCCTAACTCTGCAGACCTCGTCCTCTGAGCCGCGCTCTGGAGGCATTGGAACT
CTGCAATTTATTGAGGAGTTTGTGCCATCGGTCTACTTTAACCCCTTCTCGGGACCTCCCGG
CCACTATCCGGATCAATTTATTCCTAACTTTGACGCGGTAAAGGACTCGGCGGACGGCTACG
ACTGAATGTTAAGTGGAGAGGCAGAGCAACTGCGCCTGAAACACCTGGTCCACTGTCGCCGC
CACAAGTGCTTTGCCCGCGACTCCGGTGAGTTTTGCTACTTTGAATTGCCCGAGGATCATAT
CGAGGGCCCGGCGCACGGCGTCCGGCTTACCGCCCAGGGAGAGCTTGCCCGTAGCCTGATTC
GGGAGTTTACCCAGCGCCCCCTGCTAGTTGAGCGGGACAGGGGACCCTGTGTTCTCACTGTG
ATTTGCAACTGTCCTAACCTTGGATTACATCAAGATCCTCTAGTTATAACTAGAGTACCCGG
GGATCTTATTCCCTTTAACTAATAAAAAAAAATAATAAAGCATCACTTACTTAAAATCAGTT
AGCAAATTTCTGTCCAGTTTATTCAGCAGCACCTCCTTGCCCTCCTCCCAGCTCTGGTATTG
CAGCTTCCTCCTGGCTGCAAACTTTCTCCACAATCTAAATGGAATGTCAGTTTCCTCCTGTT
CCTGTCCATCCGCACCCACTATCTTCATGTTGTTGCAGATACCGGTATAACTTCGTATATGG
TTTCTTATACGAAGTTATCTCGAGAACTATCTTCATGTTGTTGCAGATGAAGCGCGCAAGAC
CGTCTGAAGATACCTTCAACCCCGTGTATCCATATGACACGGAAACCGGTCCTCCAACTGTG
CCTTTTCTTACTCCTCCCTTTGTATCCCCCAATGGGTTTCAAGAGAGTCCCCCTGGGGTACT
CTCTTTGCGCCTATCCGAACCTCTAGTTACCTCCAATGGCATGCTTGCGCTCAAAATGGGCA
ACGGCCTCTCTCTGGACGAGGCCGGCAACCTTACCTCCCAAAATGTAACCACTGTGAGCCCA
CCTCTCAAAAAAACCAAGTCAAACATAAACCTGGAAATATCTGCACCCCTCACAGTTACCTC
AGAAGCCCTAACTGTGGCTGCCGCCGCACCTCTAATGGTCGCGGGCAACACACTCACCATGC
AATCACAGGCCCCGCTAACCGTGCACGACTCCAAACTTAGCATTGCCACCCAAGGACCCCTC
ACAGTGTCAGAAGGAAAGCTAGCCCTGCAAACATCAGGCCCCCTCACCACCACCGATAGCAG
TACCCTTACTATCACTGCCTCACCCC
```

FIG. 30 (13 of 16)

```
CTCTAACTACTGCCACTGGTAGCTTGGGCATTGACTTGAAAGAGCCCATTTATACACAAAAT
GGAAAACTAGGACTAAAGTACGGGGCTCCTTTGCATGTAACAGACGACCTAAACACTTTGAC
CGTAGCAACTGGTCCAGGTGTGACTATTAATAATACTTCCTTGCAAACTAAAGTTACTGGAG
CCTTGGGTTTTGATTCACAAGGCAATATGCAACTTAATGTAGCAGGAGGACTAAGGATTGAT
TCTCAAAACAGACGCCTTATACTTGATGTTAGTTATCCGTTTGATGCTCAAAACCAACTAAA
TCTAAGACTAGGACAGGGCCCTCTTTTTATAAACTCAGCCCACAACTTGGATATTAACTACA
ACAAAGGCCTTTACTTGTTTACAGCTTCAAACAATTCCAAAAAGCTTGAGGTTAACCTAAGC
ACTGCCAAGGGGTTGATGTTTGACGCTACAGCCATAGCCATTAATGCAGGAGATGGGCTTGA
ATTTGGTTCACCTAATGCACCAAACACAAATCCCCTCAAAACAAAAATTGGCCATGGCCTAG
AATTTGATTCAAACAAGGCTATGGTTCCTAAACTAGGAACTGGCCTTAGTTTTGACAGCACA
GGTGCCATTACAGTAGGAAACAAAAATAATGATAAGCTAACTTTGTGGACCACACCAGCTCC
ATCTCCTAACTGTAGACTAAATGCAGAGAAAGATGCTAAACTCACTTTGGTCTTAACAAAAT
GTGGCAGTCAAATACTTGCTACAGTTTCAGTTTTGGCTGTTAAAGGCAGTTTGGCTCCAATA
TCTGGAACAGTTCAAAGTGCTCATCTTATTATAAGATTTGACGAAAATGGAGTGCTACTAAA
CAATTCCTTCCTGGACCCAGAATATTGGAACTTTAGAAATGGAGATCTTACTGAAGGCACAG
CCTATACAAACGCTGTTGGATTTATGCCTAACCTATCAGCTTATCCAAAATCTCACGGTAAA
ACTGCCAAAAGTAACATTGTCAGTCAAGTTTACTTAAACGGAGACAAAACTAAACCTGTAAC
ACTAACCATTACACTAAGCGGTACACAGGAATCCGGAGACACAACTCCAAGTGCATACTCTA
TGTCATTTTCATGGGACTGGTCTGGCCACAACTACATTAATGAAATATTTGCCACATCCTCT
TACACTTTTTCATACATTGCCCAAGAATAAAGAAGCGGCCGCATAACTTCGTATAGCATACA
TTATACGAAGTTATACCGGTATACATTGCCCAAGAATAAAGAATCGTTTGTGTTATGTTTCA
ACGTGTTTATTTTTCAATTGCAGAAAATTTCAAGTCATTTTTCATTCAGTAGTATAGCCCCA
CCACCACATAGCTTATACAGATCACCGTACCTTAATCAAACTCACAGAACCCTAGTATTCAA
CCTGCCACCTCCCTCCCAACACACAGAGTACACAGTCCTTTCTCCCCGGCTGGCCTTAAAAA
GCATCATATCATGGGTAACAGACATATTCTTAGGTGTTATATTCCACACGGTTTCCTGTCGA
GCCAAACGCTCATCAGTGATATTAATAAACTCCCCGGGCAGCTCACTTAAGTTCATGTCGCT
GTCCAGCTGCTGAGCCACAGGCTGCTGTCCAACTTGCGGTTGCTTAACGGGCGGCGAAGGAG
AAGTCCACGCCTACATGGGGGTAGAGTCATAATCGTGCATCAGGATAGGGCGGTGGTGCTGC
AGCAGCGCGCGAATAAACTGCTGCCGCCGCCGCTCCGTCCTGCAGGAATACAACATGGCAGT
GGTCTCCTCAGCGATGATTCGCACCGCCCGCAGCATAAGGCGCCTTGTCCTCCGGGCACAGC
AGCGCACCCTGATCTCACTTAAATCAGCACAGTAACTGCAGCACAGCACCACAATATTGTTC
AAAATCCCACAGTGCAAGGCGCTGTATCCAAAGCTCATGGCGGGGACCACAGAACCCACGTG
GCCATCATACCACAAGCGCAGGTAGATTAAGTGGCGACCCCTCATAAACACGCTGGACATAA
ACATTACCTCTTTTGGCATGTTGTAATTCACCACCTCCCGGTACCATATAAACCTCTGATTA
AACATGGCGCCATCCACCACCATCCTAAACCAGCTGGCCAAAACCTGCCCGCCGGCTATACA
CTGCAGGGAACCGGGACTGGAACAATGACAGTGGAGAGCCCAGGACTCGTAACCATGGATCA
TCATGCTCGTCATGATATCAATGTTGGCACAACACAGGCACACGTGCATACACTTCCTCAGG
ATTACAAGCTCCTCCCGCGTTAGAACCATATCCCAGGGAACAACCCATTCCTGAATCAGCGT
AAATCCCACACTGCAGGGAAGACCTCGCACGTAACTCACGTTGTGCATTGTCAAAGTGTTAC
ATTCGGGCAGCAGCGGATGATCCTCCAGTATGGTAGCGCGGGTTTCTGTCTCAAAAGGAGGT
AGACGATCCCTACTGTAC
```

FIG. 30

```
GGAGTGCGCCGAGACAACCGAGATCGTGTTGGTCGTAGTGTCATGCCAAATGGAACGCCGGA
CGTAGTCATATTTCCTGAAGCAAAACCAGGTGCGGGCGTGACAAACAGATCTGCGTCTCCGG
TCTCGCCGCTTAGATCGCTCTGTGTAGTAGTTGTAGTATATCCACTCTCTCAAAGCATCCAG
GCGCCCCCTGGCTTCGGGTTCTATGTAAACTCCTTCATGCGCCGCTGCCCTGATAACATCCA
CCACCGCAGAATAAGCCACACCCAGCCAACCTACACATTCGTTCTGCGAGTCACACACGGGA
GGAGCGGGAAGAGCTGGAAGAACCATGTTTTTTTTTTATTCCAAAAGATTATCCAAAACCT
CAAAATGAAGATCTATTAAGTGAACGCGCTCCCCTCCGGTGGCGTGGTCAAACTCTACAGCC
AAAGAACAGATAATGGCATTTGTAAGATGTTGCACAATGGCTTCCAAAAGGCAAACGGCCCT
CACGTCCAAGTGGACGTAAAGGCTAAACCCTTCAGGGTGAATCTCCTCTATAAACATTCCAG
CACCTTCAACCATGCCCAAATAATTCTCATCTCGCCACCTTCTCAATATATCTCTAAGCAAA
TCCCGAATATTAAGTCCGGCCATTGTAAAAATCTGCTCCAGAGCGCCCTCCACCTTCAGCCT
CAAGCAGCGAATCATGATTGCAAAAATTCAGGTTCCTCACAGACCTGTATAAGATTCAAAAG
CGGAACATTAACAAAAATACCGCGATCCCGTAGGTCCCTTCGCAGGGCCAGCTGAACATAAT
CGTGCAGGTCTGCACGGACCAGCGCGGCCACTTCCCCGCCAGGAACCTTGACAAAAGAACCC
ACACTGATTATGACACGCATACTCGGAGCTATGCTAACCAGCGTAGCCCCGATGTAAGCTTT
GTTGCATGGGCGGCGATATAAAATGCAAGGTGCTGCTCAAAAAATCAGGCAAAGCCTCGCGC
AAAAAAGAAAGCACATCGTAGTCATGCTCATGCAGATAAAGGCAGGTAAGCTCCGGAACCAC
CACAGAAAAAGACACCATTTTTCTCTCAAACATGTCTGCGGGTTTCTGCATAAACACAAAAT
AAAATAACAAAAAAACATTTAAACATTAGAAGCCTGTCTTACAACAGGAAAAACAACCCTTA
TAAGCATAAGACGGACTACGGCCATGCCGGCGTGACCGTAAAAAAACTGGTCACCGTGATTA
AAAAGCACCACCGACAGCTCCTCGGTCATGTCCGGAGTCATAATGTAAGACTCGGTAAACAC
ATCAGGTTGATTCATCGGTCAGTGCTAAAAAGCGACCGAAATAGCCCGGGGGAATACATACC
CGCAGGCGTAGAGACAACATTACAGCCCCCATAGGAGGTATAACAAAATTAATAGGAGAGAA
AAACACATAAACACCTGAAAAACCCTCCTGCCTAGGCAAAATAGCACCCTCCCGCTCCAGAA
CAACATACAGCGCTTCACAGCGGCAGCCTAACAGTCAGCCTTACCAGTAAAAAAGAAAACCT
ATTAAAAAAACACCACTCGACACGGCACCAGCTCAATCAGTCACAGTGTAAAAAAGGGCCAA
GTGCAGAGCGAGTATATATAGGACTAAAAAATGACGTAACGGTTAAAGTCCACAAAAAACAC
CCAGAAAACCGCACGCGAACCTACGCCCAGAAACGAAAGCCAAAAAACCCACAACTTCCTCA
AATCGTCACTTCCGTTTTCCCACGTTACGTAACTTCCCATTTTAAGAAAACTACAATTCCCA
ACACATACAAGTTACTCCGCCCTAAAACCTACGTCACCCGCCCCGTTCCCACGCCCCGCGCC
ACGTCACAAACTCCACCCCCTCATTATCATATTGGCTTCAATCCAAAATAAGGTATATTATT
GATGATTTAATTAAGGATCCNNNCCTGTCCTCGACCGATGCCCTTGAGAGCCTTCAACCCAG
TCAGCTCCTTCCGGTGGGCGCGGGGCATGACTATCGTCGCCGCACTTATGACTGTCTTCTTT
ATCATGCAACTCGTAGGACAGGTGCCGGCAGCGCTCTGGGTCATTTTCGGCGAGGACCGCTT
TCGCTGGAGCGCGACGATGATCGGCCTGTCGCTTGCGGTATTCGGAATCTTGCACGCCCTCG
CTCAAGCCTTCGTCACTGGTCCCGCCACCAAACGTTTCGGCGAGAAGCAGGCCATTATCGCC
GGCATGGCGGCCGACGCGCTGGGCTACGTCTTGCTGGCGTTCGCGACGCGAGGCTGGATGGC
CTTCCCCATTATGATTCTTCTCGCTTCCGGCGGCATCGGGATGCCCGCGTTGCAGGCCATGC
TGTCCAGGCAGGTAGATGACGACCATCAGGGACAGCTTCAAGGATCGCTCGCGGCTCTTACC
AGCCTAACTTCGATCACTGGACCGCTGATCGTCACGGCGATTTATGCCGCCTCGGCGAGCAC
ATGGAACG
```

FIG. 30

```
GGTTGGCATGGATTGTAGGCGCCGCCCTATACCTTGTCTGCCTCCCCGCGTTGCGTCGCGGT
GCATGGAGCCGGGCCACCTCGACCTGAATGGAAGCCGGCGGCACCTCGCTAACGGATTCACC
ACTCCAAGAATTGGAGCCAATCAATTCTTGCGGAGAACTGTGAATGCGCAAACCAACCCTTG
GCAGAACATATCCATCGCGTCCGCCATCTCCAGCAGCCGCACGCGGCGCATCTCGGGCAGCG
TTGGGTCCTGGCCACGGGTGCGCATGATCGTGCTCCTGTCGTTGAGGACCCGGCTAGGCTGG
CGGGGTTGCCTTACTGGTTAGCAGAATGAATCACCGATACGCGAGCGAACGTGAAGCGACTG
CTGCTGCAAAACGTCTGCGACCTGAGCAACAACATGAATGGTCTTCGGTTTCCGTGTTTCGT
AAAGTCTGGAAACGCGGAAGTCAGCGCCCTGCACCATTATGTTCCGGATCTGCATCGCAGGA
TGCTGCTGGCTACCCTGTGGAACACCTACATCTGTATTAACGAAGCGCTGGCATTGACCCTG
AGTGATTTTTCTCTGGTCCCGCCGCATCCATACCGCCAGTTGTTTACCCTCACAACGTTCCA
GTAACCGGGCATGTTCATCATCAGTAACCCGTATCGTGAGCATCCTCTCTCGTTTCATCGGT
ATCATTACCCCCATGAACAGAAATTCCCCCTTACACGGAGGCATCAAGTGACCAAACAGGAA
AAAACCGCCCTTAACATGGCCCGCTTTATCAGAAGCCAGACATTAACGCTTCTGGAGAAACT
CAACGAGCTGGACGCGGATGAACAGGCAGACATCTGTGAATCGCTTCACGACCACGCTGATG
AGCTTTACCGCAGCTGCCTCGCGCGTTTCGGTGATGACGGTGAAAACCTCTGACACATGCAG
CTCCCGGAGACGGTCACAGCTTGTCTGTAAGCGGATGCCGGGAGCAGACAAGCCCGTCAGGG
CGCGTCAGCGGGTGTTGGCGGGTGTCGGGGCGCAGCCATGACCCAGTCACGTAGCGATAGCG
GAGTGTATACTGGCTTAACTATGCGGCATCAGAGCAGATTGTACTGAGAGTGCACCATATGC
GGTGTGAAATACCGCACAGATGCGTAAGGAGAAAATACCGCAT
```

FIG. 30 pShuttle (SEQ ID NO:2)

```
TTAATTAANNNTCCCTTCCAGCTCTCTGCCCCTTTTGGATTGAAGCCAATATGATAATGAGG
GGGTGGAGTTTGTGACGTGGCGCGGGGCGTGGGAACGGGGCGGGTGACGTAGTAGTGTGGCG
GAAGTGTGATGTTGCAAGTGTGGCGGAACACATGTAAGCGACGGATGTGGCAAAAGTGACGT
TTTTGGTGTGCGCCGGTGTACACAGGAAGTGACAATTTTCGCGCGGTTTTAGGCGGATGTTG
TAGTAAATTTGGGCGTAACCGAGTAAGATTTGGCCATTTTCGCGGGAAAACTGAATAAGAGG
AAGTGAAATCTGAATAATTTTGTGTTACTCATAGCGCGTAANNNCGCGTTAAGATACATTGA
TGAGTTTGGACAAACCACAACTAGAATGCAGTGAAAAAAATGCTTTATTTGTGAAATTTGTG
ATGCTATTGCTTTATTTGTAACCATTATAAGCTGCAATAAACAAGTTAACAACAACAATTGC
ATTCATTTTATGTTTCAGGTTCAGGGGGAGGTGTGGGAGGTTTTTTAAAGCAAGTAAAACCT
CTACAAATGTGGTATGGCTGATTATGATCAGTTATCTAGATCCGGTGGATCTGAGTCCGGAC
TTGTACAGCTCGTCCATGCCGAGAGTGATCCCGGCGGCGGTCACGAACTCCAGCAGGACCAT
GTGATCGCGCTTCTCGTTGGGGTCTTTGCTCAGGGCGGACTGGGTGCTCAGGTAGTGGTTGT
CGGGCAGCAGCACGGGGCCGTCGCCGATGGGGGTGTTCTGCTGGTAGTGGTCGGCGAGCTGC
ACGCTGCCGTCCTCGATGTTGTGGCGGATCTTGAAGTTCACCTTGATGCCGTTCTTCTGCTT
GTCGGCCATGATATAGACGTTGTGGCTGTTGTAGTTGTACTCCAGCTTGTGCCCCAGGATGT
TGCCGTCCTCCTTGAAGTCGATGCCCTTCAGCTCGATGCGGTTCACCAGGGTGTCGCCCTCG
AACTTCACCTCGGCGCGGGTCTTGTAGTTGCCGTCGTCCTTGAAGAAGATGGTGCGCTCCTG
GACGTAGCCTTCGGGCATGGCGGACTTGAAGAAGTCGTGCTGCTTCATGTGGTCGGGGTAGC
GGCTGAAGCACTGCACGCCGTAGGTCAGGGTGGTCACGAGGGTGGGCCAGGGCACGGGCAGC
TTGCCGGTGGTGCAGATGAACTTCAGGGTCAGCTTGCCGTAGGTGGCATCGCCCTCGCCCTC
GCCGGACACGCTGAACTTGTGGCCGTTTACGTCGCCGTCCAGCTCGACCAGGATGGGCACCA
CCCCGGTGAACAGCTCCTCGCCCTTGCTCACCATGGTGGCGACCGGTAGCGCTAGCGGATCT
GACGGTTCACTAAACCAGCTCTGCTTATATAGACCTCCCACCGTACACGCCTACCGCCCATT
TGCGTCAATGGGGCGGAGTTGTTACGACATTTTGGAAAGTCCCGTTGATTTTGGTGCCAAAA
CAAACTCCCATTGACGTCAATGGGGTGGAGACTTGGAAATCCCCGTGAGTCAAACCGCTATC
CACGCCCATTGATGTACTGCCAAAACCGCATCACCATGGTAATAGCGATGACTAATACGTAG
ATGTACTGCCAAGTAGGAAAGTCCCATAAGGTCATGTACTGGGCATAATGCCAGGCGGGCCA
TTTACCGTCATTGACGTCAATAGGGGCGTACTTGGCATATGATACACTTGATGTACTGCCA
AGTGGGCAGTTTACCGTAAATACTCCACCCATTGACGTCAATGGAAAGTCCCTATTGGCGTT
ACTATGGGAACATACGTCATTATTGACGTCAATGGGCGGGGTCGTTGGGCGGTCAGCCAGG
CGGGCCATTTACCGTAAGTTATGTAACGCGGAACTCCATATATGGGCTATGAACTAATGACC
CCGTAATTGATTACTATTANNNCTAGCAGATCTGGTACCGTCGACGCGGCCGCGATATCCTC
GAGAAGCTTTCTAGAGNNNTAAGGGTGGGAAAGAATATATAAGGTGGGGGTCTTATGTAGTT
TTGTATCTGTTTTGCAGCAGCCGCCGCCGCCATGAGCACCAACTCGTTTGATGGAAGCATTG
TGAGCTCATATTTGACAACGCGCATGCCCCATGGGCCGGGGTGCGTCAGAATGTGATGGGC
TCCAGCATTGATGGTCGCCCCGTCCTGCCCGCAAACTCTACTACCTTGACCTACGAGACCGT
GTCTGGAACGCCGTTGGAGACTGCAGCCTCCGCCGCCGCTTCAGCCGCTGCAGCCACCGCCC
GCGGGATTGTGACTGACTTTGCTTTCCTGAGCCCGCTTGCAAGCAGTGCAGCTTCCCGTTCA
TCCGCCCGCGATGACAAGTTGACGGCTCTT
```

FIG. 31 (1 of 4)

```
TTGGCACAATTGGATTCTTTGACCCGGGAACTTAATGTCGTTTCTCAGCAGCTGTTGGATCT
GCGCCAGCAGGTTTCTGCCCTGAAGGCTTCCTCCCCTCCCAATGCGGTTTAAAACATAAATA
AAAAACCAGACTCTGTTTGGATTTGGATCAAGCAAGTGTCTTGCTGTCTTTATTTAGGGGTT
TTGCGCGCGCGGTAGGCCCGGGACCAGCGGTCTCGGTCGTTGAGGGTCCTGTGTATTTTTTC
CAGGACGTGGTAAAGGTGACTCTGGATGTTCAGATACATGGGCATAAGCCCGTCTCTGGGGT
GGAGGTAGCACCACTGCAGAGCTTCATGCTGCGGGGTGGTGTTGTAGATGATCCAGTCGTAG
CAGGAGCGCTGGGCGTGGTGCCTAAAAATGTCTTTCAGTAGCAAGCTGATTGCCAGGGGCAG
GCCCTTGGTGTAAGTGTTTACAAAGCGGTTAAGCTGGGATGGGTGCATACGTGGGGATATGA
GATGCATCTTGGACTGTATTTTTAGGTTGGCTATGTTCCCAGCCATATCCCTCCGGGGATTC
ATGTTGTGCAGAACCACCAGCACAGTGTATCCGGTGCACTTGGGAAATTTGTCATGTAGCTT
AGAAGGAAATGCGTGGAAGAACTTGGAGACGCCCTTGTGACCTCCAAGATTTTCCATGCATT
CGTCCATAATGATGGCAATGGGCCCACGGGCGGCGGCCTGGGCGAAGATATTTCTGGGATCA
CTAACGTCATAGTTGTGTTCCAGGATGAGATCGTCATAGGCCATTTTTACAAAGCGCGGGCG
GAGGGTGCCAGACTGCGGTATAATGGTTCCATCCGGCCCAGGGGCGTAGTTACCCTCACAGA
TTTGCATTTCCCACGCTTTGAGTTCAGATGGGGGGATCATGTCTACCTGCGGGGCGATGAAG
AAAACGGTTTCCGGGGTAGGGGAGATCAGCTGGGAAGAAAGCAGGTTCCTGAGCAGCTGCGA
CTTACCGCAGCCGGTGGGCCCGTAAATCACACCTATTACCGGGTGCAACTGGTAGTTAAGAG
AGCTGCAGCTGCCGTCATCCCTGAGCAGGGGGGCCACTTCGTTAAGCATGTCCCTGACTCGC
ATGTTTTCCCTGACCAAATCCGCCAGAAGGCGCTCGCCGCCCAGCGATAGCAGTTCTTGCAA
GGAAGCAAAGTTTTTCAACGGTTTGAGACCGTCCGCCGTAGGCATGCTTTTGAGCGTTTGAC
CAAGCAGTTCCAGGCGGTCCCACAGCTCGGTCACCTGCTCTACGGCATCTCGATCCAGCATA
TCTCCTCGTTTCGCGGGTTGGGGCGGCTTTCGCTGTACGGCAGTAGTCGGTGCTCGTCCAGA
CGGGCCAGGGTCATGTCTTTCCACGGGCGCAGGGTCCTCGTCAGCGTAGTCTGGGTCACGGT
GAAGGGGTGCGCTCCGGGCTGCGCGCTGGCCAGGGTGCGCTTGAGGCTGGTCCTGCTGGTGC
TGAAGCGCTGCCGGTCTTCGCCCTGCGCGTCGGCCAGGTAGCATTTGACCATGGTGTCATAG
TCCAGCCCCTCCGCGGCGTGGCCCTTGGCGCGCAGCTTGCCCTTGGAGGAGGCGCCGCACGA
GGGGCAGTGCAGACTTTTGAGGGCGTAGAGCTTGGGCGCGAGAAATACCGATTCCGGGGAGT
AGGCATCCGCGCCGCAGGCCCCGCAGACGGTCTCGCATTCCACGAGCCAGGTGAGCTCTGGC
CGTTCGGGGTCAAAAACCAGGTTTCCCCCATGCTTTTTGATGCGTTTCTTACCTCTGGTTTC
CATGAGCCGGTGTCCACGCTCGGTGACGAAAAGGCTGTCCGTGTCCCCGTATACAGACTNNN
GTTTAAACGAATTCNNNTATAAAATGCAAGGTGCTGCTCAAAAAATCAGGCAAAGCCTCGCG
CAAAAAAGAAAGCACATCGTAGTCATGCTCATGCAGATAAAGGCAGGTAAGCTCCGGAACCA
CCACAGAAAAAGACACCATTTTTCTCTCAAACATGTCTGCGGGTTTCTGCATAAACACAAAA
TAAAATAACAAAAAAACATTTAAACATTAGAAGCCTGTCTTACAACAGGAAAAACAACCCTT
ATAAGCATAAGACGGACTACGGCCATGCCGGCGTGACCGTAAAAAAACTGGTCACCGTGATT
AAAAAGCACCACCGACAGCTCCTCGGTCATGTCCGGAGTCATAATGTAAGACTCGGTAAACA
CATCAGGTTGATTCATCGGTCAGTGCTAAAAAGCGACCGAAATAGCCCGGGGGAATACATAC
CCGCAGGCGTAGAGACAACATTACAGCCCCCATAGGAGGTATAACAAAATTAATAGGAGAGA
AAAACACATAAACACCTGAAAAACCCTCCTGCCTAGGCAAAATAGCACCCTCCCGCTCCAGA
ACAACATACAGCGCTTCACAGCGGCAGCCTAACAGTCAGCCTTACCAGTAAAAAGAAAACC
TATTAAAAAAAC
```

FIG. 31 (2 of 4)

```
ACCACTCGACACGGCACCAGCTCAATCAGTCACAGTGTAAAAAAGGGCCAAGTGCAGAGCGA
GTATATATAGGACTAAAAAATGACGTAACGGTTAAAGTCCACAAAAAACACCCAGAAAACCG
CACGCGAACCTACGCCCAGAAACGAAAGCCAAAAAACCCACAACTTCCTCAAATCGTCACTT
CCGTTTTCCCACGTTACGTAACTTCCCATTTTAAGAAAACTACAATTCCCAACACATACAAG
TTACTCCGCCCTAAAACCTACGTCACCCGCCCCGTTCCCACGCCCCGCGCCACGTCACAAAC
TCCACCCCCTCATTATCATATTGGCTTCAATCCAAAATAAGGTATATTATTGATGATNNNTT
AATTAAGGATCCNNNCGGTGTGAAATACCGCACAGATGCGTAAGGAGAAAATACCGCATCAG
GCGCTCTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGC
GAAACCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTA
CCATCTGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCAGTTAATAGTTTG
CGCAACGTTGTTGNNNNNNAAAAAGGATCTTCACCTAGATCCTTTTCACGTAGAAAGCCAGT
CCGCAGAAACGGTGCTGACCCCGGATGAATGTCAGCTACTGGGCTATCTGGACAAGGGAAAA
CGCAAGCGCAAAGAGAAAGCAGGTAGCTTGCAGTGGGCTTACATGGCGATAGCTAGACTGGG
CGGTTTTATGGACAGCAAGCGAACCGGAATTGCCAGCTGGGGCGCCCTCTGGTAAGGTTGGG
AAGCCCTGCAAAGTAAACTGGATGGCTTTCTCGCCGCCAAGGATCTGATGGCGCAGGGGATC
AAGCTCTGATCAAGAGACAGGATGAGGATCGTTTCGCATGATTGAACAAGATGGATTGCACG
CAGGTTCTCCGGCCGCTTGGGTGGAGAGGCTATTCGGCTATGACTGGGCACAACAGACAATC
GGCTGCTCTGATGCCGCCGTGTTCCGGCTGTCAGCGCAGGGGCGCCCGGTTCTTTTTGTCAA
GACCGACCTGTCCGGTGCCCTGAATGAACTGCAAGACGAGGCAGCGCGGCTATCGTGGCTGG
CCACGACGGGCGTTCCTTGCGCAGCTGTGCTCGACGTTGTCACTGAAGCGGGAAGGGACTGG
CTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCAT
TCGACCACCAAGCGAAACATCGCATCGAGCGAGCACGTACTCGGATGGAAGCCGGTCTTGTC
GATCAGGATGATCT
```

FIG. 31 (3 of 4)

```
GGACGAAGAGCATCAGGGGCTCGCGCCAGCCGAACTGTTCGCCAGGCTCAAGGCGAGCATGC
CCGACGGCGAGGATCTCGTCGTGACCCATGGCGATGCCTGCTTGCCGAATATCATGGTGGAA
AATGGCCGCTTTTCTGGATTCATCGACTGTGGCCGGCTGGGTGTGGCGGACCGCTATCAGGA
CATAGCGTTGGCTACCCGTGATATTGCTGAAGAGCTTGGCGGCGAATGGGCTGACCGCTTCC
TCGTGCTTTACGGTATCGCCGCTCCCGATTCGCAGCGCATCGCCTTCTATCGCCTTCTTGAC
GAGTTCTTCTGAATTTTGTTAAAATTTTTGTTAAATCAGCTCATTTTTTAACCAATAGGCCG
AAATCGGCAACATCCCTTATAAATCAAAAGAATAGACCGCGATAGGGTTGAGTGTTGTTCCA
GTTTGGAACAAGAGTCCACTATTAAAGAACGTGGACTCCAACGTCAAAGGGCGAAAAACCGT
CTATCAGGGCGATGGCCCACTACGTGAACCATCACCCAAATCAAGTTTTTTGCGGTCGAGGT
GCCGTAAAGCTCTAAATCGGAACCCTAAAGGGAGCCCCCGATTTAGAGCTTGACGGGGAAAG
CCGGCGAACGTGGCGAGAAAGGAAGGGAAGAAAGCGAAAGGAGCGGGCGCTAGGGCGCTGGC
AAGTGTAGCGGTCACGCTGCGCGTAACCACCACACCCGCGCGCTTAATGCGCCGNNNNNNNNN
NNNNNNNNNNNNNNNNNNNNNNNNNNNNNNNNNNNNNNNNNNNNNNNNNNNNNNNN
```

FIG. 31 (4 of 4)

RP-Fib (SEQ ID NO:3)

```
TCGAGAACTATCTTCATGTTGTTGCAGATGAAGCGCGCAAGACCGTCTGAAGATACCTTCAA
CCCCGTGTATCCATATGACACGGAAACCGGTCCTCCAACTGTGCCTTTTCTTACTCCTCCCT
TTGTATCCCCCAATGGGTTTCAAGAGAGTCCCCCTGGGGTACTCTCTTTGCGCCTATCCGAA
CCTCTAGTTACCTCCAATGGCATGCTTGCGCTCAAAATGGGCAACGGCCTCTCTCTGGACGA
GGCCGGCAACCTTACCTCCCAAAATGTAACCACTGTGAGCCCACCTCTCAAAAAAACCAAGT
CAAACATAAACCTGGAAATATCTGCACCCCTCACAGTTACCTCAGAAGCCCTAACTGTGGCT
GCCGCCGCACCTCTAATGGTCGCGGGCAACACACTCACCATGCAATCACAGGCCCCGCTAAC
CGTGCACGACTCCAAACTTAGCATTGCCACCCAAGGACCCCTCACAGTGTCAGAAGGAAAGC
TAGCCCTGCAAACATCAGGCCCCCTCACCACCACCGATAGCAGTACCCTTACTATCACTGCC
TCACCCCCTCTAACTACTGCCACTGGTAGCTTGGGCATTGACTTGAAAGAGCCCATTTATAC
ACAAAATGGAAAACTAGGACTAAAGTACGGGGCTCCTTTGCATGTAACAGACGACCTAAACA
CTTTGACCGTAGCAACTGGTCCAGGTGTGACTATTAATAATACTTCCTTGCAAACTAAAGTT
ACTGGAGCCTTGGGTTTTGATTCACAAGGCAATATGCAACTTAATGTAGCAGGAGGACTAAG
GATTGATTCTCAAAACAGACGCCTTATACTTGATGTTAGTTATCCGTTTGATGCTCAAAACC
AACTAAATCTAAGACTAGGACAGGGCCCTCTTTTTATAAACTCAGCCCACAACTTGGATATT
AACTACAACAAAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAATGCAGGAGATG
GGCTTGAATTTGGTTCACCTAATGCACCAAACACAAATCCCCTCAAAACAAAAATTGGCCAT
GGCCTAGAATTTGATTCAAACAAGGCTATGGTTCCTAAACTAGGAACTGGCCTTAGTTTTGA
CAGCACAGGTGCCATTACAGTAGGAAACAAAAATAATGATAAGCTAACTTTGTGGACCACAC
CAGCTCCATCTCCTAACTGTAGACTAAATGCAGAGAAAGATGCTAAACTCACTTTGGTCTTA
ACAAAATGTGGCAGTCAAATACTTGCTACAGTTTCAGTTTTGGCTGTTAAAGGCAGTTTGGC
TCCAATATCTGGAACAGTTCAAAGTGCTCATCTTATTATAAGATTTGACGAAAATGGAGTGC
TACTAAACAATTCCTTCCTGGACCCAGAATATTGGAACTTTAGAAATGGAGATCTTACTGAA
GGCACAGCCTATACAAACGCTGTTGGATTTATGCCTAACCTATCAGCTTATCCAAAATCTCA
CGGTAAAACTGCCAAAAGTAACATTGTCAGTCAAGTTTACTTAAACGGAGACAAAACTAAAC
CTGTAACACTAACCATTACACTAAGCGGTACACAGGAATCCGGAGACACAACTCCAAGTGCA
TACTCTATGTCATTTTCATGGGACTGGTCTGGCCACAACTACATTAATGAAATATTTGCCAC
ATCCTCTTACACTTTTTCATACATTGCCCAAGAATAAAGAAGCGGCCGCATAACTTCGTATA
GCATACATTATACGAACGGTAGGTACCGAGCTCGAATTCACTGGCCGTCGTTTTACAACGTC
GTGACTGGGAAAACCCTGGCGTTACCCAACTTAATCGCCTTGCAGCACATCCCCCTTTCGCC
AGCTGGCGTAATAGCGAAGAGGCCCGCACCGATCGCCCTTCCCAACAGTTGCGCAGCCTGAA
TGGCGAATGGCGCCTGATGCGGTATTTTCTCCTTACGCATCTGTGCGGTATTTCACACCGCA
TATGGTGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGACAAGC
TGTGACCGTCTCCGGGAGCTGCATGTGTCAGAGGTTTTCACCGTCATCACCGAAACGCGCGA
GACGAAAGGGCCTCGTGATACGCCTATTTTTATAGGTTAATGTCATGATAATAATGGTTTCT
TAGACGTCAGGTGGCACTTTTCGGGGAAATGTGCGCGG
```

FIG. 32 (1 of 2)

```
AACCCCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCCGTGTC
GCCCTTATTCCCTTTTTTGCGGCATTTTGCCTTCCTGTTTTTGCTCACCCAGAAACGCTGGT
GAAAGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACTTTT
AAAGTTCTGCTATGTGGCGCGGTATTATCCCGTATTGACGCCGGGCAAGAGCAACTCGGTCG
CCGCATACACTATTCTCAGAATGACTTGGTTGAGTACTCACCAGTCACAGAAAAGCATCTTA
CGGATGGCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCATACCAAACG
ACGAGCGTGACACCACGATGCCTGTAGCAATGGCAACAACGTTGCGCAAACTATTAACTGGC
GAACTACTTACTCTAGCTTCCCGGCAACAATTAATAGACTGGATGGAGGCGGATAAAGTTGC
AGGACCACTTCTGCGCTCGGCCCTTCCGGCTGGCTGGTTTATTGCTGATAAATCTGGAGCCG
GTGAGCGTGGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTT
AGATTGATTTAAAACTTCATTTTTAATTTAAAAGGATCTAGGTGAAGATCCTTTTTGATAAT
CTCATGACCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAACAAAAA
AACCACCGCTACCAGCGGTGGTTTGTTTGCCGGATCAAGAGCTACCAACTCTTTTTCCGAAG
GTAACTGGCTTCAGCAGAGCGCAGATACCAAATACTGTCCTTCTAGTGTAGCCGTAGTTAGG
CCACCACTTCAAGAACTCTGTAGCACCGCCTACATACCTCGCTCTGCTAATCCTGTTACCAG
TGGCTGCTGCCAGTGGCGATAAGTCGTGTCTTACCGGGTTGGACTCAAGACGATAGTTACCG
GATAAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCACCTCTGACTTGA
GCGTCGATTTTTGTGATGCTCGTCAGGGGGCGGAGCCTATGGAAAAACGCCAGCAACGCGG
CCTTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAATACGCAAACCGC
CTCTCCCCGCGCGTTGGCCGATTCATTAATGCAGCTGGCACGACAGGTTTCCCGACTGGAAA
GCGGGCAGTGAGCGCAACGCAATTAATGTGAGTTAGCTCACTCATTAGGCACCCCAGGCTTT
ACACTTTATGCTTCCGGCTCGTATGTTGTGTGGAATTGTGAGCGGATAACAATTTCACACAG
GAAACAGCTATGACCATGATTACGCCAAGCTTGCATGCCTGCAGGTCGACACTAGTACCGTT
CGTATATGGTTTCTTATACGAAGTTATC
```

FIG. 32 (2 of 2)

RPuc-Fib (SEQ ID NO:4)

```
CCGGTTTCCGTGTCATATGGATACACGGGGTTGAAGGTATCTTCAGACGGTCTTGCGCGCTT
CATCTGCAACAACATGAAGATAGTTCTCGAGATAACTTCGTATAAGAAACCATATACGAACG
GTACTAGTGTCGACCTGCAGGCATGCAAGCTTGGCGTAATCATGGTCATAGCTGTTTCCTGT
GTGAAATTGTTATCCGCTCACAATTCCACACAACATACGAGCCGGAAGCATAAAGTGTAAAG
CCTGGGGTGCCTAATGAGTGAGCTAACTCACATTAATTGCGTTGCGCTCACTGCCCGCTTTC
CAGTCGGGAAACCTGTCGTGCCAGCTGCATTAATGAATCGGCCAACGCGCGGGGAGAGGCGG
TTTGCGTATTGGGCGCTCTTCCGCTTCCTCGCTCACTGACTCGCTGCGCTCGGTCGTTCGGC
TGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAA
GTCAGAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTA
ACTACGGCTACACTAGAAGGACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAG
CGATCTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCGCCA
GTTAATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAA
GTGCTCATCATTGGAAAACGTTCTTCGGGGCGAAAACTCTCAAGGATCTTACCGCTGTTGAG
ATCCAGTTCGATGTAACCCACTCGTGCACCCAACTGATCTTCAGCATCTTTTACTTTCACCA
GCGTTTCTGGGTGAGCAAAAACAGGAAGGCAAAATGCCGCAAAAAAGGGAATAAGGGCGACA
CGGAAATGTTGAATACTCATACTCTTCCTTTTTCAATATTATTGAAGCATTTATCAGGGTTA
TTGTCTCATGAGCGGATACATATTTGAATGTATTTAGAAAAATAAACAAATAGGGGTTCCGC
GCACATTTCCCCGAAAAGTGCCACCTGACGTCTAAGA
```

FIG. 33

```
AACCATTATTATCATGACATTAACCTATAAAAATAGGCGTATCACGAGGCCCTTTCGTCTCG
CGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGG
GTGTCGGGGCTGGCTTAACTATGCGGCATCAGAGCAGATTGTACTGAGAGTGCACCATATGC
GGTGTGAAATACCGCACAGATGCGTAAGGAGAAAATACCGCATCAGGCGCCATTCGCCATTC
AGGCTGCGCAACTGTTGGGAAGGGCGATCGGTGCGGGCCTCTTCGCTATTACGCCAGCTGGC
GAAAGGGGGATGTGCTGCAAGGCGATTAAGTTGGGTAACGCCAGGGTTTTCCCAGTCACGAC
GTTGTAAAACGACGGCCAGTGAATTCGAGCTCGGTACCTACCGTTCGTATAATGTATGCTAT
ACGAAGTTATGCGGCCGCTTCTTTATTCTTGGGCAATGTATGAAAAAGTGTAAGAGGATGTG
GCAAATATTTCATTAATGTAGTTGTGGCCAGACCAGTCCCATGAAAATGACATAGAGTATGC
ACTTGGAGTTGTGTCTCCGGATTCCTGTGTACCGTTTAGTGTAATGGTTAGTGTTACAGGTT
TAGTTTTGTCTCCGTTTAAGTAAACTTGACTGACAATGTTACTTTTGGCAGTTTTACCGTGA
GATTTTGGATAAGCTGATAGGTTAGGCATAAATCCAACAGCGTTTGTATAGGCTGTGCCTTC
AGTAAGATCTCCATTTCTAAAGTTCCAATATTCTGGGTCCAGGAAGGAATTGTTTAGTAGCA
CTCCATTTTCGTCAAATCTTATAATAAGATGAGCACTTTGAACTGTTCCAGATATTGGAGCC
AAACTGCCTTTAACAGCCAAAACTGAAACTGTAGCAAGTATTTGACTGCCACATTTTGTTAA
GACCAAAGTGAGTTTAGCATCTTTCTCTGCATTTAGTCTACAGTTAGGAGATGGAGCTGGTG
TGGTCCACAAAGTTAGCTTATCATTATTTTTGTTTCCTACTGTAATGGCACCTGTGCTGTCA
AAACTAAGGCCAGTTCCTAGTTTAGGAACCATAGCCTTGTTTGAATCAAATTCTAGGCCATG
GCCAATTTTTGTTTTGAGGGGATTTGTGTTTGGTGCATTAGGTGAACCAAATTCAAGCCCAT
CTCCTGCATTAATGGCTATGGCTGTAGCGTCAAACATCAACCCCTTGGCAGTGCTTAGGTTA
ACCTCAAGCTTTTTGGAATTGTTTGAAGCTGTAAACAAGTAAAGGCCTTTGTTGTAGTTAAT
ATCCAAGTTGTGGGCTGAGTTTATAAAAAGAGGGCCCTGTCCTAGTCTTAGATTTAGTTGGT
TTTGAGCATCAAACGGATAACTAACATCAAGTATAAGGCGTCTGTTTTGAGAATCAATCCTT
AGTCCTCCTGCTACATTAAGTTGCATATTGCCTTGTGAATCAAAACCCAAGGCTCCAGTAAC
TTTAGTTTGCAAGGAAGTATTATTAATAGTCACACCTGGACCAGTTGCTACGGTCAAAGTGT
TTAGGTCGTCTGTTACATGCAAAGGAGCCCCGTACTTTAGTCCTAGTTTTCCATTTTGTGTA
TAAATGGGCTCTTTCAAGTCAATGCCCAAGCTACCAGTGGCAGTAGTTAGAGGGGGTGAGGC
AGTGATAGTAAGGGTACTGCTATCGGTGGTGGTGAGGGGGCCTGATGTTTGCAGGGCTAGCT
TTCCTTCTGACACTGTGAGGGGTCCTTGGGTGGCAATGCTAAGTTTGGAGTCGTGCACGGTT
AGCGGGGCCTGTGATTGCATGGTGAGTGTGTTGCCCGCGACCATTAGAGGTGCGGCGGCAGC
CACAGTTAGGGCTTCTGAGGTAACTGTGAGGGGTGCAGATATTTCCAGGTTTATGTTTGACT
TGGTTTTTTTGAGAGGTGGGCTCACAGTGGTTACATTTTGGGAGGTAAGGTTGCCGGCCTCG
TCCAGAGAGAGGCCGTTGCCCATTTTGAGCGCAAGCATGCCATTGGAGGTAACTAGAGGTTC
GGATAGGCGCAAAGAGAGTACCCCAGGGGGACTCTCTTGAAACCCATTGGGGGATACAAAGG
GAGGAGTAAGAAAAGGCACAGTTGGAGGA
```

FIG. 33 (2 of 2)

RP-Blast-Fib (SEQ ID NO:5)

```
TCGAGAACTATCTTCATGTTGTTGCAGATGAAGCGCGCAAGACCGTCTGAAGATACCTTCAA
CCCCGTGTATCCATATGACACGGAAACCGGTCCTCCAACTGTGCCTTTTCTTACTCCTCCCT
TTGTATCCCCCAATGGGTTTCAAGAGAGTCCCCCTGGGGTACTCTCTTTGCGCCTATCCGAA
CCTCTAGTTACCTCCAATGGCATGCTTGCGCTCAAAATGGGCAACGGCCTCTCTCTGGACGA
GGCCGGCAACCTTACCTCCCAAAATGTAACCACTGTGAGCCCACCTCTCAAAAAAACCAAGT
CAAACATAAACCTGGAAATATCTGCACCCCTCACAGTTACCTCAGAAGCCCTAACTGTGGCT
GCCGCCGCACCTCTAATGGTCGCGGGCAACACACTCACCATGCAATCACAGGCCCCGCTAAC
CGTGCACGACTCCAAACTTAGCATTGCCACCCAAGGACCCCTCACAGTGTCAGAAGGAAAGC
TAGCCCTGCAAACATCAGGCCCCCTCACCACCACCGATAGCAGTACCCTTACTATCACTGCC
TCACCCCCTCTAACTACTGCCACTGGTAGCTTGGGCATTGACTTGAAAGAGCCCATTTATAC
ACAAAATGGAAAACTAGGACTAAAGTACGGGGCTCCTTTGCATGTAACAGACGACCTAAACA
CTTTGACCGTAGCAACTGGTCCAGGTGTGACTATTAATAATACTTCCTTGCAAACTAAAGTT
ACTGGAGCCTTGGGTTTTGATTCACAAGGCAATATGCAACTTAATGTAGCAGGAGGACTAAG
GATTGATTCTCAAAACAGACGCCTTATACTTGATGTTAGTTATCCGTTTGATGCTCAAAACC
AACTAAATCTAAGACTAGGACAGGGCCCTCTTTTTATAAACTCAGCCCACAACTTGGATATT
AACTACAACAAAGGCCTTTACTTGTTTACAGCTTCAAACAATTCCAAAAAGCTTGAGGTTAA
CCTAAGCACTGCCAAGGGGTTGATGTTTGACGCTACAGCCATAGCCATTAATGCAGGAGATG
GGCTTGAATTTGGTTCACCTAATGCACCAAACACAAATCCCCTCAAAACAAAAATTGGCCAT
GGCCTAGAATTTGATTCAAACAAGGCTATGGTTCCTAAACTAGGAACTGGCCTTAGTTTTGA
CAGCACAGGTGCCATTACAGTAGGAAACAAAAATAATGATAAGCTAACTTTGTGGACCACAC
CAGCTCCATCTCCTAACTGTAGACTAAATGCAGAGAAAGATGCTAAACTCACTTTGGTCTTA
ACAAAATGTGGCAGTCAAATACTTGCTACAGTTTCAGTTTTGGCTGTTAAAGGCAGTTTGGC
TCCAATATCTGGAACAGTTCAAAGTGCTCATCTTATTATAAGATTTGACGAAAATGGAGTGC
TACTAAACAATTCCTTCCTGGACCCAGAATATTGGAACTTTAGAAATGGAGATCTTACTGAA
GGCACAGCCTATACAAACGCTGTTGGATTTATGCCTAACCTATCAGCTTATCCAAAATCTCA
CGGTAAAACTGCCAAAAGTAACATTGTCAGTCAAGTTTACTTAAACGGAGACAAAACTAAAC
CTGTAACACTAACCATTACACTAAGCGGTACACAGGAATCCGGAGACACAACTCCAAGTGCA
TACTCTATGTCATTTTCATGGGACTGGTCTGGCCACAACTACATTAATGAAATATTTGCCAC
ATCCTCTTACACTTTTTCATACATTGCCCAAGAATAAAGAAGCGGCCGCATAACTTCGTATA
GCATACATTATACGAACGGTAGGTACCAGGTAAGTGTACCCAATTCGCCCTATAGTGAGTCG
TATTACAATTCACTGGCCGTCGTTTTACAACGCCTGATGCGGTATTTTCTCCTTACGCATCT
GTGCGGTATTTCACACCGCATATATGGTGCACTCTCAGTACAATCTGCTCTGATGCCGCATA
GTTAAGCCAGCCCCGACACCCGCCAACACCCGCTGACGCGCCCTGACGGGCTTGTCTGCTCC
CGGCATCCGCTTACAGACAAGCTGTGACCGTCTCCGGGAGCTGCATGTGTCAGAGGTTTTCA
CCGTCATCACCGAAACGCGCGAGACGAAAGGGCCTCGTGATACGCCTATTTTTATAGGTTAA
TGTCATGATAATAATGGTTTCTTAGACGTCAGGTGGCACTTTTCGGGGAAATGTGCGCGGAA
CCCCTATTTGTTTATTTTTCTAAATACATTCAAATATGTATCCGCTCATGAGACAATAACCC
TGATAAATGCTTCAATAATATTGAAAAGGAAGAGTATG
```

FIG. 34 (1 of 3)

```
AGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAACGT
TTTCCAATGATGAGCACTTTTAAAGTTCTGCTATGTGGCGCGGTATTATCCCGTATTGACGC
CGGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAGCT
AACCGCTTTTTTGCACAACATGGGGGATCATGTAACTCGCCTTGATCGTTGGGAACCGGAGC
TGAATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGACTG
GATGGAGGCGGATAAAGTTGCAGGACCACTTCTGCGCTCGGCCCTTCCGGCTGGCTGGTTTA
TTGCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGACC
AAGTTTACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTTCCACTG
AGCGTCAGACCCCGTAGAAAAGATCAAAGGATCTTCTTGAGATCCTTTTTTTTCTGCGCGTAA
TCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCCT
TCTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCATTGAG
AAAGCGCCACGCTTCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCAC
ATGCTGGGCCCAGCCGGCCAGATCTGAGCTCGCGGCCGCGATATCGCTAGCTCGAGGTCCGT
TACATAACTTACGGTAAATGGCCCGCCTGGCTGACCGCCCAACGACCCCCGCCCATTGACGT
CAATAATGACGTATGTTCCCATAGTAACGCCAATAGGGACTTTCCATTGACGTCAATGGGTG
GAGTATTTACGGTAAACTGCCCACTTGGCAGTACATCAAGTGTATCATATGCCAAGTACGCC
CCCTATTGACGTCAATGACGGTAAATGGCCCGCCTGGCATTATGCCCAGTACATGACCTTAT
GGGACTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGTCTCCA
CCCCATTGACGTCAATGGGAGTTTGTTTTGGCACCAAAATCAACGGGACTTTCCAAAATGTC
GTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCT
CCATAGAAGACACCGGGACCGATCCAGCCTCCGCGGCCGGGAACGGTGCATTGGAACGGACC
GTGTTGACAATTAATCATCGGCATAGTATATCGGCATAGTATAATACGACAAGGTGAGGAAC
TAAACCATGGCCAAGCCTTTGTC
```

```
TCAAGAAGAATCCACCCTCATTGAAAGAGCAACGGCTACAATCAACAGCATCCCCATCTCTG
AAGACTACAGCGTCGCCAGCGCAGCTCTCTCTAGCGACGGCCGCATCTTCACTGGTGTCAAT
GTATATCATTTTACTGGGGGACCTTGTGCAGAACTCGTGGTGCTGGGCACTGCTGCTGCTGC
GGCAGCTGGCAACCTGACTTGTATCGTCGCGATCGGAAATGAGAACAGGGGCATCTTGAGCC
CCTGCGGACGGTGCCGACAGGTGCTTCTCGATCTGCATCCTGGGATCAAAGCCATAGTGAAG
GACAGTGATGGACAGCCGACGGCAGTTGGGATTCGTGAATTGCTGCCCTCTGGTTATGTGTG
GGAGGGCTAAGCACTTCGTGGCCGAGGAGCAGGACTGACACTCGACCTCGAAACTTGTTTAT
TGCAGCTTATAATGGTTACAAATAAAGCAATAGCATCACAAATTTCACAAATAAAGCATTTT
TTTCACTGCATTCTAGTTGTGGTTTGTCCAAACTCATCAATGTATCTTATCATGTCTGAATT
CCCGGGGATCCTCTAGTACCGTTCGTATATGGTTTCTTATACGAAGTTATC
```

FIG. 34 (3 of 3)

pFEX (SEQ ID NO:6)

```
TAAGGATCCNNNCCTGTCCTCGACCGATGCCCTTGAGAGCCTTCAACCCAGTCAGCTCCTTC
CGGTGGGCGCGGGGCATGACTATCGTCGCCGCACTTATGACTGTCTTCTTTATCATGCAACT
CGTAGGACAGGTGCCGGCAGCGCTCTGGGTCATTTTCGGCGAGGACCGCTTTCGCTGGAGCG
CGACGATGATCGGCCTGTCGCTTGCGGTATTCGGAATCTTGCACGCCCTCGCTCAAGCCTTC
GTCACTGGTCCCGCCACCAAACGTTTCGGCGAGAAGCAGGCCATTATCGCCGGCATGGCGGC
CGACGCGCTGGGCTACGTCTTGCTGGCGTTCGCGACGCGAGGCTGGATGGCCTTCCCCATTA
TGATTCTTCTCGCTTCCGGCGGCATCGGGATGCCCGCGTTGCAGGCCATGCTGTCCAGGCAG
GTAGATGACGACCATCAGGGACAGCTTCAAGGATCGCTCGCGGCTCTTACCAGCCTAACTTC
GATCACTGGACCGCTGATCGTCACGGCGATTTATGCCGCCTCGGCGAGCACATGGAACGGGT
TGGCATGGATTGTAGGCGCCGCCCTATACCTTGTCTGCCTCCCCGCGTTGCGTCGCGGTGCA
TGGAGCCGGGCCACCTCGACCTGAATGGAAGCCGGCGGCACCTCGCTAACGGATTCACCACT
CCAAGAATTGGAGCCAATCAATTCTTGCGGAGAACTGTGAATGCGCAAACCAACCCTTGGCA
GAACATATCCATCGCGTCCGCCATCTCCAGCAGCCGCACGCGGCGCATCTCGGGCAGCGTTG
GGTCCTGGCCACGGGTGCGCATGATCGTGCTCCTGTCGTTGAGGACCCGGCTAGGCTGGCGG
GGTTGCCTTACTGGTTAGCAGAATGAATCACCGATACGCGAGCGAACGTGAAGCGACTGCTG
CTGCAAAACGTCTGCGACCTGAGCAACAACATGAATGGTCTTCGGTTTCCGTGTTTCGTAAA
GTCTGGAAACGCGGAAGTCAGCGCCCTGCACCATTATGTTCCGGATCTGCATCGCAGGATGC
TGCTGGCTACCCTGTGGAACACCTACATCTGTATTAACGAAGCGCTGGCATTGACCCTGAGT
GATTTTCTCTGGTCCCGCCGCATCCATACCGCCAGTTGTTTACCCTCACAACGTTCCAGTA
ACCGGGCATGTTCATCATCAGTAACCCGTATCGTGAGCATCCTCTCTCGTTTCATCGGTATC
ATTACCCCCATGAACAGAAATTCCCCCTTACACGGAGGCATCAAGTGACCAAACAGGAAAAA
ACCGCCCTTAACATGGCCCGCTTTATCAGAAGCCAGACATTAACGCTTCTGGAGAAACTCAA
CGAGCTGGACGCGGATGAACAGGCAGACATCTGTGAATCGCTTCACGACCACGCTGATGAGC
TTTACCGCAGCTGCCTCGCGCGTTTCGGTGATGACGGTGAAAACCTCTGACACATGCAGCTC
CCGGAGACGGTCACAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAG
TGTATACTGGCTTAACTATGCGGCATCAGAGCAGATTGTACTGAGAGTGCACCATATGCGGT
GTGAAATACCGCACAGATGCGTAAGGAGAAAATACCGCATCAGGCGCTCTTCCGCTTCCTCG
CTCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGCC
AGCAAAAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCTCAATGCTCACGC
TGTAGGTATCTCAGTTCGGTGTAGGTCGTTCGCTCCAAGCTGGGCTGTGTGCACGAACCCCC
CGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGC
GGTGCTACAGAGTTCTTGAAGTGGTGGCCT
```

FIG. 35 (1 of 14)

```
AACTACGGCTACACTAGAAGGACAGTATTTGGTATCTGCGCTCTGCTGAAGCCAGTTACCTT
CGGAAAAAGAGTTGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATT
ATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCA
GCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGG
CTCCAGATTTATCAGCAATAAACCAGCCAGCCGGAAGGGCCGAGCGCAGAAGTGGTCCTGCA
ACTTTATCCGCCTCCATCCAGTCTATTAATTGTTGCCGGGAAGCTAGAGTAAGTAGTTCGCC
AGTTAATAGTTTGCGCAACGTTGTTGCCATTGCTGCAGGCATCGTGGTGTCACGCTCGTCGT
TTGGTATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGCGA
CCGAGTTGCTCTTGCCCGGCGTCAACACGGGATAATACCGCGCCACATAGCAGAACTTTAAA
AGTGCTCATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGAC
ACGGAAATGTTGAATACTCATACTCTTCCTTTTTCAATATTATTGAAGCATTTATCAGGGTT
ATTGTCTCATGAGCGGATACATATTTGAATGTATTTAGAAAAATAAACAAATAGGGGTTCCG
CGCACATTTCCCCGAAAAGTGCCACCTGNNNGAATTCGAATCTAGTATCGATTCGAANNNCT
TAAGGGTGGGAAAGAATATATAAGGTGGGGGTCTTATGTAGTTTTGTATCTGTTTTGCAGCA
GCCGCCGCCGCCATGAGCACCAACTCGTTTGATGGAAGCATTGTGAGCTCATATTTGACAAC
GCGCATGCCCCCATGGGCCGGGGTGCGTCAGAATGTGATGGGCTCCAGCATTGATGGTCGCC
CCGTCCTGCCCGCAAACTCTACTACCTTGACCTACGAGACCGTGTCTGGAACGCCGTTGGAG
ACTGCAGCCTCCGCCGCCGCTTCAGCCGCTGCAGCCACCGCCCGCGGGATTGTGACTGACTT
TGCTTTCCTGAGCCCGCTTGCAAGCAGTGCAGCTTCCGTTCATCCGCCCGCGATGACAAGT
TGACGGCTCTTTTGGCACAATTGGATTCTTTGACCCGGGAACTTAATGTCGTTTCTCAGCAG
CTGTTGGATCTGCGCCAGCAGGTTTCTGCCCTGAAGGCTTCCTCCCCTCCCAATGCGGTTTA
AAACATAAATAAAAAACCAGACTCTGTTTGGATTTGGATCAAGCAAGTGTCTTGCTGTCTTT
ATTTAGGGGTTTTGCGCGCGCGGTAGGCCCGGGACCAGCGGTCTCGGTCGTTGAGGGTCCTG
TGTATTTTTTCCAGGACGTGGTAAAGGTGACTCTGGATGTTCAGATACATGGGCATAAGCCC
GTCTCTGGGGTGGAGGTAGCACCACTGCAGAGCTTCATGCTGCGGGGTGGTGTTGTAGATGA
TCCAGTCGTAGCAGGAGCGCTGGGCGTGGTGCCTAAAAATGTCTTTCAGTAGCAAGCTGATT
GCCAGGGGCAGGCCCTTGGTGTAAGTGTTTACAAAGCGGTTAAGCTGGGATGGGTGCATACG
TGGGGATATGAGATGCATCTTGGACTGTATTTTAGGTTGGCTATGTTCCCAGCCATATCCC
TCCGGGGATTCATGTTGTGCAGAACCACCAGCACAGTGTATCCGGTGCACTTGGGAAATTTG
TCATGTAGCTTAGAAGGAAATGCGTGGAAGAACTTGGAGACGCCCTTGTGACCTCCAAGATT
TTCCATGCATTCGTCCATAATGATGGCAATGGGCCCACGGGCGGCGGCCTGGGCGAAGATAT
TTCTGGGATCACTAACGTCATAGTT
```

```
GTGTTCCAGGATGAGATCGTCATAGGCCATTTTTACAAAGCGCGGGCGGAGGGTGCCAGACT
GCGGTATAATGGTTCCATCCGGCCCAGGGGCGTAGTTACCCTCACAGATTTGCATTTCCCAC
GCTTTGAGTTCAGATGGGGGGATCATGTCTACCTGCGGGGCGATGAAGAAAACGGTTTCCGG
GGTAGGGGAGATCAGCTGGGAAGAAAGCAGGTTCCTGAGCAGCTGCGACTTACCGCAGCCGG
TGGGCCCGTAAATCACACCTATTACCGGGTGCAACTGGTAGTTAAGAGAGCTGCAGCTGCCG
TCATCCCTGAGCAGGGGGGCCACTTCGTTAAGCATGTCCCTGACTCGCATGTTTTCCCTGAC
CAAATCCGCCAGAAGGCGCTCGCCGCCCAGCGATAGCAGTTCTTGCAAGGAAGCAAAGTTTT
TCAACGGTTTGAGACCGTCCGCCGTAGGCATGCTTTTGAGCGTTTGACCAAGCAGTTCCAGG
CGGTCCCACAGCTCGGTCACCTGCTCTACGGCATCTCGATCCAGCATATCTCCTCGTTTCGC
GGGTTGGGGCGGCTTTCGCTGTACGGCAGTAGTCGGTGCTCGTCCAGACGGGCCAGGGTCAT
GTCTTTCCACGGGCGCAGGGTCCTCGTCAGCGTAGTCTGGGTCACGGTGAAGGGGTGCGCTC
CGGGCTGCGCGCTGGCCAGGGTGCGCTTGAGGCTGGTCCTGCTGGTGCTGAAGCGCTGCCGG
TCTTCGCCCTGCGCGTCGGCCAGGTAGCATTTGACCATGGTGTCATAGTCCAGCCCCTCCGC
GGCGTGGCCCTTGGCGCGCAGCTTGCCCTTGGAGGAGGCGCCGCACGAGGGGCAGTGCAGAC
TTTTGAGGGCGTAGAGCTTGGGCGCGAGAAATACCGATTCCGGGGAGTAGGCATCCGCGCCG
CAGGCCCCGCAGACGGTCTCGCATTCCACGAGCCAGGTGAGCTCTGGCCGTTCGGGGTCAAA
AACCAGGTTTCCCCCATGCTTTTTGATGCGTTTCTTACCTCTGGTTTCCATGAGCCGGTGTC
CACGCTCGGTGACGAAAAGGCTGTCCGTGTCCCCGTATACAGACTTGAGAGGCCTGTCCTCG
AGCGGTGTTCCGCGGTCCTCCTCGTATAGAAACTCGGACCACTCTGAGACAAAGGCTCGCGT
CCAGGCCAGCACGAAGGAGGCTAAGTGGGAGGGGTAGCGGTCGTTGTCCACTAGGGGGTCCA
CTCGCTCCAGGGTGTGAAGACACATGTCGCCCTCTTCGGCATCAAGGAAGGTGATTGGTTTG
TAGGTGTAGGCCACGTGACCGGGTGTTCCTGAAGGGGGGCTATAAAAGGGGGTGGGGGCGCG
TTCGTCCTCACTCTCTTCCGCATCGCTGTCTGCGAGGGCCAGCTGTTGGGGTGAGTACTCCC
TCTGAAAAGCGGGCATGACTTCTGCGCTAAGATTGTCAGTTTCCAAAAACGAGGAGGATTTG
ATATTCACCTGGCCCGCGGTGATGCCTTTGAGGGTGGCCGCATCCATCTGGTCAGAAAAGAC
AATCTTTTTGTTGTCAAGCTTGGTGGCAAACGACCCGTAGAGGGCGTTGGACAGCAACTTGG
CGATGGAGCGCAGGGTTTGGTTTTTGTCGCGATCGGCGCGCTCCTTGGCCGCGATGTTTAGC
TGCACGTATTCGCGCGCAACGCACCGCCATTCGGGAAAGACGGTGGTGCGCTCGTCGGGCAC
CAGGTGCACGCGCCAACCGCGGTTGTGCAGGGTGACAAGGTCAACGCTGGTGGCTACCTCTC
CGCGTAGGCGCTCGTTGGTCCAGCAGAGGCGGCCGCCCTTGCGCGAGCAGAATGGCGGTAGG
GGGTCTAGCTGCGTCTCGTCCGGGGGTCTGCGTCCACGGTAAAGACCCCGGGCAGCAGGCG
CGCGTCGAAGTAGTCTATCTTGCATCCTTGCAAGTCTAGCGCCTGCTGCCATGCGCGGGCGG
CAAGCGCGCGCTCGTATGGGTTGAGTGGGGGACCCCATGGCATGGGGTGGGTGAGCGCGGAG
GCGTACATGCCGCAAATGTCGTAAACGTAGAGGGGCTCTCTGAGTATTCCAAGATATGTAGG
GTAGCATCTTCCACCGCGGATGCTGGCGCGCACGTAATCGTATAGTTCGTGCGAGGGAGCGA
GGAGGTCGGGACCGAGGTTGCTACGGGCGGCTGCTCTGCTCGGAAGACTATCTGCCTGAAG
ATGGCATGTGAGTTGGATGATATGGTTGGACGCTGGAAGACGTTGAAGCTGGCGTCTGTGAG
ACCTACCGCGTCACGCACGAAGGAGGCGTAGGAGTCGCGCAGCTTGTTGACCAGCTCGGCGG
TGACCTGCACGTCTAGGGCGCAGTAGTCCAGGGTTTCCTTGATGATGTCATACTTATCCTGT
CCCTTTTTTTTTCCACA
```

FIG. 35 (3 of 14)

```
GCTCGCGGTTGAGGACAAACTCTTCGCGGTCTTTCCAGTACTCTTGGATCGGAAACCCGTCG
GCCTCCGAACGGTAAGAGCCTAGCATGTAGAACTGGTTGACGGCCTGGTAGGCGCAGCATCC
CTTTTCTACGGGTAGCGCGTATGCCTGCGCGGCCTTCCGGAGCGAGGTGTGGGTGAGCGCAA
AGGTGTCCCTGACCATGACTTTGAGGTACTGGTATTTGAAGTCAGTGTCGTCGCATCCGCCC
TGCTCCCAGAGCAAAAAGTCCGTGCGCTTTTTGGAACGCGGATTTGGCAGGGCGAAGGTGAC
ATCGTTGAAGAGTATCTTTCCCGCGCGAGGCATAAAGTTGCGTGTGATGCGGAAGGGTCCCG
GCACCTCGGAACGGTTGTTAATTACCTGGGCGGCGAGCACGATCTCGTCAAAGCCGTTGATG
TTGTGGCCCACAATGTAAAGTTCCAAGAAGCGCGGGATGCCCTTGATGGAAGGCAATTTTTT
AAGTTCCTCGTAGGTGAGCTCTTCAGGGGAGCTGAGCCCGTGCTCTGAAAGGGCCCAGTCTG
CAAGATGAGGGTTGGAAGCGACGAATGAGCTCCACAGGTCACGGGCCATTAGCATTTGCAGG
TGGTCGCGAAAGGTCCTAAACTGGCGACCTATGGCCATTTTTTCTGGGGTGATGCAGTAGAA
GGTAAGCGGGTCTTGTTCCCAGCGGTCCCATCCAAGGTTCGCGGCTAGGTCTCGCGCGGCAG
TCACTAGAGGCTCATCTCCGCCGAACTTCATGACCAGCATGAAGGGCACGAGCTGCTTCCCA
AAGGCCCCCATCCAAGTATAGGTCTCTACATCGTAGGTGACAAAGAGACGCTCGGTGCGAGG
ATGCGAGCCGATCGGGAAGAACTGGATCTCCCGCCACCAATTGGAGGAGTGGCTATTGATGT
GGTGAAAGTAGAAGTCCCTGCGACGGGCCGAACACTCGTGCTGGCTTTTGTAAAAACGTGCG
CAGTACTGGCAGCGGTGCACGGGCTGTACATCCTGCACGAGGTTGACCTGACGACCGCGCAC
AAGGAAGCAGAGTGGGAATTTGAGCCCCTCGCCTGGCGGGTTTGGCTGGTGGTCTTCTACTT
CGGCTGCTTGTCCTTGACCGTCTGGCTGCTCGAGGGGAGTTACGGTGGATCGGACCACCACG
CCGCGCGAGCCCAAAGTCCAGATGTCCGCGCGCGGCGGTCGGAGCTTGATGACAACATCGCG
CAGATGGGAGCTGTCCATGGTCTGGAGCTCCCGCGGCGTCAGGTCAGGCGGGAGCTCCTGCA
GGTTTACCTCGCATAGACGGGTCAGGGCGCGGGCTAGATCCAGGTGATACCTAATTTCCAGG
GGCTGGTTGGTGGCGGCGTCGATGGCTTGCAAGAGGCCGCATCCCCGCGGCGCGACTACGGT
ACCGCGCGGCGGGCGGTGGGCCGCGGGGGTGTCCTTGGATGATGCATCTAAAAGCGGTGACG
CGGGCGAGCCCCCGGAGGTAGGGGGGGCTCCGGACCCGCCGGGAGAGGGGGCAGGGGCACGT
CGGCGCCGCGCGCGGGCAGGAGCTGGTGCTGCGCGCGTAGGTTGCTGGCGAACGCGACGACG
CGGCGGTTGATCTCCTGAATCTGGCGCCTCTGCGTGAAGACGACGGGCCCGGTGAGCTTGAG
CCTGAAAGAGAGTTCGACAGAATCAATTTCGGTGTCGTTGACGGCGGCCTGGCGCAAAATCT
CCTGCACGTCTCCTGAGTTGTCTTGATAGGCGATCTCGGCCATGAACTGCTCGATCTCTTCC
TCCTGGAGATCTCCGCGTCCGGCTCGCTCCACGGTGGCGGCGAGGTCGTTGGAAATGCGGGC
CATGAGCTGCGAGAAGGCGTTGAGGCCTCCCTCGTTCCAGACGCGGCTGTAGACCACGCCCC
CTTCGGCATCGCGGGCGCGCATGACCACCTGCGCGAGATTGAGCTCCACGTGCCGGGCGAAG
ACGGCGTAGTTTCGCAGGCGCTGAAAGAGGTAGTTGAGGGTGGTGGCGGTGTGTTCTGCCAC
GAAGAAGTACATAACCCAGCGTCGCAACGTGGATTCGTTGATATCCCCCAAGGCCTCAAGGC
GCTCCATGGCCTCGTAGAAGTCCACGGCGAAGTTGAAAAACTGGGAGTTGCGCGCCGACACG
GTTAACTCCTCCTCCAGAAGACGGATGAGCTCGGCGACAGTGTCGCGCACCTCGCGCTCAAA
GGCTACAGGGGCCTCTTCTTCTTCTTCAATCTCCTCTTCCATAAGGGCCTCCCCTTCTTCTT
CTTCTGGCGGCGGTGGGGAGGGGGGACACGGCGGCGACGACGGCGCACCGGGAGGCGGTCG
ACAAAGCGCTCGATCATCTCCCCGCGGCGACGGCGCATGGTCTCGGTGACGGCGCGGCCGTT
CTCGCGGGG
```

FIG. 35 (4 of 14)

```
GCGCAGTTGGAAGACGCCGCCCGTCATGTCCCGGTTATGGGTTGGCGGGGGGCTGCCATGCG
GCAGGGATACGGCGCTAACGATGCATCTCAACAATTGTTGTGTAGGTACTCCGCCGCCGAGG
GACCTGAGCGAGTCCGCATCGACCGGATCGGAAAACCTCTCGAGAAAGGCGTCTAACCAGTC
ACAGTCGCAAGGTAGGCTGAGCACCGTGGCGGGCGGCAGCGGGCGGCGGTCGGGGTTGTTTC
TGGCGGAGGTGCTGCTGATGATGTAATTAAAGTAGGCGGTCTTGAGACGGCGGATGGTCGAC
AGAAGCACCATGTCCTTGGGTCCGGCCTGCTGAATGCGCAGGCGGTCGGCCATGCCCCAGGC
TTCGTTTTGACATCGGCGCAGGTCTTTGTAGTAGTCTTGCATGAGCCTTTCTACCGGCACTT
CTTCTTCTCCTTCCTCTTGTCCTGCATCTCTTGCATCTATCGCTGCGGCGGCGGCGGAGTTT
GGCCGTAGGTGGCGCCCTCTTCCTCCCATGCGTGTGACCCCGAAGCCCCTCATCGGCTGAAG
CAGGGCTAGGTCGGCGACAACGCGCTCGGCTAATATGGCCTGCTGCACCTGCGTGAGGGTAG
ACTGGAAGTCATCCATGTCCACAAAGCGGTGGTATGCGCCCGTGTTGATGGTGTAAGTGCAG
TTGGCCATAACGGACCAGTTAACGGTCTGGTGACCCGGCTGCGAGAGCTCGGTGTACCTGAG
ACGCGAGTAAGCCCTCGAGTCAAATACGTAGTCGTTGCAAGTCCGCACCAGGTACTGGTATC
CCACCAAAAAGTGCGGCGGCGGCTGGCGGTAGAGGGCCAGCGTAGGGTGGCCGGGGCTCCG
GGGGCGAGATCTTCCAACATAAGGCGATGATATCCGTAGATGTACCTGGACATCCAGGTGAT
GCCGGCGGCGGTGGTGGAGGCGCGCGGAAAGTCGCGGACGCGGTTCCAGATGTTGCGCAGCG
GCAAAAAGTGCTCCATGGTCGGGACGCTCTGGCCGGTCAGGCGCGCGCAATCGTTGACGCTC
TACCGTGCAAAAGGAGAGCCTGTAAGCGGGCACTCTTCCGTGGTCTGGTGGATAAATTCGCA
AGGGTATCATGGCGGACGACCGGGGTTCGAGCCCCGTATCCGGCCGTCCGCCGTGATCCATG
CGGTTACCGCCCGCGTGTCGAACCCAGGTGTGCGACGTCAGACAACGGGGGAGTGCTCCTTT
TGGCTTCCTTCCAGGCGCGGCGGCTGCTGCGCTAGCTTTTTTGGCCACTGGCCGCGCGCAGC
GTAAGCGGTTAGGCTGGAAAGCGAAAGCATTAAGTGGCTCGCTCCCTGTAGCCGGAGGGTTA
TTTTCCAAGGGTTGAGTCGCGGGACCCCCGGTTCGAGTCTCGGACCGGCCGGACTGCGGCGA
ACGGGGGTTTGCCTCCCCGTCATGCAAGACCCCGCTTGCAAATTCCTCCGGAAACAGGGACG
AGCCCCTTTTTTGCTTTTCCCAGATGCATCCGGTGCTGCGGCAGATGCGCCCCCCTCCTCAG
CAGCGGCAAGAGCAAGAGCAGCGGCAGACATGCAGGGCACCCTCCCCTCCTCCTACCGCGTC
AGGAGGGGCGACATCCGCGGTTGACGCGGCAGCAGATGGTGATTACGAACCCCCGCGGCGCC
GGGCCCGGCACTACCTGGACTTGGAGGAGGGCGAGGGCCTGGCGCGGCTAGGAGCGCCCTCT
CCTGAGCGGTACCCAAGGGTGCAGCTGAAGCGTGATACGCGTGAGGCGTACGTGCCGCGGCA
GAACCTGTTTCGCGACCGCGAGGGAGAGGAGCCCGAGGAGATGCGGGATCGAAAGTTCCACG
CAGGGCGCGAGCTGCGGCATGGCCTGAATCGCGAGCGGTTGCTGCGCGAGGAGGACTTTGAG
CCCGACGCGCGAACCGGGATTAGTCCCGCGCGCGCACACGTGGCGGCCGCCGACCTGGTAAC
CGCATACGAGCAGACGGTGAACCAGGAGATTAACTTTCAAAAAAGCTTTAACAACCACGTGC
GTACGCTTGTGGCGCGCGAGGAGGTGGCTATAGGACTGATGCATCTGTGGGACTTTGTAAGC
GCGCTGGAGCAAAACCCAAATAGCAAGCCGCTCATGGCGCAGCTGTTCCTTATAGTGCAGCA
CAGCAGGGACAACGAGGCATTCAGGGATGCGCTGCTAAACATAGTAGAGCCCGAGGGCCGCT
GGCTGCTCGATTTGATAAACATCCTGCAGAGCATAGTGGTGCAGGAGCGCAGCTTGAGCCTG
GCTGACAAGGTGGCCGCCATCAACTATTCCATGCTTAGCCTGGGCAAGTTTTACGCCCGCAA
GATATACCATACCCCTTACGTTCCCATAGACAAGGAGGTAAAGATCGAGGGGTTCTACATGC
GCATGG
```

FIG. 35 (5 of 14)

```
CGCTGAAGGTGCTTACCTTGAGCGACGACCTGGGCGTTTATCGCAACGAGCGCATCCACAAG
GCCGTGAGCGTGAGCCGGCGGCGCGAGCTCAGCGACCGCGAGCTGATGCACAGCCTGCAAAG
GGCCCTGGCTGGCACGGGCAGCGGCGATAGAGAGGCCGAGTCCTACTTTGACGCGGGCGCTG
ACCTGCGCTGGGCCCCAAGCCGACGCGCCCTGGAGGCAGCTGGGGCCGGACCTGGGCTGGCG
GTGGCACCCGCGCGCGCTGGCAACGTCGGCGGCGTGGAGGAATATGACGAGGACGATGAGTA
CGAGCCAGAGGACGGCGAGTACTAAGCGGTGATGTTTCTGATCAGATGATGCAAGACGCAAC
GGACCCGGCGGTGCGGGCGGCGCTGCAGAGCCAGCCGTCCGGCCTTAACTCCACGGACGACT
GGCGCCAGGTCATGGACCGCATCATGTCGCTGACTGCGCGCAATCCTGACGCGTTCCGGCAG
CAGCCGCAGGCCAACCGGCTCTCCGCAATTCTGGAAGCGGTGGTCCCGGCGCGCGCAAACCC
CACGCACGAGAAGGTGCTGGCGATCGTAAACGCGCTGGCCGAAAACAGGGCCATCCGGCCCG
ACGAGGCCGGCCTGGTCTACGACGCGCTGCTTCAGCGCGTGGCTCGTTACAACAGCGGCAAC
GTGCAGACCAACCTGGACCGGCTGGTGGGGATGTGCGCGAGGCCGTGGCGCAGCGTGAGCG
CGCGCAGCAGCAGGGCAACCTGGGCTCCATGGTTGCACTAAACGCCTTCCTGAGTACACAGC
CCGCCAACGTGCCGCGGGGACAGGAGGACTACACCAACTTTGTGAGCGCACTGCGGCTAATG
GTGACTGAGACACCGCAAAGTGAGGTGTACCAGTCTGGGCCAGACTATTTTTTCCAGACCAG
TAGACAAGGCCTGCAGACCGTAAACCTGAGCCAGGCTTTCAAAAACTTGCAGGGGCTGTGGG
GGGTGCGGGCTCCCACAGGCGACCGCGCGACCGTGTCTAGCTTGCTGACGCCCAACTCGCGC
CTGTTGCTGCTGCTAATAGCGCCCTTCACGGACAGTGGCAGCGTGTCCCGGGACACATACCT
AGGTCACTTGCTGACACTGTACCGCGAGGCCATAGGTCAGGCGCATGTGGACGAGCATACTT
TCCAGGAGATTACAAGTGTCAGCCGCGCGCTGGGGCAGGAGGACACGGGCAGCCTGGAGGCA
ACCCTAAACTACCTGCTGACCAACCGGCGGCAGAAGATCCCCTCGTTGCACAGTTTAAACAG
CGAGGAGGAGCGCATTTTGCGCTACGTGCAGCAGAGCGTGAGCCTTAACCTGATGCGCGACG
GGGTAACGCCCAGCGTGGCGCTGGACATGACCGCGCGCAACATGGAACCGGGCATGTATGCC
TCAAACCGGCCGTTTATCAACCGCCTAATGGACTACTTGCATCGCGCGGCCGCCGTGAACCC
CGAGTATTTCACCAATGCCATCTTGAACCCGCACTGGCTACCGCCCCCTGGTTTCTACACCG
GGGGATTCGAGGTGCCCGAGGGTAACGATGGATTCCTCTGGGACGACATAGACGACAGCGTG
TTTTCCCCGCAACCGCAGACCCTGCTAGAGTTGCAACAGCGCGAGCAGGCAGAGGCGGCGCT
GCGAAAGGAAAGCTTCCGCAGGCCAAGCAGCTTGTCCGATCTAGGCGCTGCGGCCCCGCGGT
CAGATGCTAGTAGCCCATTTCCAAGCTTGATAGGGTCTCTTACCAGCACTCGCACCACCCGC
CCGCGCCTGCTGGGCGAGGAGGAGTACCTAAACAACTCGCTGCTGCAGCCGCAGCGCGAAAA
AAACCTGCCTCCGGCATTTCCCAACAACGGGATAGAGAGCCTAGTGGACAAGATGAGTAGAT
GGAAGACGTACGCGCAGGAGCACAGGGACGTGCCAGGCCCGCGCCCGCCCACCCGTCGTCAA
AGGCACGACCGTCAGCGGGGTCTGGTGTGGGAGGACGATGACTCGGCAGACGACAGCAGCGT
CCTGGATTTGGGAGGGAGTGGCAACCCGTTTGCGCACCTTCGCCCCAGGCTGGGGAGAATGT
TTTAAAAAAAAAAAAAGCATGATGCAAAATAAAAAACTCACCAAGGCCATGGCACCGAGCGTT
GGTTTTCTTGTATTCCCCTTAGTATGCGGCGCGCGGCGATGTATGAGGAAGGTCCTCCTCCC
TCCTACGAGAGTGTGGTGAGCGCGGCGCCAGTGGCGGCGGCGCTGGGTTCTCCCTTCGATGC
TCCCCTGGACCCGCCGTTTGTGCCTCCGCGGTACCTGCGGCCTACCGGGGGGAGAAACAGCA
TCCGTTACTCTGAGTTGGCACCCCTATTCGACACCACCCGTGTGTACCTGGTGGACAACAAG
TCA
```

FIG. 35

```
ACGGATGTGGCATCCCTGAACTACCAGAACGACCACAGCAACTTTCTGACCACGGTCATTCA
AAACAATGACTACAGCCCGGGGGAGGCAAGCACACAGACCATCAATCTTGACGACCGGTCGC
ACTGGGGCGGCGACCTGAAAACCATCCTGCATACCAACATGCCAAATGTGAACGAGTTCATG
TTTACCAATAAGTTTAAGGCGCGGGTGATGGTGTCGCGCTTGCCTACTAAGGACAATCAGGT
GGAGCTGAAATACGAGTGGGTGGAGTTCACGCTGCCCGAGGGCAACTACTCCGAGACCATGA
CCATAGACCTTATGAACAACGCGATCGTGGAGCACTACTTGAAAGTGGGCAGACAGAACGGG
GTTCTGGAAAGCGACATCGGGGTAAAGTTTGACACCCGCAACTTCAGACTGGGGTTTGACCC
CGTCACTGGTCTTGTCATGCCTGGGGTATATACAAACGAAGCCTTCCATCCAGACATCATTT
TGCTGCCAGGATGCGGGGTGGACTTCACCCACAGCCGCCTGAGCAACTTGTTGGGCATCCGC
AAGCGGCAACCCTTCCAGGAGGGCTTTAGGATCACCTACGATGATCTGGAGGGTGGTAACAT
TCCCGCACTGTTGGATGTGGACGCCTACCAGGCGAGCTTGAAAGATGACACCGAACAGGGCG
GGGGTGGCGCAGGCGGCAGCAACAGCAGTGGCAGCGGCGCGGAAGAGAACTCCAACGCGGCA
GCCGCGGCAATGCAGCCGGTGGAGGACATGAACGATCATGCCATTCGCGGCGACACCTTTGC
CACACGGGCTGAGGAGAAGCGCGCTGAGGCCGAAGCAGCGGCCGAAGCTGCCGCCCCCGCTG
CGCAACCCGAGGTCGAGAAGCCTCAGAAGAAACCGGTGATCAAACCCCTGACAGAGGACAGC
AAGAAACGCAGTTACAACCTAATAAGCAATGACAGCACCTTCACCCAGTACCGCAGCTGGTA
CCTTGCATACAACTACGGCGACCCTCAGACCGGAATCCGCTCATGGACCCTGCTTTGCACTC
CTGACGTAACCTGCGGCTCGGAGCAGGTCTACTGGTCGTTGCCAGACATGATGCAAGACCCC
GTGACCTTCCGCTCCACGCGCCAGATCAGCAACTTTCCGGTGGTGGGCGCCGAGCTGTTGCC
CGTGCACTCCAAGAGCTTCTACAACGACCAGGCCGTCTACTCCCAACTCATCCGCCAGTTTA
CCTCTCTGACCCACGTGTTCAATCGCTTTCCCGAGAACCAGATTTTGGCGCGCCCGCCAGCC
CCCACCATCACCACCGTCAGTGAAAACGTTCCTGCTCTCACAGATCACGGGACGCTACCGCT
GCGCAACAGCATCGGAGGAGTCCAGCGAGTGACCATTACTGACGCCAGACGCCGCACCTGCC
CCTACGTTTACAAGGCCCTGGGCATAGTCTCGCCGCGCGTCCTATCGAGCCGCACTTTTTGA
GCAAGCATGTCCATCCTTATATCGCCCAGCAATAACACAGGCTGGGGCCTGCGCTTCCCAAG
CAAGATGTTTGGCGGGGCCAAGAAGCGCTCCGACCAACACCCAGTGCGCGTGCGCGGGCACT
ACCGCGCGCCCTGGGGCGCGCACAAACGCGGCCGCACTGGGCGCACCACCGTCGATGACGCC
ATCGACGCGGTGGTGGAGGAGGCGCGCAACTACACGCCCACGCCGCCACCAGTGTCCACAGT
GGACGCGGCCATTCAGACCGTGGTGCGCGGAGCCCGGCGCTATGCTAAAATGAAGAGACGGC
GGAGGCGCGTAGCACGTCGCCACCGCCGCCGACCCGGCACTGCCGCCCAACGCGCGGCGGCG
GCCCTGCTTAACCGCGCACGTCGCACCGGCCGACGGGCGGCCATGCGGGCCGCTCGAAGGCT
GGCCGCGGGTATTGTCACTGTGCCCCCCAGGTCCAGGCGACGAGCGGCCGCCGCAGCAGCCG
CGGCCATTAGTGCTATGACTCAGGGTCGCAGGGGCAACGTGTATTGGGTGCGCGACTCGGTT
AGCGGCCTGCGCGTGCCCGTGCGCACCCGCCCCCGCGCAACTAGATTGCAAGAAAAAACTA
CTTAGACTCGTACTGTTGTATGTATCCAGCGGCGGCGGCGCGCAACGAAGCTATGTCCAAGC
GCAAAATCAAAGAAGAGATGCTCCAGGTCATCGCGCCGGAGATCTATGGCCCCCCGAAGAAG
GAAGAGCAGGATTACAAGCCCCGAAAGCTAAAGCGGGTCAAAAAGAAAAAGAAAGATGATGA
TGATGAACTTGACGACGAGGTGGAACTGCTGCACGCTACCGCGCCCAGGCGACGGGTACAGT
GGAAAGGTCGACGCGTAAAACGTGTTTTGCGACCCGGCACCACCGTAGTCTTTACGCCCGGT
GAGC
```

```
GCTCCACCCGCACCTACAAGCGCGTGTATGATGAGGTGTACGGCGACGAGGACCTGCTTGAG
CAGGCCAACGAGCGCCTCGGGGAGTTTGCCTACGGAAAGCGGCATAAGGACATGCTGGCGTT
GCCGCTGGACGAGGGCAACCCAACACCTAGCCTAAAGCCCGTAACACTGCAGCAGGTGCTGC
CCGCGCTTGCACCGTCCGAAGAAAAGCGCGGCCTAAAGCGCGAGTCTGGTGACTTGGCACCC
ACCGTGCAGCTGATGGTACCCAAGCGCCAGCGACTGGAAGATGTCTTGGAAAAAATGACCGT
GGAACCTGGGCTGGAGCCCGAGGTCCGCGTGCGGCCAATCAAGCAGGTGGCGCCGGGACTGG
GCGTGCAGACCGTGGACGTTCAGATACCCACTACCAGTAGCACCAGTATTGCCACCGCCACA
GAGGGCATGGAGACACAAACGTCCCCGGTTGCCTCAGCGGTGGCGGATGCCGCGGTGCAGGC
GGTCGCTGCGGCCGCGTCCAAGACCTCTACGGAGGTGCAAACGGACCCGTGGATGTTTCGCG
TTTCAGCCCCCGGCGCCCGCGCGGTTCGAGGAAGTACGGCGCCGCCAGCGCGCTACTGCCC
GAATATGCCCTACATCCTTCCATTGCGCCTACCCCGGCTATCGTGGCTACACCTACCGCCC
CAGAAGACGAGCAACTACCCGACGCCGAACCACCACTGGAACCCGCCGCCGCCGTCGCCGTC
GCCAGCCCGTGCTGGCCCCGATTTCCGTGCGCAGGGTGGCTCGCGAAGGAGGCAGGACCCTG
GTGCTGCCAACAGCGCGCTACCACCCCAGCATCGTTTAAAAGCCGGTCTTTGTGGTTCTTGC
AGATATGGCCCTCACCTGCCGCCTCCGTTTCCCGGTGCCGGGATTCCGAGGAAGAATGCACC
GTAGGAGGGGCATGGCCGGCCACGGCCTGACGGGCGGCATGCGTCGTGCGCACCACCGGCGG
CGGCGCGCGTCGCACCGTCGCATGCGCGGCGGTATCCTGCCCCTCCTTATTCCACTGATCGC
CGCGGCGATTGGCGCCGTGCCCGGAATTGCATCCGTGGCCTTGCAGGCGCAGAGACACTGAT
TAAAAACAAGTTGCATGTGGAAAAATCAAAATAAAAAGTCTGGACTCTCACGCTCGCTTGGT
CCTGTAACTATTTTGTAGAATGGAAGACATCAACTTTGCGTCTCTGGCCCCGCGACACGGCT
CGCGCCCGTTCATGGGAAACTGGCAAGATATCGGCACCAGCAATATGAGCGGTGGCGCCTTC
AGCTGGGGCTCGCTGTGGAGCGGCATTAAAAATTTCGGTTCCACCGTTAAGAACTATGGCAG
CAAGGCCTGGAACAGCAGCACAGGCCAGATGCTGAGGGATAAGTTGAAAGAGCAAAATTTCC
AACAAAAGGTGGTAGATGGCCTGGCCTCTGGCATTAGCGGGGTGGTGGACCTGGCCAACCAG
GCAGTGCAAAATAAGATTAACAGTAAGCTTGATCCCCGCCCTCCCGTAGAGGAGCCTCCACC
GGCCGTGGAGACAGTGTCTCCAGAGGGGCGTGGCGAAAAGCGTCCGCGCCCCGACAGGGAAG
AAACTCTGGTGACGCAAATAGACGAGCCTCCCTCGTACGAGGAGGCACTAAAGCAAGGCCTG
CCCACCACCCGTCCCATCGCGCCCATGGCTACCGGAGTGCTGGGCCAGCACACACCCGTAAC
GCTGGACCTGCCTCCCCCCGCCGACACCCAGCAGAAACCTGTGCTGCCAGGCCCGACCGCCG
TTGTTGTAACCCGTCCTAGCCGCGCGTCCCTGCGCCGCGCCGCCAGCGGTCCGCGATCGTTG
CGGCCCGTAGCCAGTGGCAACTGGCAAAGCACACTGAACAGCATCGTGGGTCTGGGGGTGCA
ATCCCTGAAGCGCCGACGATGCTTCTGAATAGCTAACGTGTCGTATGTGTGTCATGTATGCG
TCCATGTCGCCGCCAGAGGAGCTGCTGAGCCGCCGCGCGCCCGCTTTCCAAGATGGCTACCC
CTTCGATGATGCCGCAGTGGTCTTACATGCACATCTCGGGCCAGGACGCCTCGGAGTACCTG
AGCCCCGGGCTGGTGCAGTTTGCCCGCGCCACCGAGACGTACTTCAGCCTGAATAACAAGTT
TAGAAACCCCACGGTGGCGCCTACGCACGACGTGACCACAGACCGGTCCCAGCGTTTGACGC
TGCGGTTCATCCCTGTGGACCGTGAGGATACTGCGTACTCGTACAAGGCGCGGTTCACCCTA
GCTGTGGGTGATAACCGTGTGCTGGACATGGCTTCCACGTACTTTGACATCCGCGGCGTGCT
GGACAGGGGCCCTACTTTTAAGCCCTACTCTGGCACTGCCTACAACGCCCTGGCTCCCAAGG
GTGCCCCAA
```

FIG. 35

```
ATCCTTGCGAATGGGATGAAGCTGCTACTGCTCTTGAAATAAACCTAGAAGAAGAGGACGAT
GACAACGAAGACGAAGTAGACGAGCAAGCTGAGCAGCAAAAAACTCACGTATTTGGGCAGGC
GCCTTATTCTGGTATAAATATTACAAAGGAGGGTATTCAAATAGGTGTCGAAGGTCAAACAC
CTAAATATGCCGATAAAACATTTCAACCTGAACCTCAAATAGGAGAATCTCAGTGGTACGAA
ACTGAAATTAATCATGCAGCTGGGAGAGTCCTTAAAAAGACTACCCCAATGAAACCATGTTA
CGGTTCATATGCAAAACCCACAAATGAAAATGGAGGGCAAGGCATTCTTGTAAAGCAACAAA
ATGGAAAGCTAGAAAGTCAAGTGGAAATGCAATTTTTCTCAACTACTGAGGCGACCGCAGGC
AATGGTGATAACTTGACTCCTAAAGTGGTATTGTACAGTGAAGATGTAGATATAGAAACCCC
AGACACTCATATTTCTTACATGCCCACTATTAAGGAAGGTAACTCACGAGAACTAATGGGCC
AACAATCTATGCCCAACAGGCCTAATTACATTGCTTTTAGGGACAATTTTATTGGTCTAATG
TATTACAACAGCACGGGTAATATGGGTGTTCTGGCGGGCCAAGCATCGCAGTTGAATGCTGT
TGTAGATTTGCAAGACAGAAACACAGAGCTTTCATACCAGCTTTTGCTTGATTCCATTGGTG
ATAGAACCAGGTACTTTTCTATGTGGAATCAGGCTGTTGACAGCTATGATCCAGATGTTAGA
ATTATTGAAAATCATGGAACTGAAGATGAACTTCCAAATTACTGCTTTCCACTGGGAGGTGT
GATTAATACAGAGACTCTTACCAAGGTAAAACCTAAAACAGGTCAGGAAAATGGATGGGAAA
AAGATGCTACAGAATTTTCAGATAAAAATGAAATAAGAGTTGGAAATAATTTTGCCATGGAA
ATCAATCTAAATGCCAACCTGTGGAGAAATTTCCTGTACTCCAACATAGCGCTGTATTTGCC
CGACAAGCTAAAGTACAGTCCTTCCAACGTAAAAATTTCTGATAACCCAAACACCTACGACT
ACATGAACAAGCGAGTGGTGGCTCCCGGGTTAGTGGACTGCTACATTAACCTTGGAGCACGC
TGGTCCCTTGACTATATGGACAACGTCAACCCATTTAACCACCACCGCAATGCTGGCCTGCG
CTACCGCTCAATGTTGCTGGGCAATGGTCGCTATGTGCCCTTCCACATCCAGGTGCCTCAGA
AGTTCTTTGCCATTAAAAACCTCCTTCTCCTGCCGGGCTCATACACCTACGAGTGGAACTTC
AGGAAGGATGTTAACATGGTTCTGCAGAGCTCCCTAGGAAATGACCTAAGGGTTGACGGAGC
CAGCATTAAGTTTGATAGCATTTGCCTTTACGCCACCTTCTTCCCCATGGCCCACAACACCG
CCTCCACGCTTGAGGCCATGCTTAGAAACGACACCAACGACCAGTCCTTTAACGACTATCTC
TCCGCCGCCAACATGCTCTACCCTATACCCGCCAACGCTACCAACGTGCCCATATCCATCCC
CTCCCGCAACTGGGCGGCTTTCCGCGGCTGGGCCTTCACGCGCCTTAAGACTAAGGAAACCC
CATCACTGGGCTCGGGCTACGACCCTTATTACACCTACTCTGGCTCTATACCCTACCTAGAT
GGAACCTTTTACCTCAACCACACCTTTAAGAAGGTGGCCATTACCTTTGACTCTTCTGTCAG
CTGGCCTGGCAATGACCGCCTGCTTACCCCCAACGAGTTTGAAATTAAGCGCTCAGTTGACG
GGGAGGGTTACAACGTTGCCCAGTGTAACATGACCAAAGACTGGTTCCTGGTACAAATGCTA
GCTAACTACAACATTGGCTACCAGGGCTTCTATATCCCAGAGAGCTACAAGGACCGCATGTA
CTCCTTCTTTAGAAACTTCCAGCCCATGAGCCGTCAGGTGGTGGATGATACTAAATACAAGG
ACTACCAACAGGTGGGCATCCTACACCAACACAACAACTCTGGATTTGTTGGCTACCTTGCC
CCCACCATGCGCGAAGGACAGGCCTACCCTGCTAACTTCCCCTATCCGCTTATAGGCAAGAC
CGCAGTTGACAGCATTACCCAGAAAAAGTTTCTTTGCGATCGCACCCTTTGGCGCATCCCAT
TCTCCAGTAACTTTATGTCCATGGGCGCACTCACAGACCTGGGCCAAAACCTTCTCTACGCC
AACTCCGCCCACGCGCTAGACATGACTTTTGAGGTGGATCCCATGGACGAGCCCACCCTTCT
TTATGTTTTGTTTGAAGTCTTTGACG
```

```
TGGTCCGTGTGCACCGGCCGCACCGCGGCGTCATCGAAACCGTGTACCTGCGCACGCCCTTC
TCGGCCGGCAACGCCACAACATAAAGAAGCAAGCAACATCAACAACAGCTGCCGCCATGGGC
TCCAGTGAGCAGGAACTGAAAGCCATTGTCAAAGATCTTGGTTGTGGGCCATATTTTTTGGG
CACCTATGACAAGCGCTTTCCAGGCTTTGTTTCTCCACACAAGCTCGCCTGCGCCATAGTCA
ATACGGCCGGTCGCGAGACTGGGGGCGTACACTGGATGGCCTTTGCCTGGAACCCGCACTCA
AAAACATGCTACCTCTTTGAGCCCTTTGGCTTTTCTGACCAGCGACTCAAGCAGGTTTACCA
GTTTGAGTACGAGTCACTCCTGCGCCGTAGCGCCATTGCTTCTTCCCCGACCGCTGTATAA
CGCTGGAAAAGTCCACCCAAAGCGTACAGGGGCCCAACTCGGCCGCCTGTGGACTATTCTGC
TGCATGTTTCTCCACGCCTTTGCCAACTGGCCCCAAACTCCCATGGATCACAACCCCACCAT
GAACCTTATTACCGGGGTACCCAACTCCATGCTCAACAGTCCCCAGGTACAGCCCACCCTGC
GTCGCAACCAGGAACAGCTCTACAGCTTCCTGGAGCGCCACTCGCCCTACTTCCGCAGCCAC
AGTGCGCAGATTAGGAGCGCCACTTCTTTTTGTCACTTGAAAAACATGTAAAAATAATGTAC
TAGAGACACTTTCAATAAAGGCAAATGCTTTTATTTGTACACTCTCGGGTGATTATTTACCC
CCACCCTTGCCGTCTGCGCCGTTTAAAAATCAAAGGGGTTCTGCCGCGCATCGCTATGCGCC
ACTGGCAGGGACACGTTGCGATACTGGTGTTTAGTGCTCCACTTAAACTCAGGCACAACCAT
CCGCGGCAGCTCGGTGAAGTTTTCACTCCACAGGCTGCGCACCATCACCAACGCGTTTAGCA
GGTCGGGCGCCGATATCTTGAAGTCGCAGTTGGGGCCTCCGCCCTGCGCGCGCGAGTTGCGA
TACACAGGGTTGCAGCACTGGAACACTATCAGCGCCGGGTGGTGCACGCTGGCCAGCACGCT
CTTGTCGGAGATCAGATCCGCGTCCAGGTCCTCCGCGTTGCTCAGGGCGAACGGAGTCAACT
TTGGTAGCTGCCTTCCCAAAAAGGGCGCGTGCCCAGGCTTTGAGTTGCACTCGCACCGTAGT
GGCATCAAAAGGTGACCGTGCCCGGTCTGGGCGTTAGGATACAGCGCCTGCATAAAAGCCTT
GATCTGCTTAAAAGCCACCTGAGCCTTTGCGCCTTCAGAGAAGAACATGCCGCAAGACTTGC
CGGAAAACTGATTGGCCGGACAGGCCGCGTCGTGCACGCAGCACCTTGCGTCGGTGTTGGAG
ATCTGCACCACATTTCGGCCCCACCGGTTCTTCACGATCTTGGCCTTGCTAGACTGCTCCTT
CAGCGCGCGCTGCCCGTTTTCGCTCGTCACATCCATTTCAATCACGTGCTCCTTATTTATCA
TAATGCTTCCGTGTAGACACTTAAGCTCGCCTTCGATCTCAGCGCAGCGGTGCAGCCACAAC
GCGCAGCCCGTGGGCTCGTGATGCTTGTAGGTCACCTCTGCAAACGACTGCAGGTACGCCTG
CAGGAATCGCCCCATCATCGTCACAAAGGTCTTGTTGCTGGTGAAGGTCAGCTGCAACCCGC
GGTGCTCCTCGTTCAGCCAGGTCTTGCATACGGCCGCCAGAGCTTCCACTTGGTCAGGCAGT
AGTTTGAAGTTCGCCTTTAGATCGTTATCCACGTGGTACTTGTCCATCAGCGCGCGCGCAGC
CTCCATGCCCTTCTCCCACGCAGACACGATCGGCACACTCAGCGGGTTCATCACCGTAATTT
CACTTTCCGCTTCGCTGGGCTCTTCCTCTTCCTCTTGCGTCCGCATACCACGCGCCACTGGG
TCGTCTTCATTCAGCCGCCGCACTGTGCGCTTACCTCCTTTGCCATGCTTGATTAGCACCGG
TGGGTTGCTGAAACCCACCATTTGTAGCGCCACATCTTCTCTTTCTTCCTCGCTGTCCACGA
TTACCTCTGGTGATGGCGGGCGCTCGGGCTTGGGAGAAGGGCGCTTCTTTTTCTTCTTGGGC
GCAATGGCCAAATCCGCCGCCGAGGTCGATGGCCGCGGGCTGGGTGTGCGCGGCACCAGCGC
GTCTTGTGATGAGTCTTCCTCGTCCTCGGACTCGATACGCCGCCTCATCCGCTTTTTTGGGG
GCGCCCGGGGAGGCGGCGGCGACGGGGACGGGACGACACGTCCTCCATGGTTGGGGGACGT
CGCGCCGCACCGCGTCCGCGCTCGGGGTGGTTTCGCGCTGCTCCTCTTCCCGACTGGCCAT
TTCCTTCTCCTATAGGCAGAAAAAGATCATGGAGTCAGTCGAGAAGAAGGACAGCCTAACCG
CCCCCTCTGAGTTCGCCACCACC
```

FIG. 35 (10 of 14)

```
GCCTCCACCGATGCCGCCAACGCGCCTACCACCTTCCCCGTCGAGGCACCCCCGCTTGAGGA
GGAGGAAGTGATTATCGAGCAGGACCCAGGTTTTGTAAGCGAAGACGACGAGGACCGCTCAG
TACCAACAGAGGATAAAAAGCAAGACCAGGACAACGCAGAGGCAAACGAGGAACAAGTCGGG
CGGGGGGACGAAAGGCATGGCGACTACCTAGATGTGGGAGACGACGTGCTGTTGAAGCATCT
GCAGCGCCAGTGCGCCATTATCTGCGACGCGTTGCAAGAGCGCAGCGATGTGCCCCTCGCCA
TAGCGGATGTCAGCCTTGCCTACGAACGCCACCTATTCTCACCGCGCGTACCCCCCAAACGC
CAAGAAAACGGCACATGCGAGCCCAACCCGCGCCTCAACTTCTACCCCGTATTTGCCGTGCC
AGAGGTGCTTGCCACCTATCACATCTTTTTCCAAAACTGCAAGATACCCCTATCCTGCCGTG
CCAACCGCAGCCGAGCGGACAAGCAGCTGGCCTTGCGGCAGGGCGCTGTCATACCTGATATC
GCCTCGCTCAACGAAGTGCCAAAAATCTTTGAGGGTCTTGGACGCGACGAGAAGCGCGCGGC
AAACGCTCTGCAACAGGAAAACAGCGAAAATGAAAGTCACTCTGGAGTGTTGGTGGAACTCG
AGGGTGACAACGCGCGCCTAGCCGTACTAAAACGCAGCATCGAGGTCACCCACTTTGCCTAC
CCGGCACTTAACCTACCCCCCAAGGTCATGAGCACAGTCATGAGTGAGCTGATCGTGCGCCG
TGCGCAGCCCCTGGAGAGGGATGCAAATTTGCAAGAACAAACAGAGGAGGGCCTACCCGCAG
TTGGCGACGAGCAGCTAGCGCGCTGGCTTCAAACGCGCGAGCCTGCCGACTTGGAGGAGCGA
CGCAAACTAATGATGGCCGCAGTGCTCGTTACCGTGGAGCTTGAGTGCATGCAGCGGTTCTT
TGCTGACCCGGAGATGCAGCGCAAGCTAGAGGAAACATTGCACTACACCTTTCGACAGGGCT
ACGTACGCCAGGCCTGCAAGATCTCCAACGTGGAGCTCTGCAACCTGGTCTCCTACCTTGGA
ATTTTGCACGAAAACCGCCTTGGGCAAAACGTGCTTCATTCCACGCTCAAGGGCGAGGCGCG
CCGCGACTACGTCCGCGACTGCGTTTACTTATTTCTATGCTACACCTGGCAGACGGCCATGG
GCGTTTGGCAGCAGTGCTTGGAGGAGTGCAACCTCAAGGAGCTGCAGAAACTGCTAAAGCAA
AACTTGAAGGACCTATGGACGGCCTTCAACGAGCGCTCCGTGGCCGCGCACCTGGCGGACAT
CATTTTCCCCGAACGCCTGCTTAAAACCCTGCAACAGGGTCTGCCAGACTTCACCAGTCAAA
GCATGTTGCAGAACTTTAGGAACTTTATCCTAGAGCGCTCAGGAATCTTGCCCGCCACCTGC
TGTGCACTTCCTAGCGACTTTGTGCCCATTAAGTACCGCGAATGCCCTCCGCCGCTTTGGGG
CCACTGCTACCTTCTGCAGCTAGCCAACTACCTTGCCTACCACTCTGACATAATGGAAGACG
TGAGCGGTGACGGTCTACTGGAGTGTCACTGTCGCTGCAACCTATGCACCCCGCACCGCTCC
CTGGTTTGCAATTCGCAGCTGCTTAACGAAAGTCAAATTATCGGTACCTTTGAGCTGCAGGG
TCCCTCGCCTGACGAAAAGTCCGCGGCTCCGGGGTTGAAACTCACTCCGGGGCTGTGGACGT
CGGCTTACCTTCGCAAATTTGTACCTGAGGACTACCACGCCCACGAGATTAGGTTCTACGAA
GACCAATCCCGCCCGCCAAATGCGGAGCTTACCGCCTGCGTCATTACCCAGGGCCACATTCT
TGGCCAATTGCAAGCCATCAACAAAGCCCGCCAAGAGTTTCTGCTACGAAAGGGACGGGGGG
TTTACTTGGACCCCCAGTCCGGCGAGGAGCTCAACCCAATCCCCCCGCCGCCGCAGCCCTAT
CAGCAGCAGCCGCGGGCCCTTGCTTCCCAGGATGGCACCCAAAAAGAAGCTGCAGCTGCCGC
CGCCACCCACGGACGAGGAGGAATACTGGGACAGTCAGGCAGAGGAGGTTTTGGACGAGGAG
GAGGAGGACATGATGGAAGACTGGGAGAGCCTAGACGAGGAAGCTTCCGAGGTCGAAGAGGT
GTCAGACGAAACACCGTCACCCTCGGTCGCATTCCCCTCGCCGGCGCCCCAGAAATCGGCAA
CCGGTTCCAGCATGGCTACAACCTCCGCTCCTCAGGCGCCGCCGGCACTGCCCGTTCGCCGA
CCCAACCGTAGATGGGACACCACTGGAACCAGGGCCGGTAAGTCCAAGCAGCCGCCGCCGTT
AGCCCAA
```

```
GAGCAACAACAGCGCCAAGGCTACCGCTCATGGCGCGGGCACAAGAACGCCATAGTTGCTTG
CTTGCAAGACTGTGGGGGCAACATCTCCTTCGCCCGCCGCTTTCTTCTCTACCATCACGGCG
TGGCCTTCCCCCGTAACATCCTGCATTACTACCGTCATCTCTACAGCCCATACTGCACCGGC
GGCAGCGGCAGCGGCAGCAACAGCAGCGGCCACACAGAAGCAAAGGCGACCGGATAGCAAGA
CTCTGACAAAGCCCAAGAAATCCACAGCGGCGGCAGCAGCAGGAGGAGGAGCGCTGCGTCTG
GCGCCCAACGAACCCGTATCGACCCGCGAGCTTAGAAACAGGATTTTTCCCACTCTGTATGC
TATATTTCAACAGAGCAGGGGCCAAGAACAAGAGCTGAAAATAAAAAACAGGTCTCTGCGAT
CCCTCACCCGCAGCTGCCTGTATCACAAAAGCGAAGATCAGCTTCGGCGCACGCTGGAAGAC
GCGGAGGCTCTCTTCAGTAAATACTGCGCGCTGACTCTTAAGGACTAGTTTCGCGCCCTTTC
TCAAATTTAAGCGCGAAAACTACGTCATCTCCAGCGGCCACACCCGGCGCCAGCACCTGTCG
TCAGCGCCATTATGAGCAAGGAAATTCCCACGCCCTACATGTGGAGTTACCAGCCACAAATG
GGACTTGCGGCTGGAGCTGCCCAAGACTACTCAACCCGAATAAACTACATGAGCGCGGGACC
CCACATGATATCCCGGGTCAACGGAATCCGCGCCCACCGAAACCGAATTCTCTTGGAACAGG
CGGCTATTACCACCACACCTCGTAATAACCTTAATCCCCGTAGTTGGCCCGCTGCCCTGGTG
TACCAGGAAAGTCCCGCTCCCACCACTGTGGTACTTCCCAGAGACGCCCAGGCCGAAGTTCA
GATGACTAACTCAGGGGCGCAGCTTGCGGGCGGCTTTCGTCACAGGGTGCGGTCGCCCGGGC
AGGGTATAACTCACCTGACAATCAGAGGGCGAGGTATTCAGCTCAACGACGAGTCGGTGAGC
TCCTCGCTTGGTCTCCGTCCGGACGGGACATTTCAGATCGGCGGCGCCGGCCGTCCTTCATT
CACGCCTCGTCAGGCAATCCTAACTCTGCAGACCTCGTCCTCTGAGCCGCGCTCTGGAGGCA
TTGGAACTCTGCAATTTATTGAGGAGTTTGTGCCATCGGTCTACTTTAACCCCTTCTCGGGA
CCTCCCGGCCACTATCCGGATCAATTTATTCCTAACTTTGACGCGGTAAAGGACTCGGCGGA
CGGCTACGACTGAATGTTAAGTGGAGAGGCAGAGCAACTGCGCCTGAAACACCTGGTCCACT
GTCGCCGCCACAAGTGCTTTGCCCGCGACTCCGGTGAGTTTTGCTACTTTGAATTGCCCGAG
GATCATATCGAGGGCCCGGCGCACGGCGTCCGGCTTACCGCCCAGGGAGAGCTTGCCCGTAG
CCTGATTCGGGAGTTTACCCAGCGCCCCCTGCTAGTTGAGCGGGACAGGGGACCCTGTGTTC
TCACTGTGATTTGCAACTGTCCTAACCTTGGATTACATCAAGATCCTCTAGTTATAACTAGA
GTACCCGGGGATCTTATTCCCTTTAACTAATAAAAAAAAATAATAAAGCATCACTTACTTAA
AATCAGTTAGCAAATTTCTGTCCAGTTTATTCAGCAGCACCTCCTTGCCCTCCTCCCAGCTC
TGGTATTGCAGCTTCCTCCTGGCTGCAAACTTTCTCCACAATCTAAATGGAATGTCAGTTTC
CTCCTGTTCCTGTCCATCCGCACCCACCGGTATAACTTCGTATATGGTTTCTTATACGAACG
GTAGATCTATATCTATGATCTCGCAGTCTCCGGCGAGCACCGGAGGCAGGGCATTGCCACCG
CGCTCATCAATCTCCTCAAGCATGAGGCCAACGCGCTTGGTGCTTATGTGATCTACGTGCAA
GCAGATTACGGTGACGATCCCGCAGTGGCTCTCTATACAAAGTTGGGCATACGGGAAGAAGT
GATGCACTTTGATATCGACCCAAGTACCGCCACCTAACAATTCGTTCAAGCCGAGATCGGCT
TCCCGGCCGCGGAGTTGTTCGGTAAATTGTCACAACGCCGCGGCCATCGGCATTTTCTTTTG
CGTTTTTATTTGTTAACTGTTAATTGTCCTTGTTCAAGGATGCTGTCTTTGACAACAGATGT
TTTCTTGCCTTTGATGTTCAGCAGGAAGCTTGGCGCAAACGTTGATTGTTTGTCTGCGTAGA
ATCCTCTGTTTGTCATATAGCTTGTAATCACCACGACATTGTTTCCTTTCGCTTGAGGTACA
GCGAAGTGTGAGTAAGTAAAGGTTACATCGTTAGGATCAAGATCCATTTTTAACACAAGGCC
AGTTTTGTTCAGCGGCTTGTATGGGCC
```

FIG. 35 (12 of 14)

```
AGTTAAAGAATTAGAAACATAACCAAGCATGTAAATATCGTTAGACGAAATGCCGTCAATCG
TCATTTTTGATCCGCGGGAGTCAGTGAACAGGTACCATTTGCCGTTCATTTTAAAGACGTTC
GCGCGTTCAATTTCATCTGTTACTGTGTTAGATGCAATCAGCGGTTTCATCACTTTTTTCAG
TGTGTAATCATCGTTTAGCTCAATCATACCGAGAGCGCCGTTTGCTAACTCAGCCGTGCGTT
TTTTATCGCTTTGCAGAAGTTTTTGACTTTCTTGACGGAAGAATGATGTGCTTTTGCCATAG
TATGCTTTGTTAAATAAAGATTCTTCGCCTTGGTAGCCATCTTCAGTTCCAGTGTTTGCTTC
AAATACTAAGTATTTGTGGCCTTTATCTTCTACGTAGTGAGGATCTCTCAGCGTATGGTTGT
CGCCTGAGCTGTAGTTGCCTTCATCGATGAACTGCTGTACATTTTGATACGTTTTTCCGTCA
CCGTCAAAGATTGATTTATAATCCTCTACACCGTTGATGTTCAAAGAGCTGTCTGATGCTGA
TACGTTAACTTGTGCAGTTGTCAGTGTTTGTTTGCCGTAATGTTTACCGGAGAAATCAGTGT
AGAATAAACGGATTTTTCCGTCAGATGTAAATGTGGCTGAACCTGACCATTCTTGTGTTTGG
TCTTTTAGGATAGAATCATTTGCATCGAATTTGTCGCTGTCTTTAAAGACGCGGCCAGCGTT
TTTCCAGCTGTCAATAGAAGTTTCGCCGACTTTTTGATAGAACATGTAAATCGATGTGTCAT
CCGCATTTTTAGGATCTCCGGCTAATGCAAAGACGATGTGGTAGCCGCGATAGTTTGCGACA
GTGCCGTCAGCGTTTTGTAATGGCCAGCTGTCCCAAACGTCCAGGCCTTTTGCAGAAGAGAT
ATTTTTAATTGTGGACGAATCGAATTCAGGAACTTGATATTTTTCATTTTTTTGCTGTTCAG
GGATTTGCAGCATATCATGGCGTGTAATATGGGAAATGCCGTATGTTTCCTTATATGGCTTT
TGGTTCGTTTCTTTCGCAAACGCTTGAGTTGCGCCTCCTGCCAGCAGTGCGGTAGTAAAGGT
TAATACTGTTGCTTGTTTTGCAAACTTTTTGATGTTCATCGTTCATGTCTCCTTTTTTATGT
ACTGTGTTAGCGGTCTGCTTCTTCCAGCCCTCCTGTTTGAAGATGGCAAGTTAGTTACGCAC
AATAAAAAAAGACCTAAAATATGTAAGGGGTGACGCCAAAGTATACACTTTGCCCTTTACAC
ATTTTAGGTCTTGCCTGCTTTATCAGTAACAAACCCGCGCGATTTACTTTTCGACCTCATTC
TATTAGACTCTCGTTTGGATTGCAACTGGTCTATTTTCCTCTTTTGTTTGATAGAAAATCAT
AAAAGGATTTGCAGACTACGGGCCTAAAGAACTAAAAAATCTATCTGTTTCTTTTCATTCTC
TGTATTTTTTATAGTTTCTGTTGCATGGGCATAAAGTTGCCTTTTTAATCACAATTCAGAAA
ATATCATAATATCTCATTTCACTAAATAATAGTGAACGGCAGGTATATGTGATGGGTTAAAA
AGGATCGATCCTCTAGCTAGAGTCGATCGTACCGTTCGTATAGCATACATTATACGAAGTTA
TACCGGTATACATTGCCCAAGAATAAAGAATCGTTTGTGTTATGTTTCAACGTGTTTATTTT
TCAATTGCAGAAAATTTCAAGTCATTTTTCATTCAGTAGTATAGCCCCACCACCACATAGCT
TATACAGATCACCGTACCTTAATCAAACTCACAGAACCCTAGTATTCAACCTGCCACCTCCC
TCCCAACACACAGAGTACACAGTCCTTTCTCCCCGGCTGGCCTTAAAAAGCATCATATCATG
GGTAACAGACATATTCTTAGGTGTTATATTCCACACGGTTTCCTGTCGAGCCAAACGCTCAT
CAGTGATATTAATAAACTCCCCGGGCAGCTCACTTAAGTTCATGTCGCTGTCCAGCTGCTGA
GCCACAGGCTGCTGTCCAACTTGCGGTTGCTTAACGGGCGGCGAAGGAGAAGTCCACGCCTA
CATGGGGGTAGAGTCATAATCGTGCATCAGGATAGGGCGGTGGTGCTGCAGCAGCGCGCGAA
TAAACTGCTGCCGCCGCCGCTCCGTCCTGCAGGAATACAACATGGCAGTGGTCTCCTCAGCG
ATGATTCGCACCGCCCGCAGCATAAGGCGCCTTGTCCTCCGGGCACAGCAGCGCACCCTGAT
CTCACTTAAATCAGCACAGTAACTGCAGCACAGCACCACAATATTGTTCAAAATCCCACAGT
GCAAGGCGCTGTATCCAAAGCTCATGGCGGGGACCACAGAACCCACGTGGCCATCATACCAC
AAGCGCAGGTAGATTAAGTGGCGACCCCTCATAAACACGCTGGACAT
```

FIG. 35 (13 of 14)

```
AAACATTACCTCTTTTGGCATGTTGTAATTCACCACCTCCCGGTACCATATAAACCTCTGAT
TAAACATGGCGCCATCCACCACCATCCTAAACCAGCTGGCCAAAACCTGCCCGCCGGCTATA
CACTGCAGGGAACCGGGACTGGAACAATGACAGTGGAGAGCCCAGGACTCGTAACCATGGAT
CATCATGCTCGTCATGATATCAATGTTGGCACAACACAGGCACACGTGCATACACTTCCTCA
GGATTACAAGCTCCTCCCGCGTTAGAACCATATCCCAGGGAACAACCCATTCCTGAATCAGC
GTAAATCCCACACTGCAGGGAAGACCTCGCACGTAACTCACGTTGTGCATTGTCAAAGTGTT
ACATTCGGGCAGCAGCGGATGATCCTCCAGTATGGTAGCGCGGGTTTCTGTCTCAAAAGGAG
GTAGACGATCCCTACTGTACGGAGTGCGCCGAGACAACCGAGATCGTGTTGGTCGTAGTGTC
ATGCCAAATGGAACGCCGGACGTAGTCATATTTCCTGAAGCAAAACCAGGTGCGGGCGTGAC
AAACAGATCTGCGTCTCCGGTCTCGCCGCTTAGATCGCTCTGTGTAGTAGTTGTAGTATATC
CACTCTCTCAAAGCATCCAGGCGCCCCCTGGCTTCGGGTTCTATGTAAACTCCTTCATGCGC
CGCTGCCCTGATAACATCCACCACCGCAGAATAAGCCACACCCAGCCAACCTACACATTCGT
TCTGCGAGTCACACACGGGAGGAGCGGGAAGAGCTGGAAGAACCATGTTTTTTTTTTTATTC
CAAAAGATTATCCAAAACCTCAAAATGAAGATCTATTAAGTGAACGCGCTCCCCTCCGGTGG
CGTGGTCAAACTCTACAGCCAAAGAACAGATAATGGCATTTGTAAGATGTTGCACAATGGCT
TCCAAAAGGCAAACGGCCCTCACGTCCAAGTGGACGTAAAGGCTAAACCCTTCAGGGTGAAT
CTCCTCTATAAACATTCCAGCACCTTCAACCATGCCCAAATAATTCTCATCTCGCCACCTTC
TCAATATATCTCTAAGCAAATCCCGAATATTAAGTCCGGCCATTGTAAAAATCTGCTCCAGA
GCGCCCTCCACCTTCAGCCTCAAGCAGCGAATCATGATTGCAAAAATTCAGGTTCCTCACAG
ACCTGTATAAGATTCAAAAGCGGAACATTAACAAAAATACCGCGATCCCGTAGGTCCCTTCG
CAGGGCCAGCTGAACATAATCGTGCAGGTCTGCACGGACCAGCGCGGCCACTTCCCCGCCAG
GAACCTTGACAAAAGAACCCACACTGATTATGACACGCATACTCGGAGCTATGCTAACCAGC
GTAGCCCCGATGTAAGCTTTGTTGCATGGGCGGCGATATAAAATGCAAGGTGCTGCTCAAAA
AATCAGGCAAAGCCTCGCGCAAAAAAGAAAGCACATCGTAGTCATGCTCATGCAGATAAAGG
CAGGTAAGCTCCGGAACCACCACAGAAAAAGACACCATTTTTCTCTCAAACATGTCTGCGGG
TTTCTGCATAAACACAAAATAAAATAACAAAAAAACATTTAAACATTAGAAGCCTGTCTTAC
AACAGGAAAAACAACCCTTATAAGCATAAGACGGACTACGGCCATGCCGGCGTGACCGTAAA
AAAACTGGTCACCGTGATTAAAAAGCACCACCGACAGCTCCTCGGTCATGTCCGGAGTCATA
ATGTAAGACTCGGTAAACACATCAGGTTGATTCATCGGTCAGTGCTAAAAAGCGACCGAAAT
AGCCCGGGGGAATACATACCCGCAGGCGTAGAGACAACATTACAGCCCCCATAGGAGGTATA
ACAAAATTAATAGGAGAGAAAAACACATAAACACCTGAAAAACCCTCCTGCCTAGGCAAAAT
AGCACCCTCCCGCTCCAGAACAACATACAGCGCTTCACAGCGGCAGCCTAACAGTCAGCCTT
ACCAGTAAAAAGAAAACCTATTAAAAAAACACCACTCGACACGGCACCAGCTCAATCAGTC
ACAGTGTAAAAAGGGCCAAGTGCAGAGCGAGTATATATAGGACTAAAAAATGACGTAACGG
TTAAAGTCCACAAAAAACACCCAGAAAACCGCACGCGAACCTACGCCCAGAAACGAAAGCCA
AAAAACCCACAACTTCCTCAAATCGTCACTTCCGTTTTCCCACGTTACGTAACTTCCCATTT
TAAGAAAACTACAATTCCCAACACATACAAGTTACTCCGCCCTAAAACCTACGTCACCCGCC
CCGTTCCCACGCCCCGCGCCACGTCACAAACTCCACCCCCTCATTATCATATTGGCTTCAAT
CCAAAATAAGGTATATTATTGATGATTTAAT
```

FIG. 35 (14 of 14)

SEQUENCE LISTING

<160> NUMBER OF SEQ ID NOS: 52

<210> SEQ ID NO 1
<211> LENGTH: 37941
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: modified_base
<222> LOCATION: (1254)..(1259)
<223> OTHER INFORMATION: a, c, g, t, unknown, or other
<220> FEATURE:
<221> NAME/KEY: modified_base
<222> LOCATION: (2797)..(2863)
<223> OTHER INFORMATION: a, c, g, t, unknown, or other
<220> FEATURE:
<221> NAME/KEY: modified_base
<222> LOCATION: (2872)..(2874)
<223> OTHER INFORMATION: a, c, g, t, unknown, or other
<220> FEATURE:
<221> NAME/KEY: modified_base
<222> LOCATION: (3215)..(3217)
<223> OTHER INFORMATION: a, c, g, t, unknown, or other
<220> FEATURE:
<221> NAME/KEY: modified_base
<222> LOCATION: (4805)..(4807)
<223> OTHER INFORMATION: a, c, g, t, unknown, or other
<220> FEATURE:
<221> NAME/KEY: modified_base
<222> LOCATION: (4864)..(4866)
<223> OTHER INFORMATION: a, c, g, t, unknown, or other
<220> FEATURE:
<221> NAME/KEY: modified_base
<222> LOCATION: (36237)..(36239)
<223> OTHER INFORMATION: a, c, g, t, unknown, or other

<400> SEQUENCE: 1

```
gcgctcttcc gcttcctcgc tcactgactc gctgcgctcg gtcgttcggc tgcggcgagc      60
ggtatcagct cactcaaagg cggtaatacg gttatccaca gaatcagggg ataacgcagg     120
aaagaacatg tgagcaaaag gccagcaaaa ggccaggaac cgtaaaaagg ccgcgttgct     180
ggcgtttttc cataggctcc gcccccctga cgagcatcac aaaaatcgac gctcaagtca     240
gaggtggcga aacccgacag gactataaag ataccaggcg tttccccctg gaagctccct     300
cgtgcgctct cctgttccga ccctgccgct taccggatac ctgtccgcct ttctcccttc     360
gggaagcgtg cgctttctca tagctcacg ctgtaggtat ctcagttcgg tgtaggtcgt     420
tcgctccaag ctgggctgtg tgcacgaacc ccccgttcag cccgaccgct gcgccttatc     480
cggtaactat cgtcttgagt ccaacccggt aagacacgac ttatcgccac tggcagcagc     540
cactggtaac aggattagca gagcgaggta tgtaggcggt gctacagagt tcttgaagtg     600
gtggcctaac tacggctaca ctagaaggac agtatttggt atctgcgctc tgctgaagcc     660
agttaccttc ggaaaaagag ttggtagctc ttgatccggc aaacaaacca ccgctggtag     720
cggtggtttt tttgtttgca agcagcagat tacgcgcaga aaaaaggat ctcaagaaga     780
tcctttgatc ttttctacgg ggtctgacgc tcagtggaac gaaaactcac gttaagggat     840
tttggtcatg agattatcaa aaaggatctt cacctagatc cttttaaatt aaaaatgaag     900
ttttaaatca atctaaagta tatatgagta aacttggtct gacagttacc aatgcttaat     960
cagtgaggca cctatctcag cgatctgtct atttcgttca tccatagttg cctgactccc    1020
cgtcgtgtag ataactacga tacgggaggg cttaccatct ggccccagtg ctgcaatgat    1080
accgcgagac ccacgctcac cggctccaga tttatcagca ataaaccagc cagccggaag    1140
```

```
ggccgagcgc agaagtggtc ctgcaacttt atccgcctcc atccagtcta ttaattgttg   1200
ccgggaagct agagtaagta gttcgccagt taatagtttg cgcaacgttg ttgnnnnnna   1260
aaaaggatct tcacctagat ccttttcacg tagaaagcca gtccgcagaa acggtgctga   1320
ccccggatga atgtcagcta ctgggctatc tggacaaggg aaaacgcaag cgcaaagaga   1380
aagcaggtag cttgcagtgg gcttacatgg cgatagctag actgggcggt tttatggaca   1440
gcaagcgaac cggaattgcc agctggggcg ccctctggta aggttgggaa gccctgcaaa   1500
gtaaactgga tggcttttctc gccgccaagg atctgatggc gcaggggatc aagctctgat   1560
caagagacag gatgaggatc gtttcgcatg attgaacaag atggattgca cgcaggttct   1620
ccggccgctt gggtggagag ctattcggc tatgactggg cacaacagac aatcggctgc   1680
tctgatgccg ccgtgttccg gctgtcagcg caggggcgcc cggttctttt tgtcaagacc   1740
gacctgtccg gtgccctgaa tgaactgcaa gacgaggcag cgcggctatc gtggctggcc   1800
acgacgggcg ttccttgcgc agctgtgctc gacgttgtca ctgaagcggg aagggactgg   1860
ctgctattgg gcgaagtgcc ggggcaggat ctcctgtcat ctcaccttgc tcctgccgag   1920
aaagtatcca tcatggctga tgcaatgcgg cggctgcata cgcttgatcc ggctacctgc   1980
ccattcgacc accaagcgaa acatcgcatc gagcgagcac gtactcggat ggaagccggt   2040
cttgtcgatc aggatgatct ggacgaagag catcaggggc tcgcgccagc cgaactgttc   2100
gccaggctca aggcgagcat gcccgacggc gaggatctcg tcgtgaccca tggcgatgcc   2160
tgcttgccga atatcatggt ggaaaatggc cgcttttctg gattcatcga ctgtggccgg   2220
ctgggtgtgg cggaccgcta tcaggacata gcgttggcta cccgtgatat tgctgaagag   2280
cttggcggcg aatgggctga ccgcttcctc gtgctttacg gtatcgccgc tcccgattcg   2340
cagcgcatcg ccttctatcg ccttcttgac gagttcttct gaattttgtt aaaattttg   2400 ttaaatcagc tcattttta accaataggc cgaaatcggc aacatccctt ataaatcaaa   2460
agaatagacc gcgatagggt tgagtgttgt tccagtttgg aacaagagtc cactattaaa   2520
gaacgtggac tccaacgtca aagggcgaaa aaccgtctat cagggcgatg gcccactacg   2580
tgaaccatca cccaaatcaa gttttttgcg gtcgaggtgc cgtaaagctc taaatcggaa   2640
ccctaaaggg agcccccgat ttagagcttg acggggaaag ccggcgaacg tggcgagaaa   2700
ggaagggaag aaagcgaaag gagcgggcgc tagggcgctg gcaagtgtag cggtcacgct   2760
gcgcgtaacc accacacccg cgcgcttaat gcgccgnnnn nnnnnnnnnn nnnnnnnnn   2820 nnnnnnnnnn nnnnnnnnnn nnnnnnnnnn nnnnnnnnnn nnnttaatta annntccctt   2880
ccagctctct gccccttttg gattgaagcc aatatgataa tgagggggtg gagtttgtga   2940
cgtggcgcgg ggcgtgggaa cggggcgggt gacgtagtag tgtggcggaa gtgtgatgtt   3000
gcaagtgtgg cggaacacat gtaagcgacg gatgtgcaa aagtgacgtt tttggtgtgc   3060
gccggtgtac acaggaagtg acaattttcg cgcggtttta ggcggatgtt gtagtaaatt   3120
tgggcgtaac cgagtaagat ttggccattt tcgcgggaaa actgaataag aggaagtgaa   3180
atctgaataa ttttgtgtta ctcatagcgc gtaannncgc gttaagatac attgatgagt   3240
ttggacaaac cacaactaga atgcagtgaa aaaatgctt tatttgtgaa atttgtgatg   3300
ctattgcttt atttgtaacc attataagct gcaataaaca agttaacaac aacaattgca   3360
ttcattttat gtttcaggtt caggggagg tgtgggaggt ttttaaagc aagtaaaacc   3420 tctacaaatg tggtatggct gattatgatc agttatctag atccggtgga tctgagtccg   3480
gacttgtaca gctcgtccat gccgagagtg atcccggcgg cggtcacgaa ctccagcagg   3540
```

```
accatgtgat cgcgcttctc gttggggtct ttgctcaggg cggactgggt gctcaggtag    3600
tggttgtcgg gcagcagcac ggggccgtcg ccgatggggg tgttctgctg gtagtggtcg    3660
gcgagctgca cgctgccgtc ctcgatgttg tggcggatct tgaagttcac cttgatgccg    3720
ttcttctgct tgtcggccat gatatagacg ttgtggctgt tgtagttgta ctccagcttg    3780
tgccccagga tgttgccgtc ctccttgaag tcgatgccct tcagctcgat gcggttcacc    3840
agggtgtcgc cctcgaactt cacctcggcg cgggtcttgt agttgccgtc gtccttgaag    3900
aagatggtgc gctcctggac gtagccttcg ggcatggcgg acttgaagaa gtcgtgctgc    3960
ttcatgtggt cggggtagcg gctgaagcac tgcacgccgt aggtcaggt ggtcacgagg     4020 gtgggccagg gcacgggcag cttgccggtg gtgcagatga acttcagggt cagcttgccg    4080
taggtggcat cgccctcgcc ctcgccggac acgctgaact tgtggccgtt tacgtcgccg    4140
tccagctcga ccaggatggg caccaccccg gtgaacagct cctcgccctt gctcaccatg    4200
gtggcgaccg gtagcgctag cggatctgac ggttcactaa accagctctg cttatataga    4260
cctcccaccg tacacgccta ccgcccattt gcgtcaatgg ggcggagttg ttacgacatt    4320
ttggaaagtc ccgttgattt tggtgccaaa acaaactccc attgacgtca atggggtgga    4380
gacttggaaa tccccgtgag tcaaaccgct atccacgccc attgatgtac tgccaaaacc    4440
gcatcaccat ggtaatagcg atgactaata cgtagatgta ctgccaagta ggaaagtccc    4500
ataaggtcat gtactgggca taatgccagg cgggccattt accgtcattg acgtcaatag    4560
ggggcgtact tggcatatga tacacttgat gtactgccaa gtgggcagtt taccgtaaat    4620
actccaccca ttgacgtcaa tggaaagtcc ctattggcgt tactatggga acatacgtca    4680
ttattgacgt caatgggcgg gggtcgttgg gcggtcagcc aggcgggcca tttaccgtaa    4740
gttatgtaac gcggaactcc atatatgggc tatgaactaa tgaccccgta attgattact    4800
attannncta gcagatctgg taccgtcgac gcggccgcga tatcctcgag aagctttcta    4860
gagnnntaag ggtgggaaag aatatataag gtgggggtct tatgtagtttt tgtatctgtt    4920 ttgcagcagc cgccgccgcc atgagcacca actcgtttga tggaagcatt gtgagctcat    4980
atttgacaac gcgcatgccc ccatgggccg gggtgcgtca aatgtgatg ggctccagca     5040 ttgatggtcg ccccgtcctg cccgcaaact ctactacctt gacctacgag accgtgtctg    5100
gaacgccgtt ggagactgca gcctccgccg ccgcttcagc cgctgcagcc accgccgcg     5160 ggattgtgac tgactttgct ttcctgagcc cgcttgcaag cagtgcagct tcccgttcat    5220
ccgcccgcga tgacaagttg acggctcttt tggcacaatt ggattctttg acccgggaac    5280
ttaatgtcgt ttctcagcag ctgttggatc tgcgccagca ggtttctgcc ctgaaggctt    5340
cctcccctcc caatgcggtt taaaacataa ataaaaaacc agactctgtt tggatttgga    5400
tcaagcaagt gtcttgctgt ctttatttag gggttttgcg cgcgcggtag gcccgggacc    5460
agcggtctcg gtcgttgagg gtcctgtgta tttttccag dacgtggtaa aggtgactct    5520
ggatgttcag atacatgggc ataagcccgt ctctggggtg gaggtagcac cactgcagag    5580
cttcatgctg cggggtggtg ttgtagatga tccagtcgta gcaggagcgc tgggcgtggt    5640
gcctaaaaat gtcttttcagt agcaagctga ttgccagggg caggcccttg gtgtaagtgt    5700
ttacaaagcg gttaagctgg gatgggtgca tacgtgggga tatgagatgc atcttggact    5760 gtattttag gttggctatg ttcccagcca tatccctccg gggattcatg ttgtgcagaa    5820
ccaccagcac agtgtatccg gtgcacttgg gaaatttgtc atgtagctta gaaggaaatg    5880
cgtggaagaa cttggagacg cccttgtgac ctccaagatt ttccatgcat tcgtccataa    5940
```

```
tgatggcaat gggcccacgg gcggcggcct gggcgaagat atttctggga tcactaacgt    6000
catagttgtg ttccaggatg agatcgtcat aggccatttt tacaaagcgc gggcggaggg    6060
tgccagactg cggtataatg gttccatccg gcccaggggc gtagttaccc tcacagattt    6120
gcatttccca cgctttgagt tcagatgggg ggatcatgtc tacctgcggg gcgatgaaga    6180
aaacggtttc cggggtaggg gagatcagct gggaagaaag caggttcctg agcagctgcg    6240
acttaccgca gccggtgggc ccgtaaatca cacctattac cgggtgcaac tggtagttaa    6300
gagagctgca gctgccgtca tccctgagca gggggccac ttcgttaagc atgtccctga     6360
ctcgcatgtt ttccctgacc aaatccgcca gaaggcgctc gccgcccagc gatagcagtt    6420
cttgcaagga agcaaagttt ttcaacggtt tgagaccgtc cgccgtaggc atgcttttga    6480
gcgtttgacc aagcagttcc aggcggtccc acagctcggt cacctgctct acggcatctc    6540
gatccagcat atctcctcgt ttcgcggtt ggggcggctt tcgctgtacg gcagtagtcg     6600
gtgctcgtcc agacgggcca gggtcatgtc tttccacggg cgcagggtcc tcgtcagcgt    6660
agtctgggtc acggtgaagg ggtgcgctcc gggctgcgcg ctggccaggg tgcgcttgag    6720
gctggtcctg ctggtgctga agcgctgccg gtcttcgccc tgcgcgtcgg ccaggtagca    6780
tttgaccatg gtgtcatagt ccagcccctc cgcggcgtgg cccttggcgc gcagcttgcc    6840
cttgaggag cgccgcacg aggggcagtg cagacttttg agggcgtaga gcttgggcgc      6900
gagaaatacc gattccgggg agtaggcatc cgcgccgcag gccccgcaga cggtctcgca    6960
ttccacgagc caggtgagct ctggccgttc ggggtcaaaa accaggtttc ccccatgctt    7020
tttgatgcgt ttcttacctc tggtttccat gagccggtgt ccacgctcgg tgacgaaaag    7080
gctgccgtg tccccgtata cagactactt gagaggcctg tcctcgagcg gtgttccgcg     7140
gtcctcctcg tatagaaact cggaccactc tgagacaaag gctcgcgtcc aggccagcac    7200
gaaggaggct aagtgggagg ggtagcggtc gttgtccact aggggggtcca ctcgctccag   7260
ggtgtgaaga cacatgtcgc cctcttcggc atcaaggaag gtgattggtt tgtaggtgta    7320
ggccacgtga ccgggtgttc ctgaaggggg gctataaaag ggggtgggggg gcgcgttcgtc  7380
ctcactctct tccgcatcgc tgtctgcgag ggccagctgt tggggtgagt actccctctg    7440
aaaagcgggc atgacttctg cgctaagatt gtcagtttcc aaaaacgagg aggatttgat    7500
attcacctgg cccgcggtga tgcctttgag ggtggccgca tccatctggt cagaaaagac    7560
aatcttttg ttgtcaagct tggtggcaaa cgacccgtag agggcgttgg acagcaactt     7620
ggcgatggag cgcagggttt ggttttttgtc gcgatcggcg cgctccttgg ccgcgatgtt   7680
tagctgcacg tattcgcgcg caacgcaccg ccattcggga aagacggtgg tgcgctcgtc    7740
gggcaccagg tgcacgcgcc aaccgcggtt gtgcagggtg acaaggtcaa cgctggtggc    7800
tacctctccg cgtaggcgct cgttggtcca gcagaggcgg ccgcccttgc gcgagcagaa    7860
tggcggtagg gggtctagct gcgtctcgtc cgggggtct gcgtccacgg taaagacccc     7920
gggcagcagg cgcgcgtcga agtagtctat cttgcatcct tgcaagtcta gcgcctgctg    7980
ccatgcgcgg gcggcaagcg cgcgctcgta tgggttgagt gggggacccc atggcatggg    8040
gtgggtgagc gcggaggcgt acatgccgca aatgtcgtaa acgtagaggg gctctctgag    8100
tattccaaga tatgtagggt agcatcttcc accgcggatg ctggcgcgca cgtaatcgta    8160
tagttcgtgc gagggagcga ggaggtcggg accgaggttg ctacgggcgg gctgctctgc    8220
tcggaagact atctgcctga agatggcatg tgagttggat gatatggttg gacgctggaa    8280
gacgttgaag ctggcgtctg tgagacctac cgcgtcacgc acgaaggagg cgtaggagtc    8340
```

```
gcgcagcttg ttgaccagct cggcggtgac ctgcacgtct agggcgcagt agtccagggt    8400
ttccttgatg atgtcatact tatcctgtcc ctttttttc cacagctcgc ggttgaggac     8460
aaactcttcg cggtctttcc agtactcttg gatcggaaac ccgtcggcct ccgaacggta    8520
agagcctagc atgtagaact ggttgacggc ctggtaggcg cagcatccct tttctacggg    8580
tagcgcgtat gcctgcgcgg ccttccgagg cgaggtgtgg gtgagcgcaa aggtgtccct    8640
gaccatgact ttgaggtact ggtatttgaa gtcagtgtcg tcgcatccgc cctgctccca    8700
gagcaaaaag tccgtgcgct ttttggaacg cggatttggc agggcgaagg tgacatcgtt    8760
gaagagtatc tttcccgcgc gaggcataaa gttgcgtgtg atgcggaagg gtcccggcac    8820
ctcggaacgg ttgttaatta cctgggcggc gagcacgatc tcgtcaaagc cgttgatgtt    8880
gtggcccaca atgtaaagtt ccaagaagcg cgggatgccc ttgatggaag gcaattttt    8940 aagttcctcg taggtgagct cttcagggga gctgagcccg tgctctgaaa gggcccagtc    9000
tgcaagatga gggttggaag cgacgaatga gctccacagg tcacgggcca ttagcatttg    9060
caggtggtcg cgaaaggtcc taaactggcg acctatggcc attttttctg gggtgatgca    9120
gtagaaggta agcgggtctt gttcccagcg gtcccatcca aggttcgcgg ctaggtctcg    9180
cgcggcagtc actagaggct catctccgcc gaacttcatg accagcatga agggcacgag    9240
ctgcttccca aaggccccca tccaagtata ggtctctaca tcgtaggtga caaagagacg    9300
ctcggtgcga ggatgcgagc cgatcgggaa gaactggatc tcccgccacc aattggagga    9360
gtggctattg atgtggtgaa agtagaagtc cctgcgacgg gccgaacact cgtgctggct    9420
tttgtaaaaa cgtgcgcagt actggcagcg gtgcacgggc tgtacatcct gcacgaggtt    9480
gacctgacga ccgcgcacaa ggaagcagag tgggaatttg agccccctcgc ctggcgggtt   9540 tggctggtgg tcttctactt cggctgcttg tccttgaccg tctggctgct cgaggggagt    9600
tacggtggat cggaccacca cgccgcgcga gcccaaagtc cagatgtccg cgcgcggcgg    9660
tcggagcttg atgacaacat cgcgcagatg ggagctgtcc atggtctgga gctcccgcgg    9720
cgtcaggtca ggcgggagct cctgcaggtt tacctcgcat agacgggtca gggcgcgggc    9780
tagatccagg tgatacctaa tttccagggg ctggttggtg gcggcgtcga tggcttgcaa    9840
gaggccgcat cccgcggcg cgactacggt accgcgcggc gggcggtggg ccgcgggggt    9900
gtccttggat gatgcatcta aaagcggtga cgcgggcgag ccccggagg tagggggggc     9960 tccggacccg ccgggagagg gggcaggggc acgtcggcgc cgcgcgcggg caggagctgg   10020
tgctgcgcgc gtaggttgct ggcgaacgcg acgacgcggc ggttgatctc ctgaatctgg   10080
cgcctctgcg tgaagacgac gggcccggtg agcttgagcc tgaaagagag ttcgacagaa   10140
tcaatttcgg tgtcgttgac ggcggcctgg cgcaaaatct cctgcacgtc tcctgagttg   10200
tcttgatagg cgatctcggc catgaactgc tcgatctctt cctcctggag atctccgcgt   10260
ccggctcgct ccacggtggc ggcgaggtcg ttggaaatgc gggccatgag ctgcgagaag   10320
gcgttgaggc ctcccctcgtt ccagacgcgc ctgtagacca cgcccccttc ggcatcgcgg   10380
gcgcgcatga ccacctgcgc gagattgagc tccacgtgcc gggcgaagac ggcgtagttt   10440
cgcaggcgct gaaagaggta gttgagggtg tggcggtgt gttctgccac gaagaagtac    10500
ataacccagc gtcgcaacgt ggattcgttg atatccccca aggcctcaag cgcgctccatg  10560 gcctcgtaga agtccacggc gaagttgaaa aactgggagt tgcgcgccga cacggttaac   10620
tcctcctcca gaagacggat gagctcggcg acagtgtcgc gcacctcgcg ctcaaaggct   10680
acaggggcct cttcttcttc ttcaatctcc tcttccataa gggcctcccc ttcttcttct   10740
```

```
tctggcggcg gtgggggagg ggggacacgg cggcgacgac ggcgcaccgg gaggcggtcg   10800
acaaagcgct cgatcatctc cccgcggcga cggcgcatgg tctcggtgac ggcgcggccg   10860
ttctcgcggg ggcgcagttg gaagacgccg cccgtcatgt cccggttatg ggttggcggg   10920
gggctgccat gcggcaggga tacggcgcta acgatgcatc tcaacaattg ttgtgtaggt   10980
actccgccgc cgagggacct gagcgagtcc gcatcgaccg gatcggaaaa cctctcgaga   11040
aaggcgtcta accagtcaca gtcgcaaggt aggctgagca ccgtggcggg cggcagcggg   11100
cggcggtcgg ggttgtttct ggcggaggtg ctgctgatga tgtaattaaa gtaggcggtc   11160
ttgagacggc ggatggtcga cagaagcacc atgtccttgg gtccggcctg ctgaatgcgc   11220
aggcggtcgg ccatgcccca ggcttcgttt tgacatcggc gcaggtcttt gtagtagtct   11280
tgcatgagcc tttctaccgg cacttcttct tctccttcct cttgtcctgc atctcttgca   11340
tctatcgctg cggcggcggc ggagtttggc cgtaggtggc gccctcttcc tcccatgcgt   11400
gtgaccccga agcccctcat cggctgaagc agggctaggt cggcgacaac gcgctcggct   11460
aatatggcct gctgcacctg cgtgagggta gactggaagt catccatgtc cacaaagcgg   11520
tggtatgcgc ccgtgttgat ggtgtaagtg cagttggcca taacggacca gttaacggtc   11580
tggtgacccg gctgcgagag ctcggtgtac ctgagacgcg agtaagccct cgagtcaaat   11640
acgtagtcgt tgcaagtccg caccaggtac tggtatccca ccaaaaagtg cggcggcggc   11700
tggcggtaga ggggccagcg tagggtggcc ggggctccgg gggcgagatc ttccaacata   11760
aggcgatgat atccgtagat gtacctggac atccaggtga tgccggcggc ggtggtggag   11820
gcgcgcggaa agtcgcggac gcggttccag atgttgcgca gcggcaaaaa gtgctccatg   11880
gtcgggacgc tctggccggt caggcgcgcg caatcgttga cgctctaccg tgcaaaagga   11940
gagcctgtaa gcgggcactc ttccgtggtc tggtggataa attcgcaagg gtatcatggc   12000
ggacgaccgg ggttcgagcc ccgtatccgg ccgtccgccg tgatccatgc ggttaccgcc   12060
cgcgtgtcga acccaggtgt gcgacgtcag acaacggggg agtgctcctt ttggcttcct   12120
tccaggcgcg gcgctgctg cgctagcttt tttggccact ggccgcgcgc agcgtaagcg   12180
gttaggctgg aaagcgaaag cattaagtgg ctcgctccct gtagccggag ggttattttc   12240
caagggttga gtcgcgggac ccccggttcg agtctcggac cggccggact gcggcgaacg   12300
ggggtttgcc tccccgtcat gcaagacccc gcttgcaaat tcctccggaa acagggacga   12360 gcccctttt tgcttttccc agatgcatcc ggtgctgcgg cagatgcgcc cccctcctca   12420
gcagcggcaa gagcaagagc agcggcagac atgcagggca ccctcccctc ctcctaccgc   12480
gtcaggaggg gcgacatccg cggttgacgc ggcagcagat ggtgattacg aaccccgcg   12540 gcgccgggcc cggcactacc tggacttgga ggagggcgag ggcctggcgc ggctaggagc   12600
gccctctcct gagcggtacc caagggtgca gctgaagcgt gatacgcgtg aggcgtacgt   12660
gccgcggcag aacctgtttc gcgaccgcga gggagaggag cccgaggaga tgcgggatcg   12720
aaagttccac gcagggcgcg agctgcggca tggcctgaat cgcgagcggt tgctgcgcga   12780
ggaggacttt gagcccgacg cgcgaaccgg gattagtccc gcgcgcgcac acgtggcggc   12840
cgccgacctg gtaaccgcat acgagcagac ggtgaaccag gagattaact ttcaaaaaag   12900
ctttaacaac cacgtgcgta cgcttgtggc gcgcgaggag gtggctatag gactgatgca   12960
tctgtgggac tttgtaagcg cgctggagca aaacccaaat agcaagccgc tcatggcgca   13020
gctgttcctt atagtgcagc acagcaggga caacgaggca ttcagggatg cgctgctaaa   13080
catagtagag cccgagggcc gctggctgct cgatttgata aacatcctgc agagcatagt   13140
```

```
ggtgcaggag cgcagcttga gcctggctga caaggtggcc gccatcaact attccatgct   13200
tagcctgggc aagttttacg cccgcaagat ataccatacc ccttacgttc ccatagacaa   13260
ggaggtaaag atcgaggggt tctacatgcg catggcgctg aaggtgctta ccttgagcga   13320
cgacctgggc gtttatcgca acgagcgcat ccacaaggcc gtgagcgtga gccggcggcg   13380
cgagctcagc gaccgcgagc tgatgcacag cctgcaaagg gccctggctg cacgggcag    13440
cggcgataga gaggccgagt cctactttga cgcgggcgct gacctgcgct gggccccaag   13500
ccgacgcgcc ctggaggcag ctggggccgg acctgggctg gcggtggcac ccgcgcgcgc   13560
tggcaacgtc ggcggcgtgg aggaatatga cgaggacgat gagtacgagc cagaggacgg   13620
cgagtactaa gcggtgatgt ttctgatcag atgatgcaag acgcaacgga cccgcggtg    13680
cgggcggcgc tgcagagcca gccgtccggc cttaactcca cggacgactg cgccaggtc    13740
atggaccgca tcatgtcgct gactgcgcgc aatcctgacg cgttccggca gcagccgcag   13800
gccaaccggc tctccgcaat tctggaagcg gtggtcccgg cgcgcgcaaa ccccacgcac   13860
gagaaggtgc tggcgatcgt aaacgcgctg gccgaaaaca gggccatccg gcccgacgag   13920
gccggcctgg tctacgacgc gctgcttcag cgcgtggctc gttacaacag cggcaacgtg   13980
cagaccaacc tggaccggct ggtgggggat gtgcgcgagg ccgtggcgca gcgtgagcgc   14040
gcgcagcagc agggcaaccc gggctccatg gttgcactaa acgccttcct gagtacacag   14100
cccgccaacg tgccgcgggg acaggaggac tacaccaact tgtgagcgc actgcggcta    14160
atggtgactg agacaccgca aagtgaggtg taccagtctg gccagacta ttttttccag    14220
accagtagac aaggcctgca gaccgtaaac ctgagccagg ctttcaaaaa cttgcagggg   14280
ctgtgggggg tgcgggctcc cacaggcgac cgcgcgaccg tgtctagctt gctgacgccc   14340
aactcgcgcc tgttgctgct gctaatagcg cccttcacgg acagtggcag cgtgtcccgg   14400
gacacatacc taggtcactt gctgacactg taccgcgagg ccataggtca ggcgcatgtg   14460
gacgagcata cttttccagga gattacaagt gtcagccgcg cgctggggca ggaggacacg   14520
ggcagcctgg aggcaaccct aaactacctg ctgaccaacc ggcggcagaa gatcccctcg   14580
ttgcacagtt taaacagcga ggaggagcgc attttgcgct acgtgcagca gagcgtgagc   14640
cttaacctga tgcgcgacgg ggtaacgccc agcgtggcgc tggacatgac cgcgcgcaac   14700
atggaaccgg gcatgtatgc ctcaaaccgg ccgtttatca accgcctaat ggactacttg   14760
catcgcgcgg ccgccgtgaa ccccgagtat ttcaccaatg ccatcttgaa cccgcactgg   14820
ctaccgcccc ctggttttcta caccggggga ttcgaggtgc ccgagggtaa cgatggattc   14880
ctctgggacg acatagacga cagcgtgttt tccccgcaac cgcagaccct gctagagttg   14940
caacagcgcg agcaggcaga ggcggcgctg cgaaaggaaa gcttccgcag gccaagcagc   15000
ttgtccgatc taggcgctgc ggccccgcgg tcagatgcta gtagcccatt tccaagcttg   15060
atagggtctc ttaccagcac tcgcaccacc cgcccgcgcc tgctgggcga ggaggagtac   15120
ctaaacaact cgctgctgca gccgcagcgc gaaaaaaacc tgcctccggc atttcccaac   15180
aacgggatag agagcctagt ggacaagatg agtagatgga agacgtacgc gcaggagcac   15240
agggacgtgc caggcccgcg cccgcccacc cgtcgtcaaa ggcacgaccg tcagcggggt   15300
ctggtgtggg aggacgatga ctcggcagac gacagcagcc tcctggatt tgggagggagt  15360
ggcaacccgt ttgcgcacct tcgccccagg ctggggagaa tgttttaaaa aaaaaaagc   15420
atgatgcaaa ataaaaaact caccaaggcc atggcaccga cgttggtttt cttgtattc   15480
cccttagtat gcggcgcgcg gcgatgtatg aggaaggtcc tcctccctcc tacgagagtg   15540
```

```
tggtgagcgc ggcgccagtg gcggcggcgc tgggttctcc cttcgatgct ccccctggacc    15600 cgccgtttgt gcctccgcgg tacctgcggc ctaccggggg gagaaacagc atccgttact    15660
ctgagttggc acccctattc gacaccaccc gtgtgtacct ggtggacaac aagtcaacgg    15720
atgtggcatc cctgaactac cagaacgacc acagcaactt tctgaccacg gtcattcaaa    15780
acaatgacta cagcccgggg gaggcaagca cacagaccat caatcttgac gaccggtcgc    15840 actgggcgg cgacctgaaa accatcctgc ataccaacat gccaaatgtg aacgagttca    15900
tgtttaccaa taagtttaag gcgcgggtga tggtgtcgcg cttgcctact aaggacaatc    15960
aggtggagct gaaatacgag tgggtggagt tcacgctgcc cgagggcaac tactccgaga    16020
ccatgaccat agaccttatg aacaacgcga tcgtggagca ctacttgaaa gtgggcagac    16080
agaacggggt tctggaaagc gacatcgggg taaagtttga cacccgcaac ttcagactgg    16140
ggtttgaccc cgtcactggt cttgtcatgc ctggggtata tacaaacgaa gccttccatc    16200
cagacatcat tttgctgcca ggatgcgggg tggacttcac ccacagccgc ctgagcaact    16260
tgttgggcat ccgcaagcgg caacccttcc aggagggctt taggatcacc tacgatgatc    16320
tggagggtgg taacattccc gcactgttgg atgtggacgc ctaccaggcg agcttgaaag    16380
atgacaccga acagggcggg ggtggcgcag gcggcagcaa cagcagtggc agcggcgcgg    16440
aagagaactc caacgcggca gccgcggcaa tgcagccggt ggaggacatg aacgatcatg    16500
ccattcgcgg cgacaccttt gccacacggg ctgaggagaa gcgcgctgag gccgaagcag    16560
cggccgaagc tgccgccccc gctgcgcaac ccgaggtcga gaagcctcag aagaaaccgg    16620
tgatcaaacc cctgacagag gacagcaaga aacgcagtta caacctaata agcaatgaca    16680
gcaccttcac ccagtaccgc agctggtacc ttgcatacaa ctacggcgac cctcagaccg    16740
gaatccgctc atggaccctg cttttgcactc ctgacgtaac ctgcggctcg gagcaggtct    16800
actggtcgtt gccagacatg atgcaagacc ccgtgacctt ccgctccacg cgccagatca    16860
gcaactttcc ggtggtgggc gccgagctgt tgcccgtgca ctccaagagc ttctacaacg    16920
accaggccgt ctactcccaa ctcatccgcc agtttacctc tctgacccac gtgttcaatc    16980
gctttcccga gaaccagatt ttggcgcgcc cgccagcccc caccatcacc accgtcagtg    17040
aaaacgttcc tgctctcaca gatcacggga cgctaccgct cgcaacagc atcggaggag    17100 tccagcgagt gaccattact gacgccagac gccgcacctg cccctacgtt tacaaggccc    17160
tgggcatagt ctcgccgcgc gtcctatcga gccgcacttt ttgagcaagc atgtccatcc    17220
ttatatcgcc cagcaataac acaggctggg gcctgcgctt cccaagcaag atgtttggcg    17280
gggccaagaa gcgctccgac caacacccag tgcgcgtgcg cgggcactac cgcgcgccct    17340
ggggcgcgca caaacgcggc cgcactgggc gcaccaccgt cgatgacgcc atcgacgcgg    17400
tggtggagga ggcgcgcaac tacacgccca cgccgccacc agtgtccaca gtggacgcgg    17460
ccattcagac cgtggtgcgc ggagcccggc gctatgctaa aatgaagaga cggcggaggc    17520
gcgtagcacg tcgccaccgc cgccgacccg gcactgccgc caacgcgcg gcggcggccc    17580 tgcttaaccg cgcacgtcgc accggccgac gggcggccat gcgggccgct cgaaggctgg    17640 ccgcggggtat tgtcactgtg ccccccaggt ccaggcgacg agcggccgcc gcagcagccg    17700
cggccattag tgctatgact cagggtcgca ggggcaacgt gtattgggtg cgcgactcgg    17760
ttagcggcct gcgcgtgccc gtgcgcaccc gccccccgcg caactagatt gcaagaaaaa    17820
actacttaga ctcgtactgt tgtatgtatc cagcggcggc ggcgcgcaac gaagctatgt    17880
ccaagcgcaa aatcaaagaa gagatgctcc aggtcatcgc gccggagatc tatggccccc    17940
```

```
cgaagaagga agagcaggat tacaagcccc gaaagctaaa gcgggtcaaa aagaaaaaga   18000
aagatgatga tgatgaactt gacgacgagg tggaactgct gcacgctacc gcgcccaggc   18060
gacgggtaca gtggaaaggt cgacgcgtaa aacgtgtttt gcgacccggc accaccgtag   18120
tctttacgcc cggtgagcgc tccacccgca cctacaagcg cgtgtatgat gaggtgtacg   18180
gcgacgagga cctgcttgag caggccaacg agcgcctcgg ggagtttgcc tacgaaaagc   18240
ggcataagga catgctggcg ttgccgctgg acgagggcaa cccaacacct agcctaaagc   18300
ccgtaacact gcagcaggtg ctgcccgcgc ttgcaccgtc cgaagaaaag cgcggcctaa   18360
agcgcgagtc tggtgacttg gcacccaccg tgcagctgat ggtacccaag cgccagcgac   18420
tggaagatgt cttggaaaaa atgaccgtgg aacctgggct ggagcccgag gtccgcgtgc   18480
ggccaatcaa gcaggtggcg ccgggactgg gcgtgcagac cgtggacgtt cagataccca   18540
ctaccagtag caccagtatt gccaccgcca cagagggcat ggagacacaa acgtccccgg   18600
ttgcctcagc ggtggcggat gccgcggtgc aggcggtcgc tgcggccgcg tccaagacct   18660
ctacggaggt gcaaacggac ccgtggatgt ttcgcgtttc agccccccgg cgcccgcgcg   18720
gttcgaggaa gtacgcgcc gccagcgcgc tactgcccga atatgcccta catccttcca   18780
ttgcgcctac ccccggctat cgtggctaca cctaccgccc cagaagacga gcaactaccc   18840
gacgccgaac caccactgga acccgccgcc gcgtcgccg tcgccagccc gtgctggccc   18900
cgatttccgt gcgcagggtg gctcgcgaag gaggcaggac cctggtgctg ccaacagcgc   18960
gctaccaccc cagcatcgtt taaaagccgg tctttgtggt tcttgcagat atggccctca   19020
cctgccgcct ccgtttcccg gtgccgggat tccgaggaag aatgcaccgt aggaggggca   19080
tggccggcca cggcctgacg ggcggcatgc gtcgtgcgca ccaccggcgg cggcgcgcgt   19140
cgcaccgtcg catgcgcggc ggtatcctgc ccctccttat tccactgatc gccgcggcga   19200
ttggcgccgt gcccggaatt gcatccgtgg ccttgcaggc gcagagacac tgattaaaaa   19260
caagttgcat gtggaaaaat caaaataaaa agtctggact ctcacgctcg cttggtcctg   19320
taactatttt gtagaatgga agacatcaac tttgcgtctc tggccccgcg acacggctcg   19380
cgcccgttca tgggaaactg gcaagatatc ggcaccagca atatgagcgg tggcgccttc   19440
agctggggct cgctgtggag cggcattaaa aatttcggtt ccaccgttaa gaactatggc   19500
agcaaggcct ggaacagcag cacaggccag atgctgaggg ataagttgaa agagcaaaat   19560
ttccaacaaa aggtggtaga tggcctggcc tctggcatta gcggggtggt ggacctggcc   19620
aaccaggcag tgcaaaataa gattaacagt aagcttgatc cccgccctcc cgtagaggag   19680
cctccaccgg ccgtggagac agtgtctcca gaggggcgtg gcgaaaagcg tccgcgcccc   19740
gacagggaag aaactctggt gacgcaaata gacgagcctc cctcgtacga ggaggcacta   19800
aagcaaggcc tgcccaccac ccgtcccatc gcgcccatgg ctaccggagt gctgggccag   19860
cacacacccg taacgctgga cctgcctccc cccgccgaca cccagcagaa acctgtgctg   19920
ccaggcccga ccgccgttgt tgtaaccgt cctagccgcg cgtccctgcg ccgcgccgcc   19980
agcggtccgc gatcgttgcg gcccgtagcc agtggcaact ggcaaagcac actgaacagc   20040
atcgtgggtc tggggtgca atccctgaag cgccgacgat gcttctgaat agctaacgtg   20100
tcgtatgtgt gtcatgtatg cgtccatgtc gccgccagag gagctgctga gccgccgcgc   20160
gcccgctttc caagatggct acccccttcga tgatgccgca gtggtcttac atgcacatct   20220
cgggccagga cgcctcggag tacctgagcc ccggctggt gcagtttgcc cgcgccaccg   20280
agacgtactt cagcctgaat aacaagttta gaaacccac ggtggcgcct acgcacgacg   20340
```

```
tgaccacaga ccggtcccag cgtttgacgc tgcggttcat ccctgtggac cgtgaggata   20400
ctgcgtactc gtacaaggcg cggttcaccc tagctgtggg tgataaccgt gtgctggaca   20460
tggcttccac gtactttgac atccgcggcg tgctggacag gggccctact tttaagccct   20520
actctggcac tgcctacaac gccctggctc ccaagggtgc cccaaatcct tgcgaatggg   20580
atgaagctgc tactgctctt gaaataaacc tagaagaaga ggacgatgac aacgaagacg   20640
aagtagacga gcaagctgag cagcaaaaaa ctcacgtatt tgggcaggcg ccttattctg   20700
gtataaatat tacaaaggag ggtattcaaa taggtgtcga aggtcaaaca cctaaatatg   20760
ccgataaaac atttcaacct gaacctcaaa taggagaatc tcagtggtac gaaactgaaa   20820
ttaatcatgc agctgggaga gtccttaaaa agactacccc aatgaaacca tgttacggtt   20880
catatgcaaa acccacaaat gaaaatggag ggcaaggcat tcttgtaaag caacaaaatg   20940
gaaagctaga aagtcaagtg gaaatgcaat ttttctcaac tactgaggcg accgcaggca   21000
atggtgataa cttgactcct aaagtggtat tgtacagtga agatgtagat atagaaaccc   21060
cagacactca tatttcttac atgcccacta ttaaggaagg taactcacga gaactaatgg   21120
gccaacaatc tatgcccaac aggcctaatt acattgcttt tagggacaat tttattggtc   21180
taatgtatta caacagcacg ggtaatatgg gtgttctggc gggccaagca tcgcagttga   21240
atgctgttgt agatttgcaa gacagaaaca cagagctttc ataccagctt ttgcttgatt   21300
ccattggtga tagaaccagg tacttttcta tgtggaatca ggctgttgac agctatgatc   21360
cagatgttag aattattgaa aatcatggaa ctgaagatga acttccaaat tactgctttc   21420
cactgggagg tgtgattaat acagagactc ttaccaaggt aaaacctaaa acaggtcagg   21480
aaaatggatg ggaaaaagat gctacagaat tttcagataa aaatgaaata agagttggaa   21540
ataattttgc catggaaatc aatctaaatg ccaacctgtg gagaaatttc ctgtactcca   21600
acatagcgct gtatttgccc gacaagctaa agtacagtcc ttccaacgta aaaatttctg   21660
ataacccaaa cacctacgac tacatgaaca agcgagtggt ggctcccggg ttagtggact   21720
gctacattaa ccttggagca cgctggtccc ttgactatat ggacaacgtc aacccattta   21780
accaccaccg caatgctggc ctgcgctacc gctcaatgtt gctgggcaat ggtcgctatg   21840
tgcccttcca catccaggtg cctcagaagt tctttgccat taaaaacctc cttctcctgc   21900
cgggctcata cacctacgag tggaacttca ggaaggatgt taacatggtt ctgcagagct   21960
ccctaggaaa tgacctaagg gttgacggag ccagcattaa gtttgatagc atttgccttt   22020
acgccacctt cttccccatg gcccacaaca ccgcctccac gcttgaggcc atgcttagaa   22080
acgacaccaa cgaccagtcc tttaacgact atctctccgc cgccaacatg ctctacccta   22140
tacccgccaa cgctaccaac gtgcccatat ccatcccctc ccgcaactgg gcggctttcc   22200
gcggctgggc cttcacgcgc cttaagacta aggaaacccc atcactgggc tcgggctacg   22260
accctattta cacctactct ggctctatac cctacctaga tggaaccttt tacctcaacc   22320
acacctttaa gaaggtggcc attacctttg actcttctgt cagctggcct ggcaatgacc   22380
gcctgcttac ccccaacgag tttgaaatta gcgctcagt  tgacggggag ggttacaacg   22440
ttgcccagtg taacatgacc aaagactggt tcctggtaca aatgctagct aactacaaca   22500
ttggctacca gggcttctat atcccagaga gctacaagga ccgcatgtac tccttctttc   22560
gaaacttcca gcccatgagc cgtcaggtgg tggatgatac taaatacaag gactaccaac   22620
aggtgggcat cctacaccaa cacaacaact ctggatttgt tggctacctt gcccccacca   22680
tgcgcgaagg acaggcctac cctgctaact tcccctatcc gcttataggc aagaccgcag   22740
```

```
ttgacagcat tacccagaaa aagtttcttt gcgatcgcac cctttggcgc atcccattct   22800
ccagtaactt tatgtccatg ggcgcactca cagacctggg ccaaaacctt ctctacgcca   22860
actccgccca cgcgctagac atgacttttg aggtggatcc catggacgag cccacccttc   22920
tttatgtttt gtttgaagtc tttgacgtgg tccgtgtgca ccggccgcac cgcggcgtca   22980
tcgaaaccgt gtacctgcgc acgcccttct cggccggcaa cgccacaaca taaagaagca   23040
agcaacatca acaacagctg ccgccatggg ctccagtgag caggaactga aagccattgt   23100
caaagatctt ggttgtgggc cataattttt gggcacctat gacaagcgct ttccaggctt   23160
tgtttctcca cacaagctcg cctgcgccat agtcaatacg gccggtcgcg agactggggg   23220
cgtacactgg atggcctttg cctggaaccc gcactcaaaa acatgctacc tctttgagcc   23280
ctttggctttt tctgaccagc gactcaagca ggtttaccag tttgagtacg agtcactcct   23340
gcgccgtagc gccattgctt cttccccccga ccgctgtata acgctggaaa agtccaccca   23400
aagcgtacag gggcccaact cggccgcctg tggactattc tgctgcatgt ttctccacgc   23460
ctttgccaac tggcccccaaa ctcccatgga tcacaacccc accatgaacc ttattaccgg   23520
ggtacccaac tccatgctca acagtcccca ggtacagccc accctgcgtc gcaaccagga   23580
acagctctac agcttcctgg agcgccactc gccctacttc cgcagccaca gtgcgcagat   23640
taggagcgcc acttcttttt gtcacttgaa aaacatgtaa aaataatgta ctagagacac   23700
tttcaataaa ggcaaatgct tttatttgta cactctcggg tgattattta ccccccaccct   23760
tgccgtctgc gccgttaaa aatcaaaggg gttctgccgc gcatcgctat gcgccactgg   23820
cagggacacg ttgcgatact ggtgtttagt gctccactta aactcaggca caaccatccg   23880
cggcagctcg gtgaagtttt cactccacag gctgcgcacc atcaccaacg cgtttagcag   23940
gtcgggcgcc gatatcttga agtcgcagtt ggggcctccg ccctgcgcgc gcgagttgcg   24000
atacacaggg ttgcagcact ggaacactat cagcgcgggg tggtgcacgc tggccagcac   24060
gctcttgtcg gagatcagat ccgcgtccag gtcctccgcg ttgctcaggg cgaacggagt   24120
caactttggt agctgccttc ccaaaaaggg cgcgtgccca ggctttgagt tgcactcgca   24180
ccgtagtggc atcaaaaggt gaccgtgccc ggtctgggcg ttaggataca cgcctgcat   24240
aaaagccttg atctgcttaa aagccaccctg agcctttgcg ccttcagaga agaacatgcc   24300
gcaagacttg ccggaaaact gattggccgg acaggccgcg tcgtgcacgc agcaccttgc   24360
gtcggtgttg gagatctgca ccacatttcg gccccaccgg ttcttcacga tcttggcctt   24420
gctagactgc tccttcagcg cgcgctgccc gttttcgctc gtcacatcca tttcaatcac   24480
gtgctcctta tttatcataa tgcttccgtg tagacactta agctcgcctt cgatctcagc   24540
gcagcggtgc agccacaacg cgcagcccgt gggctcgtga tgcttgtagg tcacctctgc   24600
aaacgactgc aggtacgcct gcaggaatcg ccccatcatc gtcacaaagg tcttgttgct   24660
ggtgaaggtc agctgcaacc gcggtgctc ctcgttcagc caggtcttgc atacggccgc   24720
cagagcttcc acttggtcag gcagtagttt gaagttcgcc tttagatcgt tatccacgtg   24780
gtacttgtcc atcagcgcgc gcgcagcctc catgccttc tcccacgcag acacgatcgg   24840
cacactcagc gggttcatca ccgtaatttc actttccgct tcgctgggct cttcctcttc   24900
ctcttgcgtc cgcataccac gcgccactgg gtcgtcttca ttcagccgcc gcactgtgcg   24960
cttacctcct ttgccatgct tgattagcac cggtgggttg ctgaaaccca ccattttgtag   25020
cgccacatct tctctttctt cctcgctgtc cacgattacc tctggtgatg gcgggcgctc   25080
gggcttggga gaagggcgct tcttttttctt cttgggcgca atggccaaat ccgccgccga   25140
```

```
ggtcgatggc cgcgggctgg gtgtgcgcgg caccagcgcg tcttgtgatg agtcttcctc   25200
gtcctcggac tcgatacgcc gcctcatccg ctttttttggg ggcgcccggg gaggcggcgg   25260
cgacggggac ggggacgaca cgtcctccat ggttggggga cgtcgcgccg caccgcgtcc   25320
gcgctcgggg gtggtttcgc gctgctcctc ttcccgactg gccatttcct tctcctatag   25380
gcagaaaaag atcatggagt cagtcgagaa gaaggacagc ctaaccgccc cctctgagtt   25440
cgccaccacc gcctccaccg atgccgccaa cgcgcctacc accttccccg tcgaggcacc   25500
cccgcttgag gaggaggaag tgattatcga gcaggaccca ggttttgtaa gcgaagacga   25560
cgaggaccgc tcagtaccaa cagaggataa aaagcaagac caggacaacg cagaggcaaa   25620
cgaggaacaa gtcgggcggg gggacgaaag gcatggcgac tacctagatg tgggagacga   25680
cgtgctgttg aagcatctgc agcgccagtg cgccattatc tgcgacgcgt tgcaagagcg   25740
cagcgatgtg cccctcgcca tagcggatgt cagccttgcc tacgaacgcc acctattctc   25800
accgcgcgta cccccaaac gccaagaaaa cggcacatgc gagcccaacc cgcgcctcaa   25860
cttctacccc gtatttgccg tgccagaggt gcttgccacc tatcacatct ttttccaaaa   25920
ctgcaagata cccctatcct gccgtgccaa ccgcagccga gcgacaagc agctggcctt   25980
gcggcagggc gctgtcatac ctgatatcgc ctcgctcaac gaagtgccaa aaatctttga   26040
gggtcttgga cgcgacgaga agcgcgcggc aaacgctctg caacaggaaa acagcgaaaa   26100
tgaaagtcac tctggagtgt tggtggaact cgagggtgac aacgcgcgcc tagccgtact   26160
aaaacgcagc atcgaggtca cccactttgc ctacccggca cttaacctac cccaaggt   26220
catgagcaca gtcatgagtg agctgatcgt gcgccgtgcg cagcccctgg agagggatgc   26280
aaatttgcaa gaacaaacag aggagggcct acccgcagtt ggcgacgagc agctagcgcg   26340
ctggcttcaa acgcgcgagc ctgccgactt ggaggagcga cgcaaactaa tgatggccgc   26400
agtgctcgtt accgtggagc ttgagtgcat gcagcggttc tttgctgacc cggagatgca   26460
gcgcaagcta gaggaaacat tgcactacac ctttcgacag ggctacgtac gccaggcctg   26520
caagatctcc aacgtggagc tctgcaacct ggtctcctac cttggaattt tgcacgaaaa   26580
ccgccttggg caaaacgtgc ttcattccac gctcaagggc gaggcgcgcc gcgactacgt   26640
ccgcgactgc gtttacttat ttctatgcta cacctggcag acggccatgg gcgtttggca   26700
gcagtgcttg gaggagtgca acctcaagga gctgcagaaa ctgctaaagc aaaacttgaa   26760
ggacctatgg acggccttca acgagcgctc cgtggccgcg cacctggcgg acatcatttt   26820
ccccgaacgc ctgcttaaaa ccctgcaaca gggtctgcca gacttcacca gtcaaagcat   26880
gttgcagaac tttaggaact ttatcctaga gcgctcagga atcttgcccg ccacctgctg   26940
tgcacttcct agcgactttg tgcccattaa gtaccgcgaa tgccctccgc cgctttgggg   27000
ccactgctac cttctgcagc tagccaacta ccttgcctac cactctgaca ataatggaaga   27060
cgtgagcggt acggtctac tggagtgtca ctgtcgctgc aacctatgca cccgcaccg   27120
ctccctggtt tgcaattcgc agctgcttaa cgaaagtcaa attatcggta cctttgagct   27180
gcagggtccc tcgcctgacg aaaagtccgc ggctccgggg ttgaaactca ctccggggct   27240
gtggacgtcg gcttaccttc gcaaatttgt acctgaggac taccacgccc acgagattag   27300
gttctacgaa gaccaatccc gcccgccaaa tgcggagctt accgcctgcg tcattaccca   27360
gggccacatt cttggccaat gcaagccat caacaaagcc cgccaagagt ttctgctacg   27420
aaagggacgg ggggtttact tggacccca gtccggcgag gagctcaacc caatcccccc   27480
gccgccgcag ccctatcagc agcagccgcg ggcccttgct tcccaggatg gcacccaaaa   27540
```

```
agaagctgca gctgccgccg ccacccacgg acgaggagga atactgggac agtcaggcag    27600
aggaggtttt ggacgaggag gaggaggaca tgatggaaga ctgggagagc ctagacgagg    27660
aagcttccga ggtcgaagag gtgtcagacg aaacaccgtc accctcggtc gcattcccct    27720
cgccggcgcc ccagaaatcg gcaaccggtt ccagcatggc tacaacctcc gctcctcagg    27780
cgccgccggc actgcccgtt cgccgaccca accgtagatg ggacaccact ggaaccaggg    27840
ccggtaagtc caagcagccg ccgccgttag cccaagagca acaacagcgc caaggctacc    27900
gctcatggcg cgggcacaag aacgccatag ttgcttgctt gcaagactgt ggggcaaca    27960 tctccttcgc ccgccgcttt cttctctacc atcacggcgt ggccttcccc cgtaacatcc    28020
tgcattacta ccgtcatctc tacagcccat actgcaccgg cggcagcggc agcggcagca    28080
acagcagcgg ccacacagaa gcaaaggcga ccggatagca agactctgac aaagcccaag    28140
aaatccacag cggcggcagc agcaggagga ggagcgctgc gtctggcgcc caacgaaccc    28200
gtatcgaccc gcgagcttag aaacaggatt tttcccactc tgtatgctat atttcaacag    28260
agcaggggcc aagaacaaga gctgaaaata aaaaacaggt ctctgcgatc cctcacccgc    28320
agctgcctgt atcacaaaag cgaagatcag cttcggcgca cgctggaaga gcggaggct    28380 ctcttcagta aatactgcgc gctgactctt aaggactagt ttcgcgccct ttctcaaatt    28440
taagcgcgaa aactacgtca tctccagcgg ccacacccgg cgccagcacc tgtcgtcagc    28500
gccattatga gcaaggaaat tcccacgccc tacatgtgga gttaccagcc acaaatggga    28560
cttgcggctg gagctgccca agactactca acccgaataa actacatgag cgcgggaccc    28620
cacatgatat cccgggtcaa cggaatccgc gcccaccgaa accgaattct cttggaacag    28680
gcggctatta ccaccacacc tcgtaataac cttaatcccc gtagttggcc cgctgccctg    28740
gtgtaccagg aaagtcccgc tcccaccact gtggtacttc ccagagacgc ccaggccgaa    28800
gttcagatga ctaactcagg ggcgcagctt gcgggcggct ttcgtcacag ggtgcggtcg    28860
cccgggcagg gtataactca cctgacaatc agagggcgag gtattcagct caacgacgag    28920
tcggtgagct cctcgcttgg tctccgtccg gacgggacat ttcagatcgg cggcgccggc    28980
cgtccttcat tcacgcctcg tcaggcaatc ctaactctgc agacctcgtc ctctgagccg    29040
cgctctggag gcattggaac tctgcaattt attgaggagt ttgtgccatc ggtctacttt    29100
aaccccttct cgggacctcc cggccactat ccggatcaat ttattcctaa ctttgacgcg    29160
gtaaaggact cggcggacgg ctacgactga atgttaagtg gagaggcaga gcaactgcgc    29220
ctgaaacacc tggtccactg tcgccgccac aagtgctttg cccgcgactc cggtgagttt    29280
tgctactttg aattgcccga ggatcatatc gagggcccgg cgcacggcgt ccggcttacc    29340
gcccagggag agcttgcccg tagcctgatt cgggagttta cccagcgccc cctgctagtt    29400
gagcgggaca ggggaccctg tgttctcact gtgatttgca actgtcctaa ccttggatta    29460
catcaagatc ctctagttat aactagagta cccggggatc ttattccctt taactaataa    29520
aaaaaaataa taaagcatca cttacttaaa atcagtttagc aaatttctgt ccagtttatt    29580
cagcagcacc tccttgccct cctcccagct ctggtattgc agcttcctcc tggctgcaaa    29640 cttttctccac aatctaaatg gaatgtcagt ttcctcctgt tcctgtccat ccgcacccac    29700
cggtataact tcgtatatgg tttccttatac gaacggtaca agaacaagag ctgaaaataa    29760
aaaacaggtc tctgcgatcc ctcacccgca gctgcctgta tcacaaaagc gaagatcagc    29820
ttcggcgcac gctggaagac gcggaggctc tcttcagtaa atactgcgcg ctgactctta    29880
aggactagtt tcgcgccctt tctcaaattt aagcgcgaaa actacgtcat ctccagcggc    29940
```

```
cacacccggc gccagcacct gtcgtcagcg ccattatgag caaggaaatt cccacgccct   30000
acatgtggag ttaccagcca caaatgggac ttgcggctgg agctgcccaa gactactcaa   30060
cccgaataaa ctacatgagc gcgggacccc acatgatatc ccgggtcaac ggaatccgcg   30120
cccaccgaaa ccgaattctc ttggaacagg cggctattac caccacacct cgtaataacc   30180
ttaatccccg tagttggccc gctgccctgg tgtaccagga aagtcccgct cccaccactg   30240
tggtacttcc cagagacgcc caggccgaag ttcagatgac taactcaggg gcgcagcttg   30300
cgggcggctt tcgtcacagg gtgcggtcgc ccgggcaggg tataactcac ctgacaatca   30360
gagggcgagg tattcagctc aacgacgagt cggtgagctc ctcgcttggt ctccgtccgg   30420
acgggacatt tcagatcggc ggcgccggcc gtccttcatt cacgcctcgt caggcaatcc   30480
taactctgca gacctcgtcc tctgagccgc gctctggagg cattggaact ctgcaattta   30540
ttgaggagtt tgtgccatcg gtctacttta accccttctc gggacctccc ggccactatc   30600
cggatcaatt tattcctaac tttgacgcgg taaaggactc ggcggacggc tacgactgaa   30660
tgttaagtgg agaggcagag caactgcgcc tgaaacacct ggtccactgt cgccgccaca   30720
agtgctttgc ccgcgactcc ggtgagtttt gctactttga attgcccgag gatcatatcg   30780
agggcccggc gcacggcgtc cggcttaccg cccagggaga gcttgcccgt agcctgattc   30840
gggagtttac ccagcgcccc ctgctagttg agcgggacag gggaccctgt gttctcactg   30900
tgatttgcaa ctgtcctaac cttggattac atcaagatcc tctagttata actagagtac   30960
ccggggatct tattcccttt aactaataaa aaaaataat aaagcatcac ttacttaaaa   31020
tcagttagca aatttctgtc cagtttattc agcagcacct ccttgccctc ctcccagctc   31080
tggtattgca gcttcctcct ggctgcaaac tttctccaca atctaaatgg aatgtcagtt   31140
tcctcctgtt cctgtccatc cgcacccact atcttcatgt tgttgcagat accggtataa   31200
cttcgtatat ggtttcttat acgaagttat ctcgagaact atcttcatgt tgttgcagat   31260
gaagcgcgca agaccgtctg aagatacctt caaccccgtg tatccatatg acacggaaac   31320
cggtcctcca actgtgcctt tcttactcc tcccttgta tccccaatg ggtttcaaga   31380 gagtccccct ggggtactct cttgcgcct atccgaacct ctagttacct ccaatggcat   31440
gcttgcgctc aaaatgggca acggcctctc tctggacgag gccggcaacc ttacctccca   31500
aaatgtaacc actgtgagcc cacctctcaa aaaaccaag tcaaacataa acctggaaat   31560
atctgcaccc ctcacagtta cctcagaagc cctaactgtg gctgccgccg cacctctaat   31620
ggtcgcgggc aacacactca ccatgcaatc acaggccccg ctaaccgtgc acgactccaa   31680
acttagcatt gccacccaag gacccctcac agtgtcagaa ggaaagctag ccctgcaaac   31740
atcaggcccc ctcaccacca ccgatagcag taccttact atcactgcct cacccctct   31800 aactactgcc actggtagct tgggcattga cttgaaagag cccatttata cacaaaatgg   31860
aaaactagga ctaaagtacg gggctccttt gcatgtaaca gacgacctaa acactttgac   31920
cgtagcaact ggtccaggtg tgactattaa taatacttcc ttgcaaacta agttactgg   31980 agccttgggt tttgattcac aaggcaatat gcaacttaat gtagcaggag gactaaggat   32040
tgattctcaa aacagacgcc ttatacttga tgttagttat ccgtttgatg ctcaaaacca   32100
actaaatcta agactaggac agggccctct ttttataaac tcagcccaca acttggatat   32160
taactacaac aaaggccttt acttgtttac agcttcaaac aattccaaaa gcttgaggt   32220 taacctaagc actgccaagg ggttgatgtt tgacgctaca gccatagcca ttaatgcagg   32280
agatgggctt gaatttggtt cacctaatgc accaaacaca aatcccctca aaacaaaaat   32340
```

```
tggccatggc ctagaatttg attcaaacaa ggctatggtt cctaaactag gaactggcct    32400
tagttttgac agcacaggtg ccattacagt aggaaacaaa aataatgata agctaacttt    32460
gtggaccaca ccagctccat ctcctaactg tagactaaat gcagagaaag atgctaaact    32520
cactttggtc ttaacaaaat gtggcagtca aatacttgct acagtttcag ttttggctgt    32580
taaaggcagt ttggctccaa tatctggaac agttcaaagt gctcatctta ttataagatt    32640
tgacgaaaat ggagtgctac taaacaattc cttcctggac ccagaatatt ggaactttag    32700
aaatggagat cttactgaag gcacagccta tacaaacgct gttggattta tgcctaacct    32760
atcagcttat ccaaaatctc acggtaaaac tgccaaaagt aacattgtca gtcaagttta    32820
cttaaacgga gacaaaacta aacctgtaac actaaccatt acactaagcg gtacacagga    32880
atccggagac acaactccaa gtgcatactc tatgtcattt tcatgggact ggtctggcca    32940
caactacatt aatgaaatat ttgccacatc ctcttacact ttttcataca ttgcccaaga    33000
ataaagaagc ggccgcataa cttcgtatag catacattat acgaagttat accggtatac    33060
attgcccaag aataaagaat cgtttgtgtt atgtttcaac gtgtttattt ttcaattgca    33120
gaaaatttca agtcattttt cattcagtag tatagcccca ccaccacata gcttatacag    33180
atcaccgtac cttaatcaaa ctcacagaac cctagtattc aacctgccac ctccctccca    33240
acacacagag tacacagtcc tttctccccg gctggcctta aaaagcatca tatcatgggt    33300
aacagacata ttcttaggtg ttatattcca cacggttttcc tgtcgagcca acgctcatc    33360 agtgatatta ataaactccc cgggcagctc acttaagttc atgtcgctgt ccagctgctg    33420
agccacaggc tgctgtccaa cttgcggttg cttaacgggc ggcgaaggag aagtccacgc    33480
ctacatgggg gtagagtcat aatcgtgcat caggataggg cggtggtgct gcagcagcgc    33540
gcgaataaac tgctgccgcc gccgctccgt cctgcaggaa tacaacatgg cagtggtctc    33600
ctcagcgatg attcgcaccg cccgcagcat aaggcgcctt gtcctccggg cacagcagcg    33660
caccctgatc tcacttaaat cagcacagta actgcagcac agcaccacaa tattgttcaa    33720
aatcccacag tgcaaggcgc tgtatccaaa gctcatggcg gggaccacag aacccacgtg    33780
gccatcatac cacaagcgca ggtagattaa gtggcgaccc ctcataaaca cgctggacat    33840
aaacattacc tcttttggca tgttgtaatt caccacctcc cggtaccata taaacctctg    33900
attaaacatg gcgccatcca ccaccatcct aaaccagctg gccaaaacct gcccgccggc    33960
tatacactgc agggaaccgg gactggaaca atgacagtgg agagcccagg actcgtaacc    34020
atggatcatc atgctcgtca tgatatcaat gttggcacaa cacaggcaca cgtgcataca    34080
cttcctcagg attacaagct cctcccgcgt tagaaccata tcccagggaa caacccattc    34140
ctgaatcagc gtaaatccca cactgcaggg aagacctcgc acgtaactca cgttgtgcat    34200
tgtcaaagtg ttacattcgg gcagcagcgg atgatcctcc agtatggtag cgcgggtttc    34260
tgtctcaaaa ggaggtagac gatccctact gtacggagtg cgccgagaca accgagatcg    34320
tgttggtcgt agtgtcatgc caaatggaac gccggacgta gtcatatttc ctgaagcaaa    34380
accaggtgcg ggcgtgacaa acagatctgc gtctccggtc tcgccgctta gatcgctctg    34440
tgtagtagtt gtagtatatc cactctctca aagcatccag gcgccccctg gcttcgggtt    34500
ctatgtaaac tccttcatgc gccgctgccc tgataacatc caccaccgca gaataagcca    34560
cacccagcca acctacacat tcgttctgcg agtcacacac gggaggagcg ggaagagctg    34620
gaagaaccat gttttttttt ttattccaaa agattatcca aaacctcaaa atgaagatct    34680
attaagtgaa cgcgctcccc tccggtggcg tggtcaaact ctacagccaa agaacagata    34740
```

```
atggcatttg taagatgttg cacaatggct tccaaaaggc aaacggccct cacgtccaag    34800
tggacgtaaa ggctaaaccc ttcagggtga atctcctcta taaacattcc agcaccttca    34860
accatgccca ataattctc atctcgccac cttctcaata tatctctaag caaatcccga     34920
atattaagtc cggccattgt aaaaatctgc tccagagcgc cctccacctt cagcctcaag    34980
cagcgaatca tgattgcaaa aattcaggtt cctcacagac ctgtataaga ttcaaaagcg    35040
gaacattaac aaaaataccg cgatcccgta ggtcccttcg cagggccagc tgaacataat    35100
cgtgcaggtc tgcacggacc agcgcggcca cttccccgcc aggaaccttg acaaagaac     35160 ccacactgat tatgacacgc atactcggag ctatgctaac cagcgtagcc ccgatgtaag    35220
ctttgttgca tgggcggcga tataaaatgc aaggtgctgc tcaaaaaatc aggcaaagcc    35280
tcgcgcaaaa aagaaagcac atcgtagtca tgctcatgca gataaaggca ggtaagctcc    35340
ggaaccacca cagaaaaaga caccattttt ctctcaaaca tgtctgcggg tttctgcata    35400
aacacaaaat aaaataacaa aaaaacattt aaacattaga agcctgtctt acaacaggaa    35460
aaacaaccct tataagcata agacggacta cggccatgcc ggcgtgaccg taaaaaaact    35520
ggtcaccgtg attaaaaagc accaccgaca gctcctcggt catgtccgga gtcataatgt    35580
aagactcggt aaacacatca ggttgattca tcggtcagtg ctaaaaagcg accgaaatag    35640 cccggggaa tacatacccg caggcgtaga gacaacatta cagcccccat aggaggtata    35700
acaaaattaa taggagagaa aaacacataa acacctgaaa aaccctcctg cctaggcaaa    35760
atagcaccct cccgctccag aacaacatac agcgcttcac agcggcagcc taacagtcag    35820
ccttaccagt aaaaagaaa acctattaaa aaaacaccac tcgacacggc accagctcaa    35880
tcagtcacag tgtaaaaag ggccaagtgc agagcgagta tatataggac taaaaaatga     35940
cgtaacggtt aaagtccaca aaaaacaccc agaaaccgc acgcgaacct acgcccagaa    36000
acgaaagcca aaaaacccac aacttcctca aatcgtcact tccgttttcc cacgttacgt    36060
aacttcccat tttaagaaaa ctacaattcc caacacatac aagttactcc gccctaaaac    36120
ctacgtcacc cgccccgttc ccacgccccg cgccacgtca caaactccac cccctcatta    36180
tcatattggc ttcaatccaa aataaggtat attattgatg atttaattaa ggatccnnnc    36240
ctgtcctcga ccgatgccct tgagagcctt caacccagtc agctccttcc ggtgggcgcg    36300
gggcatgact atcgtcgccg cacttatgac tgtcttcttt atcatgcaac tcgtaggaca    36360
ggtgccggca gcgctctggg tcattttcgg cgaggaccgc tttcgctgga gcgcgacgat    36420
gatcggcctg tcgcttgcgg tattcggaat cttgcacgcc ctcgctcaag ccttcgtcac    36480
tggtcccgcc accaaacgtt tcggcgagaa gcaggccatt atcgccggca tggcggccga    36540
cgcgctgggc tacgtcttgc tggcgttcgc gacgcgaggc tggatggcct tccccattat    36600
gattcttctc gcttccggcg gcatcgggat gcccgcgttg caggccatgc tgtccaggca    36660
ggtagatgac gaccatcagg gacagcttca aggatcgctc gcggctctta ccagcctaac    36720
ttcgatcact ggaccgctga tcgtcacggc gatttatgcc gcctcggcga gcacatggaa    36780
cgggttggca tggattgtag cgccgccct ataccttgtc tgcctcccg cgttgcgtcg      36840 cggtgcatgg agccgggcca cctcgacctg aatggaagcc ggcggcacct cgctaacgga    36900
ttcaccactc caagaattgg agccaatcaa ttcttgcgga gaactgtgaa tgcgcaaacc    36960 aaccccttggc agaacatatc catcgcgtcc gccatctcca gcagccgcac gcggcgcatc    37020
tcgggcagcg ttgggtcctg gccacggggtg cgcatgatcg tgctcctgtc gttgaggacc    37080
cggctaggct ggcgggggttg ccttactggt tagcagaatg aatcaccgat acgcgagcga    37140
```

```
acgtgaagcg actgctgctg caaaacgtct gcgacctgag caacaacatg aatggtcttc   37200
ggtttccgtg tttcgtaaag tctggaaacg cggaagtcag cgccctgcac cattatgttc   37260
cggatctgca tcgcaggatg ctgctggcta ccctgtggaa cacctacatc tgtattaacg   37320
aagcgctggc attgaccctg agtgattttt ctctggtccc gccgcatcca taccgccagt   37380
tgtttaccct cacaacgttc cagtaaccgg gcatgttcat catcagtaac ccgtatcgtg   37440
agcatcctct ctcgtttcat cggtatcatt accccatga acagaaattc cccctacac    37500 ggaggcatca agtgaccaaa caggaaaaaa ccgcccttaa catggcccgc tttatcagaa   37560
gccagacatt aacgcttctg gagaaactca acgagctgga cgcggatgaa caggcagaca   37620
tctgtgaatc gcttcacgac cacgctgatg agctttaccg cagctgcctc gcgcgtttcg   37680
gtgatgacgg tgaaaacctc tgacacatgc agctcccgga cacggtcaca gcttgtctgt   37740
aagcggatgc cgggagcaga caagcccgtc agggcgcgtc agcgggtgtt ggcgggtgtc   37800
ggggcgcagc catgacccag tcacgtagcg atagcggagt gtatactggc ttaactatgc   37860
ggcatcagag cagattgtac tgagagtgca ccatatgcgg tgtgaaatac cgcacagatg   37920
cgtaaggaga aataccgca t                                               37941
```

```
<210> SEQ ID NO 2
<211> LENGTH: 8172
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: modified_base
<222> LOCATION: (9)..(11)
<223> OTHER INFORMATION: a, c, g, t, unknown, or other
<220> FEATURE:
<221> NAME/KEY: modified_base
<222> LOCATION: (352)..(354)
<223> OTHER INFORMATION: a, c, g, t, unknown, or other
<220> FEATURE:
<221> NAME/KEY: modified_base
<222> LOCATION: (1942)..(1944)
<223> OTHER INFORMATION: a, c, g, t, unknown, or other
<220> FEATURE:
<221> NAME/KEY: modified_base
<222> LOCATION: (2001)..(2003)
<223> OTHER INFORMATION: a, c, g, t, unknown, or other
<220> FEATURE:
<221> NAME/KEY: modified_base
<222> LOCATION: (4244)..(4246)
<223> OTHER INFORMATION: a, c, g, t, unknown, or other
<220> FEATURE:
<221> NAME/KEY: modified_base
<222> LOCATION: (4261)..(4263)
<223> OTHER INFORMATION: a, c, g, t, unknown, or other
<220> FEATURE:
<221> NAME/KEY: modified_base
<222> LOCATION: (5246)..(5248)
<223> OTHER INFORMATION: a, c, g, t, unknown, or other
<220> FEATURE:
<221> NAME/KEY: modified_base
<222> LOCATION: (5263)..(5265)
<223> OTHER INFORMATION: a, c, g, t, unknown, or other
<220> FEATURE:
<221> NAME/KEY: modified_base
<222> LOCATION: (6566)..(6571)
<223> OTHER INFORMATION: a, c, g, t, unknown, or other
<220> FEATURE:
<221> NAME/KEY: modified_base
<222> LOCATION: (8109)..(8172)
<223> OTHER INFORMATION: a, c, g, t, unknown, or other

<400> SEQUENCE: 2
```

```
ttaattaann ntcccttcca gctctctgcc cctttggat tgaagccaat atgataatga    60
gggggtggag tttgtgacgt ggcgcgggc gtgggaacgg ggcgggtgac gtagtagtgt   120
ggcggaagtg tgatgttgca agtgtggcgg aacacatgta agcgacggat gtggcaaaag   180
tgacgttttt ggtgtgcgcc ggtgtacaca ggaagtgaca attttcgcgc ggttttaggc   240
ggatgttgta gtaaatttgg gcgtaaccga gtaagatttg gccattttcg cgggaaaact   300
gaataagagg aagtgaaatc tgaataattt tgtgttactc atagcgcgta anncgcgtt   360 aagatacatt gatgagtttg gacaaaccac aactagaatg cagtgaaaaa aatgctttat   420
ttgtgaaatt tgtgatgcta ttgctttatt tgtaaccatt ataagctgca ataaacaagt   480
taacaacaac aattgcattc attttatgtt tcaggttcag ggggaggtgt gggaggtttt   540
ttaaagcaag taaaacctct acaaatgtgg tatggctgat tatgatcagt tatctagatc   600
cggtggatct gagtccggac ttgtacagct cgtccatgcc gagagtgatc ccggcggcgg   660
tcacgaactc cagcaggacc atgtgatcgc gcttctcgtt ggggtctttg ctcagggcgg   720
actgggtgct caggtagtgg ttgtcgggca gcagcacggg gccgtcgccg atggggtgt   780 tctgctggta gtggtcggcg agctgcacgc tgccgtcctc gatgttgtgg cggatcttga   840
agttcacctt gatgccgttc ttctgcttgt cggccatgat atagacgttg tggctgttgt   900
agttgtactc cagcttgtgc cccaggatgt tgccgtcctc cttgaagtcg atgcccttca   960
gctcgatgcg gttcaccagg gtgtcgccct cgaacttcac ctcggcgcgg tcttgtagt   1020 tgccgtcgtc cttgaagaag atggtgcgct cctggacgta gccttcgggc atggcggact  1080
tgaagaagtc gtgctgcttc atgtggtcgg ggtagcggct gaagcactgc acgccgtagg  1140
tcagggtggt cacgagggtg ggccagggca cgggcagctt gccggtggtg cagatgaact  1200
tcagggtcag cttgccgtag gtggcatcgc cctcgccctc gccggacacg ctgaacttgt  1260
ggccgtttac gtcgccgtcc agctcgacca ggatgggcac caccccggtg aacagctcct  1320
cgcccttgct caccatggtg gcgaccggta gcgctagcgg atctgacggt tcactaaacc  1380
agctctgctt atatagacct cccaccgtac acgcctaccg cccatttgcg tcaatggggc  1440
ggagttgtta cgacattttg gaaagtcccg ttgattttgg tgccaaaaca aactcccatt  1500
gacgtcaatg gggtggagac ttggaaatcc ccgtgagtca aaccgctatc cacgcccatt  1560
gatgtactgc caaaaccgca tcaccatggt aatagcgatg actaatacgt agatgtactg  1620
ccaagtagga aagtcccata aggtcatgta ctgggcataa tgccaggcgg gccatttacc  1680
gtcattgacg tcaataggg gcgtacttgg catatgatac acttgatgta ctgccaagtg  1740
ggcagtttac cgtaaatact ccacccattg acgtcaatgg aaagtcccta ttggcgttac  1800
tatgggaaca tacgtcatta ttgacgtcaa tgggcgggg tcgttgggcg gtcagccagg  1860
cgggccattt accgtaagtt atgtaacgcg gaactccata tatgggctat gaactaatga  1920
ccccgtaatt gattactatt annnctagca gatctggtac cgtcgacgcg gccgcgatat  1980
cctcgagaag ctttctagag nnntaagggt gggaaagaat atataaggtg ggggtcttat  2040
gtagttttgt atctgttttg cagcagccgc gccgccatg agcaccaact cgtttgatgg  2100
aagcattgtg agctcatatt tgacaacgcg catgcccca tgggccgggg tgcgtcagaa  2160
tgtgatgggc tccagcattg atggtcgccc cgtcctgccc gcaaactcta ctaccttgac  2220
ctacgagacc gtgtctggaa cgccgttgga gactgcagcc tccgccgccg cttcagccgc  2280
tgcagccacc gcccgcggga ttgtgactga ctttgctttc ctgagcccgc ttgcaagcag  2340
tgcagcttcc cgttcatccg cccgcgatga caagttgacg gctcttttgg cacaattgga  2400
```

```
ttctttgacc cgggaactta atgtcgtttc tcagcagctg ttggatctgc gccagcaggt    2460
ttctgccctg aaggcttcct ccctcccaa tgcggtttaa aacataaata aaaaaccaga    2520
ctctgtttgg atttggatca agcaagtgtc ttgctgtctt tatttagggg ttttgcgcgc    2580
gcggtaggcc cgggaccagc ggtctcggtc gttgagggtc ctgtgtattt tttccaggac    2640
gtggtaaagg tgactctgga tgttcagata catgggcata agcccgtctc tggggtggag    2700
gtagcaccac tgcagagctt catgctgcgg gtggtgttg tagatgatcc agtcgtagca    2760
ggagcgctgg gcgtggtgcc taaaaatgtc tttcagtagc aagctgattg ccaggggcag    2820
gcccttggtg taagtgttta caaagcggtt aagctgggat gggtgcatac gtggggatat    2880
gagatgcatc ttggactgta ttttaggtt ggctatgttc ccagccatat ccctccgggg    2940
attcatgttg tgcagaacca ccagcacagt gtatccggtg cacttgggaa atttgtcatg    3000
tagcttagaa ggaaatgcgt ggaagaactt ggagacgccc ttgtgacctc caagattttc    3060
catgcattcg tccataatga tggcaatggg cccacgggcg gcggcctggg cgaagatatt    3120
tctgggatca ctaacgtcat agttgtgttc caggatgaga tcgtcatagg ccatttttac    3180
aaagcgcggg cggagggtgc cagactgcgg tataatggtt ccatccggcc caggggcgta    3240
gttaccctca cagatttgca tttcccacgc tttgagttca gatgggggga tcatgtctac    3300
ctgcggggca tgaagaaaaa cggttttccgg ggtaggggag atcagctggg aagaaagcag    3360
gttcctgagc agctgcgact taccgcagcc ggtgggcccg taaatcacac ctattaccgg    3420
gtgcaactgg tagttaagag agctgcagct gccgtcatcc ctgagcaggg gggccacttc    3480
gttaagcatg tccctgactc gcatgttttc cctgaccaaa tccgcagaa ggcgctcgcc    3540
gcccagcgat agcagttctt gcaaggaagc aaagttttc aacggtttga accgtccgc    3600
cgtaggcatg cttttgagcg tttgaccaag cagttccagg cggtcccaca gctcggtcac    3660
ctgctctacg gcatctcgat ccagcatatc tcctcgtttc gcgggttggg gcggctttcg    3720
ctgtacggca gtagtcggtg ctcgtccaga cgggccaggt tcatgtcttt ccacgggcgc    3780
agggtcctcg tcagcgtagt ctgggtcacg gtgaagggt gcgctccggg ctgcgcgctg    3840
gccagggtgc gcttgaggct ggtcctgctg gtgctgaagc gctgccggtc ttcgccctgc    3900
gcgtcggcca ggtagcattt gaccatggtg tcatagtcca gcccctccgc ggcgtggccc    3960
ttggcgcgca gcttgccctt ggaggaggcg ccgcacgagg ggcagtgcag acttttgagg    4020
gcgtagagct tgggcgcgag aaataccgat tccggggagt aggcatccgc gccgcaggcc    4080
ccgcagacgt ctctcgcattc cacgagccag gtgagctctg gccgttcggg gtcaaaaacc    4140
aggtttcccc catgcttttt gatgcgtttc ttacctctgg tttccatgag ccggtgtcca    4200
cgctcggtga cgaaaaggct gtccgtgtcc ccgtatacag actnnngttt aaacgaattc    4260
nnntataaaa tgcaaggtgc tgctcaaaaa atcaggcaaa gcctcgcgca aaaagaaag    4320
cacatcgtag tcatgctcat gcagataaag gcagtaagc tccggaacca ccacagaaaa    4380
agacaccatt tttctctcaa acatgtctgc gggtttctgc ataaacacaa aataaaataa    4440
caaaaaaaca tttaaacatt agaagcctgt cttacaacag gaaaaacaac ccttataagc    4500
ataagacgga ctacggccat gccggcgtga ccgtaaaaaa actggtcacc gtgattaaaa    4560
agcaccaccg cacagctcctc ggtcatgtcc ggagtcataa tgtaagactc ggtaaacaca    4620
tcaggttgat tcatcggtca gtgctaaaaa gcgaccgaaa tagcccgggg gaatacatac    4680
ccgcaggcgt agagacaaca ttacagcccc cataggaggt ataacaaaat taataggaga    4740
gaaaaacaca taaacacctg aaaaaccctc ctgcctaggc aaaatagcac cctcccgctc    4800
```

```
cagaacaaca tacagcgctt cacagcggca gcctaacagt cagccttacc agtaaaaaag    4860
aaaacctatt aaaaaaacac cactcgacac ggcaccagct caatcagtca cagtgtaaaa    4920
aagggccaag tgcagagcga gtatatatag gactaaaaaa tgacgtaacg gttaaagtcc    4980
acaaaaaaca cccagaaaac cgcacgcgaa cctacgccca gaaacgaaag ccaaaaaacc    5040
cacaacttcc tcaaatcgtc acttccgttt tcccacgtta cgtaacttcc cattttaaga    5100
aaactacaat tcccaacaca tacaagttac tccgccctaa aacctacgtc acccgccccg    5160
ttcccacgcc ccgcgccacg tcacaaactc caccccctca ttatcatatt ggcttcaatc    5220
caaaataagg tatattattg atgatnnntt aattaaggat ccnnncggtg tgaaataccg    5280
cacagatgcg taaggagaaa ataccgcatc aggcgctctt ccgcttcctc gctcactgac    5340
tcgctgcgct cggtcgttcg gctgcggcga gcggtatcag ctcactcaaa ggcggtaata    5400
cggttatcca cagaatcagg ggataacgca ggaaagaaca tgtgagcaaa aggccagcaa    5460
aaggccagga accgtaaaaa ggccgcgttg ctggcgtttt tccataggct ccgcccccct    5520
gacgagcatc acaaaaatcg acgctcaagt cagaggtggc gaaacccgac aggactataa    5580
agataccagg cgtttccccc tggaagctcc ctcgtgcgct ctcctgttcc gaccctgccg    5640
cttaccggat acctgtccgc ctttctccct tcgggaagcg tggcgctttc tcatagctca    5700
cgctgtaggt atctcagttc ggtgtaggtc gttcgctcca agctgggctg tgtgcacgaa    5760
ccccccgttc agcccgaccg ctgcgcctta tccggtaact atcgtcttga gtccaacccg    5820
gtaagacacg acttatcgcc actggcagca gccactggta acaggattag cagagcgagg    5880
tatgtaggcg gtgctacaga gttcttgaag tggtggccta actacggcta cactagaagg    5940
acagtatttg gtatctgcgc tctgctgaag ccagttacct tcggaaaaag agttggtagc    6000
tcttgatccg gcaaacaaac caccgctggt agcggtggtt tttttgtttg caagcagcag    6060
attacgcgca gaaaaaaagg atctcaagaa gatcctttga tcttttctac ggggtctgac    6120
gctcagtgga acgaaaactc acgttaaggg attttggtca tgagattatc aaaaaggatc    6180
ttcacctaga tccttttaaa ttaaaaatga agttttaaat caatctaaag tatatatgag    6240
taaacttggt ctgacagtta ccaatgctta atcagtgagg cacctatctc agcgatctgt    6300
ctatttcgtt catccatagt tgcctgactc ccgtcgtgt agataactac gatacgggag    6360
ggcttaccat ctggccccag tgctgcaatg ataccgcgag acccacgctc accggctcca    6420
gatttatcag caataaacca gccagccgga agggccgagc gcagaagtgg tcctgcaact    6480
ttatccgcct ccatccagtc tattaattgt tgccgggaag ctagagtaag tagttcgcca    6540
gttaatagtt tgcgcaacgt tgttgnnnnn naaaaaggat cttcacctag atccttttca    6600
cgtagaaagc cagtccgcag aaacggtgct gaccccggat gaatgtcagc tactgggcta    6660
tctggacaag ggaaaacgca agcgcaaaga gaaagcaggt agcttgcagt gggcttacat    6720
ggcgatagct agactgggcg gttttatgga cagcaagcga accggaattg ccagctgggg    6780
cgccctctgg taaggttggg aagccctgca agtaaactg gatggctttc tcgccgccaa    6840
ggatctgatg cgcagggga tcaagctctg atcaagagac aggatgagga tcgtttcgca    6900
tgattgaaca agatggattg cacgcaggtt ctccggccgc ttgggtggag aggctattcg    6960
gctatgactg gcacaacag acaatcggct gctctgatgc cgccgtgttc cggctgtcag    7020
cgcaggggcg cccggttctt tttgtcaaga ccgacctgtc cggtgccctg aatgaactgc    7080
aagacgaggc agcgcggcta tcgtggctgg ccacgacggg cgttccttgc gcagctgtgc    7140
tcgacgttgt cactgaagcg ggaagggact ggctgctatt gggcgaagtg ccggggcagg    7200
```

```
atctcctgtc atctcacctt gctcctgccg agaaagtatc catcatggct gatgcaatgc    7260
ggcggctgca tacgcttgat ccggctacct gcccattcga ccaccaagcg aaacatcgca    7320
tcgagcgagc acgtactcgg atggaagccg gtcttgtcga tcaggatgat ctggacgaag    7380
agcatcaggg gctcgcgcca gccgaactgt tcgccaggct caaggcgagc atgcccgacg    7440
gcgaggatct cgtcgtgacc catggcgatg cctgcttgcc gaatatcatg gtggaaaatg    7500
gccgcttttc tggattcatc gactgtggcc ggctgggtgt ggcggaccgc tatcaggaca    7560
tagcgttggc tacccgtgat attgctgaag agcttggcgg cgaatgggct gaccgcttcc    7620
tcgtgcttta cggtatcgcc gctcccgatt cgcagcgcat cgccttctat cgccttcttg    7680
acgagttctt ctgaattttg ttaaattttt tgttaaatca gctcattttt taaccaatag    7740
gccgaaatcg gcaacatccc ttataaatca aagaataga ccgcgatagg gttgagtgtt    7800
gttccagttt ggaacaagag tccactatta agaacgtgg actccaacgt caagggcga    7860 aaaaccgtct atcagggcga tggcccacta cgtgaaccat cacccaaatc aagtttttg    7920 cggtcgaggt gccgtaaagc tctaaatcgg aaccctaaag ggagcccccg atttagagct    7980
tgacggggaa agccggcgaa cgtggcgaga aggaaggga agaaagcgaa aggagcgggc    8040
gctagggcgc tggcaagtgt agcggtcacg ctgcgcgtaa ccaccacacc cgcgcgctta    8100
atgcgccgnn nnnnnnnnn nnnnnnnnnn nnnnnnnnnn nnnnnnnnnn nnnnnnnnnn    8160
nnnnnnnnnn nn                                                       8172

<210> SEQ ID NO 3
<211> LENGTH: 4530
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3
tcgagaacta tcttcatgtt gttgcagatg aagcgcgcaa gaccgtctga agataccttc      60
aaccccgtgt atccatatga cacggaaacc ggtcctccaa ctgtgccttt tcttactcct     120 cccttttgtat cccccaatgg gtttcaagag agtcccctg gggtactctc tttgcgccta     180
tccgaacctc tagttacctc caatggcatg cttgcgctca aaatgggcaa cggcctctct     240
ctggacgagg ccggcaacct tacctcccaa aatgtaacca ctgtgagccc acctctcaaa     300 aaaccaagt caaacataaa cctggaaata tctgcacccc tcacagttac ctcagaagcc     360
ctaactgtgg ctgccgccgc acctctaatg gtcgcgggca acacactcac catgcaatca     420
caggccccgc taaccgtgca cgactccaaa cttagcattg ccacccaagg accccctcaca    480 gtgtcagaag gaaagctagc cctgcaaaca tcaggccccc tcaccaccac cgatagcagt     540
acccttacta tcactgcctc acccctctca actactgcca ctggtagctt gggcattgac     600
ttgaaagagc ccatttatac acaaaatgga aaactaggac taaagtacgg ggctcctttg     660
catgtaacag acgacctaaa cactttgacc gtagcaactg gtccaggtgt gactattaat     720
aatacttcct tgcaaactaa agttactgga gccttgggtt ttgattcaca aggcaatatg     780
caacttaatg tagcaggagg actaaggatt gattctcaaa acagacgcct tatacttgat     840
gttagttatc cgtttgatgc tcaaaaccaa ctaaatctaa gactaggaca gggccctctt     900
tttataaact cagcccacaa cttggatatt aactacaaca aaggcctta cttgtttaca     960 gcttcaaaca attccaaaaa gcttgaggtt aacctaagca ctgccaaggg gttgatgttt    1020
gacgctacag ccatagccat taatgcagga gatgggcttg aatttggttc acctaatgca    1080
```

```
ccaaacacaa atcccctcaa aacaaaaatt ggccatggcc tagaatttga ttcaaacaag    1140
gctatggttc ctaaactagg aactggcctt agttttgaca gcacaggtgc cattacagta    1200
ggaaacaaaa ataatgataa gctaactttg tggaccacac cagctccatc tcctaactgt    1260
agactaaatg cagagaaaga tgctaaactc actttggtct taacaaaatg tggcagtcaa    1320
atacttgcta cagtttcagt tttggctgtt aaaggcagtt tggctccaat atctggaaca    1380
gttcaaagtg ctcatcttat tataagattt gacgaaaatg gagtgctact aaacaattcc    1440
ttcctggacc cagaatattg gaactttaga aatggagatc ttactgaagg cacagcctat    1500
acaaacgctg ttggatttat gcctaaccta tcagcttatc caaaatctca cggtaaaact    1560
gccaaaagta acattgtcag tcaagtttac ttaaacggag acaaaactaa acctgtaaca    1620
ctaaccatta cactaagcgg tacacaggaa tccgagacaa caactccaag tgcatactct    1680
atgtcatttt catgggactg gtctggccac aactacatta atgaaatatt tgccacatcc    1740
tcttacactt tttcatacat tgcccaagaa taaagaagcg gccgcataac ttcgtatagc    1800
atacattata cgaacggtag gtaccgagct cgaattcact ggccgtcgtt ttacaacgtc    1860
gtgactggga aaaccctggc gttacccaac ttaatcgcct tgcagcacat ccccctttcg    1920
ccagctggcg taatagcgaa gaggcccgca ccgatcgccc ttcccaacag ttgcgcagcc    1980
tgaatggcga atggcgcctg atgcggtatt ttctccttac gcatctgtgc ggtatttcac    2040
accgcatatg gtgcactctc agtacaatct gctctgatgc cgcatagtta agccagcccc    2100
gacacccgcc aacacccgct gacgcgccct gacgggcttg tctgctcccg gcatccgctt    2160
acagacaagc tgtgaccgtc tccgggagct gcatgtgtca gaggttttca ccgtcatcac    2220
cgaaacgcgc gagacgaaag gcctcgtga tacgcctatt tttataggtt aatgtcatga    2280
taataatggt ttcttagacg tcaggtggca cttttcgggg aaatgtgcgc ggaacccta    2340 tttgtttatt tttctaaata cattcaaata tgtatccgct catgagacaa taaccctgat    2400
aaatgcttca ataatattga aaaggaaga gtatgagtat tcaacatttc cgtgtcgccc    2460
ttattccctt ttttgcggca ttttgccttc ctgttttgc tcacccagaa acgctggtga    2520
aagtaaaaga tgctgaagat cagttgggtg cacgagtggg ttacatcgaa ctggatctca    2580
acagcggtaa gatccttgag agttttcgcc ccgaagaacg ttttccaatg atgagcactt    2640
ttaaagttct gctatgtggc gcggtattat cccgtattga cgccgggcaa gagcaactcg    2700
gtcgccgcat acactattct cagaatgact tggttgagta ctcaccagtc acagaaaagc    2760
atcttacgga tggcatgaca gtaagagaat tatgcagtgc tgccataacc atgagtgata    2820
acactgcggc caacttactt ctgacaacga tcggaggacc gaaggagcta accgcttttt    2880
tgcacaacat gggggatcat gtaactcgcc ttgatcgttg ggaaccggag ctgaatgaag    2940
ccataccaaa cgacgagcgt gacaccacga tgcctgtagc aatggcaaca acgttgcgca    3000
aactattaac tggcgaacta cttactctag cttcccggca caattaata gactggatgg    3060 aggcggataa agttgcagga ccacttctgc gctcggccct tccggctggc tggtttattg    3120
ctgataaatc tggagccggt gagcgtgggt ctcgcggtat cattgcagca ctggggccag    3180
atggtaagcc ctcccgtatc gtagttatct acacgacggg gagtcaggca actatggatg    3240
aacgaaatag acagatcgct gagataggtg cctcactgat taagcattgg taactgtcag    3300
accaagttta ctcatatata ctttagattg atttaaaact tcattttta tttaaaagga    3360 tctaggtgaa gatcctttt gataatctca tgaccaaaat cccttaacgt gagttttcgt    3420
tccactgagc gtcagacccc gtagaaaaga tcaaaggatc ttcttgagat cctttttttc    3480
```

```
tgcgcgtaat ctgctgcttg caaacaaaaa aaccaccgct accagcggtg gtttgtttgc    3540
cggatcaaga gctaccaact cttttttccga aggtaactgg cttcagcaga gcgcagatac   3600
caaatactgt ccttctagtg tagccgtagt taggccacca cttcaagaac tctgtagcac    3660
cgcctacata cctcgctctg ctaatcctgt taccagtggc tgctgccagt ggcgataagt    3720
cgtgtcttac cgggttggac tcaagacgat agttaccgga taaggcgcag cggtcgggct    3780 gaacggggg ttcgtgcaca cagcccagct tggagcgaac gacctacacc gaactgagat     3840
acctacagcg tgagctatga aaagcgcca cgcttcccga agggagaaag gcggacaggt     3900
atccggtaag cggcagggtc ggaacaggag agcgcacgag ggagcttcca gggggaaacg    3960
cctggtatct ttatagtcct gtcgggtttc gccacctctg acttgagcgt cgatttttgt    4020
gatgctcgtc agggggggcgg agcctatgga aaaacgccag caacgcggcc ttttttacggt  4080 tcctggcctt tgctggcct tttgctcaca tgttctttcc tgcgttatcc cctgattctg     4140
tggataaccg tattaccgcc tttgagtgag ctgataccgc tcgccgcagc cgaacgaccg    4200
agcgcagcga gtcagtgagc gaggaagcgg aagagcgccc aatacgcaaa ccgcctctcc    4260
ccgcgcgttg gccgattcat taatgcagct ggcacgacag gtttcccgac tggaaagcgg    4320
gcagtgagcg caacgcaatt aatgtgagtt agctcactca ttaggcaccc caggctttac    4380
actttatgct tccggctcgt atgttgtgtg gaattgtgag cggataacaa tttcacacag    4440
gaaacagcta tgaccatgat tacgccaagc ttgcatgcct gcaggtcgac actagtaccg    4500
ttcgtatatg gtttcttata cgaagttatc                                     4530
```

```
<210> SEQ ID NO 4
<211> LENGTH: 4530
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4
```

```
ccggtttccg tgtcatatgg atacacgggg ttgaaggtat cttcagacgg tcttgcgcgc     60
ttcatctgca acaacatgaa gatagttctc gagataactt cgtataagaa accatatacg    120
aacggtacta gtgtcgacct gcaggcatgc aagcttggcg taatcatggt catagctgtt    180
tcctgtgtga aattgttatc cgctcacaat tccacacaac atacgagccg aagcataaa     240 gtgtaaagcc tggggtgcct aatgagtgag ctaactcaca ttaattgcgt tgcgctcact    300
gcccgctttc cagtcgggaa acctgtcgtg ccagctgcat taatgaatcg gccaacgcgc    360
ggggagaggc ggtttgcgta ttgggcgctc ttccgcttcc tcgctcactg actcgctgcg    420
ctcggtcgtt cggctgcggc gagcggtatc agctcactca aaggcggtaa tacggttatc    480
cacagaatca ggggataacg caggaaagaa catgtgagca aaaggccagc aaaaggccag    540
gaaccgtaaa aaggccgcgt tgctggcgtt tttccatagg ctccgccccc ctgacgagca    600
tcacaaaaat cgacgctcaa gtcagaggtg gcgaaacccg acaggactat aaagatacca    660
ggcgtttccc cctggaagct ccctcgtgcg ctctcctgtt ccgaccctgc cgcttaccgg    720
atacctgtcc gcctttctcc cttcgggaag cgtggcgctt tctcatagct cacgctgtag    780
gtatctcagt tcggtgtagg tcgttcgctc caagctgggc tgtgtgcacg aaccccccgt    840
tcagcccgac cgctgcgcct tatccggtaa ctatcgtctt gagtccaacc cggtaagaca    900
cgacttatcg ccactggcag cagccactgg taacaggatt agcagagcga ggtatgtagg    960
```

```
cggtgctaca gagttcttga agtggtggcc taactacggc tacactagaa ggacagtatt    1020
tggtatctgc gctctgctga agccagttac cttcggaaaa agagttggta gctcttgatc    1080
cggcaaacaa accaccgctg gtagcggtgg ttttttttgtt tgcaagcagc agattacgcg    1140
cagaaaaaaa ggatctcaag aagatccttt gatcttttct acggggtctg acgctcagtg    1200
gaacgaaaac tcacgttaag ggattttggt catgagatta tcaaaaagga tcttcaccta    1260 gatccttttta aattaaaaat gaagttttaa atcaatctaa agtatatatg agtaaacttg    1320
gtctgacagt taccaatgct taatcagtga ggcacctatc tcagcgatct gtctatttcg    1380
ttcatccata gttgcctgac tccccgtcgt gtagataact acgatacggg agggcttacc    1440
atctggcccc agtgctgcaa tgataccgcg agacccacgc tcaccggctc cagatttatc    1500
agcaataaac cagccagccg gaagggccga gcgcagaagt ggtcctgcaa ctttatccgc    1560
ctccatccag tctattaatt gttgccggga agctagagta agtagttcgc cagttaatag    1620
tttgcgcaac gttgttgcca ttgctacagg catcgtggtg tcacgctcgt cgtttggtat    1680
ggcttcattc agctccggtt cccaacgatc aaggcgagtt acatgatccc ccatgttgtg    1740
caaaaaagcg gttagctcct tcggtcctcc gatcgttgtc agaagtaagt tggccgcagt    1800
gttatcactc atggttatgg cagcactgca taattctctt actgtcatgc catccgtaag    1860
atgcttttct gtgactggtg agtactcaac caagtcattc tgagaatagt gtatgcggcg    1920
accgagttgc tcttgcccgg cgtcaatacg ggataatacc gcgccacata gcagaacttt    1980
aaaagtgctc atcattggaa aacgttcttc ggggcgaaaa ctctcaagga tcttaccgct    2040
gttgagatcc agttcgatgt aacccactcg tgcacccaac tgatcttcag catcttttac    2100
tttcaccagc gtttctgggt gagcaaaaac aggaaggcaa aatgccgcaa aaaagggaat    2160
aagggcgaca cggaaatgtt gaatactcat actcttcctt tttcaatatt attgaagcat    2220
ttatcagggt tattgtctca tgagcggata catatttgaa tgtatttaga aaaataaaca    2280
aataggggtt ccgcgcacat ttccccgaaa agtgccacct gacgtctaag aaaccattat    2340
tatcatgaca ttaacctata aaaataggcg tatcacgagg ccctttcgtc tcgcgcgttt    2400
cggtgatgac ggtgaaaacc tctgacacat gcagctcccg gagacggtca cagcttgtct    2460
gtaagcggat gccgggagca gacaagcccg tcagggcgcg tcagcgggtg ttggcgggtg    2520
tcggggctgg cttaactatg cggcatcaga gcagattgta ctgagagtgc accatatgcg    2580
gtgtgaaata ccgcacagat gcgtaaggag aaaataccgc atcaggcgcc attcgccatt    2640
caggctgcgc aactgttggg aagggcgatc ggtgcgggcc tcttcgctat tacgccagct    2700
ggcgaaaggg ggatgtgctg caaggcgatt aagttgggta acgccagggt tttcccagtc    2760
acgacgttgt aaaacgacgg ccagtgaatt cgagctcggt acctaccgtt cgtataatgt    2820
atgctatacg aagttatgcg gccgcttctt tattcttggg caatgtatga aaaagtgtaa    2880
gaggatgtgg caaatatttc attaatgtag ttgtggccag accagtccca tgaaaatgac    2940
atagagtatg cacttggagt tgtgtctccg gattcctgtg taccgtttag tgtaatggtt    3000
agtgttacag gttagtttt gtctccgttt aagtaaactt gactgacaat gttacttttg    3060
gcagttttac cgtgagattt tggataagct gataggttag gcataaatcc aacagcgttt    3120
gtataggctg tgccttcagt aagatctcca tttctaaagt tccaatattc tgggtccagg    3180
aaggaattgt ttagtagcac tccattttcg tcaaatctta taataagatg agcactttga    3240
actgttccag atattggagc caaactgcct ttaacagcca aaactgaaac tgtagcaagt    3300
atttgactgc cacattttgt taagaccaaa gtgagtttag catctttctc tgcatttagt    3360
```

```
ctacagttag gagatggagc tggtgtggtc cacaaagtta gcttatcatt attttttgttt    3420 cctactgtaa tggcacctgt gctgtcaaaa ctaaggccag ttcctagttt aggaaccata    3480
gccttgtttg aatcaaattc taggccatgg ccaattttg ttttgagggg atttgtgttt     3540
ggtgcattag gtgaaccaaa ttcaagccca tctcctgcat taatggctat ggctgtagcg    3600
tcaaacatca accccttggc agtgcttagg ttaacctcaa gcttttttgga attgtttgaa   3660 gctgtaaaca gtaaaggcc tttgttgtag ttaatatcca agttgtgggc tgagtttata     3720
aaaagagggc cctgtcctag tcttagattt agttggtttt gagcatcaaa cggataacta    3780
acatcaagta taaggcgtct gttttgagaa tcaatcctta gtcctcctgc tacattaagt    3840
tgcatattgc cttgtgaatc aaaacccaag gctccagtaa ctttagtttg caaggaagta    3900
ttattaatag tcacacctgg accagttgct acggtcaaag tgtttaggtc gtctgttaca    3960
tgcaaaggag ccccgtactt tagtcctagt tttccatttt gtgtataaat gggctctttc    4020
aagtcaatgc ccaagctacc agtggcagta gttagagggg gtgaggcagt gatagtaagg    4080
gtactgctat cggtggtggt gagggggcct gatgtttgca gggctagctt tccttctgac    4140
actgtgaggg gtccttgggt ggcaatgcta agttttggagt cgtgcacggt tagcggggcc    4200
tgtgattgca tggtgagtgt gttgcccgcg accattagag gtgcggcggc agccacagtt    4260
agggcttctg aggtaactgt gaggggtgca gatatttcca ggtttatgtt tgacttggtt    4320
tttttgagag gtgggctcac agtggttaca ttttgggagg taaggttgcc ggcctcgtcc    4380
agagagaggc cgttgcccat tttgagcgca agcatgccat tggaggtaac tagaggttcg    4440
gataggcgca aagagagtac cccaggggga ctctcttgaa acccattggg ggatacaaag    4500
ggaggagtaa gaaaaggcac agttggagga                                    4530
```

<210> SEQ ID NO 5
<211> LENGTH: 5383
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5

```
tcgagaacta tcttcatgtt gttgcagatg aagcgcgcaa gaccgtctga agataccttc      60
aaccccgtgt atccatatga cacggaaacc ggtcctccaa ctgtgccttt tcttactcct     120
ccctttgtat cccccaatgg gtttcaagag agtccccctg gggtactctc tttgcgccta     180
tccgaacctc tagttacctc caatggcatg cttgcgctca aaatgggcaa cggcctctct     240
ctggacgagg ccggcaacct tacctcccaa aatgtaacca ctgtgagccc acctctcaaa    300
aaaaccaagt caaacataaa cctggaaata tctgcacccc tcacagttac ctcagaagcc     360
ctaactgtgg ctgccgccgc acctctaatg gtcgcgggca acacactcac catgcaatca    420
caggccccgc taaccgtgca cgactccaaa cttagcattg ccacccaagg accctcaca    480 gtgtcagaag gaaagctagc cctgcaaaca tcaggccccc tcaccaccac cgatagcagt    540
acccttacta tcactgcctc accccctcta actactgcca ctggtagctt gggcattgac    600
ttgaaagagc ccatttatac acaaaatgga aaactaggac taaagtacgg ggctcctttg    660
catgtaacag acgacctaaa cactttgacc gtagcaactg tccaggtgt gactattaat     720 aatacttcct tgcaaactaa agttactgga gccttgggtt ttgattcaca aggcaatatg    780
caacttaatg tagcaggagg actaaggatt gattctcaaa acagacgcct tatacttgat    840
gttagttatc cgtttgatgc tcaaaaccaa ctaaatctaa gactaggaca gggccctctt    900
```

```
tttataaact cagcccacaa cttggatatt aactacaaca aaggccttta ccttgtttaca      960
gcttcaaaca attccaaaaa gcttgaggtt aacctaagca ctgccaaggg gttgatgttt     1020
gacgctacag ccatagccat taatgcagga gatgggcttg aatttggttc acctaatgca     1080
ccaaacacaa atccctcaa aacaaaaatt ggccatggcc tagaatttga ttcaaacaag      1140
gctatggttc ctaaactagg aactggcctt agttttgaca gcacaggtgc cattacagta     1200
ggaaacaaaa ataatgataa gctaactttg tggaccacac cagctccatc tcctaactgt     1260
agactaaatg cagagaaaga tgctaaactc actttggtct taacaaaatg tggcagtcaa     1320
atacttgcta cagtttcagt tttggctgtt aaaggcagtt tggctccaat atctggaaca     1380
gttcaaagtg ctcatcttat tataagattt gacgaaaatg gagtgctact aaacaattcc     1440
ttcctggacc cagaatattg gaactttaga aatggagatc ttactgaagg cacagcctat     1500
acaaacgctg ttggatttat gcctaaccta tcagcttatc caaatctca cggtaaaact     1560
gccaaaagta acattgtcag tcaagtttac ttaaacggag acaaaactaa acctgtaaca     1620
ctaaccatta cactaagcgg tacacaggaa tccggagaca caactccaag tgcatactct     1680
atgtcatttt catgggactg gtctggccac aactacatta tgaaatatt tgccacatcc      1740
tcttacactt tttcatacat tgcccaagaa taaagaagcg gccgcataac ttcgtatagc     1800
atacattata cgaacggtag gtaccaggta agtgtaccca attcgcccta tagtgagtcg     1860
tattacaatt cactggccgt cgttttacaa cgcctgatgc ggtattttct ccttacgcat     1920
ctgtgcggta tttcacaccg catatatggt gcactctcag tacaatctgc tctgatgccg     1980
catagttaag ccagccccga cacccgccaa cacccgctga cgcgccctga cgggcttgtc     2040
tgctcccggc atccgcttac agacaagctg tgaccgtctc cggagctgc atgtgtcaga     2100
ggttttcacc gtcatcaccg aaacgcgcga gacgaaaggg cctcgtgata cgcctatttt     2160
tataggttaa tgtcatgata taatggttt cttagacgtc aggtggcact tttcggggaa      2220
atgtgcgcgg aacccctatt tgtttatttt tctaaataca ttcaaatatg tatccgctca     2280
tgagacaata accctgataa atgcttcaat aatattgaaa aaggaagagt atgagtattc     2340
aacatttccg tgtcgccctt attcctttt ttgcggcatt ttgccttcct gtttttgctc      2400
acccagaaac gctggtgaaa gtaaaagatg ctgaagatca gttgggtgca cgagtgggtt     2460
acatcgaact ggatctcaac agcggtaaga tccttgagag ttttcgcccc gaagaacgtt     2520
ttccaatgat gagcactttt aaagttctgc tatgtggcgc ggtattatcc cgtattgacg     2580
ccgggcaaga gcaactcggt cgccgcatac actattctca gaatgacttg gttgagtact     2640
caccagtcac agaaaagcat cttacggatg gcatgacagt aagagaatta tgcagtgctg     2700
ccataaccat gagtgataac actgcggcca acttacttct gacaacgatc ggaggaccga     2760
aggagctaac cgcttttttg cacaacatgg gggatcatgt aactcgcctt gatcgttggg     2820
aaccggagct gaatgaagcc ataccaaacg acgagcgtga ccacgatgg cctgtagcaa      2880
tggcaacaac gttgcgcaaa ctattaactg gcgaactact tactctagct tcccggcaac     2940
aattaataga ctggatggag gcggataaag ttgcaggacc acttctgcgc tcggcccttc     3000
cggctggctg gtttattgct gataaatctg gagccggtga gcgtgggtct cgcggtatca     3060
ttgcagcact ggggccagat ggtaagccct cccgtatcgt agttatctac acgacgggga     3120
gtcaggcaac tatggatgaa cgaaatagac agatcgctga gataggtgcc tcactgatta     3180
agcattggta actgtcagac caagtttact catatatact ttagattgat ttaaaacttc     3240
attttttaatt taaaaggatc taggtgaaga tcctttttga taatctcatg accaaaatcc     3300
```

```
cttaacgtga gttttcgttc cactgagcgt cagaccccgt agaaaagatc aaaggatctt    3360
cttgagatcc ttttttttctg cgcgtaatct gctgcttgca acaaaaaaaa ccaccgctac   3420
cagcggtggt ttgtttgccg gatcaagagc taccaactct ttttccgaag gtaactggct   3480
tcagcagagc gcagatacca atactgtcc ttctagtgta gccgtagtta ggccaccact    3540
tcaagaactc tgtagcaccg cctacatacc tcgctctgct aatcctgtta ccagtggctg   3600
ctgccagtgg cgataagtcg tgtcttaccg ggttggactc aagacgatag ttaccggata   3660
aggcgcagcg tcgggctga acgggggggtt cgtgcacaca gcccagcttg gagcgaacga   3720
cctacaccga actgagatac ctacagcgtg agcattgaga aagcgccacg cttcccgaag   3780
ggagaaaggc ggacaggtat ccggtaagcg gcagggtcgg aacaggagag cgcacgaggg   3840
agcttccagg gggaaacgcc tggtatcttt atagtcctgt cgggtttcgc cacctctgac   3900
ttgagcgtcg attttttgtga tgctcgtcag ggggcggag cctatggaaa aacgccagca   3960
acgcggcctt tttacggttc ctggccttttt gctggccttt tgctcacatg ctgggcccag   4020
ccggccagat ctgagctcgc ggccgcgata tcgctagctc gaggtccgtt acataactta   4080
cggtaaatgg cccgcctggc tgaccgccca acgacccccg cccattgacg tcaataatga   4140
cgtatgttcc catagtaacg ccaatagggga ctttccattg acgtcaatgg gtggagtatt   4200
tacggtaaac tgcccacttg gcagtacatc aagtgtatca tatgccaagt acgcccccta   4260
ttgacgtcaa tgacggtaaa tggcccgcct ggcattatgc ccagtacatg accttatggg   4320
actttcctac ttggcagtac atctacgtat tagtcatcgc tattaccatg gtgatgcggt   4380
tttggcagta catcaatggg cgtggatagc ggtttgactc acggggattt ccaagtctcc   4440
accccattga cgtcaatggg agtttgtttt ggcaccaaaa tcaacgggac tttccaaaat   4500
gtcgtaacaa ctccgcccca ttgacgcaaa tgggcggtag gcgtgtacgg tgggaggtct   4560
atataagcag agctcgttta gtgaaccgtc agatcgcctg gagacgccat ccacgctgtt   4620
ttgacctcca tagaagacac cgggaccgat ccagcctccg cggccgggaa cggtgcattg   4680
gaacggaccg tgttgacaat taatcatcgg catagtatat cggcatagta taatacgaca   4740
aggtgaggaa ctaaaccatg ccaagccctt tgtctcaaga agaatccacc ctcattgaaa   4800
gagcaacggc tacaatcaac agcatcccca tctctgaaga ctacagcgtc gccagcgcag   4860
ctctctctag cgacggccgc atcttcactg gtgtcaatgt atatcatttt actgggggac   4920
cttgtgcaga actcgtggtg ctgggcactg ctgctgctgc ggcagctggc aacctgactt   4980
gtatcgtcgc gatcggaaat gagaacaggg gcatcttgag cccctgcgga cggtgccgac   5040
aggtgcttct cgatctgcat cctgggatca aagccatagt gaaggacagt gatggacagc   5100
cgacggcagt tgggattcgt gaattgctgc cctctggtta tgtgtgggag ggctaagcac   5160
ttcgtggccg aggagcagga ctgacactcg acctcgaaac ttgttttattg cagcttataa   5220 tggttacaaa taaagcaata gcatcacaaa tttcacaaat aaagcatttt tttcactgca   5280
ttctagttgt ggtttgtcca aactcatcaa tgtatcttat catgtctgaa ttcccgggga   5340
tcctctagta ccgttcgtat atggtttctt atacgaagtt atc                     5383
```

<210> SEQ ID NO 6
<211> LENGTH: 33991
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:

```
<221> NAME/KEY: modified_base
<222> LOCATION: (10)..(12)
<223> OTHER INFORMATION: a, c, g, t, unknown, or other
<220> FEATURE:
<221> NAME/KEY: modified_base
<222> LOCATION: (3655)..(3657)
<223> OTHER INFORMATION: a, c, g, t, unknown, or other
<220> FEATURE:
<221> NAME/KEY: modified_base
<222> LOCATION: (3684)..(3686)
<223> OTHER INFORMATION: a, c, g, t, unknown, or other

<400> SEQUENCE: 6
```

| | | | | | |
|---|---|---|---|---|---|
| taaggatccn | nncctgtcct | cgaccgatgc | ccttgagagc | cttcaaccca | gtcagctcct | 60 |
| tccggtgggc | gcggggcatg | actatcgtcg | ccgcacttat | gactgtcttc | tttatcatgc | 120 |
| aactcgtagg | acaggtgccg | gcagcgctct | gggtcatttt | cggcgaggac | cgctttcgct | 180 |
| ggagcgcgac | gatgatcggc | ctgtcgcttg | cggtattcgg | aatcttgcac | gccctcgctc | 240 |
| aagccttcgt | cactggtccc | gccaccaaac | gtttcggcga | gaagcaggcc | attatcgccg | 300 |
| gcatggcggc | cgacgcgctg | ggctacgtct | tgctggcgtt | cgcgacgcga | ggctggatgg | 360 |
| ccttccccat | tatgattctt | ctcgcttccg | gcggcatcgg | gatgcccgcg | ttgcaggcca | 420 |
| tgctgtccag | gcaggtagat | gacgaccatc | agggacagct | tcaaggatcg | ctcgcggctc | 480 |
| ttaccagcct | aacttcgatc | actggaccgc | tgatcgtcac | ggcgatttat | gccgcctcgg | 540 |
| cgagcacatg | gaacgggttg | gcatggattg | taggcgccgc | cctatacctt | gtctgcctcc | 600 |
| ccgcgttgcg | tcgcggtgca | tggagccggg | ccacctcgac | ctgaatggaa | gccggcggca | 660 |
| cctcgctaac | ggattcacca | ctccaagaat | tggagccaat | caattcttgc | ggagaactgt | 720 |
| gaatgcgcaa | accaacccctt | ggcagaacat | atccatcgcg | tccgccatct | ccagcagccg | 780 |
| cacgcggcgc | atctcgggca | gcgttgggtc | ctggccacgg | gtgcgcatga | tcgtgctcct | 840 |
| gtcgttgagg | accggctag | gctggcgggg | ttgccttact | ggttagcaga | atgaatcacc | 900 |
| gatacgcgag | cgaacgtgaa | gcgactgctg | ctgcaaaacg | tctgcgacct | gagcaacaac | 960 |
| atgaatggtc | ttcggtttcc | gtgtttcgta | aagtctggaa | acgcggaagt | cagcgccctg | 1020 |
| caccattatg | ttccggatct | gcatcgcagg | atgctgctgg | ctaccctgtg | gaacacctac | 1080 |
| atctgtatta | acgaagcgct | ggcattgacc | ctgagtgatt | tttctctggt | cccgccgcat | 1140 |
| ccataccgcc | agttgtttac | cctcacaacg | ttccagtaac | cgggcatgtt | catcatcagt | 1200 |
| aacccgtatc | gtgagcatcc | tctctcgttt | catcggtatc | attaccccca | tgaacagaaa | 1260 |
| ttccccctta | cacggaggca | tcaagtgacc | aaacaggaaa | aaaccgccct | taacatggcc | 1320 |
| cgctttatca | gaagccagac | attaacgctt | ctggagaaac | tcaacgagct | ggacgcggat | 1380 |
| gaacaggcag | acatctgtga | atcgcttcac | gaccacgctg | atgagcttta | ccgcagctgc | 1440 |
| ctcgcgcgtt | tcggtgatga | cggtgaaaac | ctctgacaca | tgcagctccc | ggagacggtc | 1500 |
| acagcttgtc | tgtaagcgga | tgccgggagc | agacaagccc | gtcagggcgc | gtcagcgggt | 1560 |
| gttggcgggt | gtcggggcgc | agccatgacc | cagtcacgta | gcgatagcgg | agtgtatact | 1620 |
| ggcttaacta | tgcggcatca | gagcagattg | tactgagagt | gcaccatatg | cggtgtgaaa | 1680 |
| taccgcacag | atgcgtaagg | agaaaatacc | gcatcaggcg | ctcttccgct | tcctcgctca | 1740 |
| ctgactcgct | gcgctcggtc | gttcggctgc | ggcgagcggt | atcagctcac | tcaaaggcgg | 1800 |
| taatacggtt | atccacagaa | tcaggggata | acgcaggaaa | gaacatgtga | gcaaaaggcc | 1860 |
| agcaaaaggc | caggaaccgt | aaaaaggccg | cgttgctggc | gtttttccat | aggctccgcc | 1920 |
| cccctgacga | gcatcacaaa | aatcgacgct | caagtcagag | gtggcgaaac | ccgacaggac | 1980 |

```
tataaagata ccaggcgttt cccccctggaa gctccctcgt gcgctctcct gttccgaccc    2040
tgccgcttac cggatacctg tccgcctttc tcccttcggg aagcgtggcg ctttctcaat    2100
gctcacgctg taggtatctc agttcggtgt aggtcgttcg ctccaagctg gctgtgtgc    2160
acgaaccccc cgttcagccc gaccgctgcg cctatccgg taactatcgt cttgagtcca    2220
acccggtaag acacgactta tcgccactgg cagcagccac tggtaacagg attagcagag    2280
cgaggtatgt aggcggtgct acagagttct gaagtggtg gcctaactac ggctacacta    2340
gaaggacagt atttggtatc tgcgctctgc tgaagccagt taccttcgga aaaagagttg    2400
gtagctcttg atccggcaaa caaaccaccg ctggtagcgg tggttttttt gtttgcaagc    2460
agcagattac gcgcagaaaa aaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt taaatcaatc taaagtatat    2640
atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg ggaagctaga gtaagtagtt    2940
cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa acaggaagg caaaatgccg    3480
caaaaaaggg aataagggcg acacggaaat gttgaatact catactcttc cttttttcaat    3540
attattgaag catttatcag ggttattgtc tcatgagcgg atacatattt gaatgtattt    3600
agaaaaataa acaaataggg gttccgcgca catttccccg aaaagtgcca cctgnnngaa    3660
ttcgaatcta gtatcgattc gaannnctta agggtgggaa agaatatata aggtgggggt    3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg ctttcctgag cccgcttgca    4020
agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctcccct cccaatgcgg tttaaaacat aaataaaaaa    4200
ccagactctg tttggatttg gatcaagcaa gtgtcttgct gtctttattt aggggttttg    4260
cgcgcgcggt aggcccggga ccagcggtct cggtcgttga gggtcctgtg tattttttcc    4320
aggacgtggt aaaggtgact ctggatgttc agatacatgg gcataagccc gtctctgggg    4380
```

```
tggaggtagc accactgcag agcttcatgc tgcggggtgg tgttgtagat gatccagtcg    4440
tagcaggagc gctgggcgtg gtgcctaaaa atgtctttca gtagcaagct gattgccagg    4500
ggcaggccct tggtgtaagt gtttacaaag cggttaagct gggatgggtg catacgtggg    4560
gatatgagat gcatcttgga ctgtatttt aggttggcta tgttcccagc catatccctc    4620
cggggattca tgttgtgcag aaccaccagc acagtgtatc cggtgcactt gggaaatttg    4680
tcatgtagct tagaaggaaa tgcgtggaag aacttggaga cgcccttgtg acctccaaga    4740
ttttccatgc attcgtccat aatgatggca atgggcccac gggcggcggc ctgggcgaag    4800
atatttctgg gatcactaac gtcatagttg tgttccagga tgagatcgtc ataggccatt    4860
tttacaaagc gcgggcggag ggtgccagac tgcggtataa tggttccatc cggcccaggg    4920
gcgtagttac cctcacagat ttgcatttcc cacgctttga gttcagatgg ggggatcatg    4980
tctacctgcg gggcgatgaa gaaaacggtt tccggggtag gggagatcag ctgggaagaa    5040
agcaggttcc tgagcagctg cgacttaccg cagccggtgg gcccgtaaat cacacctatt    5100
accgggtgca actggtagtt aagagagctg cagctgccgt catccctgag cagggggggcc    5160
acttcgttaa gcatgtccct gactcgcatg ttttccctga ccaaatccgc cagaaggcgc    5220
tcgccgccca gcgatagcag ttcttgcaag gaagcaaagt ttttcaacgg tttgagaccg    5280
tccgccgtag gcatgctttt gagcgtttga ccaagcagtt ccaggcggtc ccacagctcg    5340
gtcacctgct ctacggcatc tcgatccagc atatctcctc gtttcgcggg ttggggcggc    5400
tttcgctgta cggcagtagt cggtgctcgt ccagacgggc cagggtcatg tctttccacg    5460
ggcgcagggt cctcgtcagc gtagtctggg tcacggtgaa ggggtgcgct ccgggctgcg    5520
cgctggccag ggtgcgcttg aggctggtcc tgctggtgct gaagcgctgc cggtcttcgc    5580
cctgcgcgtc ggccaggtag catttgacca tggtgtcata gtccagcccc tccgcggcgt    5640
ggcccttggc gcgcagcttg cccttggagg aggcgccgca cgaggggcag tgcagacttt    5700
tgagggcgta gagcttgggc gcgagaaata ccgattccgg ggagtaggca tccgcgccgc    5760
aggccccgca gacggtctcg cattccacga gccaggtgag ctctggccgt tcggggtcaa    5820
aaaccaggtt tccccccatgc tttttgatgc gtttcttacc tctggtttcc atgagccggt    5880
gtccacgctc ggtgacgaaa aggctgtccg tgtccccgta tacagacttg agaggcctgt    5940
cctcgagcgg tgttccgcgg tcctcctcgt atagaaactc ggaccactct gagacaaagg    6000
ctcgcgtcca ggccagcacg aaggaggcta agtgggaggg gtagcggtcg ttgtccacta    6060
gggggtccac tcgctccagg gtgtgaagac acatgtcgcc ctcttcggca tcaaggaagg    6120
tgattggttt gtaggtgtag gccacgtgac cgggtgttcc tgaagggggg ctataaaagg    6180
gggtgggggc gcgttcgtcc tcactctctt ccgcatcgct gtctgcgagg ccagctgtt    6240
ggggtgagta ctcccctctga aaagcgggca tgacttctgc gctaagattg tcagttttcca    6300
aaaacgagga ggatttgata ttcacctggc ccgcggtgat gcctttgagg gtggccgcat    6360
ccatctggtc agaaaagaca atcttttttgt tgtcaagctt ggtggcaaac gacccgtaga    6420
gggcgttgga cagcaacttg gcgatggagc gcagggtttg gttttttgtcg cgatcggcgc    6480
gctccttggc cgcgatgttt agctgcacgt attcgcgcgc aacgcaccgc cattcgggaa    6540
agacggtggt gcgctcgtcg ggcaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggggtctg    6720
cgtccacggt aaagaccccg ggcagcaggc gcgcgtcgaa gtagtctatc ttgcatcctt    6780
```

| | | | | |
|---|---|---|---|---|
| gcaagtctag | cgcctgctgc | catgcgcggg | cggcaagcgc | gcgctcgtat gggttgagtg | 6840 |
| ggggacccca | tgggcatgggg | tgggtgagcg | cggaggcgta | catgccgcaa atgtcgtaaa | 6900 |
| cgtagagggg | ctctctgagt | attccaagat | atgtagggta | gcatcttcca ccgcggatgc | 6960 |
| tggcgcgcac | gtaatcgtat | agttcgtgcg | agggagcgag | gaggtcggga ccgaggttgc | 7020 |
| tacgggcggg | ctgctctgct | cggaagacta | tctgcctgaa | gatggcatgt gagttggatg | 7080 |
| atatggttgg | acgctggaag | acgttgaagc | tggcgtctgt | gagacctacc gcgtcacgca | 7140 |
| cgaaggaggc | gtaggagtcg | cgcagcttgt | tgaccagctc | ggcggtgacc tgcacgtcta | 7200 |
| gggcgcagta | gtccagggtt | tccttgatga | tgtcatactt | atcctgtccc tttttttttcc | 7260 |
| acagctcgcg | gttgaggaca | aactcttcgc | ggtctttcca | gtactcttgg atcggaaacc | 7320 |
| cgtcggcctc | cgaacggtaa | gagcctagca | tgtagaactg | gttgacggcc tggtaggcgc | 7380 |
| agcatccctt | ttctacgggt | agcgcgtatg | cctgcgcggc | cttccggagc gaggtgtggg | 7440 |
| tgagcgcaaa | ggtgtccctg | accatgactt | tgaggtactg | gtatttgaag tcagtgtcgt | 7500 |
| cgcatccgcc | ctgctcccag | agcaaaaagt | ccgtgcgctt | tttggaacgc ggatttggca | 7560 |
| gggcgaaggt | gacatcgttg | aagagtatct | ttcccgcgcg | aggcataaag ttgcgtgtga | 7620 |
| tgcggaaggg | tcccggcacc | tcggaacggt | tgttaattac | ctgggcggcg agcacgatct | 7680 |
| cgtcaaagcc | gttgatgttg | tggcccacaa | tgtaaagttc | caagaagcgc gggatgccct | 7740 |
| tgatggaagg | caattttttta | agttcctcgt | aggtgagctc | ttcaggggag ctgagcccgt | 7800 |
| gctctgaaag | ggcccagtct | gcaagatgag | ggttggaagc | gacgaatgag ctccacaggt | 7860 |
| cacgggccat | tagcatttgc | aggtggtcgc | gaaaggtcct | aaactggcga cctatggcca | 7920 |
| ttttttctgg | ggtgatgcag | tagaaggtaa | gcgggtcttg | ttcccagcgg tcccatccaa | 7980 |
| ggttcgcggc | taggtctcgc | gcggcagtca | ctagaggctc | atctccgccg aacttcatga | 8040 |
| ccagcatgaa | gggcacgagc | tgcttcccaa | aggcccccat | ccaagtatag gtctctacat | 8100 |
| cgtaggtgac | aaagagacgc | tcggtgcgag | gatgcgagcc | gatcgggaag aactggatct | 8160 |
| cccgccacca | attggaggag | tggctattga | tgtggtgaaa | gtagaagtcc ctgcgacggg | 8220 |
| ccgaacactc | gtgctggctt | ttgtaaaaac | gtgcgcagta | ctggcagcgg tgcacgggct | 8280 |
| gtacatcctg | cacgaggttg | acctgacgac | cgcgcacaag | gaagcagagt gggaatttga | 8340 |
| gccccctcgcc | tggcgggttt | ggctggtggt | cttctactttc | ggctgcttgt ccttgaccgt | 8400 |
| ctggctgctc | gagggagtt | acggtggatc | ggaccaccac | gccgcgcgag cccaaagtcc | 8460 |
| agatgtccgc | gcgcggcggt | cggagcttga | tgacaacatc | gcgcagatgg gagctgtcca | 8520 |
| tggtctggag | ctcccgcggc | gtcaggtcag | gcgggagctc | ctgcaggttt acctcgcata | 8580 |
| gacgggtcag | ggcgcgggct | agatccaggt | gataccctaat | ttccaggggc tggttggtgg | 8640 |
| cggcgtcgat | ggcttgcaag | aggccgcatc | cccgcggcgc | gactacggta ccgcgcggcg | 8700 |
| ggcggtgggc | cgcgggggtg | tccttggatg | atgcatctaa | aagcggtgac gcgggcgagc | 8760 |
| ccccggaggt | agggggggct | ccggacccgc | cgggagaggg | ggcaggggca cgtcggcgcc | 8820 |
| gcgcgcgggc | aggagctggt | gctgcgcgcg | taggttgctg | gcgaacgcga cgacgcggcg | 8880 |
| gttgatctcc | tgaatctggc | gcctctgcgt | gaagacgacg | ggcccggtga gcttgagcct | 8940 |
| gaaagagagt | tcgacagaat | caatttcggt | gtcgttgacg | gcggcctggc gcaaaatctc | 9000 |
| ctgcacgtct | cctgagttgt | cttgataggc | gatctcggcc | atgaactgct cgatctcttc | 9060 |
| ctcctggaga | tctccgcgtc | cggctcgctc | cacggtggcg | gcgaggtcgt tggaaatgcg | 9120 |
| ggccatgagc | tgcgagaagg | cgttgaggcc | tccctcgttc | cagacgcggc tgtagaccac | 9180 |

-continued

| | | | | | |
|---|---|---|---|---|---|
| gcccccttcg | gcatcgcggg | cgcgcatgac | cacctgcgcg | agattgagct | ccacgtgccg | 9240 |
| ggcgaagacg | gcgtagtttc | gcaggcgctg | aaagaggtag | ttgagggtgg | tggcggtgtg | 9300 |
| ttctgccacg | aagaagtaca | taacccagcg | tcgcaacgtg | gattcgttga | tatcccccaa | 9360 |
| ggcctcaagg | cgctccatgg | cctcgtagaa | gtccacggcg | aagttgaaaa | actgggagtt | 9420 |
| gcgcgccgac | acggttaact | cctcctccag | aagacggatg | agctcggcga | cagtgtcgcg | 9480 |
| cacctcgcgc | tcaaaggcta | cagggggcctc | ttcttcttct | tcaatctcct | cttccataag | 9540 |
| ggcctcccct | tcttcttctt | ctggcggcgg | tgggggaggg | gggacacggc | ggcgacgacg | 9600 |
| gcgcaccgga | aggcggtcga | caaagcgctc | gatcatctcc | ccgcggcgac | ggcgcatggt | 9660 |
| ctcggtgacg | gcgcggccgt | tctcgcgggg | gcgcagttgg | aagacgccgc | ccgtcatgtc | 9720 |
| ccggttatgg | gttggcgggg | ggctgccatg | cggcagggat | acggcgctaa | cgatgcatct | 9780 |
| caacaattgt | tgtgtaggta | ctccgccgcc | gagggacctg | agcgagtccg | catcgaccgg | 9840 |
| atcggaaaac | ctctcgagaa | aggcgtctaa | ccagtcacag | tcgcaaggta | ggctgagcac | 9900 |
| cgtggcgggc | ggcagcgggc | ggcggtcggg | gttgtttctg | gcggaggtgc | tgctgatgat | 9960 |
| gtaattaaag | taggcggtct | tgagacgcg | gatggtcgac | agaagcacca | tgtccttggg | 10020 |
| tccggcctgc | tgaatgcgca | ggcggtcggc | catgccccag | gcttcgtttt | gacatcggcg | 10080 |
| caggtctttg | tagtagtctt | gcatgagcct | ttctaccggc | acttcttctt | ctccttcctc | 10140 |
| ttgtcctgca | tctcttgcat | ctatcgctgc | ggcggcggcg | gagtttggcc | gtaggtggcg | 10200 |
| ccctcttcct | cccatgcgtg | tgaccccgaa | gccctcatc | ggctgaagca | gggctaggtc | 10260 |
| ggcgacaacg | cgctcggcta | atatggcctg | ctgcacctgc | gtgagggtag | actggaagtc | 10320 |
| atccatgtcc | acaaagcggt | ggtatgcgcc | cgtgttgatg | gtgtaagtgc | agttggccat | 10380 |
| aacggaccag | ttaacggtct | ggtgacccgg | ctgcagagc | tcggtgtacc | tgagacgcga | 10440 |
| gtaagccctc | gagtcaaata | cgtagtcgtt | gcaagtccgc | accaggtact | ggtatcccac | 10500 |
| caaaaagtgc | ggcggcggct | ggcggtagag | gggccagcgt | agggtggccg | gggctccggg | 10560 |
| ggcgagatct | tccaacataa | ggcgatgata | tccgtagatg | tacctggaca | tccaggtgat | 10620 |
| gccggcggcg | gtggtggagg | cgcgcggaaa | gtcgcggacg | cggttccaga | tgttgcgcag | 10680 |
| cggcaaaaag | tgctccatgg | tcgggacgct | ctggccggtc | aggcgcgcgc | aatcgttgac | 10740 |
| gctctaccgt | gcaaaggag | agcctgtaag | cgggcactct | tccgtggtct | ggtggataaa | 10800 |
| ttcgcaaggg | tatcatggcg | gacgaccggg | gttcgagccc | cgtatccggc | cgtccgccgt | 10860 |
| gatccatgcg | gttaccgccc | gcgtgtcgaa | cccaggtgtg | cgacgtcaga | caacggggga | 10920 |
| gtgctccttt | tggcttcctt | ccaggcgcgg | cggctgctgc | gctagctttt | ttggccactg | 10980 |
| gccgcgcgca | gcgtaagcgg | ttaggctgga | aagcgaaagc | attaagtggc | tcgctccctg | 11040 |
| tagccggagg | gttattttcc | aagggttgag | tcgcgggacc | cccggttcga | gtctcggacc | 11100 |
| ggccggactg | cggcgaacgg | gggttttgcct | cccgtcatg | caagaccccg | cttgcaaatt | 11160 |
| cctccggaaa | cagggacgag | cccctttttt | gcttttccca | gatgcatccg | gtgctgcggc | 11220 |
| agatgcgccc | ccctcctcag | cagcggcaag | agcaagagca | gcggcagaca | tgcagggcac | 11280 |
| cctcccctcc | tcctaccgcg | tcaggagggg | cgacatccgc | ggttgacgcg | gcagcagatg | 11340 |
| gtgattacga | accccgcgg | cgccgggccc | ggcactacct | ggacttggag | gagggcgagg | 11400 |
| gcctggcgcg | gctaggagcg | ccctctcctg | agcggtaccc | aagggtgcag | ctgaagcgtg | 11460 |
| atacgcgtga | ggcgtacgtg | ccgcggcaga | acctgtttcg | cgaccgcgag | ggagaggagc | 11520 |
| ccgaggagat | gcgggatcga | aagttccacg | cagggcgcga | gctgcggcat | ggcctgaatc | 11580 |

```
gcgagcggtt gctgcgcgag gaggactttg agcccgacgc gcgaaccggg attagtcccg   11640
cgcgcgcaca cgtggcggcc gccgacctgg taaccgcata cgagcagacg gtgaaccagg   11700
agattaactt tcaaaaaagc tttaacaacc acgtgcgtac gcttgtggcg cgcgaggagg   11760
tggctatagg actgatgcat ctgtgggact ttgtaagcgc gctggagcaa aacccaaata   11820
gcaagccgct catggcgcag ctgttcctta tagtgcagca cagcagggac aacgaggcat   11880
tcagggatgc gctgctaaac atagtagagc ccgagggccg ctggctgctc gatttgataa   11940
acatcctgca gagcatagtg gtgcaggagc gcagcttgag cctggctgac aaggtggccg   12000
ccatcaacta ttccatgctt agcctgggca agttttacgc ccgcaagata taccatccc    12060 cttacgttcc catagacaag gaggtaaaga tcgaggggtt ctacatgcgc atggcgctga   12120
aggtgcttac cttgagcgac gacctggcg tttatcgcaa cgagcgcatc cacaaggccg    12180
tgagcgtgag ccggcggcgc gagctcagcg accgcgagct gatgcacagc ctgcaaaggg   12240
ccctggctgg cacgggcagc ggcgatagag aggccgagtc ctactttgac gcgggcgctg   12300
acctgcgctg ggccccaagc cgacgcgccc tggaggcagc tggggccgga cctgggctgg   12360
cggtggcacc cgcgcgcgct ggcaacgtcg gcggcgtgga ggaatatgac gaggacgatg   12420
agtacgagcc agaggacggc gagtactaag cggtgatgtt tctgatcaga tgatgcaaga   12480
cgcaacggac ccggcggtgc gggcggcgct gcagagccag ccgtccggcc ttaactccac   12540
ggacgactgg cgccaggtca tggaccgcat catgtcgctg actgcgcgca atcctgacgc   12600
gttccggcag cagccgcagg ccaaccggct ctccgcaatt ctggaagcgg tggtcccggc   12660
gcgcgcaaac cccacgcacg agaaggtgct ggcgatcgta aacgcgctgg ccgaaaacag   12720
ggccatccgg cccgacgagg ccggcctggt ctacgacgcg ctgcttcagc gcgtggctcg   12780
ttacaacagc ggcaacgtgc agaccaacct ggaccggctg gtggggatg tgcgcgaggc    12840 cgtggcgcag cgtgagcgcg cgcagcagca gggcaacctg gctccatgg ttgcactaaa    12900 cgccttcctg agtacacagc ccgccaacgt gccgcgggga caggaggact acaccaactt   12960
tgtgagcgca ctgcggctaa tggtgactga gacaccgcaa agtgaggtgt accagtctgg   13020
gccagactat ttttttccaga ccagtagaca aggcctgcag accgtaaacc tgagccaggc   13080
tttcaaaaac ttgcaggggc tgtgggggt gcgggctccc acaggcgacc gcgcgaccgt    13140
gtctagcttg ctgacgccca actcgcgcct gttgctgctg ctaatagcgc ccttcacgga   13200
cagtggcagc gtgtcccggg acacatacct aggtcacttg ctgacactgt accgcgaggc   13260
cataggtcag gcgcatgtgg acgagcatac tttccaggag attacaagtg tcagccgcgc   13320
gctggggcag gaggacacgg gcagcctgga ggcaaccta aactacctgc tgaccaaccg    13380
gcggcagaag atcccctcgt tgcacagttt aaacagcgag gaggagcgca ttttgcgcta   13440
cgtgcagcag agcgtgagcc ttaacctgat gcgcgacggg gtaacgccca cgtggcgct    13500 ggacatgacc gcgcgcaaca tggaaccggg catgtatgcc tcaaaccggc cgtttatcaa   13560
ccgcctaatg gactacttgc atcgcgcggc cgccgtgaac cccgagtatt tcaccaatgc   13620
catcttgaac ccgcactggc taccgccccc tggtttctac accggggat tcgaggtgcc    13680 cgagggtaac gatggattcc tctgggacga catagacgac agcgtgtttt ccccgcaacc   13740
gcagaccctg ctagagttgc aacagcgcga caggcagag gcggcgctgc gaaaggaaag    13800
cttccgcagg ccaagcagct tgtccgatct aggcgctgcg ccccgcggt cagatgctag    13860 tagcccattt ccaagcttga tagggtctct taccagcact cgcaccaccc gcccgcgcct   13920
gctgggcgag gaggagtacc taaacaactc gctgctgcag ccgcagcgcg aaaaaaacct   13980
```

```
gcctccggca tttcccaaca acgggataga gagcctagtg gacaagatga gtagatggaa   14040
gacgtacgcg caggagcaca gggacgtgcc aggcccgcgc ccgcccaccc gtcgtcaaag   14100
gcacgaccgt cagcggggtc tggtgtggga ggacgatgac tcggcagacg acagcagcgt   14160
cctggatttg ggagggagtg gcaacccgtt tgcgcacctt cgcccaggc tggggagaat    14220 gttttaaaaa aaaaaaagca tgatgcaaaa taaaaaactc accaaggcca tggcaccgag   14280
cgttggtttt cttgtattcc ccttagtatg cggcgcgcgg cgatgtatga ggaaggtcct   14340
cctccctcct acgagagtgt ggtgagcgcg cgccagtgg cggcggcgct gggttctccc    14400
ttcgatgctc ccctggaccc gccgtttgtg cctccgcggt acctgcggcc taccgggggg   14460
agaaacagca tccgttactc tgagttggca ccctattcg acaccacccg tgtgtacctg    14520
gtggacaaca agtcaacgga tgtggcatcc ctgaactacc agaacgacca cagcaacttt   14580
ctgaccacgg tcattcaaaa caatgactac agcccggggg aggcaagcac acagaccatc   14640
aatcttgacg accggtcgca ctggggcggc gacctgaaaa ccatcctgca taccaacatg   14700
ccaaatgtga acgagttcat gtttaccaat aagtttaagg cgcgggtgat ggtgtcgcgc   14760
ttgcctacta aggacaatca ggtggagctg aaatacgagt gggtggagtt cacgctgccc   14820
gagggcaact actccgagac catgaccata gaccttatga caacgcgat cgtggagcac    14880 tacttgaaag tgggcagaca gaacgggtt ctggaaagcg catcggggt aaagtttgac     14940 acccgcaact tcagactggg gtttgacccc gtcactggtc ttgtcatgcc tggggtatat   15000
acaaacgaag ccttccatcc agacatcatt ttgctgccag gatgcggggt ggacttcacc   15060
cacagccgcc tgagcaactt gttgggcatc cgcaagcggc aacccttcca ggagggcttt   15120
aggatcacct acgatgatct ggaggtggt aacattcccg cactgttgga tgtggacgcc    15180
taccaggcga gcttgaaaga tgacaccgaa cagggcgggg gtggcgcagg cggcagcaac   15240
agcagtggca gcggcgcgga agagaactcc aacgcggcag ccgcggcaat gcagccggtg   15300
gaggacatga acgatcatgc cattcgcggc gacacctttg ccacacgggc tgaggagaag   15360
cgcgctgagg ccgaagcagc ggccgaagct gccgccccg ctgcgcaacc cgaggtcgag    15420
aagcctcaga gaaaccggt gatcaaaccc ctgacagagg acagcaagaa acgcagttac    15480
aacctaataa gcaatgacag caccttcacc cagtaccgca gctggtacct tgcatacaac   15540 tacgcgacc ctcagaccgg aatccgctca tggaccctgc tttgcactcc tgacgtaacc    15600
tgcggctcgg agcaggtcta ctggtcgttg ccagacatga tgcaagaccc cgtgaccttc   15660
cgctccacgc gccagatcag caactttccg gtggtgggcg ccgagctgtt gcccgtgcac   15720
tccaagagct tctacaacga ccaggccgtc tactcccaac tcatccgcca gtttacctct   15780
ctgacccacg tgttcaatcg ctttcccgag aaccagattt ggcgcgccc gccagccccc   15840 accatcacca ccgtcagtga aaacgttcct gctctcacag atcacgggac gctaccgctg   15900
cgcaacagca tcggaggagt ccagcgagtg accattactg acgccagacg ccgcacctgc   15960
ccctacgttt acaaggccct gggcatagtc tcgccgcgcg tcctatcgag ccgcactttt   16020
tgagcaagca tgtccatcct tatatcgccc agcaataaca caggctgggg cctgcgcttc   16080
ccaagcaaga tgtttggcgg ggccaagaag cgctccgacc aacacccagt gcgcgtgcgc   16140
gggcactacc gcgcgccctg gggcgcgcac aaacgcggcc gcactgggcg caccaccgtc   16200
gatgacgcca tcgacgcggt ggtggaggag gcgcgcaact acacgcccac gccgccacca   16260
gtgtccacag tggacgcggc cattcagacc gtggtgcgcg gagcccggcg ctatgctaaa   16320
atgaagagac ggcggaggcg cgtagcacgt cgccaccgcc gccgaccegg cactgccgcc   16380
```

```
caacgcgcgg cggcggccct gcttaaccgc gcacgtcgca ccggccgacg ggcggccatg   16440
cgggccgctc gaaggctggc cgcgggtatt gtcactgtgc cccccaggtc caggcgacga   16500
gcggccgccg cagcagccgc ggccattagt gctatgactc agggtcgcag gggcaacgtg   16560
tattgggtgc gcgactcggt tagcggcctg cgcgtgcccg tgcgcacccg ccccccgcgc   16620
aactagattg caagaaaaaa ctacttagac tcgtactgtt gtatgtatcc agcggcggcg   16680
gcgcgcaacg aagctatgtc caagcgcaaa atcaaagaag agatgctcca ggtcatcgcg   16740
ccggagatct atgcccccc gaagaaggaa gagcaggatt acaagccccg aaagctaaag   16800
cgggtcaaaa agaaaaagaa agatgatgat gatgaacttg acgacgaggt ggaactgctg   16860
cacgctaccg cgcccaggcg acgggtacag tggaaaggtc gacgcgtaaa acgtgttttg   16920
cgacccggca ccaccgtagt ctttacgccc ggtgagcgct ccacccgcac ctacaagcgc   16980
gtgtatgatg aggtgtacgg cgacgaggac ctgcttgagc aggccaacga gcgcctcggg   17040
gagtttgcct acgaaagcg gcataaggac atgctggcgt tgccgctgga cgagggcaac   17100
ccaacaccta gcctaaagcc cgtaacactg cagcaggtgc tgcccgcgct tgcaccgtcc   17160
gaagaaaagc gcggcctaaa gcgcgagtct ggtgacttgg cacccaccgt gcagctgatg   17220
gtacccaagc gccagcgact ggaagatgtc ttggaaaaaa tgaccgtgga acctgggctg   17280
gagcccgagg tccgcgtgcg gccaatcaag caggtggcgc cgggactggg cgtgcagacc   17340
gtggacgttc agatacccac taccagtagc accagtattg ccaccgccac agagggcatg   17400
gagacacaaa cgtccccggt tgcctcagcg gtggcggatg ccgcggtgca ggcggtcgct   17460
gcggccgcgt ccaagacctc tacggaggtg caaacggacc cgtggatgtt tcgcgtttca   17520
gccccccggc gccgcgcgg ttcgaggaag tacggcgccg ccagcgcgct actgcccgaa   17580
tatgccctac atccttccat tgcgcctacc cccggctatc gtggctacac ctaccgcccc   17640
agaagacgag caactacccg acgccgaacc accactggaa cccgccgccg ccgtcgccgt   17700
cgccagcccg tgctggcccc gatttccgtg cgcagggtgg ctcgcgaagg aggcaggacc   17760
ctggtgctgc caacagcgcg ctaccacccc agcatcgttt aaaagccggt ctttgtggtt   17820
cttgcagata tggccctcac ctgccgcctc cgtttcccgg tgccgggatt ccgaggaaga   17880
atgcaccgta ggaggggcat ggccggccac ggcctgacgg gcggcatgcg tcgtgcgcac   17940
caccggcggc ggcgcgcgtc gcaccgtcgc atgcgcggcg gtatcctgcc cctccttatt   18000
ccactgatcg ccgcggcgat tggcgccgtg cccggaattg catccgtggc cttgcaggcg   18060
cagagacact gattaaaaac aagttgcatg tggaaaaatc aaaataaaaa gtctggactc   18120
tcacgctcgc ttggtcctgt aactattttg tagaatggaa gacatcaact ttgcgtctct   18180
ggccccgcga cacggctcgc gcccgttcat gggaaactgg caagatatcg gcaccagcaa   18240
tatgagcggt ggcgccttca gctggggctc gctgtggagc ggcattaaaa atttcggttc   18300
caccgttaag aactatggca gcaaggcctg gaacagcagc acaggccaga tgctgaggga   18360
taagttgaaa gagcaaaatt tccaacaaaa ggtggtagat ggcctggcct ctggcattag   18420
cggggtggtg gacctggcca accaggcagt gcaaaataag attaacagta agcttgatcc   18480
ccgccctccc gtagaggagc ctccaccggc cgtggagaca gtgtctccag aggggcgtgg   18540
cgaaaagcgt ccgcgcccg acagggaaga aactctggtg acgcaaatag acgagcctcc   18600
ctcgtacgag gaggcactaa agcaaggcct gcccaccacc gtcccatcg cgcccatggc   18660 taccggagtg ctgggccagc acacacccgt aacgctggac ctgcctcccc ccgccgacac   18720
ccagcagaaa cctgtgctgc caggcccgac cgccgttgtt gtaacccgtc ctagccgcgc   18780
```

```
gtccctgcgc cgcgccgcca gcggtccgcg atcgttgcgg cccgtagcca gtggcaactg    18840
gcaaagcaca ctgaacagca tcgtgggtct gggggtgcaa tccctgaagc gccgacgatg    18900
cttctgaata gctaacgtgt cgtatgtgtg tcatgtatgc gtccatgtcg ccgccagagg    18960
agctgctgag ccgccgcgcg cccgcttccc aagatggcta ccccttcgat gatgccgcag    19020
tggtcttaca tgcacatctc gggccaggac gcctcggagt acctgagccc cgggctggtg    19080
cagtttgccc gcgccaccga gacgtacttc agcctgaata caagtttag aaaccccacg     19140 gtggcgccta cgcacgacgt gaccacagac cggtcccagc gtttgacgct gcggttcatc    19200
cctgtggacc gtgaggatac tgcgtactcg tacaaggcgc ggttcacccct agctgtgggt    19260 gataaccgtg tgctggacat ggcttccacg tactttgaca tccgcggcgt gctggacagg    19320
ggccctactt ttaagcccta ctctggcact gcctacaacg ccctggctcc caagggtgcc    19380
ccaaatcctt gcgaatggga tgaagctgct actgctcttg aaataaacct agaagaagag    19440
gacgatgaca acgaagacga agtagacgag caagctgagc agcaaaaaac tcacgtattt    19500
gggcaggcgc cttattctgg tataaatatt acaaggagg gtattcaaat aggtgtcgaa      19560
ggtcaaacac ctaaatatgc cgataaaaca tttcaacctg aacctcaaat aggagaatct    19620
cagtggtacg aaactgaaat taatcatgca gctgggagag tccttaaaaa gactacccca    19680
atgaaaccat gttacggttc atatgcaaaa cccacaaatg aaaatggagg gcaaggcatt    19740
cttgtaaagc aacaaaatgg aaagctagaa agtcaagtgg aaatgcaatt tttctcaact    19800
actgaggcga ccgcaggcaa tggtgataac ttgactccta aagtggtatt gtacagtgaa    19860
gatgtagata tagaaacccc agacactcat atttcttaca tgcccactat taaggaaggt    19920
aactcacgag aactaatggg ccaacaatct atgcccaaca ggcctaatta cattgctttt    19980
agggacaatt ttattggtct aatgtattac aacagcacgg gtaatatggg tgttctggcg    20040
ggccaagcat cgcagttgaa tgctgttgta gatttgcaag acagaaacac agagcttttca    20100 taccagctt tgcttgattc cattggtgat agaaccaggt acttttctat gtggaatcag    20160
gctgttgaca gctatgatcc agatgttaga attattgaaa atcatggaac tgaagatgaa    20220
cttccaaatt actgctttcc actgggaggt gtgattaata cagagactct taccaaggta    20280
aaacctaaaa caggtcagga aaatggatgg gaaaagatg ctacagaatt ttcagataaa     20340
aatgaaataa gagttggaaa taattttgcc atggaaatca atctaaatgc caacctgtgg    20400
agaaatttcc tgtactccaa catagcgctg tatttgcccg acaagctaaa gtacagtcct    20460
tccaacgtaa aaatttctga taacccaaac acctacgact acatgaacaa gcgagtggtg    20520
gctcccgggt tagtggactg ctacattaac cttggagcac gctggtccct tgactatatg    20580
gacaacgtca acccatttaa ccaccaccgc aatgctggcc tgcgctaccg ctcaatgttg    20640
ctgggcaatg gtcgctatgt gcccttccac atccaggtgc ctcagaagtt ctttgccatt    20700
aaaaacctcc ttctcctgcc gggctcatac acctacgagt ggaacttcag gaaggatgtt    20760
aacatggttc tgcagagctc cctaggaaat gacctaaggg ttgacggagc cagcattaag    20820
tttgatagca tttgcctta cgccaccttc ttccccatgg cccacaacac cgcctccacg    20880
cttgaggcca tgcttagaaa cgacaccaac gaccagtcct ttaacgacta tctctccgcc    20940
gccaacatgc tctaccctat acccgccaac gctaccaacg tgcccatatc catccccctcc    21000 cgcaactggg cggctttccg cggctgggcc ttcacgcgcc ttaagactaa ggaaacccca    21060
tcactgggct cgggctacga ccctattac acctactctg gctctatacc ctacctagat    21120 ggaaccttt acctcaacca caccttaag aaggtggcca ttaccttga ctcttctgtc        21180
```

```
agctggcctg gcaatgaccg cctgcttacc cccaacgagt ttgaaattaa gcgctcagtt     21240
gacggggagg gttacaacgt tgcccagtgt aacatgacca aagactggtt cctggtacaa     21300
atgctagcta actacaacat tggctaccag ggcttctata tcccagagag ctacaaggac     21360
cgcatgtact ccttctttag aaacttccag cccatgagcc gtcaggtggt ggatgatact     21420
aaatacaagg actaccaaca ggtgggcatc ctacaccaac acaacaactc tggatttgtt     21480
ggctaccttg cccccaccat gcgcgaagga caggcctacc ctgctaactt cccctatccg     21540
cttataggca agaccgcagt tgacagcatt acccagaaaa agtttctttg cgatcgcacc     21600 cttggcgca tcccattctc cagtaacttt atgtccatgg gcgcactcac agacctgggc     21660
caaaaccttc tctacgccaa ctccgcccac gcgctagaca tgacttttga ggtggatccc     21720
atggacgagc ccaccctttct ttatgttttg tttgaagtct ttgacgtggt ccgtgtgcac     21780
cggccgcacc gcggcgtcat cgaaaccgtg tacctgcgca cgcccttctc ggccggcaac     21840
gccacaacat aaagaagcaa gcaacatcaa caacagctgc cgccatgggc tccagtgagc     21900
aggaactgaa agccattgtc aaagatcttg gttgtgggcc atattttttg ggcacctatg     21960
acaagcgctt tccaggcttt gtttctccac acaagctcgc ctgcgccata gtcaatacgg     22020
ccggtcgcga gactggggggc gtacactgga tggccttttgc ctggaacccg cactcaaaaa     22080
catgctacct ctttgagccc tttggctttt ctgaccagcg actcaagcag gtttaccagt     22140
ttgagtacga gtcactcctg cgccgtagcg ccattgcttc ttcccccgac cgctgtataa     22200
cgctggaaaa gtccacccaa agcgtacagg ggcccaactc ggccgcctgt ggactattct     22260
gctgcatgtt tctccacgcc tttgccaact ggccccaaac tcccatggat cacaaccccca     22320 ccatgaacct tattaccggg gtacccaact ccatgctcaa cagtccccag gtacagccca     22380
ccctgcgtcg caaccaggaa cagctctaca gcttcctgga gcgccactcg ccctacttcc     22440
gcagccacag tgcgcagatt aggagcgcca cttctttttg tcacttgaaa aacatgtaaa     22500
aataatgtac tagagacact ttcaataaag gcaaatgctt ttatttgtac actctcgggt     22560
gattatttac ccccacccctt gccgtctgcg ccgtttaaaa atcaaagggg ttctgccgcg     22620
catcgctatg cgccactggc agggacacgt tgcgatactg tgtttagtg ctccacttaa     22680 actcaggcac aaccatccgc ggcagctcgg tgaagttttc actccacagg ctgcgcacca     22740
tcaccaacgc gtttagcagg tcgggcgccg atatcttgaa gtcgcagttg gggcctccgc     22800
cctgcgcgcg cgagttgcga tacacagggt tgcagcactg gaacactatc agcgccgggt     22860
ggtgcacgct ggccagcacg ctcttgtcgg agatcagatc cgcgtccagg tcctccgcgt     22920
tgctcagggc gaacggagtc aactttggta gctgccttcc caaaagggc gcgtgcccag     22980 gctttgagtt gcactcgcac cgtagtggca tcaaaaggtg accgtgcccg gtctgggcgt     23040
taggatacag cgcctgcata aaagccttga tctgcttaaa agccacctga gcctttgcgc     23100
cttcagagaa gaacatgccg caagacttgc cggaaaactg attggccgga caggccgcgt     23160
cgtgcacgca gcaccttgcg tcggtgttgg agatctgcac cacatttcgg ccccaccggt     23220
tcttcacgat cttggccttg ctagactgct ccttcagcgc gcgctgcccg ttttcgctcg     23280
tcacatccat ttcaatcacg tgctccttat ttatcataat gcttccgtgt agacacttaa     23340
gctcgccttc gatctcagcg cagcggtgca gccacaacgc gcagcccgtg ggctcgtgat     23400
gcttgtaggt cacctctgca aacgactgca ggtacgcctg caggaatcgc cccatcatcg     23460
tcacaaaggt cttgttgctg gtgaaggtca gctgcaaccc gcggtgctcc tcgttcagcc     23520
aggtcttgca tacggccgcc agagcttcca cttggtcagg cagtagtttg aagttcgcct     23580
```

-continued

```
ttagatcgtt atccacgtgg tacttgtcca tcagcgcgcg cgcagcctcc atgcccttct   23640
cccacgcaga cacgatcggc acactcagcg ggttcatcac cgtaatttca ctttccgctt   23700
cgctgggctc ttcctcttcc tcttgcgtcc gcataccacg cgccactggg tcgtcttcat   23760
tcagccgccg cactgtgcgc ttacctcctt tgccatgctt gattagcacc ggtgggttgc   23820
tgaaacccac catttgtagc gccacatctt ctctttcttc ctcgctgtcc acgattacct   23880
ctggtgatgg cgggcgctcg ggcttgggag aagggcgctt cttttcttc ttgggcgcaa    23940
tggccaaatc cgccgccgag gtcgatggcc gcgggctggg tgtgcgcggc accagcgcgt   24000
cttgtgatga gtcttcctcg tcctcggact cgatacgccg cctcatccgc tttttggg     24060
gcgcccgggg aggcggcggc gacggggacg gggacgacac gtcctccatg gttggggac    24120
gtcgcgccgc accgcgtccg cgctcggggg tggtttcgcg ctgctcctct tcccgactgg   24180
ccatttcctt ctcctatagg cagaaaaaga tcatggagtc agtcgagaag aaggacagcc   24240
taaccgcccc ctctgagttc gccaccaccg cctccaccga tgccgccaac gcgcctacca   24300
ccttccccgt cgaggcaccc ccgcttgagg aggaggaagt gattatcgag caggacccag   24360
gttttgtaag cgaagacgac gaggaccgct cagtaccaac agaggataaa aagcaagacc   24420
aggacaacgc agaggcaaac gaggaacaag tcgggcgggg ggacgaaagg catggcgact   24480
acctagatgt gggagacgac gtgctgttga agcatctgca gcgccagtgc gccattatct   24540
gcgacgcgtt gcaagagcgc agcgatgtgc ccctcgccat agcggatgtc agccttgcct   24600
acgaacgcca cctattctca ccgcgcgtac cccccaaacg ccaagaaaac ggcacatgcg   24660
agcccaaccc gcgcctcaac ttctaccccg tatttgccgt gccagaggtg cttgccacct   24720
atcacatctt tttccaaaac tgcaagatac ccctatcctg ccgtgccaac cgcagccgag   24780
cggacaagca gctggccttg cggcagggcg ctgtcatacc tgatatcgcc tcgctcaacg   24840
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc ccccaaggtc atgagcacag tcatgagtga gctgatcgtg cgccgtgcgc   25080
agcccctgga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
cggccatggg cgtttggcag cagtgcttgg aggagtgcaa cctcaaggag ctgcagaaac   25560
tgctaaagca aaacttgaag gacctatgga cggccttcaa cgagcgctcc gtggccgcgc   25620
acctggcgga catcatttc cccgaacgcc tgcttaaaac cctgcaacag ggtctgccag   25680
acttcaccag tcaaagcatg ttgcagaact ttaggaactt tatcctagag cgctcaggaa   25740
tcttgccccgc cacctgctgt gcacttccta gcgactttgt gcccattaag taccgcgaat   25800
gccctccgcc gctttggggc cactgctacc ttctgcagct agccaactac cttgcctacc   25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
```

```
ttatcggtac ctttgagctg cagggtccct cgcctgacga aaagtccgcg gctccggggt    26040
tgaaactcac tccggggctg tggacgtcgg cttaccttcg caaatttgta cctgaggact    26100
accacgccca cgagattagg ttctacgaag accaatcccg cccgccaaat gcggagctta    26160
ccgcctgcgt cattacccag ggccacattc ttggccaatt gcaagccatc aacaaagccc    26220
gccaagagtt tctgctacga aagggacggg gggtttactt ggaccccag tccggcgagg     26280
agctcaaccc aatcccccg ccgccgcagc cctatcagca gcagccgcgg gcccttgctt      26340
cccaggatgg cacccaaaaa gaagctgcag ctgccgccgc cacccacgga cgaggaggaa    26400
tactgggaca gtcaggcaga ggaggttttg gacgaggagg aggaggacat gatgaagac     26460
tgggagagcc tagacgagga agcttccgag gtcgaagagg tgtcagacga aacaccgtca    26520
ccctcggtcg cattccctc gccggcgccc cagaaatcgg caaccggttc cagcatggct     26580
acaacctccg ctcctcaggc gccgccggca ctgcccgttc gccgacccaa ccgtagatgg    26640
gacaccactg gaaccagggc cggtaagtcc aagcagccgc cgccgttagc ccaagagcaa    26700
caacagcgcc aaggctaccg ctcatggcgc gggcacaaga acgccatagt tgcttgcttg    26760
caagactgtg ggggcaacat ctccttcgcc cgccgctttc ttctctacca tcacggcgtg    26820
gccttccccc gtaacatcct gcattactac cgtcatctct acagcccata ctgcaccggc    26880
ggcagcggca gcggcagcaa cagcagcggc cacacagaag caaaggcgac cggatagcaa    26940
gactctgaca aagcccaaga atccacagc ggcggcagca gcaggaggag gagcgctgcg      27000
tctggcgccc aacgaacccg tatcgacccg cgagcttaga aacaggattt ttcccactct    27060
gtatgctata tttcaacaga gcaggggcca agaacaagag ctgaaaataa aaacaggtc     27120
tctgcgatcc ctcaccccgca gctgcctgta tcacaaaagc gaagatcagc ttcggcgcac   27180
gctggaagac gcggaggctc tcttcagtaa atactgcgcg ctgactctta aggactagtt    27240
tcgcgccctt tctcaaattt aagcgcgaaa actacgtcat ctccagcggc cacacccggc    27300
gccagcacct gtcgtcagcg ccattatgag caaggaaatt cccacgccct acatgtggag    27360
ttaccagcca caaatgggac ttgcggctgg agctgcccaa gactactcaa cccgaataaa    27420
ctacatgagc gcgggacccc acatgatatc ccgggtcaac ggaatccgcg cccaccgaaa    27480
ccgaattctc ttggaacagg cggctattac caccacacct cgtaataacc ttaatccccg    27540
tagttggccc gctgccctgg tgtaccagga aagtcccgct cccaccactg tggtacttcc    27600
cagagacgcc caggccgaag ttcagatgac taactcaggg gcgcagcttg cgggcggctt    27660
tcgtcacagg gtgcggtcgc ccgggcaggg tataactcac ctgacaatca gagggcgagg    27720
tattcagctc aacgacgagt cggtgagctc ctcgcttggt ctccgtccgg acgggacatt    27780
tcagatcggc ggcgccggcc gtccttcatt cacgcctcgt caggcaatcc taactctgca    27840
gacctcgtcc tctgagccgc gctctggagg cattggaact ctgcaattta ttgaggagtt    27900
tgtgccatcg gtctacttta acccttctc gggacctccc ggccactatc cggatcaatt     27960
tattcctaac tttgacgcgg taaggactc ggcggacggc tacgactgaa tgttaagtgg      28020
agaggcagag caactgcgcc tgaaacacct ggtccactgt cgccgccaca agtgctttgc    28080
ccgcgactcc ggtgagtttt gctactttga attgcccgag gatcatatcg agggcccggc    28140
gcacggcgtc cggcttaccg cccagggaga gcttgcccgt agcctgattc gggagtttac    28200
ccagcgcccc ctgctagttg agcgggacag gggaccctgt gttctcactg tgatttgcaa    28260
ctgtcctaac cttggattac atcaagatcc tctagttata actagagtac ccggggatct    28320
tattcccttt aactaataaa aaaaataat aaagcatcac ttacttaaaa tcagttagca      28380
```

```
aatttctgtc cagtttattc agcagcacct ccttgccctc ctcccagctc tggtattgca   28440
gcttcctcct ggctgcaaac tttctccaca atctaaatgg aatgtcagtt tcctcctgtt   28500
cctgtccatc cgcacccacc ggtataactt cgtatatggt ttcttatacg aacggtagat   28560
ctatatctat gatctcgcag tctccggcga gcaccggagg cagggcattg ccaccgcgct   28620
catcaatctc ctcaagcatg aggccaacgc gcttggtgct tatgtgatct acgtgcaagc   28680
agattacggt gacgatcccg cagtggctct ctatacaaag ttgggcatac gggaagaagt   28740
gatgcacttt gatatcgacc caagtaccgc cacctaacaa ttcgttcaag ccgagatcgg   28800
cttcccggcc gcggagttgt tcggtaaatt gtcacaacgc cgcggccatc ggcatttttct  28860
tttgcgtttt tatttgttaa ctgttaattg tccttgttca aggatgctgt ctttgacaac   28920
agatgttttc ttgcctttga tgttcagcag gaagcttggc gcaaacgttg attgtttgtc   28980
tgcgtagaat cctctgtttg tcatatagct tgtaatcacc acgacattgt ttcctttcgc   29040
ttgaggtaca gcgaagtgtg agtaagtaaa ggttacatcg ttaggatcaa gatccatttt   29100
taacacaagg ccagttttgt tcagcggctt gtatgggcca gttaaagaat tagaaacata   29160
accaagcatg taaatatcgt tagacgaaat gccgtcaatc gtcatttttg atccgcggga   29220
gtcagtgaac aggtaccatt tgccgttcat tttaaagacg ttcgcgcgtt caatttcatc   29280
tgttactgtg ttagatgcaa tcagcggttt catcactttt ttcagtgtgt aatcatcgtt   29340
tagctcaatc ataccgagag cgccgtttgc taactcagcc gtgcgttttt tatcgctttg   29400
cagaagtttt tgactttctt gacggaagaa tgatgtgctt ttgccatagt atgctttgtt   29460
aaataaagat tcttcgcctt ggtagccatc ttcagttcca gtgtttgctt caaatactaa   29520
gtatttgtgg cctttatctt ctacgtagtg aggatctctc agcgtatggt tgtcgcctga   29580
gctgtagttg ccttcatcga tgaactgctg tacattttga tacgttttc cgtcaccgtc    29640
aaagattgat ttataatcct ctacaccgtt gatgttcaaa gagctgtctg atgctgatac   29700
gttaacttgt gcagttgtca gtgtttgttt gccgtaatgt ttaccggaga aatcagtgta   29760
gaataaacgg attttccgt cagatgtaaa tgtggctgaa cctgaccatt cttgtgtttg     29820
gtcttttagg atagaatcat ttgcatcgaa tttgtcgctg tctttaaaga gcggccagc    29880
gttttttccag ctgtcaatag aagtttcgcc gactttttga tagaacatgt aaatcgatgt  29940
gtcatccgca tttttaggat ctccggctaa tgcaaagacg atgtggtagc cgcgatagtg   30000
tgcgacagtg ccgtcagcgt tttgtaatgg ccagctgtcc caaacgtcca ggccttttgc   30060
agaagagata ttttttaattg tggacgaatc gaattcagga acttgatatt tttcattttt  30120
ttgctgttca gggatttgca gcatatcatg gcgtgtaata tgggaaatgc cgtatgtttc   30180
cttatatggc ttttggttcg tttctttcgc aaacgcttga gttgcgcctc ctgccagcag   30240
tgcggtagta aaggttaata ctgttgcttg ttttgcaaac ttttttgatgt tcatcgttca  30300
tgtctccttt tttatgtact gtgttagcgg tctgcttctt ccagccctcc tgtttgaaga   30360
tggcaagtta gttacgcaca ataaaaaaag acctaaaata tgtaaggggt gacgccaaag   30420
tatacacttt gcccttttaca cattttaggt cttgcctgct ttatcagtaa caaacccgcg   30480
cgatttactt ttcgacctca ttctattaga ctctcgtttg gattgcaact ggtctatttt   30540
cctcttttgt ttgatagaaa atcataaaag gatttgcaga ctacgggcct aaagaactaa   30600
aaaatctatc tgtttctttt cattctctgt atttttata gtttctgttg catgggcata    30660
aagttgcctt tttaatcaca attcagaaaa tatcataata tctcatttca ctaaataata   30720
gtgaacggca ggtatatgtg atgggttaaa aaggatcgat cctctagcta gagtcgatcg   30780
```

```
taccgttcgt atagcataca ttatacgaag ttataccggt atacattgcc caagaataaa    30840
gaatcgtttg tgttatgttt caacgtgttt atttttcaat tgcagaaaat ttcaagtcat    30900
ttttcattca gtagtatagc cccaccacca catagcttat acagatcacc gtaccttaat    30960
caaactcaca gaaccctagt attcaacctg ccacctccct cccaacacac agagtacaca    31020
gtcctttctc cccggctggc cttaaaaagc atcatatcat gggtaacaga catattctta    31080
ggtgttatat tccacacggt ttcctgtcga gccaaacgct catcagtgat attaataaac    31140
tccccgggca gctcacttaa gttcatgtcg ctgtccagct gctgagccac aggctgctgt    31200
ccaacttgcg gttgcttaac gggcggcgaa ggagaagtcc acgcctacat gggggtagag    31260
tcataatcgt gcatcaggat agggcggtgg tgctgcagca gcgcgcgaat aaactgctgc    31320
cgccgccgct ccgtcctgca ggaatacaac atggcagtgg tctcctcagc gatgattcgc    31380
accgcccgca gcataaggcg ccttgtcctc cgggcacagc agcgcaccct gatctcactt    31440
aaatcagcac agtaactgca gcacagcacc acaatattgt tcaaaatccc acagtgcaag    31500
gcgctgtatc caaagctcat ggcggggacc acagaaccca cgtggccatc ataccacaag    31560
cgcaggtaga ttaagtggcg acccctcata aacacgctgg acataaacat tacctctttt    31620
ggcatgttgt aattcaccac ctcccggtac catataaacc tctgattaaa catggcgcca    31680
tccaccacca tcctaaacca gctggccaaa acctgcccgc cggctataca ctgcagggaa    31740
ccgggactgg aacaatgaca gtggagagcc caggactcgt aaccatggat catcatgctc    31800
gtcatgatat caatgttggc acaacacagg cacacgtgca tacacttcct caggattaca    31860
agctcctccc gcgttagaac catatcccag ggaacaaccc attcctgaat cagcgtaaat    31920
cccacactgc agggaagacc tcgcacgtaa ctcacgttgt gcattgtcaa agtgttacat    31980
tcgggcagca gcggatgatc ctccagtatg gtagcgcggg tttctgtctc aaaaggaggt    32040
agacgatccc tactgtacgg agtgcgccga gacaaccgag atcgtgttgg tcgtagtgtc    32100
atgccaaatg gaacgccgga cgtagtcata tttcctgaag caaaaccagg tgcgggcgtg    32160
acaaacagat ctgcgtctcc ggtctcgccg cttagatcgc tctgtgtagt agttgtagta    32220
tatccactct ctcaaagcat ccaggcgccc cctggcttcg ggttctatgt aaactccttc    32280
atgcgccgct gccctgataa catccaccac cgcagaataa gccacaccca gccaacctac    32340
acattcgttc tgcgagtcac acacgggagg agcgggaaga gctggaagaa ccatgttttt    32400 tttttttattc caaagagatta tccaaaacct caaaatgaag atctattaag tgaacgcgct    32460
cccctccggt ggcgtggtca aactctacag ccaaagaaca gataatggca tttgtaagat    32520
gttgcacaat ggcttccaaa aggcaaacgg ccctcacgtc caagtggacg taaaggctaa    32580
acccttcagg gtgaatctcc tctataaaca ttccagcacc ttcaaccatg cccaaataat    32640
tctcatctcg ccaccttctc aatatatctc taagcaaatc ccgaatatta agtccggcca    32700
ttgtaaaaat ctgctccaga gcgccctcca ccttcagcct caagcagcga atcatgattg    32760
caaaaattca ggttcctcac agacctgtat aagattcaaa agcggaacat taacaaaaat    32820
accgcgatcc cgtaggtccc ttcgcagggc cagctgaaca taatcgtgca ggtctgcacg    32880
gaccagcgcg gccacttccc cgccaggaac cttgacaaaa gaacccacac tgattatgac    32940
acgcatactc ggagctatgc taaccagcgt agccccgatg taagctttgt tgcatgggcg    33000
gcgatataaa atgcaaggtg ctgctcaaaa aatcaggcaa agcctcgcgc aaaaaagaaa    33060
gcacatcgta gtcatgctca tgcagataaa ggcaggtaag ctccggaacc accacagaaa    33120
aagacaccat ttttctctca aacatgtctg cgggtttctg cataaacaca aataaaaata    33180
```

-continued

```
acaaaaaaac atttaaacat tagaagcctg tcttacaaca ggaaaaacaa cccttataag    33240
cataagacgg actacggcca tgccggcgtg accgtaaaaa aactggtcac cgtgattaaa    33300
aagcaccacc gacagctcct cggtcatgtc cggagtcata atgtaagact cggtaaacac    33360
atcaggttga ttcatcggtc agtgctaaaa agcgaccgaa atagcccggg ggaatacata    33420
cccgcaggcg tagagacaac attacagccc ccataggagg tataacaaaa ttaataggag    33480
agaaaaacac ataaacacct gaaaacccct cctgcctagg caaaatagca ccctcccgct    33540
ccagaacaac atacagcgct tcacagcggc agcctaacag tcagccttac cagtaaaaaa    33600
gaaaacctat taaaaaaaca ccactcgaca cggcaccagc tcaatcagtc acagtgtaaa    33660
aaagggccaa gtgcagagcg agtatatata ggactaaaaa atgacgtaac ggttaaagtc    33720
cacaaaaaac acccagaaaa ccgcacgcga acctacgccc agaaacgaaa gccaaaaaac    33780
ccacaacttc ctcaaatcgt cacttccgtt ttcccacgtt acgtaacttc ccattttaag    33840
aaaactacaa ttcccaacac atacaagtta ctccgcccta aaacctacgt cacccgcccc    33900
gttcccacgc cccgcgccac gtcacaaact ccacccctc attatcatat tggcttcaat     33960
ccaaaataag gtatattatt gatgatttaa t                                    33991
```

<210> SEQ ID NO 7
<211> LENGTH: 88
<212> TYPE: DNA
<213> ORGANISM: Artificial Sequence
<220> FEATURE:
<223> OTHER INFORMATION: Description of Artificial Sequence: Synthetic primer

<400> SEQUENCE: 7

```
tcgagaacta tcttcatgtt gttgcagatg aagcgcgcaa gaccgtctga agataccttc    60
aaccccgtgt atccatatga cacggaaa                                        88
```

<210> SEQ ID NO 8
<211> LENGTH: 88
<212> TYPE: DNA
<213> ORGANISM: Artificial Sequence
<220> FEATURE:
<223> OTHER INFORMATION: Description of Artificial Sequence: Synthetic primer

<400> SEQUENCE: 8

```
ccggtttccg tgtcatatgg atacacgggg ttgaaggtat cttcagacgg tcttgcgcgc    60
ttcatctgca acaacatgaa gatagttc                                        88
```

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9

```
ataacttcgt atagcataca ttatacgaag ttat                                 34
```

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 10
ataacttcgt ataatgtatg ctatacgaag ttat                                34

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ataacttcgt atagtataca ttatacgaag ttat                                34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ataacttcgt atagcataca ttatacgaac ggta                                34

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taccgttcgt atagcataca ttatacgaag ttat                                34

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taccgttcgt atatggtttc ttatacgaag ttat                                34

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ataacttcgt atatggtttc ttatacgaac ggta                                34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
```

```
taccgttcgt atatggtttc ttatacgaac ggta                              34
```

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
taccgttcgt atagcataca ttatacgaac ggta                              34
```

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
ataacttcgt atatggtttc ttatacgaag ttat                              34
```

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
cgtaccgttc gtatagcata cattatacga agttata                           37
```

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
ccggtataac ttcgtataat gtatgctata cgaacggtac gat                    43
```

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
ccggtataac ttcgtatatg gtttcttata cgaacggta                         39
```

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gatctaccgt tcgtataaga aaccatatac gaagttata                         39
```

```
<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaccggtata cattgcccaa gaataaag                                          28

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcataagtgc ggcgacgata                                                   20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttgtgtgga attgtgagcg g                                                 21

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
catgtaccgg tgggtgcgga tggacaggaa c                                      31

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctaacaattc gttcaagccg                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcagcggttt catcactttt                                                   20

<210> SEQ ID NO 29
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgaccattc ttgtgtttgg                                                   20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtctcctttt ttatgtactg tg                                                22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttatacgaag ttataccggt                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aataaactgc tgccgccgcc                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atcaatgttg gcacaacaca                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgcagaata agccacaccc                                                   20

<210> SEQ ID NO 35
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 35
taacaaaaat accgcgatcc                                            20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acagctcctc ggtcatgtcc                                            20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgttttccca cgttacgtaa                                            20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cactataggg cgaattgggc                                            20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39 gcccttttt acactgtgac                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tttatgcaga aacccgcaga                                            20

<210> SEQ ID NO 41
<211> LENGTH: 20
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 41
atattgagaa ggtggcgaga                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgtttgtcac gcccgcacct                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agaggtttat atggtaccgg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acttaagtga gctgcccggg                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttatgcccat gcaacagaaa                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tattacacgc catgatatgc                                                    20

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 47
cggtgtagag gattataaat caatc                                          25

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
catgcttggt tatgtttcta                                                20

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctagtaccgt tcgtatatgg tttcttatac gaagttatc                           39

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tcgagataac ttcgtataag aaaccatata cgaacggta                           39

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggccgcataa cttcgtatag catacattat acgaacggta g                        41

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtacctaccg ttcgtataat gtatgctata cgaagttatg c                        41
```

ADENOVIRAL FIBER EXCHANGE SHUTTLE SYSTEM

RELATED APPLICATIONS

This application is a continuation of PCT Application PCT/US06/10025, filed Mar. 16, 2006 which claims the benefit of U.S. Provisional Application No. 60/662,168, filed Mar. 16, 2005. The entire contents of the aforementioned applications are hereby expressly incorporated herein by reference.

GOVERNMENT SUPPORT

This work was supported, in part, by grants from the National Cancer Institute (2P50CA58236-09A1) and the Prostate Cancer Foundation (DAMD17-03-2-0033). Accordingly, the government may have certain rights to this invention.

BACKGROUND OF THE INVENTION

Recombinant adenoviruses are currently used for a variety of purposes, including gene transfer in vitro, vaccination in vivo, and gene therapy. Several features of adenovirus biology have made such viruses the vectors of choice for certain of these applications. For example, adenoviruses transfer genes to a broad spectrum of cell types, and gene transfer is not dependent on active cell division. Additionally, high titers of virus and high levels of transgene expression can generally be obtained.

Decades of study of adenovirus biology have resulted in a detailed picture of the viral life cycle and the functions of the majority of viral proteins. The genome of the most commonly used human adenovirus (serotype 5) consists of a linear, 36 kb, double-stranded DNA molecule. Both strands are transcribed and nearly all transcripts are heavily spliced. Viral transcription units are conventionally referred to as early (E1, E2, E3 and E4) and late, depending on their temporal expression relative to the onset of viral DNA replication. The high density and complexity of the viral transcription units poses problems for recombinant manipulation, which is therefore usually restricted to specific regions, particularly E1, E2A, E3, and E4. In most recombinant vectors, transgenes are introduced in place of E1 or E3, the former supplied exogenously. The E1 deletion renders the viruses defective for replication and incapable of producing infectious viral particles in target cells; the E3 region encodes proteins involved in evading host immunity, and is dispensable for viral production per se.

Two approaches have traditionally been used to generate recombinant adenoviruses. The first involves direct ligation of DNA fragments of the adenoviral genome to restriction endonuclease fragments containing a transgene. The low efficiency of large fragment ligations and the scarcity of unique restriction sites have made this approach technically challenging. The second and more widely used method involves homologous recombination in mammalian cells capable of complementing defective adenoviruses ("packaging lines"). Homologous recombination results in a defective adenovirus which can replicate in the packaging line (e.g., 293 or 911 cells) which supplies the missing gene products (e.g., E1). The desired recombinants are identified by screening individual plaques generated in a lawn of packaging cells. The low efficiency of homologous recombination, the need for repeated rounds of plaque purification, and the long times required for completion of the viral production process have hampered more widespread use of adenoviral vector technology. Thus there is a need in the art for more efficient and flexible techniques for generating recombinant adenoviruses.

SUMMARY OF THE INVENTION

The instant invention provides a methods for making recombinant viral vectors and provides methods and compositions for using these vectors.

Accordingly, in one aspect, the instant invention provides methods for generating a recombinant adenoviral vector comprising a desired gene, comprising the steps of co-transforming a cell expressing RecA with a linearized shuttle plasmid comprising a selectable marker, and a transfer plasmid wherein the transfer plasmid comprises a fiber gene, thereby allowing recombination of the plasmids to generate a recombinant adenoviral vector.

In one embodiment, the transfer plasmid is constructed by co-transforming a donor plasmid and a acceptor plasmid into a cell expressing a Cre recombinase, wherein the acceptor plasmid comprises a nucleic acid segment encoding a negatively selectable marker flanked by lox sites, and a first selectable marker, and the donor plasmid comprises a nucleic acid segment encoding the fiber gene flanked by lox sites and a second selectable marker, thereby allowing for recombination of the fiber gene and the negatively selectable marker.

In a related embodiment, the lox sites are incompatible. In an further related embodiment, the lox sites are mutated to result in unidirectional recombination. In exemplary embodiments, the donor plasmid lox sites are Lox m2/66 and Lox 71 and the acceptor plasmid lox sites are Lox m2/71 and Lox 66.

In one embodiment, the negatively selectable marker is SacB.

In another embodiment, the fiber gene is modified. In one embodiment, the fiber gene is modified to incorporate a unique restriction site. In an exemplary embodiment, the unique restriction site is in the HI loop. In a further exemplary embodiment, the unique restriction site is a BspEI site.

In one embodiment, the acceptor plasmid contains a kanamycin selectable marker. In another embodiment, the donor plasmid contains a ampicillin selectable marker.

In another embodiment, the method further comprises selecting recombinant adenoviral vectors using the selectable marker. In one embodiment, the selectable marker is kanamycin.

In one embodiment, the cell is a bacterial cell, e.g., an *E. coli* cell. In other embodiments, the cell is a mammalian cell.

In one embodiment, the shuttle plasmid comprises a resistance gene and a nucleic acid segment encoding a desired product. In exemplary embodiments the desired product is a polypeptide or fragment thereof, a nucleic acid, a siRNA, an RNAi, an shRNA, or an aptamer. In specific exemplary embodiments, the desired product is a polypeptide, e.g., a therapeutic polypeptide.

In another embodiment, the nucleic acid segment is under control of a promoter. In a related embodiment, the promoter is a tissue specific promoter.

In another embodiment, the shuttle plasmid contains a unique restriction site located between RecA recombination sites. In an exemplary embodiment, the unique restriction site is a Pme I site. In another embodiment, this Pme I site can be used to linearize the plasmid.

In another embodiment, the shuttle plasmid further comprises RecA homologous recombination sites, e.g., Ad5 left and Ad5 right. In a related embodiment, the transfer plasmid further comprises RecA homologous recombination sites, e.g., Ad5 left and Ad5 right.

In another aspect, the instant invention provides methods for generating a recombinant adenoviral vector comprising a desired gene, comprising the steps of co-transforming a cell expressing RecA with a linearized shuttle plasmid comprising a selectable marker and a transfer plasmid wherein the transfer plasmid comprises a fiber gene, wherein the transfer plasmid is constructed by co-transforming a donor plasmid and a acceptor plasmid into a cell expressing Cre recombinase, wherein the acceptor plasmid comprises a nucleic acid segment encoding a negatively selectable marker flanked by lox sites, and a first selectable marker, and the donor plasmid comprises a nucleic acid segment encoding the fiber gene flanked by lox sites and a second selectable marker, thereby allowing for recombination of the fiber gene and the negatively selectable marker, thereby allowing recombination of the plasmids to generate a recombinant adenoviral vector.

In another aspect, the instant invention provides methods of generating a recombinant adenoviral vector comprising a desired gene, comprising the steps of co-transforming a cell expressing the Cre recombinase with a donor plasmid comprising a nucleic acid segment encoding the fiber gene flanked by lox sites and a shuttle-acceptor plasmid comprising a nucleic acid segment encoding a negatively selectable marker flanked by lox sites, and a nucleic acid segment encoding a desired product, thereby allowing recombination of the plasmids to generate a recombinant adenoviral vector.

In a related aspect, the desired product is a polypeptide, polypeptides, or fragments thereof, a nucleic acid, a siRNA, an RNAi, an shRNA, or an aptamer.

In one embodiment, the shuttle-acceptor plasmid is constructed by co-transforming a cell expressing RecA with a linearized shuttle plasmid and an acceptor plasmid comprising a negatively selectable marker.

In one embodiment, the lox sites are incompatible. In a related embodiment, the lox sites are mutated to result in unidirectional recombination. In an exemplary embodiment, the donor plasmid lox sites are Lox m2/66 and Lox 71 and the acceptor plasmid lox sites are Lox m2/71 and Lox 66.

In one embodiment, the negatively selectable marker is SacB.

In another embodiment the fiber gene is modified. In a related embodiment, the fiber gene is modified to include a unique restriction site in the HI loop. In an exemplary embodiment, the restriction site is a BspEI site.

In one embodiment, the acceptor plasmid contains a kanamycin selectable marker.

In another embodiment, the donor plasmid contains an ampicillin selectable marker.

In one embodiment, the methods further comprise selecting recombinant adenoviral vectors using the selectable marker. In an exemplary embodiment, the selectable marker is kanamycin.

In one embodiment, the cell is a bacterial cell, e.g., an *E. coli* cell. In another embodiment, the cell is a mammalian cell.

In one embodiment, the shuttle plasmid comprises a resistance gene and a nucleic acid segment encoding a desired product. In a related embodiment, the product is a polypeptide, polypeptides, or fragments thereof, a nucleic acid, an aptamer, a siRNA, RNAi, an shRNA, or an aptamer. In a specific embodiment, the product is a polypeptide.

In certain embodiments, the peptide is a therapeutic polypeptide.

In one embodiment, nucleic acid segment is under control of a promoter. In a related embodiment, the promoter is a tissue specific promoter.

In one embodiment, the resistance gene is not the same as the resistance gene in the acceptor plasmid.

In one embodiment, the shuttle plasmid contains a unique restriction site located between the RecA homologous recombination sites. In an exemplary embodiment, the unique restriction site is a Pme I site. In another related embodiment, the shuttle plasmid is linearized with Pme I.

In one embodiment, the acceptor plasmid further comprises RecA homologous recombination sites. In an exemplary embodiment, the RecA homologous recombination sites are Ad5 left and Ad5 right. In another embodiment, the shuttle plasmid further comprises RecA homologous recombination sites. In an exemplary embodiment, the RecA homologous recombination sites are Ad5 left and Ad5 right.

In one aspect, the invention also provides shuttle plasmids.

In another aspect the instant invention also provides acceptor plasmids.

In yet another aspect, the instant invention provides, shuttle-acceptor plasmids.

In yet another aspect, the instant invention provides donor plasmids.

In yet another aspect, the instant invention provides transfer plasmids.

In yet another aspect, the instant invention provides recombinant viral vectors comprising a resistance gene located between RecA homologous recombination sites, and a nucleic acid segment encoding a desired product.

In one embodiment, the invention provides a viral vector consisting of the nucleic acid molecule set forth as SEQ ID NO: 1.

In another embodiment, the invention provides a shuttle plasmid consisting of the nucleic acid sequence set forth as SEQ ID NO:2.

In another embodiment, the invention provides a donor plasmid consisting of the nucleic acid sequence set forth as SEQ ID NO:3.

In another embodiment, the invention provides a donor plasmid consisting of the nucleic acid sequence set forth as SEQ ID NO:4.

In another embodiment, the invention provides a donor plasmid consisting of the nucleic acid sequence set forth as SEQ ID NO: 5.

In another embodiment, the invention provides an acceptor plasmid consisting of the nucleic acid sequence set forth as SEQ ID NO:6.

In another aspect, the instant invention provides methods of creating virus comprising linearizing the viral vectors described herein and transfecting the linearized vector into a cell, thereby creating a virus.

The invention also provides methods of making psuedotyped virus using the viral vectors described herein.

In another aspect, the invention provides methods of treating an individual in need of treatment by administering to the individual a viral vector or a virus described herein.

DESCRIPTION OF THE DRAWINGS

FIGS. 2A-B depict various lox sequences. FIG. 2A depicts lox sequences with half-site mutations in italics. FIG. 2B depicts spacer sequences with mutations in italics (SEQ ID NOS.9 and 11-13).

FIG. 23 depicts detargeted AdTrack-Fib2 virus which was generated by pseudotyped AdTrack-Fex recombination with Rpuc-Fib2 in Cre recombinase expressing mammalian cells.

FIG. 24 is Table 1 entitled Primers for Constructing and Sequencing pFex (SEQ ID NOS.19-48).

FIG. 25 is Table 2 entitled Primers for Constructing and Sequencing Fiber Shuttles (SEQ ID NOS.49-52).

FIG. 26 is Table 3 entitled Fiber Shuttle Vectors.
FIG. 27 is Table 4 entitled Total Transformants from 294 co-transfections.

FIG. 28 is Table 5 entitled Percent Recombinants of Large pAdTrack-Fex Vector.

FIG. 29 is Table 6 entitled pFex and AdEasy based virus.
FIG. 30 depicts the nucleic acid sequence of pShuttle-Fib (SEQ ID NO: 1).

FIG. 31 depicts the nucleic acid sequence of pShuttle (SEQ ID NO:2).

FIG. 32 depicts the nucleic acid sequence of RP-Fib (SEQ ID NO:3).

FIG. 33 depicts the nucleic acid sequence of RPuc-Fib (SEQ ID NO:4).

FIG. 34 depicts the nucleic acid sequence of RP-Blast-Fib (SEQ ID NO: 5).

FIG. 35 depicts the nucleic acid sequence of pFEX (SEQ ID NO:6).

DETAILED DESCRIPTION OF THE INVENTION

Figure 1:
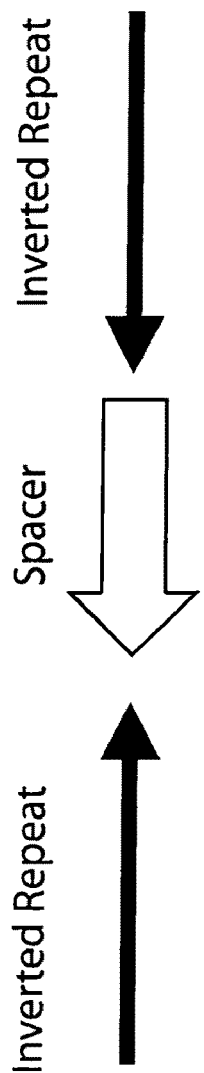
FIG. 1 is a schematic representation of a lox site showing two inverted repeats separated by a spacer region (SEQ ID NO.9).

The instant invention is based, at least in part, on the discovery of methods for generating adenoviral vectors which are more efficient and more flexible than current systems for producing recombinant viral vectors. These methods and vectors are compatible with current technology as described in U.S. Pat. No. 5,922,576, the contents of which is expressly incorporated herein by reference.

Though several systems for generating recombinant viruses through Cre-mediated or homologous recombination in yeast or bacteria have been described in the literature, the instant invention provides a two-stage recombination system for making recombinant adenoviral vectors that has several advantages in terms of ease, sensitivity and flexibility. The instant invention provides methods of producing recombinant adenoviral vectors that offer the practitioner the flexibility to adapt the system to their particular needs. They skilled artisan may introduce the desired product into an already completed transfer vector and select for a recombinant adenoviral vector, or introduce the desired product into the acceptor vector as the initial step in the method, thereby allowing them the flexibility that other systems do not provide. Moreover, the ability to recover very small numbers of recombinant viral particles amongst many transformants is particularly advantageous.

Publications describing various aspects of adenovirus biology and/or techniques relating to adenovirus include the following. Graham and Van de Eb (1973) Virology 52:456-467; Takiff et al. (1981) Lancet ii:832-834; Berkner and Sharp (1983) Nucleic Acid Research 6003-6020; Graham (1984) EMBO J. 3:2917-2922; Bett et al. (1993) J. Virology 67:5911-5921; and Bett et al. (1994) Proc. Natl. Acad. Sci. USA 91:8802-8806 describe adenoviruses that have been genetically modified to produce replication-defective gene transfer vehicles. In these vehicles, the early adenovirus gene products E1A and E1B are deleted and provided in trans by the packaging cell line 293 developed by Frank Graham (Graham et al. (1987) J. Gen. Birol. 36:59-72 and Graham (1977) J. Genetic Virology 68:937-940). The gene to be transduced is commonly inserted into adenovirus in the deleted E1A and E1B region of the virus genome Bett et al. (1994), supra. Adenovirus vectors as vehicles for efficient transduction of genes have been described by Stratford-Perricaudet (1990) Human Gene Therapy 1:2-256; Rosenfeld (1991) Science 252:431-434; Wang et al. (1991) Adv. Exp. Med. Biol. 309: 61-66; Jaffe et al. (1992) Nat. Gent. 1:372-378; Quantin et al. (1992) Proc Natl. Acad. Sci. USA 89:2581-2584; Rosenfeld et al. (1992) Cell 68:143-155; Stratford-Perricaudet et al. (1992) J. Clin. Invest. 90:626-630; Le Gal La Salle et al. (1993) Science 259:988-990; Mastrangeli et al. (1993) J. Clin. Invest. 91:225-234; Ragot et al. (1993) Nature 361:647-650; Hayaski et al. (1994) J. Biol. Chem. 269:23872-23875.

The present invention utilizes recombination, e.g., recombination in bacteria, to combine plasmid DNA molecules containing a desired product to form an adenoviral vector. In specific embodiments, the instant invention provides methods for generating recombinant adenoviral vectors that utilizes RecA and Cre mediated homologous recombination. Recombination is a process in which two DNA molecules become joined and nucleic acid is exchanged. Homologous recombination occurs between two sequences having regions of homology. Bacterial recombination is particularly robust. In order to facilitate recombination between the DNA molecules, i.e., plasmids, identical sequences must be present in both. Using standard methods in the art, segments of the adenoviral genome can be put in the plasmids to create regions of homology.

An "adenovirus vector" or "adenoviral vector" (used interchangeably) is a term well understood in the art and generally comprises a polynucleotide comprising all or a portion of an adenovirus genome. As used herein, "adenovirus" refers to the virus itself or derivatives thereof. The term covers all serotypes and subtypes and both naturally occurring and recombinant forms, except where otherwise indicated. An adenoviral vector of the present invention can be in any of several forms, including, but not limited to, naked DNA; an adenoviral vector encapsulated in an adenovirus coat; packaged in another viral or viral-like form (such as herpes simplex virus and AAV); encapsulated in a liposome; complexed with polylysine or other biocompatible polymer; complexed with synthetic polycationic molecules; conjugated with transferrin; complexed with compounds such as PEG to immunologically "mask" the molecule and/or increase half-life, or conjugated to a non-viral protein. An adenoviral vector of this invention may be in the form of any of the delivery vehicles described herein. Such vectors are one embodiment of the invention. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The term "plasmid" denotes an extrachromosomal circular DNA capable of autonomous replication in a given cell. The range of suitable plasmids is very large. Preferably, the plasmid is designed for amplification in bacteria and for expression in an eukaryotic target cell. Such plasmids can be purchased from a variety of manufacturers. Exemplary plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193-201). Plasmids can also be engineered by standard molecular biology techniques (Sambrook et al., Laboratory Manual, Cold Spring Harbor Laboratory Press, Cold Spring Harbor (1989), N.Y.). It may also comprise a selection gene in order to select for or identify the transfected cells (e.g., by complementation of a cell auxotrophy or by antibiotic resistance), stabilizing elements (e.g., cer sequence; Summers and Sherrat, 1984, Cell 36, 1097-1103) or integrative elements (e.g., LTR viral sequences and transposons).

As used herein the term "shuttle plasmid" is intended to mean a plasmid comprising a unique restriction site between RecA homologous recombination sites and used to insert a desired nucleic acid molecule, i.e., a nucleic acid molecule encoding a desired product, into a recombinant adenoviral vector. The RecA homologous recombination sites can be, for example, Ad5 right and Ad5 left. In further embodiments, the shuttle plasmid may have a tissue specific promoter which controls the expression of the desired nucleic acid molecule. The shuttle plasmid also contains a majority of the viral genes necessary to form viral particles. However, the shuttle plasmid does not contain all necessary genes to form viral particles. An exemplary shuttle plasmid is referred to as pShuttle herein.

As used herein, RecA mediated homologous recombination is used to exemplify enzyme mediated homologous recombination. Other enzymes capable of mediating homologous recombination are known in the art and can be used to design the vectors of the invention, and can further be used in the methods of the invention. For example, homologous recombination enzymes are known in eukaryotes, e.g., Rad51, Rad57, Rad55 and DMC1, in Archaea, e.g., RadA and RadB, and in phage, e.g., vsX in phage T4. These enzymes and homologs and orthologs of these enzymes are envisioned for use in the methods of the present invention.

As used herein the term "transfer plasmid" is intended to mean the plasmid that results from the Cre mediated recombination of the donor plasmid and the acceptor plasmid. The transfer plasmid has the fiber gene, or other gene in the fiber location, inserted in place of the negatively selectable marker. Moreover, the transfer plasmid has RecA homologous recombination sites to allow for insertion of a desired nucleic acid molecule by RecA mediated homologous recombination with the shuttle plasmid. The transfer plasmid also has a selectable marker, i.e., ampicillin located between the RecA homologous recombination sites. The RecA homologous recombination sites can be, for example, Ad5 right and Ad5 left. An exemplary transfer plasmid is referred to as pFex-Fib herein.

As used herein the term "nucleic acid molecule encoding fiber" is intended to mean a nucleic acid segment encoding viral capsid protein that is responsible for mediating high-affinity attachment of adenovirus to a target cell. The amino acid sequence of fiber is available as GenBank Accession number P03275, and is further described by Herisse, J., et al. (1981) Nucleic Acids Res. 9:4023-4042. In specific embodiments, the fiber gene used in the methods and compositions of the invention can be a functional fragment of the fiber protein, i.e., a fragment that retains the ability to allow the attachment of a virus to a cell.

As used herein the term "donor plasmid" is intended to mean a plasmid containing a donor gene flanked on either side by lox sites. In exemplary embodiments of the invention the donor gene is a fiber gene, or fragment thereof. However, one skilled in the art would understand that other genes can be used in place of fiber. For example, another gene that encodes a cell surface recognition protein can be used in place of fiber. Also, a nucleic acid molecule encoding a toxin can be used in place of fiber. In order to select for the transfer plasmid, the donor plasmid has a different selectable marker than the acceptor plasmid. In exemplary embodiments, the donor plasmid has ampicillin, kanamycin, or blastocidin resistance. Exemplary donor plasmids are referred to as RP-Fib, RPuc-Fib, and Rblast-Fib herein.

As used herein the term "acceptor plasmid" is intended to mean a plasmid containing a negatively selectable marker flanked by lox sites and a selectable marker, e.g., ampicillin, located between RecA homologous recombination sites. The negatively selectable marker can be, for example, SacB. An exemplary acceptor plasmid is referred to as pFex herein.

As used herein the term "shuttle-acceptor plasmid" is intended to mean the recombination product of RecA mediated recombination of a shuttle plasmid and an acceptor plasmid. The shuttle-acceptor plasmids of the invention comprise a negatively selectable marker located between two lox sites, a resistance marker, and a nucleic acid molecule encoding a desired product. An exemplary shuttle-acceptor plasmid is referred to as pShuttle-Fex herein.

In one embodiment, the "desired product" in use in the present invention, encodes a gene product of therapeutic interest. A "desired product" can have a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition. It is within the reach of the man skilled in the art to select a gene encoding an appropriate gene product of therapeutic interest, depending on the disease or condition to be treated. In a general manner, his choice may be based on the results previously obtained, so that he can reasonably expect, without undue experimentation, i.e., other than practicing the invention as claimed, to obtain such therapeutic properties.

In the context of the invention, the desired product can be homologous or heterologous to the host cell into which it is introduced. Advantageously, it encodes a polypeptide, a ribozyme or anti-sense RNA, RNAi, an aptamer or the like. The term "polypeptide" is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

The regulatory elements controlling the expression of the desired gene may further comprise additional elements, such as exon/intron sequences, targeting sequences, transport sequences, secretion signal sequences, nuclear localization signal sequences, IRES, polyA transcription termination sequences, tripartite leader sequences, sequences involved in replication or integration. These elements have been reported in the literature and can be readily obtained by those skilled in the art.

As used herein the term "lox sites" is intended to mean a nucleic acid sequence that the Cre recombinase recognizes. The canonical lox site is the loxP site. Lox sites are 34 nucleotides in length and have a 13 base pair inverted repeat separated by an 8 base pair spacer (see FIG. 1). Wild-type lox sites are unaltered following recombination thereby allowing for a reversible reaction. The instant invention uses "incompatible" lox sites which have a mutation such that intrageneic recombination, i.e. recombination within a plasmid which can result in deletion or inversion of flanked nucleic acid, can not occur. Exemplary mutations include those to the spacer that result in non-functional lox sites following recombination (see FIGS. 2A-B). The instant invention also applies "half-mutant" lox sites, which when correctly recombined, produce one fully mutant lox site and one wild type lox site, resulting in a non-functional lox site, thus preventing the reverse reaction. Specific exemplary incompatible lox sites for uni-directional insertion include the Lox m2/66 and Lox 71 on the donor fragment and Lox m2/71 with Lox66 on the acceptor fragment (see, for example, Langer, S. J. et al. (2002) *Nucleic Acid Research* 20:3067-77)

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A key step in the generation of adenoviral plasmids according to the present invention is the co-transformation of bacteria with precursor DNA vectors. Transformation is the introduction of DNA into a bacterial cell. Transformation can be carried out by a number of techniques known in the art. Such methods include but are not limited to electroporation (exposure of a cell suspension to an electrical field), the use of calcium phosphate solutions, and the use of lipids to package the DNA and fuse with the cell membrane. Co-transformation refers to the introduction of two different species of DNA molecule into the same cell.

The plasmid desirably comprises one or more desired product. In addition, segments of DNA consisting of adenoviral sequences flank the desired product to promote homologous recombination with other nucleic acid molecules to ultimately produce an adenoviral vector.

The adenoviral vector typically contains most of the adenoviral genome. The adenoviral vector may also contain a bacterial origin of replication. Portions of the wild-type adenoviral genome may be deleted to permit insertion of desired products and the packaging of recombinant adenoviral vectors containing the desired genes.

The invention provides alternative methods for producing recombinant adenoviral vectors. The methods rely on two homologous recombination steps, one mediated by Cre and the other mediated by RecA. In alternate embodiments, the instant invention provides methods in which the Cre mediated recombination must precede the RecA recombination, methods in which the RecA mediated recombination must precede the Cre mediated recombination, and finally methods in which the order of recombination events in immaterial. The order of recombination events is dictated by the resistance genes on the precursor plasmids. For example, if the donor and shuttle plasmids have the same resistance gene, the Cre mediated recombination must be preformed first (see, for example, the schematic set forth in FIG. 4). In an alternate embodiment, if the donor and acceptor plasmids have the same resistance gene, the RecA mediated recombination must occur first (see, for example, the schematic set forth in FIG. 5). Lastly, if the donor has a different resistance gene than both the acceptor and shuttle plasmids, the order of recombination steps is at the discretion of the skilled artisan (for example, if the donor plasmid had blasticidin resistance as described in the examples).

In one embodiment, a Cre expressing cell is transformed with a donor and acceptor plasmid such that Cre mediated recombination results in the formation of a transfer plasmid. The donor plasmid contains a fiber gene, or other gene product to target the recombinant virus to a specific cell, flanked by lox sites. The acceptor plasmid has a negatively selectable marker, such as SacB, flanked by lox sites. In preferred embodiments of the invention, the lox sites are engineered, i.e., mutated, to result in irreversible, uni-directional recombination and to prevent intragenic recombination.

Cells containing the recombinant transfer plasmid are selected by growth in media containing a substrate for the negatively selectable marker and an antibiotic for which the resulting transfer plasmid carries a resistance gene. In exemplary embodiments, the negatively selectable gene is SacB and the antibiotic resistance is to ampicillin, and cells containing the recombinant transfer plasmid are selected by growth in media containing sucrose and ampicillin. Once cells containing transfer plasmids are isolated, the transfer plasmids can be isolated and transformed into a RecA expressing cell with linear shuttle plasmids. Linear shuttle plasmids are formed by digesting shuttle plasmids with one or more restriction enzymes. In one embodiment, the shuttle plasmid is linearized using a restriction enzyme that has a single restriction site in the plasmid. Alternatively, shuttle plasmids may not be linearized prior to introducing them into a cell for recombination. Recombinant adenoviral vectors formed as a result of RecA mediated recombination are selected by growing cells in the presence of an antibiotic which the recombinant adenoviral vectors carry a resistance gene against. This resistance gene was originally contained on the shuttle plasmid and is integrated into the recombinant viral vector during RecA mediated recombination. A schematic of this embodiment is set forth in FIG. 4.

In an alternate embodiment, the recombinant viral vectors are produced by transforming a cell expressing RecA with a linear shuttle plasmid and an acceptor plasmid. Cells containing a shuttle-acceptor plasmid are selected in media containing an antibiotic to which the resulting shuttle-acceptor plasmid confers resistance. Recombinant shuttle-acceptor plasmids are isolated and transformed into a cell expressing Cre along with a donor plasmid. Recombinant adenoviral vectors are selected using by growing cells in media containing a substrate for the negatively selectable marker and an antibiotic which recombinant adenoviral vectors carry a resistance gene against. This resistance gene was originally contained on the donor plasmid and is integrated into the recombinant viral vector during Cre mediated recombination. A schematic of this embodiment is set forth in FIG. 5.

In other embodiments, the Cre-recombinase mediate exchange is not limited to bacteria or plasmids. For example, fiberless acceptor plasmids can be packaged into working virus through complementary cell lines that express fiber protein (a process known as psuedotyping). These pseudotyped acceptor plasmids can then be used to infect Cre expressing cells, e.g., mammalian cells such as 293cre57, that have been transfected with fiber exchange vectors, i.e. donor vectors. Cell lysate and supernatant are then harvested and used to infect a non-Cre expressing packaging line, immediately generating a recombinant adenovirus.

Adenoviral particles can be prepared according to any conventional technique in the field of the art, such as homologous recombination in a permissive cell line (e.g., as described in Graham and Prevect, 1991, Methods in Molecular Biology, Vol 7, Gene Transfer and Expression Protocols; Ed E. J. Murray, The Human Press Inc, Clinton, N.J.) or in *Escherichia coli* (as described in WO96/17070). Propagation is advantageously performed in a complementing cell line or in the presence of a helper virus providing complementation in trans. "Complementing" or "complementation" denotes that the capability to encode and/or express functions that are defective in the vector but necessary for generating viable viral particles. The cell lines 293 (Graham et al., 1977, J. Gen. Virol. 36, 59-72) and PERC6 (Fallaux et al., 1998, Human Gene Therapy 9, 1909-1917) are commonly used to complement the E1 function. Other cell lines have been engineered to complement doubly defective vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; EP919627 and WO97/04119). The adenoviral particles can be recovered from the culture supernatant but also from the cells after lysis and optionally further purified according to standard techniques (e.g., chromatography, ultracentrifugation, as described in WO96/27677, WO98/00524 and WO98/26048). Furthermore, the virions may be amplified by successive passage in a permissive cell in order to generate a high titer viral stock that may be used in the preparation of clinical lots.

The recombinant adenovirus vector generated as described above may be used to transfect mammalian cells. Techniques for transfection are well known. Available techniques include but are not limited to electroporation, the use of calcium chloride, and packaging of the vector together with lipid for fusion with the cells of interest. Cells may be transfected with the vector either in vitro or in vivo. The design of the recombinant adenoviral vector may place specific constraints on cells to be transfected. If production of viral particles is desired, a special packaging cell must be used that produces the adenoviral gene products which the adenoviral vector lacks. Which packaging cells are employed to replicate the virus will depend on the composition of the adenoviral vector used. The adenoviral vector may have specific portions of the adenoviral genome deleted, in order to make room for the desired gene in the recombinant vector. Suitable deletions which may be used include those of all or part of adenoviral transcription units E1, E3, and E4. The packaging cells preferably stably express the adenoviral proteins coded by the deleted transcription units. Techniques are known in the art for stably transfecting a cell line with whichever adenoviral sequences are required, i.e., by incorporation of the genes into the cell's genome. If virus particle production is not required, then packaging cell lines need not be used. For example, if cells are to express the desired product, production of viral particles need not be achieved. Thus for in vivo gene therapy, the recipient cells need not be able to complement the defective viruses.

Genes encoding a detectable marker may be present in adenoviral vector to allow for detection of the recombinant vector once produced. Preferably, a marker is used which is easy to monitor. More preferably a marker is used which can be detected even when present at very low levels. Use of a detectable marker permits monitoring of the transfection process. In an exemplary embodiment the detectable marker is β-galactosidase or green fluorescent protein (GFP). Detection of GFP can be achieved, for example, by fluorescence microscopy of cultured cells.

Genes encoding a selectable product can also be used as linked markers to the desired product. A selectable product is necessary for growth under a particular set of conditions. Thus it can be used to selectively grow only those cells that have been transformed or transfected. A preferred selectable product is an antibiotic resistance enzyme, such as those for ampicillin, kanamycin, or blastocidin.

The adenoviral vector of the invention can also be used to produce a pseudotyped viral particle, i.e., a viral particle that contains one or more structural genes that are not derived from the adenoviral genome. The viral vectors described herein can be made by recombination in intact viral genomes thereby producing pseudotyped virus.

Cell type-specific targeting may be achieved with vectors derived from viruses having a broad host range by the modification of viral surface proteins. For example, the specificity of infection of adenoviruses is determined by the attachment to cellular receptors present at the surface of permissive cells. In this regard, the fiber gene is exemplified throughout the instant application. However, those of skill in the art will recognize that many other genes can be used in place of fiber to achieve cell-type specific targeting. For example, penton plays a critical role in cellular attachment (Defer et al. J. Virol. 64 (1990) 3661-3673). Thus, cell targeting of adenoviruses can be carried out by genetic modification of a viral gene, e.g., fiber and/or penton, to generate modified proteins capable of specific interaction with unique cell surface polypeptides. Examples of such modifications are described in literature (for example in Wickam et al., 1997, J. Virol. 71, 8221-8229; Arnberg et al., 1997, Virol. 227, 239-244; Michael et al., 1995, Gene Therapy 2, 660-668; WO94/10323). Moreover, a exemplary penton mutant is described herein and called pFex-p* (mutation D342E).

The present invention also provides a host cell comprising an adenoviral vector of the invention, a polynucleotide or an expression vector as defined in connection with the use of the invention or infected by a viral particle of the invention. The vector may be inserted into the cellular genome or not (episome). A host cell may be unique type of cells or a group of different types of cells and encompass cultured cell lines, primary cells and proliferative cells, with a special preference for cells of human origin.

The present invention also provides compositions, e.g., pharmaceutical compositions, comprising as an agent an adenoviral vector according to the invention, a polynucleotide or an expression vector as described in connection with the use of the invention, a host cell or a viral particle according to the invention or prepared according to the method of the invention.

The composition according to the invention may be manufactured in a conventional manner for a variety of modes of administration including systemic, topical and local administration. Referring to systemic administration, injection is preferred, e.g., intravenous, intraperitoneal, intragastric, subcutaneous, intracardiac, intraarterial, intracoronary, intravascular, intraarterial, intramuscular, intrathecal, intratumoral, intranasal, intrapulmonary or intratracheal routes. Local administration include aerosolization instillation and oral routes of administration. The administration may take place in a single dose or a dose repeated one or several times after a certain time interval. The appropriate administration route and dosage vary in accordance with various parameters, for example, with the individual, the condition or disease to be treated, the stage to which it has progressed, the need for prevention or therapy and the gene of interest to be transferred. As an indication, a composition based on viral particles may be formulated in the form of doses of between $10^4$ and $10^{14}$ iu (infectious unit), advantageously between $10^5$ and $10^{13}$ iu and preferably between $10^6$ and $10^{12}$ iu. The titer may be determined by conventional techniques. The doses of DNA vector are preferably comprised between 0.01 and 10 mg/kg, and more especially between 0.5 and 2 mg/kg. The composition of the invention can be in various forms, e.g., solid (powder, lyophilized form) or liquid (e.g., aqueous).

In a preferred embodiment, the composition comprises a pharmaceutically acceptable carrier, allowing its use in a method for the therapeutic treatment of humans or animals. In this particular case, the carrier is preferably a pharmaceutically suitable injectable carrier or diluent which is non-toxic to a human or animal organism at the dosage and concentration employed (for examples, see Remington's Pharmaceutical Sciences, 16.sup.th ed. 1980, Mack Publishing Co). It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g., Tris-HCl, acetate, phosphate), emulsifiers, solubilizers, excipients or adjuvants. The pH of the composition is suitably adjusted and buffered in order to be appropriate for use in humans or animals. Representative examples of carriers or diluents for an injectable composition include water, isotonic saline solutions which are preferably buffered at a physiological pH (such as phosphate buffered saline, Tris buffered saline, mannitol, dextrose, glycerol containing or not polypeptides or proteins such as human serum albumin). For example, such a composition may comprise 10 mg/ml mannitol, 1 mg/ml HSA, 20 mM Tris pH 7.2 and 150 mM NaCl.

In addition, the composition according to the present invention may include one or more stabilizing substance(s), such as lipids (e.g., cationic lipids, liposomes, lipids as described in WO98/44143; Felgner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, 647-654), nuclease inhibitors, hydrogel, hyaluronidase (WO98/53853), collagenase, polymers, chelating agents (EP890362), in order to preserve its degradation within the animal/human body and/or improve delivery into the host cell. Such substances may be used alone or in combination (e.g., cationic and neutral lipids). It may also comprise substances susceptible to facilitate gene transfer for special applications, such as a gel complex of polylysine and lactose facilitating delivery by intraarterial route (Midoux et al., 1993, Nucleic Acid Res. 21, 871-878) or poloxamer 407 (Pastore, 1994, Circulation 90, 1-517). It has also be shown that adenovirus proteins are capable of destabilizing endosomes and enhancing the uptake of DNA into cells. The mixture of adenoviruses to solutions containing a lipid-complexed plasmid vector or the binding of DNA to polylysine covalently attached to adenoviruses using protein cross-linking agents may substantially improve the uptake and expression of the vector (Curiel et al., 1992, Am. J. Respir. Cell. Mol. Biol. 6, 247-252).

The present invention also provides the use of an adenoviral vector according to the invention, a polynucleotide or an expression vector, as described in connection with the use according to the invention, a viral particle or a host cell according to the invention for the preparation of a medicament intended for gene transfer, preferably into a human or animal body. Within the scope of the present invention, "gene transfer" has to be understood as a method for introducing any gene of interest into a cell. Thus, it also includes immunotherapy that relates to the introduction of a potentially antigenic epitope into a cell to induce an immune response which can be cellular or humoral or both.

For this purpose, the adenoviral vector, the polynucleotide and expression vector or the viral particle of the present invention may be delivered in vivo to the human or animal organism by specific delivery means adapted to the pathology to be treated. For example, a balloon catheter or a stent coated with the adenoviral vector, the expression vector carrying the polynucleotide or the viral particle may be employed to efficiently reach the cardiovascular system (as described in Riessen et al., 1993, Hum Gene Ther. 4, 749-758; Feldman and Steg, 1996, Medecine/Science 12, 47-55). It is also possible to deliver said therapeutic agents by direct administration, e.g., intravenously, in an accessible tumor, in the lungs by aerosolization and the like. Alternatively, one may employ eukaryotic host cells that have been engineered ex vivo to contain the adenoviral vector, the expression vector carrying the polynucleotide or the viral particle according to the invention. Methods for introducing such elements into an eukaryotic cell are well known to those skilled in the art and include microinjection of minute amounts of DNA into the nucleus of a cell (Capechi et al., 1980, Cell 22, 479-488), transfection with $CaPO_4$ (Chen and Okayama, 1987, Mol. Cell. Biol. 7, 2745-2752), electroporation (Chu et al., 1987, Nucleic Acid Res. 15, 1311-1326), lipofection/liposome fusion (Felgner et al., 1987, Proc. Natl. Acad. Sci. USA 84, 7413-7417) and particle bombardement (Yang et al., 1990, Proc. Natl. Acad. Sci. USA 87, 9568-9572). The graft of engineered cells is also possible in the context of the present invention (Lynch et al, 1992, Proc. Natl. Acad. Sci. USA 89, 1138-1142).

The present invention also relates to a method for the treatment of a human or animal organism, comprising administering to said organism a therapeutically effective amount of an adenoviral vector of the invention, the polynucleotide or expression vector as described in connection with the use according to the invention, a viral particle or an eukaryotic cell according to the invention.

A "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes and for therapeutic applications relative to the diseases or conditions listed above. The present method is particularly useful to prevent or reduce the establishment of an inflammatory response following administration of a conventional gene-therapy vector. It is to be understood that the present method can be carried out by any of a variety of approaches. Advantageously, the vector, viral particle, cell or the pharmaceutical composition of the invention can be administered directly in vivo by any conventional and physiologically acceptable administration route, for example by intravenous injection, by direct injection into an accessible tumor or by means of an appropriate catheter into the vascular system, etc. Alternatively, the ex vivo approach may also be adopted which consists of introducing the adenoviral vector, the polynucleotide or the viral particle according to the invention into cells, growing the transfected/infected cells in vitro and then reintroducing them into the patient to be treated.

A kit according to the invention comprises one or more of the described plasmids, e.g., a shuttle plasmid, a transfer plasmid, a donor plasmid, and/or an acceptor plasmid, useful in the generation of recombinant adenoviral vectors. A user of the kit may insert one or more desired genes into the shuttle plasmid using, for example, a restriction endonuclease and a DNA ligase. The kit may also comprise a packaging cell line for producing virus particles from the defective adenoviral vector and/or the recombinant adenoviral vectors produced containing the desired product. The kit may also comprise bacterial cells which can be used for co-transformation. Preferably the bacterial cells are homologous-recombination proficient and highly competent to receive transforming DNA.

Typically, each kit component is separately packaged to avoid premature mixing. Further, all individually packaged components are provided in a box or other container which holds the other components. Instructions for making a recombinant adenovirus vector according to the methods disclosed herein may also be included in the kit. Reference to instructions may also be provided in the kit, for example to a text or webpage.

Kits may also contain the recombinant adenoviral vectors, or viral particles, produced by the methods of the invention and instructions for the administration of the vectors or viral particles to a subject for therapeutic or preventative purposes.

EXAMPLES

It should be appreciated that the invention should not be construed to be limited to the examples that are now described; rather, the invention should be construed to include any and all applications provided herein and all equivalent variations within the skill of the ordinary artisan.

Example 1

The Cre recombinase from bacteriophage P1 is an enzyme which mediates the excision and integration of DNA based on specific sequence binding sites (lox) through stepwise cleavage and ligation involving Holiday Junction intermediates (Ghosh, K. and Van Duyne, G. D. (2002) Methods, 28: 374-383). Though nearly 100 related tyrosine recombinases have been identified by sequence homology, Cre recombinase is among the best studied. Lox binding sites are 34 base pairs in length, but are solely sufficient to target Cre binding and recombination with the corresponding Lox sites. The canonical Lox site is the LoxP site. It has a 13 bp inverted repeat and an 8 bp spacer (FIG. 1). The 8 bp spacer is asymetrical and hence has orientation (actual direction of arrow is arbitrary). Two-loxP sites flanking a gene are called "floxing". If a gene is floxed by two identical sites facing the same direction, it will be deleted with Cre recombinase. If a gene is floxed by Lox sites facing opposite directions, it will be reversed in its orientation with Cre recombinase. If two separate genes are floxed by identical sites, the genes may be exchanged with Cre recombinase. This is known as recombinase mediated cassette exchange (RMCE). Because the lox sites remain unaltered following recombination, these reactions are reversible or bidirectional.

Figure 2A:
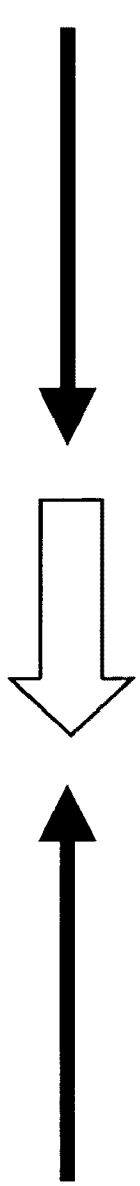

In order to maximize gene replacement, without favoring spontaneous excision, two Lox sites have to be used which are incompatible. This can be accomplished by mutating the spacer (FIG. 2B). In addition, half site mutations in the inverted repeat section can lead to a unidirectional recombination event by resulting in a non-functional lox site following recombination (FIG. 2A). By combining these two methods, a highly efficient unidirectional gene replacement can be achieved (Langer, S. J. et al. (2002) *Nucleic Acids Res,* 30: 3067-3077.).

Figure 3:
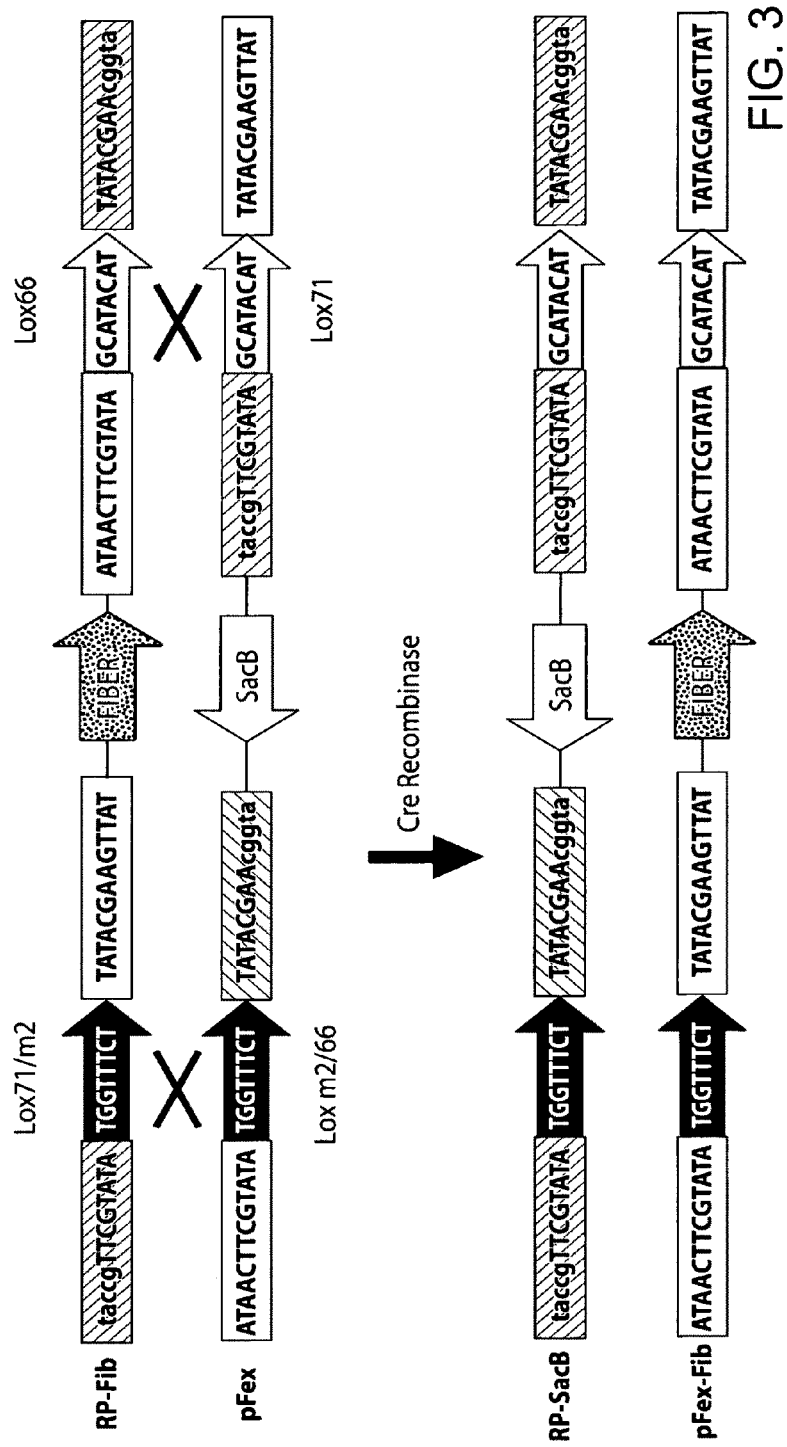
FIG. 3 is a schematic depicting two non-compatible spacer sequences (black arrows) that force gene exchange rather than excision. The reaction of two half-mutant lox sites (shaded with mutations in lower case) results in a dually mutated lox site (PR-SacB) and a unidirectional reaction (SEQ ID NOS.12-15).

This invention applies Cre recombinase and half mutant lox sites with incompatible spacers to uni-directionally exchange modified targeting genes into the fiber region of adenoviral vectors. As delineated by Langer et al, the use of a Lox m2/66 and Lox 71 on the donor fragment; and a Lox m2/71 with Lox 66 on the acceptor fragment results in a unidirectional gene exchange with maintained orientation and lack of alternative recombination events (Langer, supra). Here the acceptor vector, pFEX, has a Lox m2/66 3' of the SacB gene and a Lox 71 on the 5'-side. When induced by media containing 5% sucrose, SacB is lethal in a wide range of Gram negative bacteria, and thus permits selection for loss of the vector (Quandt, J. and Hynes, M. F. (1993) *Gene,* 127: 15-21). The donor vector, RP-Fib, contains a lox m2/71 site 5' of the Fiber gene and a Lox 66 site on the 3'-side (FIG. 3). The combination of the unidirectional recombination with a negative selectable marker results in extremely high numbers of desired recombinants. The system is directly compatible with the existing AdEasy system. The acceptor vector, named pFex, is similar to AdEasy-1, but it has the fiber gene replaced with a floxed negative selectable marker, the SacB gene. The smaller donor vector, RP-Fib, contains a modified fiber gene, which is also floxed. Several variations of the smaller donor include a unique BspEI site in the HI loop for the incorporation of targeting ligands and/or a mutation in the receptor binding region of fiber. Additionally, the donor contains many convenient restriction enzyme recognition sites so genes other than fiber can be efficiently shuttled into pFex. The numerous shuttle vectors are described in detail below.

Using the described system, the fiber gene can be transferred into pFex either before (FIG. 4) or after (FIG. 5) the recombination with the E1 shuttle vector. Two separate fiber shuttle scaffolds have been constructed for either transfer stage. RP-Fib, which is kanamycin resistant, is applied for recombination prior to the E1 shuttle recombination (FIG. 4), and RPuc-Fib, which is ampicillin resistant, is applied for recombination after the E1 shuttle recombination. To increase the efficiency of the E1 shuttle recombination, pFex stable *E. coli* called bFex, can be used to overcome limitations in large plasmid transformation efficiency. This option is available for any pFex vector, after fiber exchange, if multiple E1 variations are needed. Both recombination pathways result in the same product, which can then be linearized with Pac I digestion, and transfected into a mammalian cell packaging cell line, such as 293-HEK, for the creation of virus. A third fiber shuttle, RP-Blast-Fib, has been designed to allow for blasticidin selection at either stage of recombination.

Figure 6:
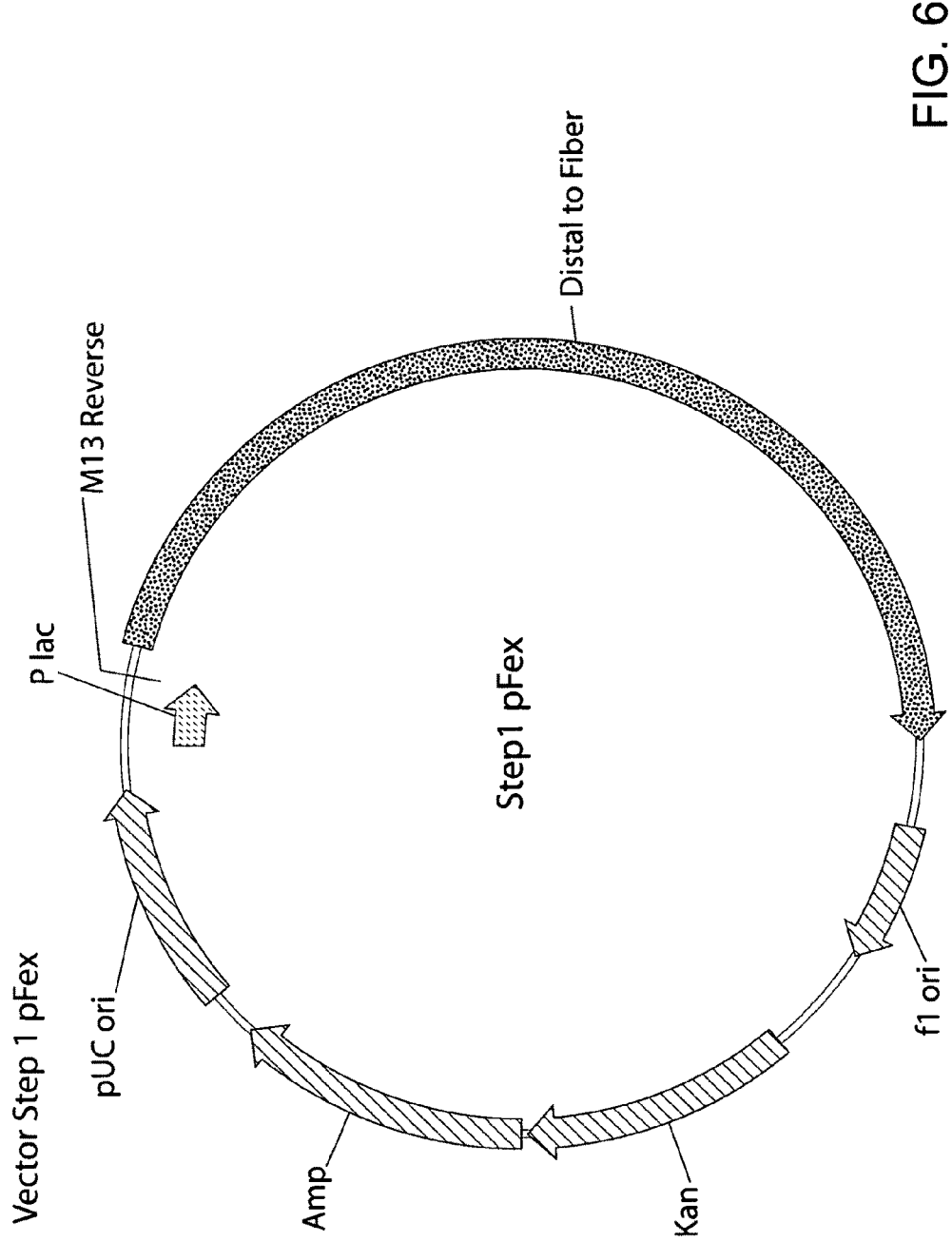
FIG. 6 is a schematic depicting step 1 of pFex assembly.

B. Design and Methods for Producing pFex Components.

pFex was assembled through several steps. First, a segment called 'distal to fiber Age I' was created by PCR amplification of the adenovirus serotype 5 genome with primers AdE-Dist 5' and AdE-Dist 3' (Table 1). This product was then cloned into the TOPO-TA vector pCR-2.1, using TA cloning, to produce the vector Step 1 pFex (FIG. 6).

Figure 7:
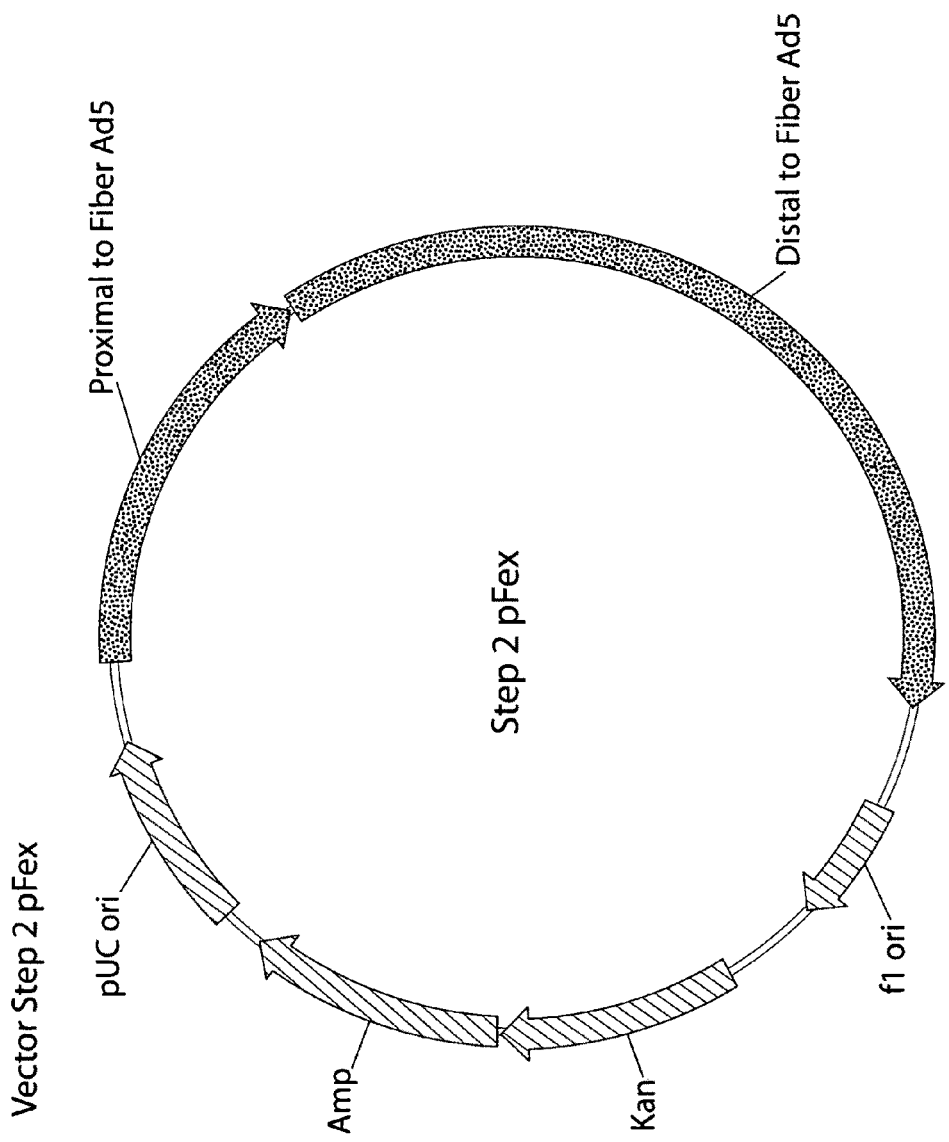
FIG. 7 is a schematic depicting step 2 of pFex assembly.

Second, a segment called 'proximal to fiber' was created by PCR amplification of the adenovirus serotype 5 genome with primers loxmve1 and loxmve2 (Table 1). This product was then cloned into Step 1 pFex using the Spe I and Age I restriction sites. The resulting vector is Step 2 pFex (FIG. 7).

Figure 8:
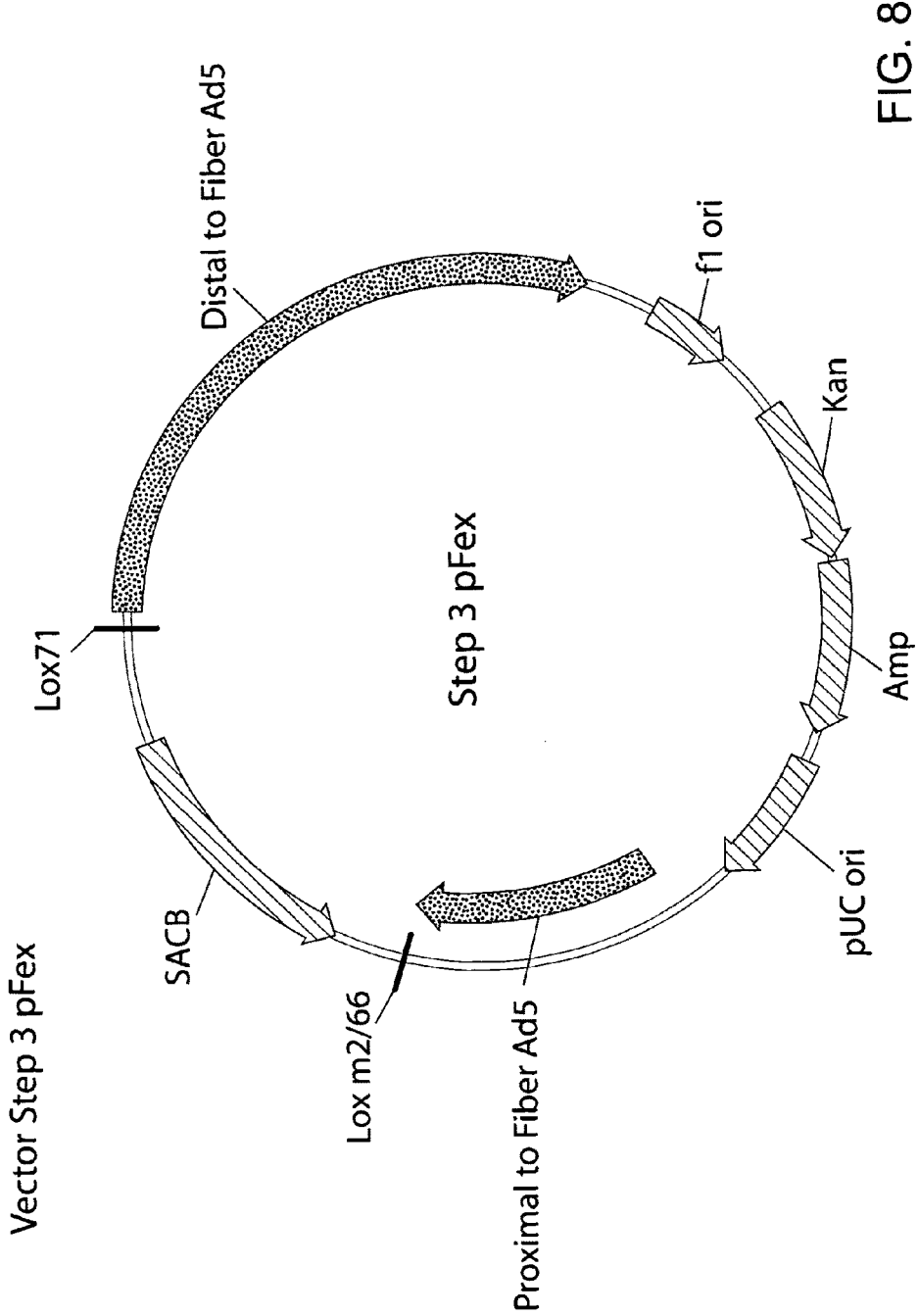
FIG. 8 is a schematic depicting step 3 of pFex assembly.

The SacB gene was isolated from the vector pAJ200 using the Bgl II and Pvu I restriction sites. Next, the two half mutant lox sites, lox m2/66 and lox 71, were added by ligation with self annealed linkers 5' lox m2/66 and 3' lox m2/66, and 5' lox 71 and 3' lox 71, respectively (Table 1). The resulting floxed SacB gene was then subcloned into Step 2 pFex to create Step 3 pFex (FIG. 8).

Figure 9:
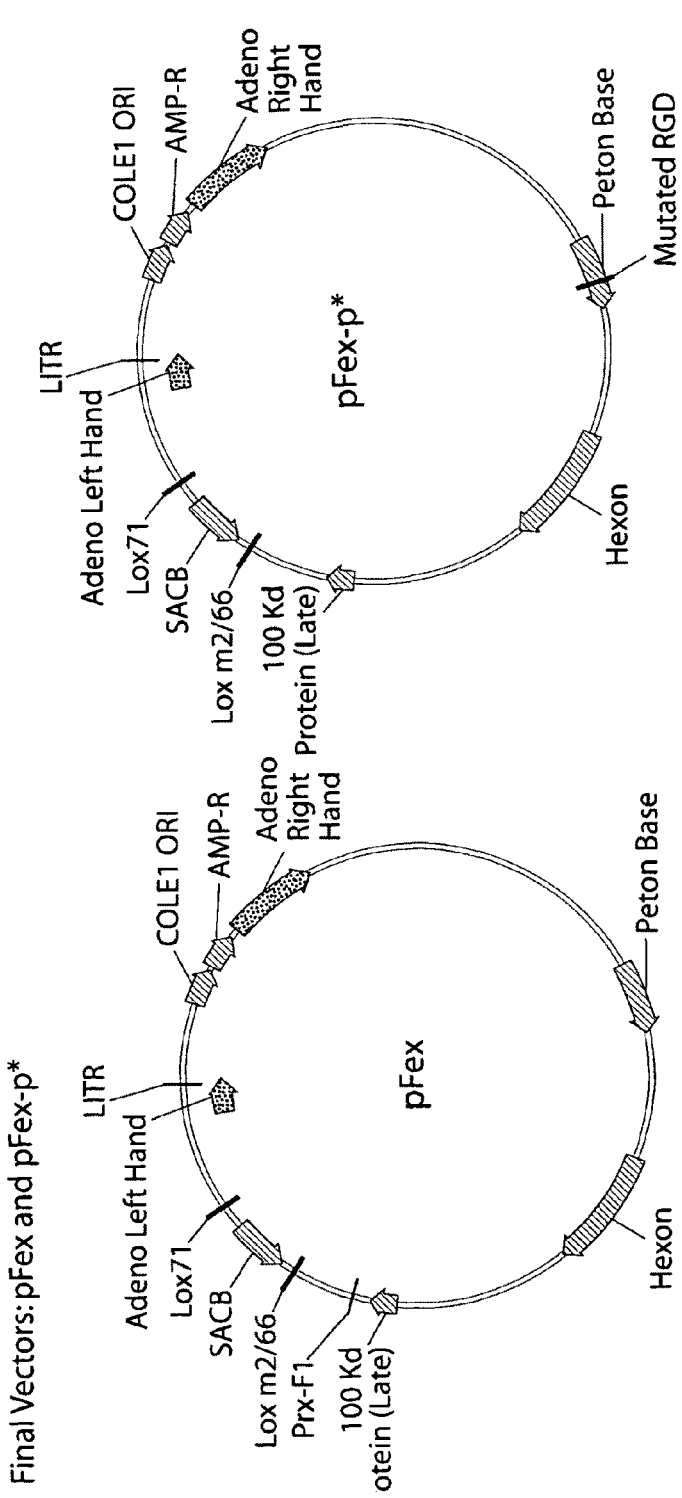
FIG. 9 is a schematic showing vectors pFex and pFex-p*.

Finally, the modified AdEasy segment containing SacB in place of fiber was removed with a double digest of SpeI and PacI. This product was then exchanged for the pre-existing region of fiber in pAdEasy-1. The final vector construct is called pFEX (FIG. 9). The final product was verified by sequencing using primers pFEX for 01-11 and pFEXrev01-11 (Table 1). Finally, a second version of pFEX, termed pFEX-p*, contains a mutation in the integrin binding domain of the penton gene, where RGD is mutated to RGE (FIG. 9).

Figure 10:
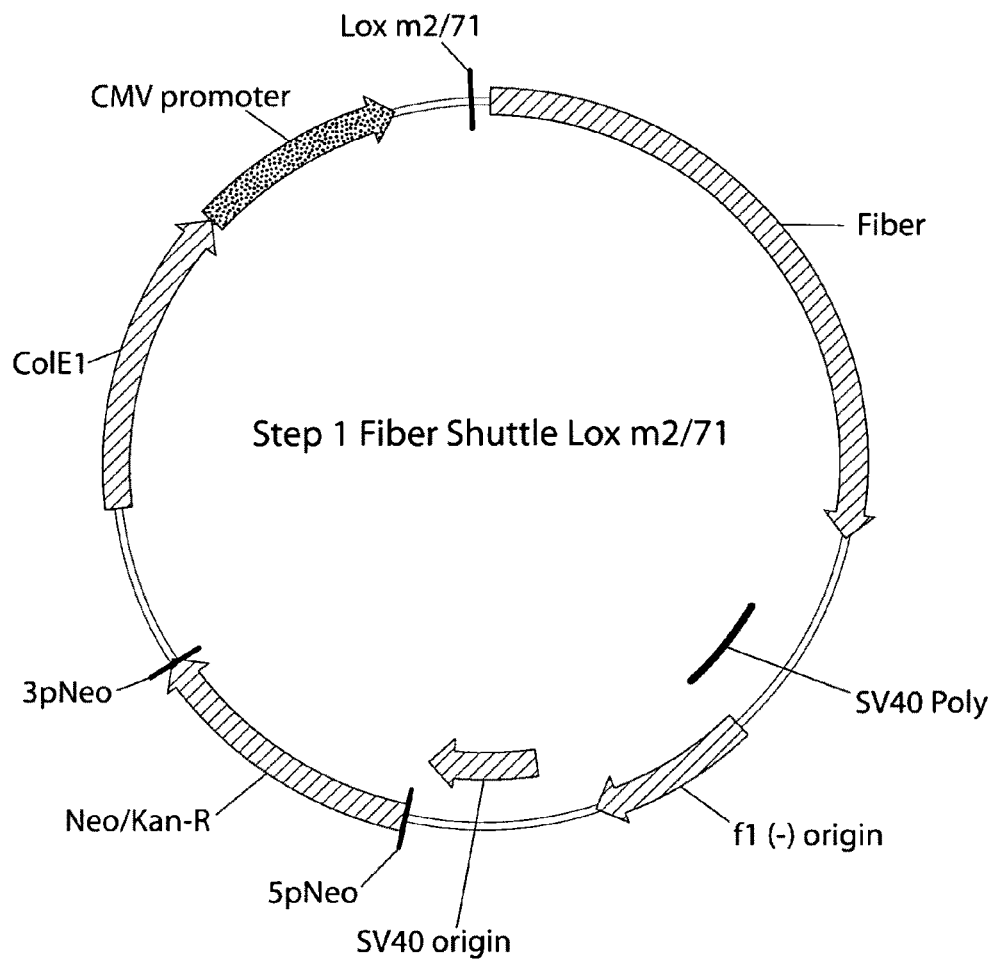
FIG. 10 is a schematic depicting Fiber Shuttle Lox m2/71.
Figure 11:
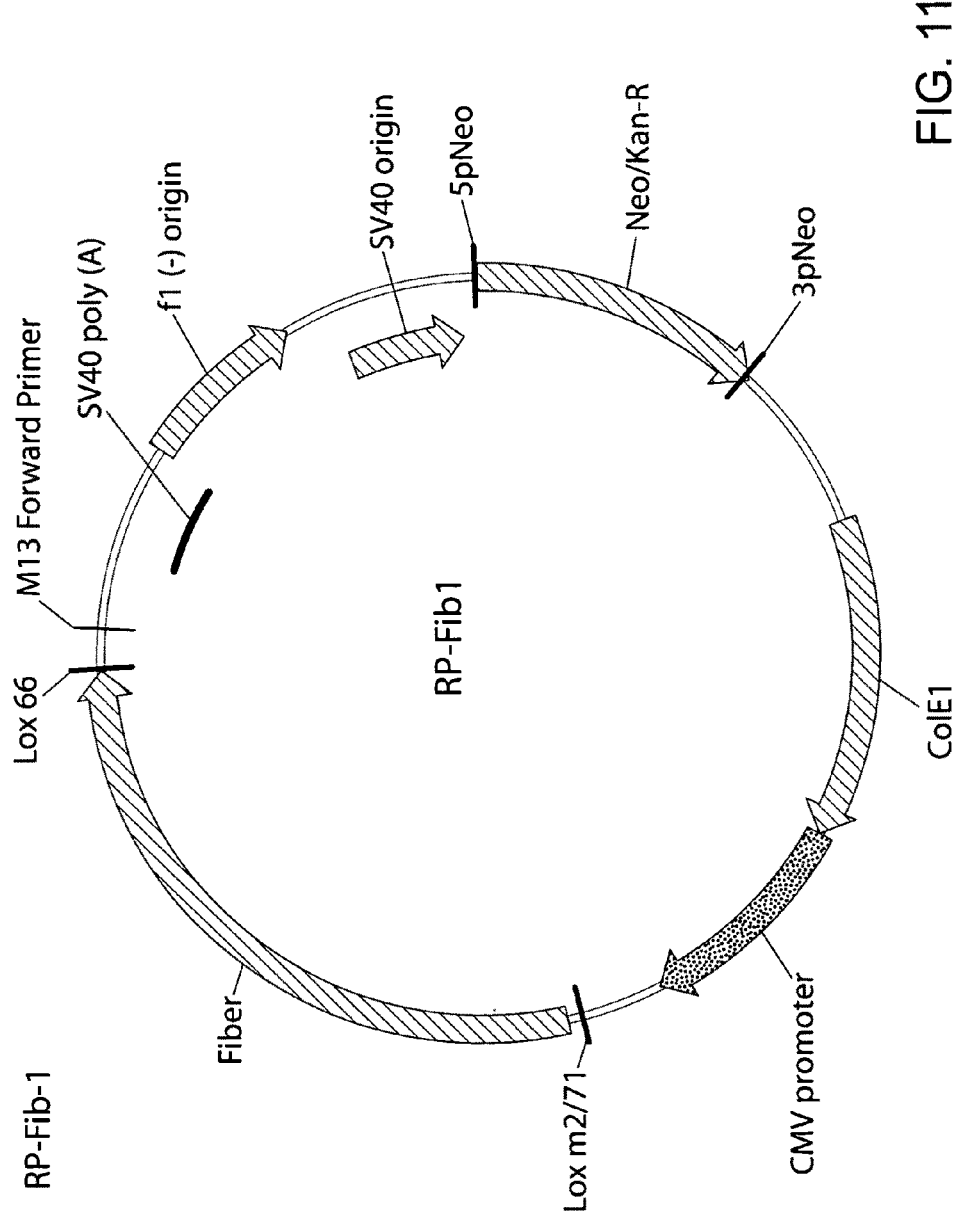
FIG. 11 is a schematic of RP-Fib-1.

The fiber shuttle vectors were also constructed in a stepwise manner. An existing adenovirus serotype 5 fiber vector, pBK-CMV-Fiber, was first digested with the restriction enzymes Spe I and Xho I. The linkers S-lox m2/71-X5 and S-lox m2/71-X5 (Table 2) were self annealed and then inserted into the vector at these sites, creating Step 1 Fiber Shuttle Lox m2/71 (FIG. 10). This product was then digested with restriction enzymes Acc65 I and Not I, and the linkers N-Lox 66-A-5 and N-Lox 66-A-3 (Table 2), were then ligated into this site. The final product was named RP-Fib (FIG. 11). Finally, the tripartite leader splice acceptor site was inserted downstream of the lox m2/71 site by annealing the primers splce1 (TCGAGAACTATCTTCATGTTGTTGCA-GATGAAGCGCGCAAGACCGTCTGAA-GATACCTTCAACCCCGTGTATC CATATGACACG-GAAA) (SEQ ID NO.7) and splce 2 (CCGGTTTCCGTGTCATATGGATA-CACGGGGTTGAAGGTATCTTCAGACG-GTCTTGCGCGCTTCATCTGCAACAACATGAAG ATAGTTC) (SEQ ID NO.8) and cloning this into XhoI/AgeI sites of all fiber shuttle vectors. All of the described RP-Fib vectors have a mutated fiber gene that contains a unique BspEI site in the gene's HI loop for the incorporation of targeting peptide sequences (FIG. 11). Additionally, some vectors have a mutated fiber gene were the coding region for $T_{489}AYT_{492}$, a known Coxsackie and Adenovirus Receptor (CAR) binding site, has been deleted (Roelvink, P. W. et al. (1999) *Science,* 286: 1568-1571).

Figure 4:
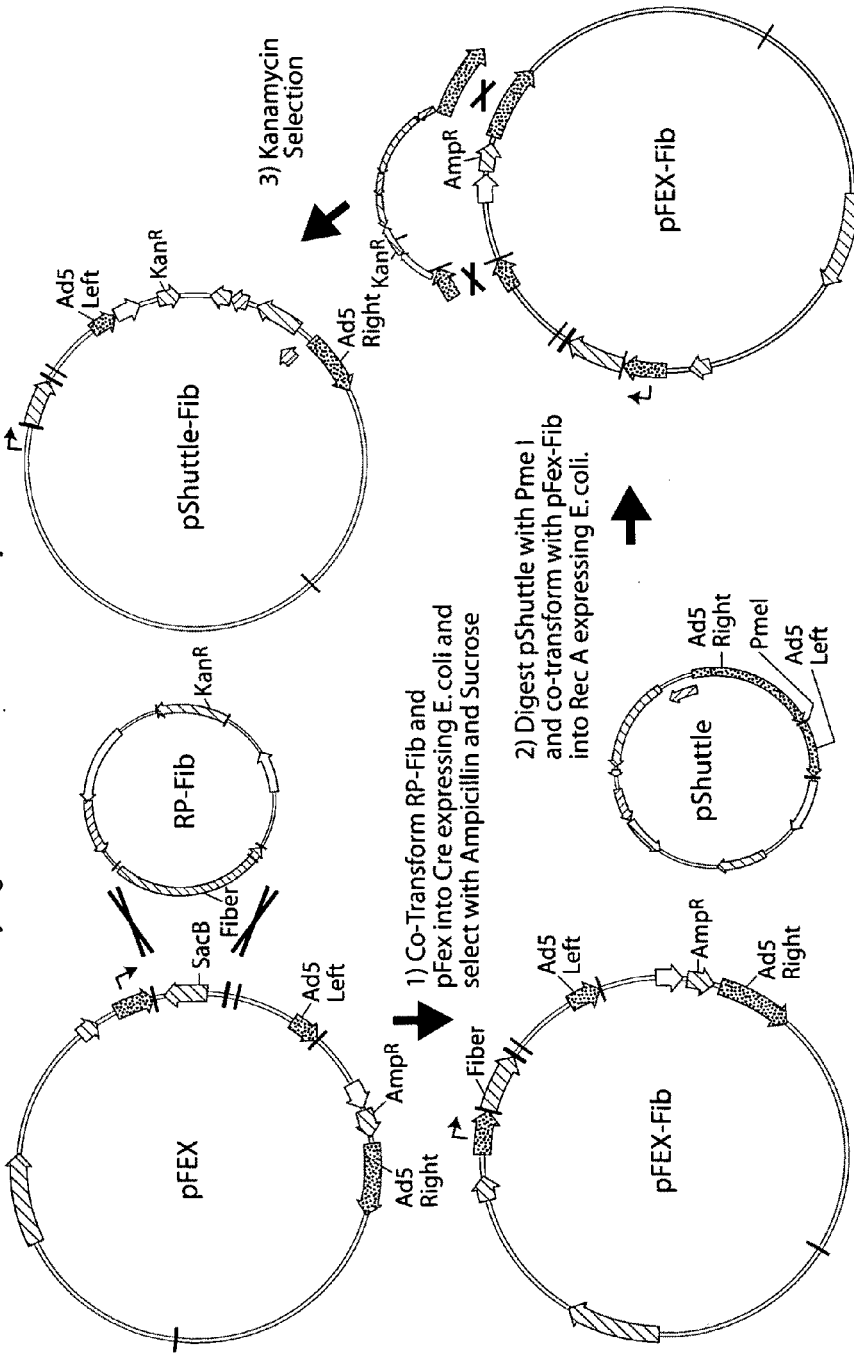
FIG. 4 is a schematic of pFex fiber exchange followed by RecA recombination resulting in pShuffle-Fib, an adenoviral vector. This vector can be digested with Pac I and transfected into a desired cell line to create virus.
Figure 5:
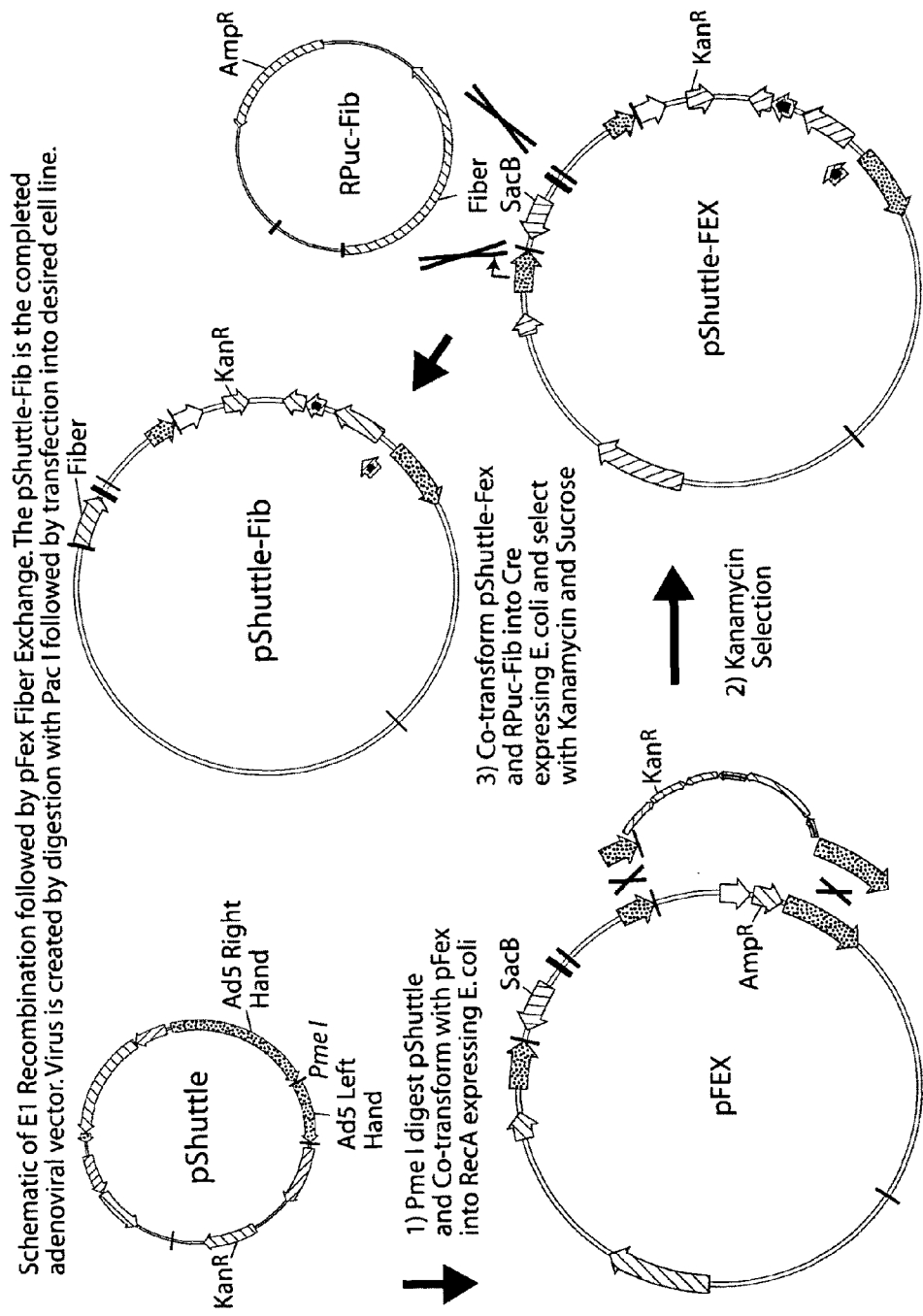
FIG. 5 is a schematic of Rec A recombination followed by pFex fiber exchange. The pshuttle-Fib is the completed adenoviral vector. This vector can be digested with Pac I and transfected into a desired cell line to create virus.
Figure 12:
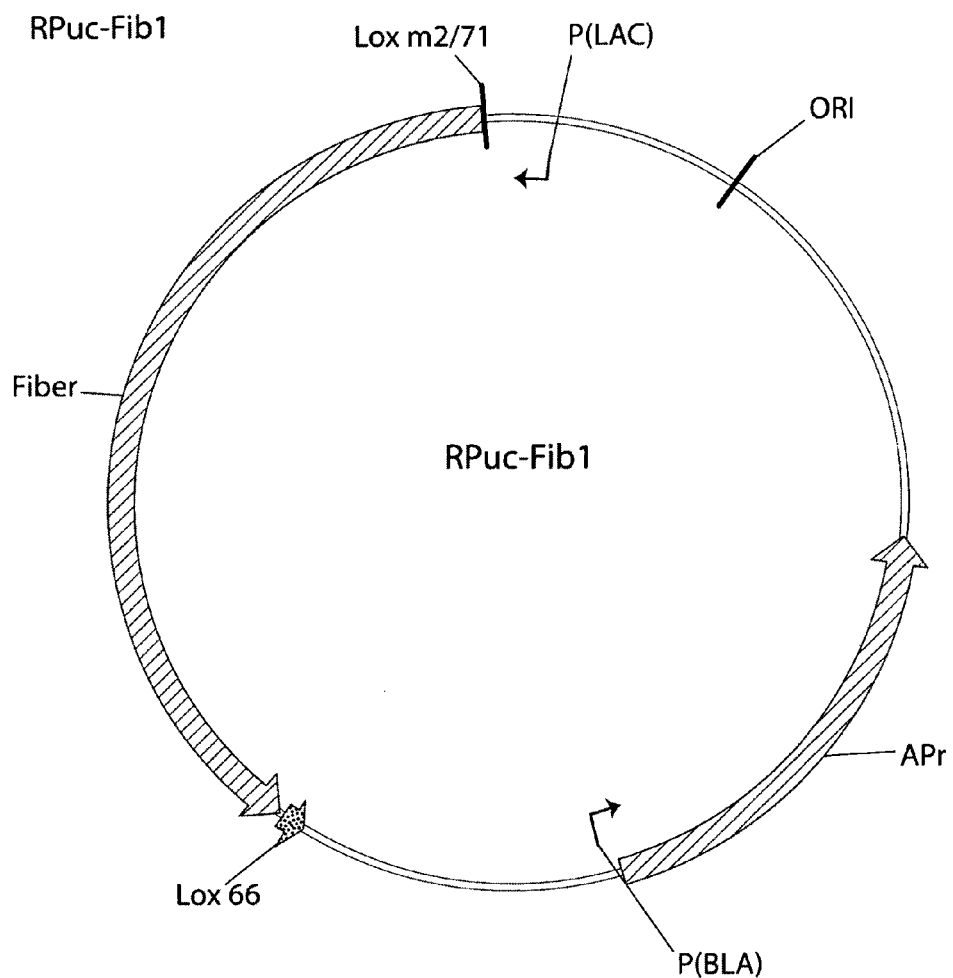
FIG. 12 is a schematic of RPuc-Fib-1.

The current fiber shuttle vectors are summarized in Table 3. All RP-Fib vectors contain genes encoding kanamycin resistance. A separate set of vectors, RPuc-Fib, contain the same floxed fiber genes; however, the vector base is pUC-19, which is amplicillin resistant (FIG. 12). These two separate selection antibiotics allow for fiber gene exchange to occur at multiple steps (FIGS. 4 & 5).

C. Recombination of pFex with E1 Shuttle Vectors

Figure 13:
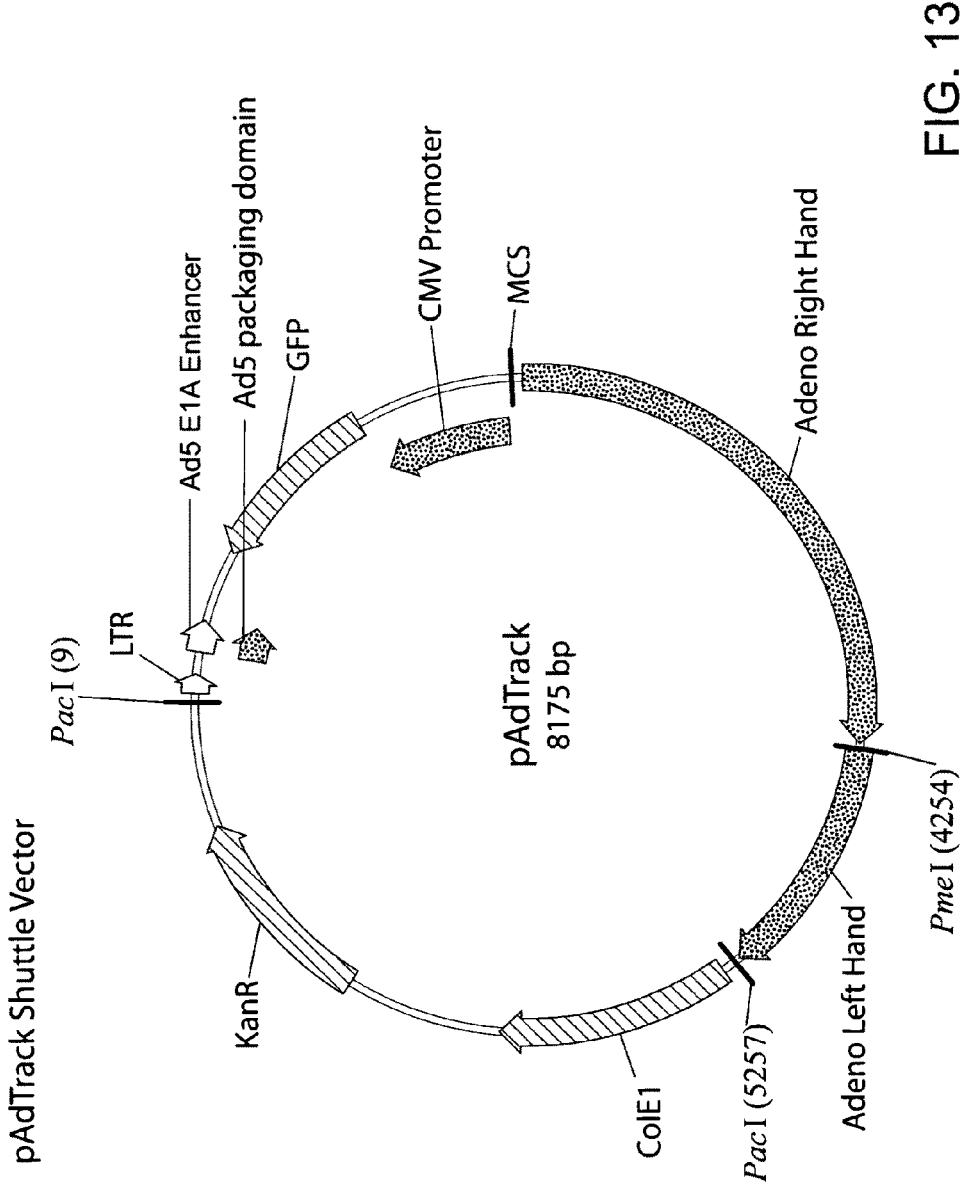
FIG. 13 is a schematic of pAdTrack shuttle vector.
Figure 14:
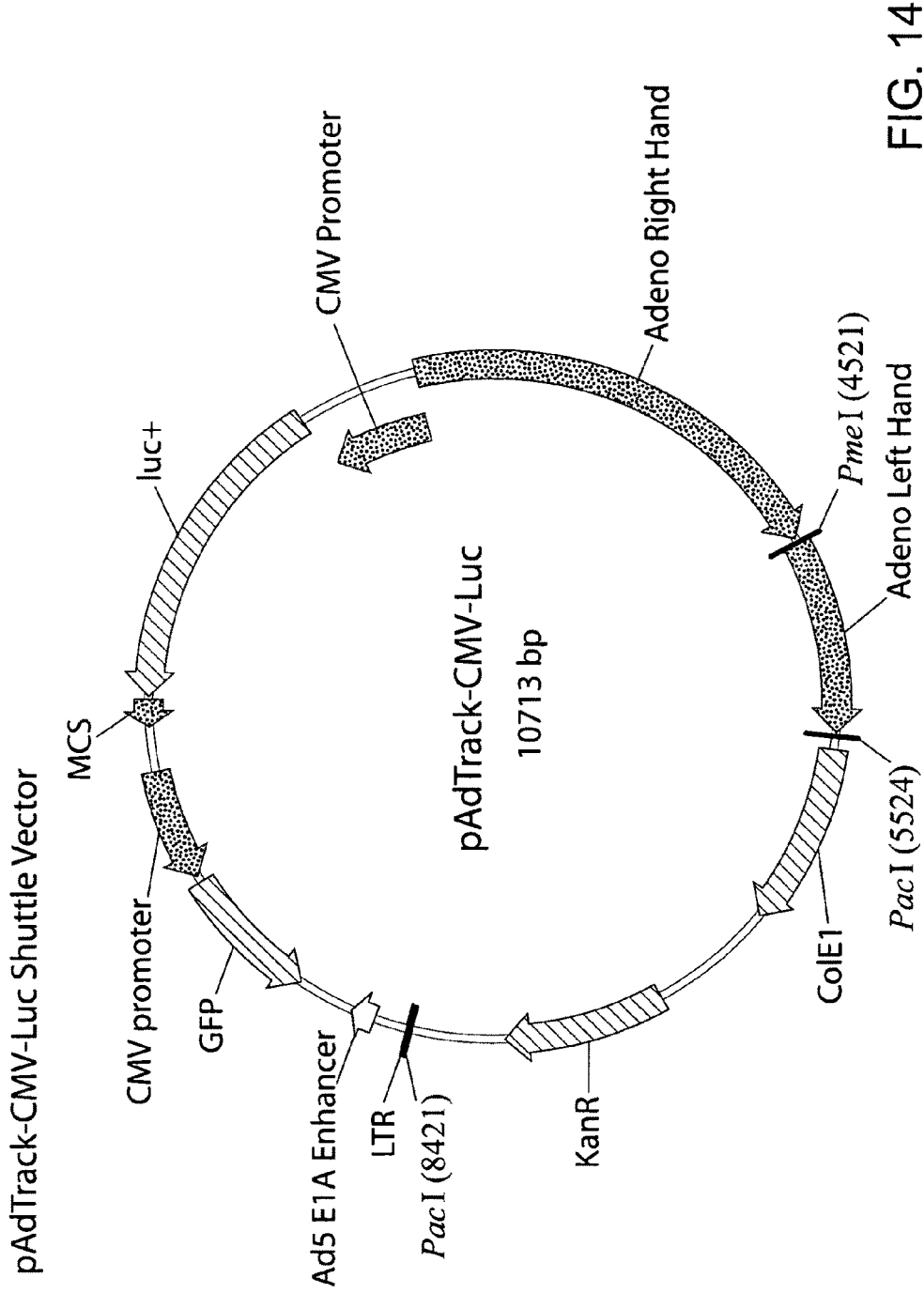
FIG. 14 is a schematic of pAdTrack-CMV-Luc shuttle vector.

The pFex vector was recombined with two E1 region shuttle vectors, pAdTrack (FIG. 13) and pAdTrack-CMV-Luc (FIG. 14) to demonstrate working recombination in these regions. This recombination step is based on the previously described AdEasy system (He, T. C. et al. (1998) *Proc Natl Acad Sci USA,* 95: 2509-2514).

Figure 15:
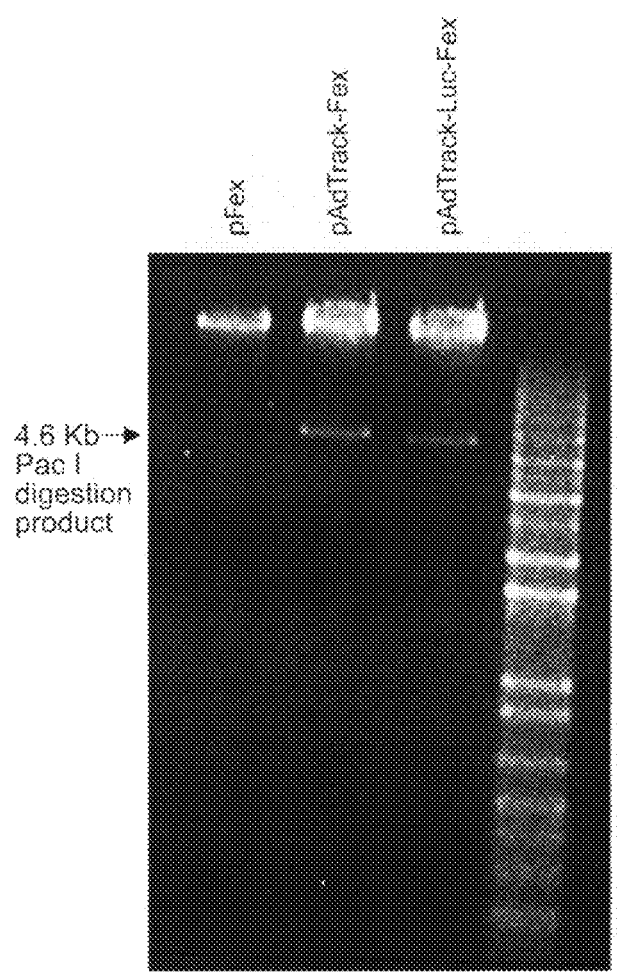
FIG. 15 depicts the results of restriction digests demonstrating pFex recombination with pAdTrack vectors.
Figure 16:
FIG. 16 depicts the results of restriction digests demonstrating ColE1/Ad Right hand recombination.

To increase the chances of recombination, the RecA positive bacterial line BJ5183 was first stably transfected with pFex. This technique has been shown to significantly increase the number of recombinants with the AdEasy vectors (Zeng, M. et al. (2001) *Biotechniques,* 31: 260-262). Each pAdTrack vector was then transformed into pFex stable BJ5183 cells, followed by selection on 50 µg/ml Kanamycin. There are two desired recombination products that replace the Ampicillin resistance cassette of pFex, one where recombination takes place between the homologous adenoviral left and right hand regions, or a second where the homologous replication origins and adenoviral right hand regions recombine. Either product is acceptable as Pac I digestion produces the same desired adenoviral genome product. Here, all products were the result of recombination between the origins of replication and the adenoviral right hand region (FIG. 15). Recombination between the adenoviral left and right hand portions would have produced a Pac I digestion product 1.7 Kb smaller without an additional Nde I site. Later whole viral genome products demonstrate four bands following Nde I digestion, indicating the recombination between the origins of replication and adenoviral right hand regions (FIG. 16).

D. Recombination of pFex with Fiber Shuttle Vectors

Figure 17:
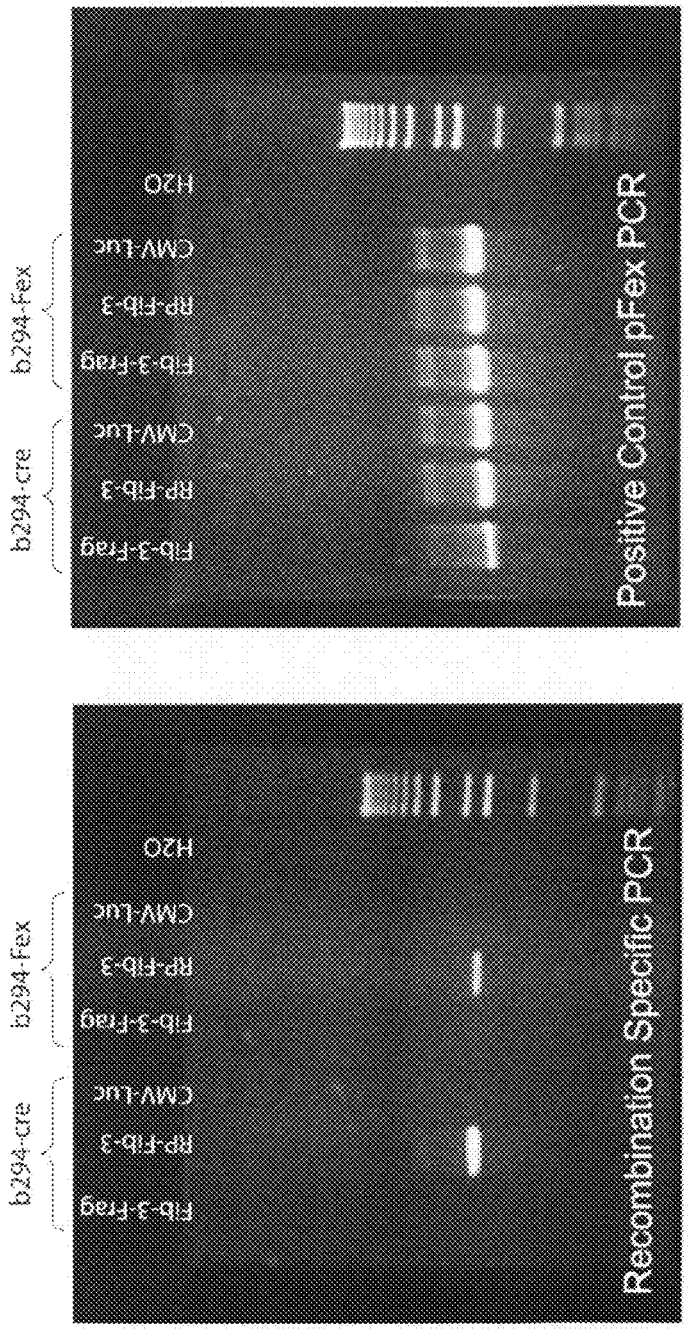
FIG. 17 depicts the results of restriction digests indicating the expected products by co-transformation of fiber shuttle and pFex into 294cre cells or by transformation of fiber shuttle into pFex stable 294cre cells (b294-fex).

The pFex vector was then recombined with the kanamycin resistant shuttle vectors Rp-Fib-1, Rp-Fib-2, Rp-Fib-3, and Rp-Fib-4 to demonstrate working Cre lox recombination. This fiber exchange reaction was facilitated by the Cre expressing bacteria, 294cre. For each shuttle vector, pFex and molar excess of the Fiber shuttle were co-transformed into 294cre cells by electroporation. These cells were then heat shocked for 20 minutes at 42° C. to induce Cre expression, and then incubated at 37° C., while shaking, for 2 hours to continue Cre expression and Cre based recombination. The formation of expected recombinants could be demonstrated by PCR amplification of a product using primers within pFex and Fiber (FIG. 17). This reaction was also equally successful with 294cre cells stably transformed with pFex. Primer sets with pFex demonstrate the presence of pFex in all samples. Here, an Mfe I+Rsr II fragment of the fiber shuttle, which still retains the floxed Fiber gene, was unable to recombine with pFex; although, it was later found that this fragment could produce recombinants, but with less efficiency than intact shuttle plasmid. There were no recombination specific products in a control reaction containing pFex and a CMV-Luc vector.

Figure 18:
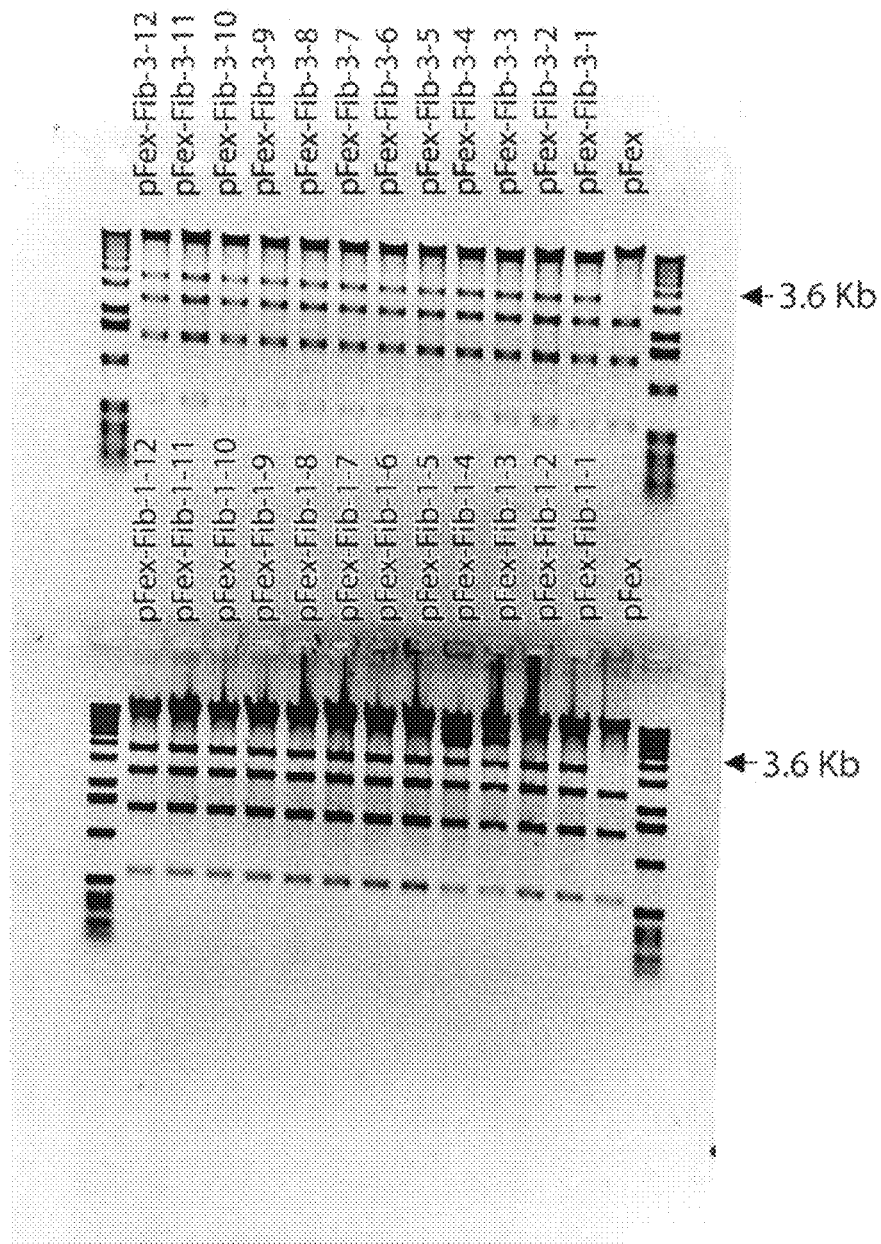
FIG. 18 depicts the results of restriction digests indicating that transformants contained the desired products.

Each transformation was then selected on LB plates with 100 µg/ml ampicillin and 7% sucrose. A small number of colonies were found for each pFex recombination with Rp-Fib shuttle plasmids, indicating that approximately 1% of the pFex plasmids successfully recombined with Rp-Fib shuttles. It has been determined that the recombination products must be further transformed into a more stable, Cre recombinase negative bacterial line, such as DH5α, to isolate the desired products. We found 24/24 ampicillin and sucrose resistant DH5α colonies to contain the desired recombinants without any contaminating aberrant recombination products (FIG. 18). We have successfully recombined all four Rp-Fib shuttle vectors with pFex.

E. Recombination of pAdTrack-Fex and pAdTrack-Luc Fex with RPuc-Fib Shuttles

Figure 19:
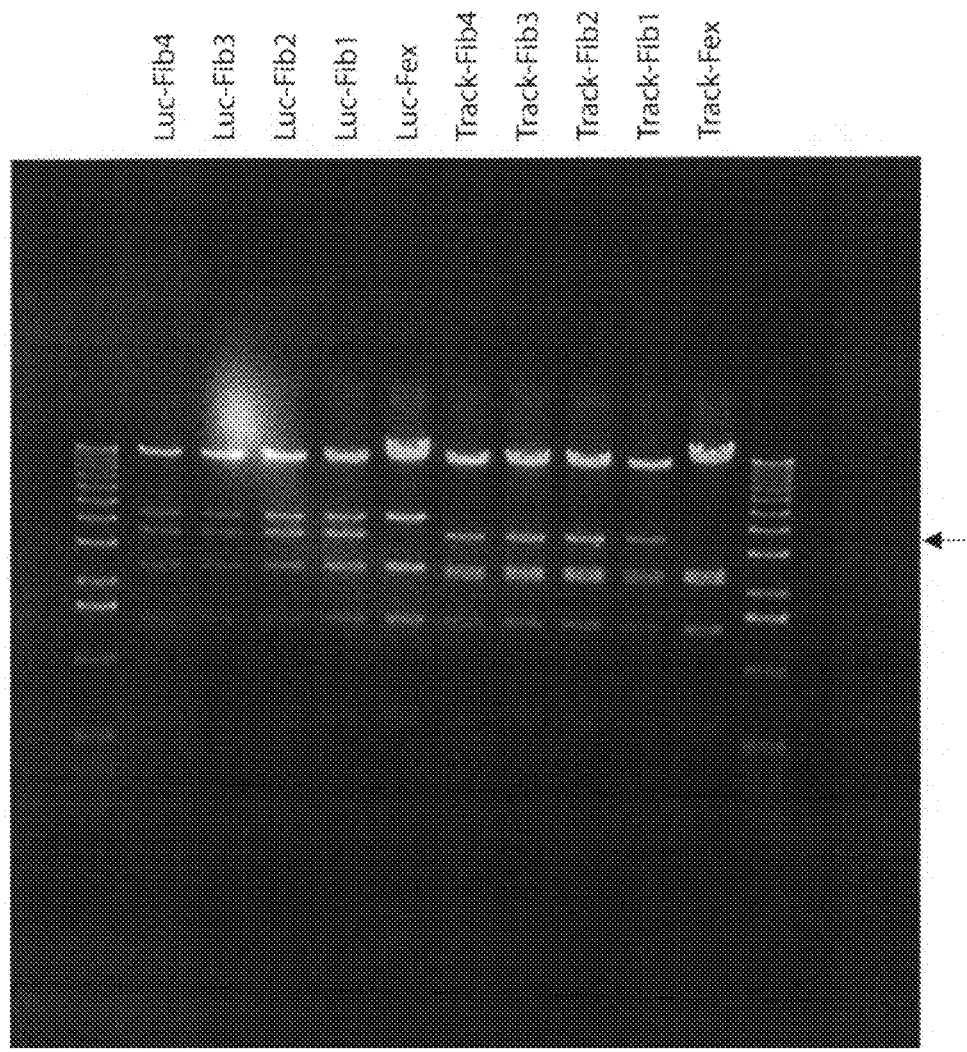
FIG. 19 depicts the results of restriction digests indicating that all products have the expected molecular weight. Track-Fib refers to pAdTrack recombinants and Luc-Fib refers to the pAdTrack-Luc-Fib recombinants.

To demonstrate that the pFex vector can be recombined in both the E1 and Fiber region, the pAdTrack recombination products pAdTrack-Fex and pAdTrack-Luc Fex were recombined with all four RPuc-Fib shuttle vectors. As before, the larger pAdTrack-Fex vectors were co-transformed into 294cre cells with molar excess RPuc-Fib shuttle vectors. Cre expression was induced by heat shock at 42° C. for 20 minutes, followed by 2 hour incubation at 37° C. with shaking at 225 rpm. Recombination efficiency was assessed by selection on a variety of antibiotics, with and without sucrose selection (Table 4). These results indicate that approximately 0.5-7% of the large pAdTrack-Fex and pAdTrack-Luc-Fex vectors recombined successfully with the RPuc-Fib shuttle vectors (Table 5). This efficiency will be significantly improved with further optimization of the Cre recombination reaction and sucrose selection. One colony from each kanamycin and sucrose selection plate were amplified, the DNA isolated and then transformed into the more stable DH5α cell lines, followed by a final colony selection on kanamycin and sucrose. Xho I digestion of these products reveals that all are the result of fiber exchange, giving the desired 3.6 Kb product (FIG. 19). Further, sequencing confirmed both that Cre lox recombination occurred as predicted, and that the expected Fiber modification was incorporated into the viral genome for each shuttle vector.

F. Generation of Adenovirus

Figure 20:
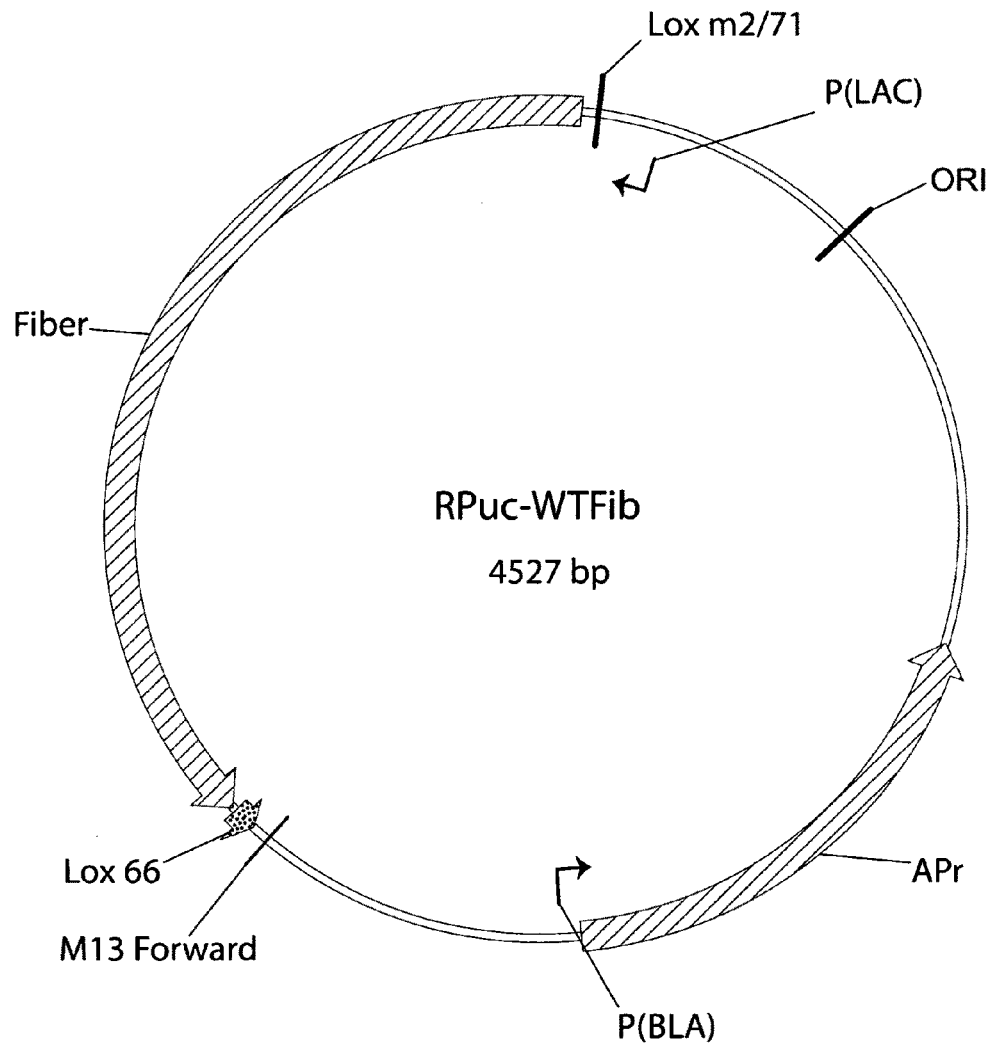
FIG. 20 is a schematic of Rpuc-WTFib, a fiber shuttle that contains wild-type fiber cDNA.
Figure 21:
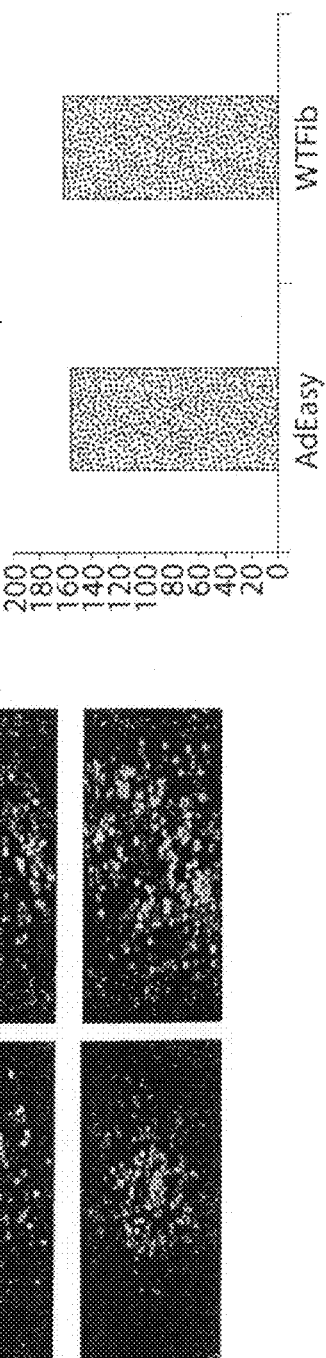
FIG. 21 depicts a comparison of the plaque size of AdTrack-AdEasy and AdTrack-WTFib by fluorescent microscopy.

Adenovirus containing wild type fiber was generated with pFex for the purpose of directly comparing AdEasy and pFex derived virus. The E1 shuttle vector, pAdTrack, was recombined into the E1 region of both AdEasy-1 and pFex. The resulting pAdTrack-Fex vector was then recombined with a fiber shuttle encoding the Wild Type Fiber, Rpuc-WTFib (FIG. 20). The resulting pFex-based viral genome was termed "pAdTrack-WTFib". Both pAdTrack-WTFib and pAdTrack-AdEasy viral plasmids were linearized with PacI and separately transfected into 293 cells for viral production. Both plasmids generated viable virus. These were concurrently amplified, harvested, and titered. The resulting viral titers were identical between AdTrack-AdEasy and AdTrack-WT-fib virus (Table 6). Further, both virus were applied to 293 cells at low multiplicity of infection (MOI) and plaques size was compared by fluorescent microscopy (GFP) to determine if there were any pFex-related deleterious effects on viral replication. Both virus had identical plaque size (FIG. 21). Therefore, there appear to be no deleterious effects of the lox sites on viral production or lifecycle.

G. Cre Mediated Fiber Exchange in Mammalian Cells

Figure 22:
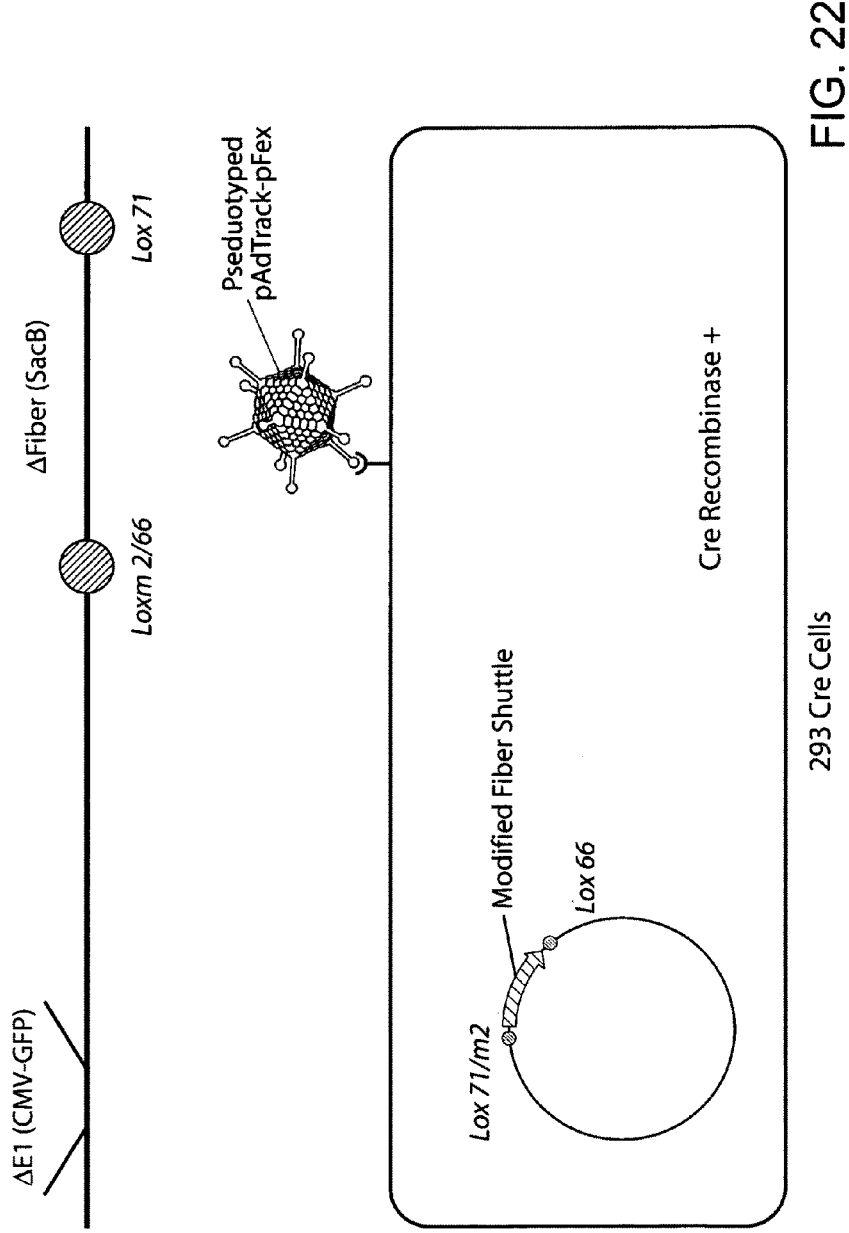
FIG. 22 depicts CRE mediated fiber exchange into viral genome in mammalian 293-cre cells through the use of a pseudotyped pAdTrack-pFex virus.

The Cre-recombinase mediate fiber exchange is not limited to E. coli or plasmids. Fiberless pFex viral vectors can be packaged into working virus through complementary cell lines that express wild type fiber protein (a process known as psuedotyping). These pseudotyped pFex viral vectors can then be used to infect Cre expressing mammalian cells (293cre57) that have been transfected with fiber donor vectors (FIG. 22). Following recombination (2-5 days), cell lysate and supernatant are harvested and used to infect a non-Cre expressing packaging line, such as 293, 911, or 911-S11. The efficiency of recombination is such that 0.01% wild type fiber shuttle, in the background of mutant fiber shuttle, can be detected. This efficiency is great enough to generate an adenoviral peptide display library.

This strategy was used to generate a CAR de-targeted adenovirus, AdTrack-Fib2. To achieve this, 293cre57 cells were simultaneously transfected with 3 µg RPuc-Fib2 (ΔTAYT) and infected with pseudotyped AdTrack-Fex virus at an MOI of 1. Five days post transfection-infection, cell and supernatant were harvested and freeze-thawed. This was used to infect 911-S11 cells, a packaging cell line which expresses an anti-fiber single chain antibody (scFv) for internalization of CAR de-targeted virus. The resulting virus was plaque purified, amplified, and titered in 911-S11 cells. FIG. 23 demonstrates the de-targeted viral production where equal particle numbers (1000 particles per cell) were applied to 293 cells or anti-fiber scFv 911-S11 cells. The lack of infection in 293 cells demonstrates CAR de-targeting, while the 911-S11 cell infection demonstrates viable fiber-containing virus. A control virus, AdTrack-WTFib, demonstrates equal infectivity of 293 and 911-S11.

H. Conclusions

The pFex system offers a unique and highly efficient means of creating fiber-modified or re-targeted adenoviral vectors. This system is fully compatible with the existing AdEasy gene vector system, which is currently applied in the majority of adenoviral vector laboratories. The system is very flexible, allowing Fiber gene transfer before or after E1 cassette exchange. Further, modified fiber gene can be shuttled into intact viral genomes in Cre recombinase expressing mammalian cell lines. This system is ideal for generating and screening modified fiber adenoviral vectors. There is a great need for re-targeted vectors on all levels of biological research, from gene transfer into a traditionally difficult to infect or transfect cell line to the development of systemically targeted therapeutic virus. pFex offers a simple and efficient means to create viral vectors to reach these goals.

Incorporation By Reference

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for generating a recombinant adenoviral vector encoding a desired product, comprising the step(s) of co-transforming a cell expressing an enzyme that mediates homologous recombination with a) a linearized shuttle plasmid encoding a selectable marker, and b) a transfer plasmid, wherein the transfer plasmid comprises a fiber gene, and wherein the fiber gene is modified to contain a unique restriction site in the HI loop;

thereby allowing recombination of the plasmids to generate the recombinant adenoviral vector.

2. The method of claim 1, wherein the enzyme that mediates homologous recombination is RecA.

3. The method of claim 1, wherein the transfer plasmid is constructed by co-transforming into a cell expressing Cre recombinase
   a) a donor plasmid, wherein the donor plasmid encodes the fiber gene flanked by lox sites and a second selectable marker, and
   b) an acceptor plasmid, wherein the acceptor plasmid encodes a negatively selectable marker flanked by lox sites and a first selectable marker, and wherein the acceptor plasmid does not encode the fiber gene;
   thereby allowing for recombination of the fiber gene and the negatively selectable marker.

4. The method of claim 3, wherein the lox sites are incompatible.

5. The method of claim 3, wherein the lox sites are mutated to result in unidirectional recombination.

6. The method of claim 3, wherein the negatively selectable marker is SacB.

7. The method of claim 1, wherein the unique restriction site is a BspEI site.

8. The method of claim 3, wherein the donor plasmid lox sites are Lox m2/66 and Lox 71.

9. The method of claim 3, wherein the acceptor plasmid lox sites are Lox m2/71 and Lox 66.

10. The method of claim 3, wherein the acceptor plasmid contains a kanamycin selectable marker.

11. The method of claim 3, wherein the donor plasmid contains an ampicillin selectable marker.

12. The method of claim 1, wherein the method further comprises selecting recombinant adenoviral vectors using the selectable marker.

13. The method of claim 12, wherein the selectable marker is kanamycin.

14. The method of claim 1, wherein the cell is a bacterial cell.

15. The method of claim 14, wherein the bacterial cell is an *E. coli* cell.

16. The method of claim 3, wherein the cell is a bacterial cell.

17. The method of claim 16, wherein the bacterial cell is an *E. coli* cell.

18. The method of claim 3, wherein the cell is a mammalian cell.

19. The method of claim 1, wherein the shuttle plasmid comprises a resistance gene and a nucleic acid segment encoding the desired product.

20. The method of claim 19, wherein the product is selected from the group consisting of a polypeptide, polypeptides, or fragments thereof, a nucleic acid, an aptamer, an RNAi, an siRNA, and an shRNA.

21. The method of claim 20, wherein the desired product is a polypeptide.

22. The method of claim 21, wherein the desired polypeptide is a therapeutic polypeptide.

23. The method of claim 19, wherein the nucleic acid segment is under control of a promoter.

24. The method of claim 23, wherein the promoter is a tissue specific promoter.

25. The method of claim 19, wherein the transfer plasmid comprises a resistance gene, and wherein the resistance gene in the shuttle plasmid is not the same as the resistance gene in the transfer plasmid.

26. The method of claim 2, wherein the shuttle plasmid contains a unique restriction site located between RecA recombination sites.

27. The method of claim 26, wherein the unique restriction site in the shuttle plasmid is a Pme I site.

28. The method of claim 1, wherein the shuttle plasmid is linearized with Pme I.

29. The method of claim 1, wherein the shuttle plasmid further comprises homologous recombination sites.

30. The method of claim 29, wherein the homologous recombination sites are RecA homologous recombination sites.

31. The method of claim 30, wherein the RecA homologous recombination sites are Ad5 left and Ad5 right.

32. The method of claim 1, wherein the transfer plasmid further comprises homologous recombination sites.

33. The method of claim 32, wherein the homologous recombination sites are RecA homologous recombination sites.

34. The method of claim 33, wherein the RecA homologous recombination sites are Ad5 left and Ad5 right.

35. A method for generating a recombinant adenoviral vector encoding a desired gene product, the method comprising the step(s) of co-transforming a cell expressing Cre recombinase with
   a) a donor plasmid, wherein the donor plasmid encodes a fiber gene flanked by lox sites, wherein the fiber gene is modified to contain a unique restriction site in the HI loop, and
   b) a shuttle-acceptor plasmid encoding a negatively selectable marker, wherein the shuttle-acceptor plasmid does not encode the fiber gene;
   thereby allowing for recombination of the fiber gene and the negatively selectable marker to generate the recombinant adenoviral vector.

36. The method of claim 35, wherein the shuttle-acceptor plasmid encoding the negatively selectable marker is constructed by co-transforming a cell expressing an enzyme that mediates homologous recombination with
   a) an acceptor plasmid, wherein the acceptor plasmid encodes the negatively selectable marker flanked by lox sites and a first selectable marker, and
   b) a linearized shuttle plasmid encoding a second selectable marker,
   thereby allowing for recombination of the first selectable marker and the second selectable marker to generate the shuttle-acceptor plasmid encoding the negatively selectable marker.

37. The method of claim 36, wherein the enzyme that mediates homologous recombination is RecA.

38. The method of claim 35, wherein the lox sites are incompatible.

39. The method of claim 35, wherein the lox sites are mutated to result in unidirectional recombination.

40. The method of claim 35, wherein the negatively selectable marker is SacB.

41. The method of claim 35, wherein the unique restriction site is a BspEI site.

42. The method of claim 35, wherein the donor plasmid lox sites are Lox m2/66 and Lox 71.

43. The method of claim 36, wherein the acceptor plasmid lox sites are Lox m2/71 and Lox 66.

44. The method of claim 36, wherein the acceptor plasmid contains a kanamycin selectable marker.

45. The method of claim 35, wherein the donor plasmid contains an ampicillin selectable marker.

46. The method of claim 36, wherein the method further comprises selecting recombinant adenoviral vectors using the second selectable marker or the negatively selectable marker.

47. The method of claim 46, wherein the second selectable marker is kanamycin and the negatively selectable marker is SacB.

48. The method of claim 35, wherein the cell is a bacterial cell.

49. The method of claim 48, wherein the bacterial cell is an *E. coli* cell.

50. The method of claim 36, wherein the cell is a bacterial cell.

51. The method of claim 50, wherein the bacterial cell is an *E. coli* cell.

52. The method of claim 35, wherein the cell is a mammalian cell.

53. The method of claim 36, wherein the shuttle plasmid comprises a resistance gene and a nucleic acid segment encoding the desired product.

54. The method of claim 53, wherein the desired product is selected from the group consisting of a polypeptide, polypeptides, or fragments thereof, a nucleic acid, an aptamer, an RNAi, an siRNA, and an shRNA.

55. The method of claim 54, wherein the desired product is a polypeptide.

56. The method of claim 55, wherein the desired polypeptide is a therapeutic polypeptide.

57. The method of claim 53, wherein the nucleic acid segment is under control of a promoter.

58. The method of claim 57, wherein the promoter is a tissue specific promoter.

59. The method of claim 37, wherein the shuttle plasmid contains a unique restriction site located between RecA recombination sites.

60. The method of claim 59, wherein the unique restriction site in the shuttle plasmid is a Pme I site.

61. The method of claim 36, wherein the shuttle plasmid is linearized with Pme I.

* * * * *